(12) United States Patent
Shoshtaev

(10) Patent No.: US 12,329,652 B2
(45) Date of Patent: Jun. 17, 2025

(54) EXPANDABLE FUSION DEVICE WITH INDEPENDENT EXPANSION SYSTEMS

(71) Applicant: INTEGRITY IMPLANTS INC., Palm Beach Gardens, FL (US)

(72) Inventor: Eugene Shoshtaev, Del Mar, CA (US)

(73) Assignee: Integrity Implants Inc., Palm Beach Gardens, FL (US)

( * ) Notice: Subject to any disclaimer, the term of this patent is extended or adjusted under 35 U.S.C. 154(b) by 0 days.

(21) Appl. No.: 17/380,897

(22) Filed: Jul. 20, 2021

(65) Prior Publication Data
US 2022/0015923 A1 Jan. 20, 2022

Related U.S. Application Data

(60) Provisional application No. 63/054,229, filed on Jul. 20, 2020.

(51) Int. Cl.
*A61F 2/44* (2006.01)
*A61F 2/30* (2006.01)

(52) U.S. Cl.
CPC .. *A61F 2/4455* (2013.01); *A61F 2002/30266* (2013.01); *A61F 2002/3055* (2013.01); *A61F 2002/30556* (2013.01); *A61F 2002/30579* (2013.01)

(58) Field of Classification Search
CPC .............................. A61F 2/4455–2/447; A61F 2250/0004–2250/001; A61F 2250/0048
See application file for complete search history.

(56) References Cited

U.S. PATENT DOCUMENTS

| | | | |
|---|---|---|---|
| 4,309,777 A | 1/1982 | Patil | |
| 4,733,665 A | 3/1988 | Palmaz | |
| 4,759,766 A | 7/1988 | Buettner-Janz et al. | |
| 4,820,305 A | 4/1989 | Harms et al. | |
| 4,997,432 A | 3/1991 | Keller | |
| 5,192,327 A | 3/1993 | Brantigan | |

(Continued)

FOREIGN PATENT DOCUMENTS

| CN | 101909548 | 7/2014 |
|---|---|---|
| DE | 10 2018 206693 | 2/2019 |

(Continued)

OTHER PUBLICATIONS

U.S. Appl. No. 17/546,816, filed Jul. 2017, To—owned by Applicant.

(Continued)

*Primary Examiner* — Ellen C Hammond
(74) *Attorney, Agent, or Firm* — McNees Wallace & Nurick LLC

(57) ABSTRACT

A variety of expandable cage improvements are provided. The cages can have a width expansion assembly that operates independently of a height expansion assembly and the wedges and ramps do not need to make contact with each other. Wedges, or movable spacers with pivotal link connections, can be used, and any portion of the cage can be expanded in width or in height in an amount that differs from other portions of the cage to provide any of a multitude of desired cage shapes. Interdigitating fingers, slidable and/or pivoting, are provided to distribute stresses over a vertebral endplate as desired.

7 Claims, 73 Drawing Sheets

(56) References Cited

U.S. PATENT DOCUMENTS

| | | |
|---|---|---|
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,126,689 A | 10/2000 | Brett |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,425,919 B1 | 7/2002 | Lambrecht et al. |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,491,724 B1 | 12/2002 | Ferree |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr. et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 | 5/2007 | Branch |
| 7,316,686 B2 | 1/2008 | Dorchak et al. |
| 7,544,208 B1 | 6/2009 | Mueller et al. |
| 7,621,950 B1 | 11/2009 | Globerman et al. |
| 7,643,884 B2 | 1/2010 | Pond et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 4/2011 | Hamada |
| 7,951,202 B2 | 5/2011 | Ralph et al. |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O+3 Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 | 9/2012 | Cipoletti et al. |
| 8,273,129 B2 | 9/2012 | Baynham et al. |
| 8,353,961 B2 | 1/2013 | McClintock |
| 8,353,963 B2 | 1/2013 | Glerum |
| 8,398,713 B2 | 3/2013 | Weiman |
| 8,435,298 B2 | 5/2013 | Weiman |
| 8,491,659 B2 | 7/2013 | Weiman et al. |
| 8,518,120 B2 | 8/2013 | Glerum et al. |
| 8,523,944 B2 | 9/2013 | Jimenez et al. |
| 8,551,173 B2 | 10/2013 | Lechmann et al. |
| 8,556,979 B2 | 10/2013 | Glerum et al. |
| 8,628,578 B2 | 1/2014 | Miller et al. |
| 8,632,595 B2 | 1/2014 | Weiman |
| 8,663,332 B1 | 3/2014 | To |
| 8,685,098 B2 | 4/2014 | Glerum et al. |
| 8,777,993 B2 | 7/2014 | Siegal et al. |
| 8,845,731 B2 | 9/2014 | Weiman |
| 8,852,279 B2 | 10/2014 | Weiman et al. |
| 8,882,840 B2 | 11/2014 | Mcclintock et al. |
| 8,894,712 B2 | 11/2014 | Varela |
| 8,900,307 B2 | 12/2014 | Hawkins et al. |
| 8,906,099 B2 | 12/2014 | Poulos |
| 8,926,704 B2 | 1/2015 | Glerum et al. |
| 8,936,641 B2 | 1/2015 | Cain |
| 8,940,048 B2 | 1/2015 | Butler |
| 8,940,052 B2 | 1/2015 | Lechmann et al. |
| 8,986,387 B1 | 3/2015 | To |
| 9,034,041 B2 | 5/2015 | Wolters |
| 9,039,771 B2 | 5/2015 | Glerum et al. |
| 9,044,342 B2 | 6/2015 | Perloff et al. |
| 9,060,876 B1 | 6/2015 | To |
| 9,066,813 B2 | 6/2015 | Farris et al. |
| 9,138,328 B2 | 9/2015 | Butler et al. |
| 9,155,628 B2 | 10/2015 | Glerum et al. |
| 9,186,259 B2 | 11/2015 | To |
| 9,216,095 B2 | 12/2015 | Glerum et al. |
| 9,241,806 B2 | 1/2016 | Suh |
| 9,278,008 B2 | 3/2016 | Perloff et al. |
| 9,320,610 B2 | 4/2016 | Alheidt et al. |
| 9,333,092 B2 | 5/2016 | To |
| 9,351,848 B2 | 5/2016 | Glerum et al. |
| 9,402,733 B1 | 8/2016 | To |
| 9,402,739 B2 | 8/2016 | Weiman et al. |
| 9,421,110 B2 | 8/2016 | Masson |
| 9,439,782 B2 | 9/2016 | Kleiner |
| 9,445,918 B1 | 9/2016 | Lin et al. |
| 9,463,052 B2 | 10/2016 | Geist |
| 9,474,625 B2 | 10/2016 | Weiman |
| 9,480,574 B2 | 11/2016 | Lee et al. |
| 9,480,576 B2 | 11/2016 | Pepper et al. |
| 9,545,316 B2 | 1/2017 | Ashley et al. |
| 9,561,116 B2 | 2/2017 | Weiman et al. |
| 9,566,168 B2 | 2/2017 | Glerum et al. |
| 9,597,200 B2 | 3/2017 | Glerum et al. |
| 9,636,154 B2 | 5/2017 | Overes et al. |
| 9,655,744 B1 | 5/2017 | Pimenta |
| 9,662,224 B2 | 5/2017 | Weiman et al. |
| 9,675,466 B2 | 6/2017 | Overes et al. |
| 9,675,469 B2 | 6/2017 | Landry et al. |
| 9,717,601 B2 | 8/2017 | Miller |
| 9,730,803 B2 | 8/2017 | DiMauro et al. |
| 9,737,411 B2 | 8/2017 | Loebl et al. |
| 9,795,493 B1 | 10/2017 | Bannigan |
| 9,801,640 B2 | 10/2017 | O+3 Neil et al. |
| 9,801,733 B2 | 10/2017 | Wolters et al. |
| 9,801,734 B1 | 10/2017 | Stein et al. |
| 9,839,528 B2 | 12/2017 | Weiman et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 | 3/2018 | Thommen et al. |
| 9,913,736 B2 | 3/2018 | To |
| 9,974,662 B2 | 5/2018 | Hessler et al. |
| 9,987,143 B2 | 6/2018 | Robinson et al. |
| 9,999,517 B2 | 6/2018 | To |
| 10,052,215 B2 | 8/2018 | Hessler et al. |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 | 10/2018 | Koch et al. |
| 10,137,007 B2 | 11/2018 | Dewey et al. |
| 10,143,565 B2 | 12/2018 | Farris et al. |
| 10,143,569 B2 | 12/2018 | Weiman et al. |

(56) References Cited

U.S. PATENT DOCUMENTS

| | | |
|---|---|---|
| 10,149,773 B2 | 12/2018 | To |
| 10,154,911 B2 | 12/2018 | Predick et al. |
| 10,182,851 B2 | 1/2019 | Robie et al. |
| 10,206,788 B2 | 2/2019 | Field et al. |
| 10,226,356 B2 | 3/2019 | Grotz |
| 10,226,360 B2 | 3/2019 | Baynham |
| 10,238,503 B2 | 3/2019 | Branch et al. |
| 10,251,759 B2 | 4/2019 | Butler et al. |
| 10,265,192 B2 | 4/2019 | Eastlack et al. |
| 10,322,014 B2 | 6/2019 | To |
| 10,342,675 B2 | 7/2019 | Alheidt |
| 10,383,743 B2 | 8/2019 | To |
| 10,413,419 B2 | 9/2019 | Thibodeau |
| 10,426,634 B1 | 10/2019 | Al-Jazaeri et al. |
| 10,441,430 B2 | 10/2019 | Ludwig et al. |
| 10,470,891 B2 | 11/2019 | Sharifi-Mehr et al. |
| 10,470,894 B2 | 11/2019 | Foley et al. |
| 10,485,675 B2 | 11/2019 | Sharifi-Mehr et al. |
| 10,492,918 B2 | 12/2019 | DiMauro et al. |
| 10,531,964 B2 | 1/2020 | Miller et al. |
| 10,624,756 B2 | 4/2020 | Bernard et al. |
| 10,631,996 B2 | 4/2020 | Bernard et al. |
| 10,682,239 B2 | 6/2020 | Hsu et al. |
| 10,687,876 B2 | 6/2020 | Vrionis et al. |
| 10,869,769 B2 | 12/2020 | Eisen et al. |
| 10,898,340 B2 | 1/2021 | Koch et al. |
| 11,076,968 B2 | 8/2021 | To |
| 2002/0035400 A1 | 3/2002 | Bryan et al. |
| 2002/0040243 A1 | 4/2002 | Attali |
| 2003/0074075 A1 | 4/2003 | Thomas et al. |
| 2003/0083746 A1 | 5/2003 | Kuslich |
| 2004/0010315 A1 | 1/2004 | Song |
| 2004/0024463 A1 | 2/2004 | Thomas et al. |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0281551 A1 | 5/2009 | Frey |
| 2009/0222043 A1 | 9/2009 | Altarac |
| 2009/0234389 A1 | 9/2009 | Chuang |
| 2010/0010542 A1 | 1/2010 | Jackson |
| 2010/0010633 A1 | 1/2010 | Kohm |
| 2010/0042218 A1 | 2/2010 | Nebosky et al. |
| 2010/0082109 A1 | 4/2010 | Greenhalgh et al. |
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1* | 11/2010 | Lechmann ............ A61F 2/4425 623/17.11 |
| 2010/0292796 A1 | 11/2010 | Greenhalgh |
| 2011/0022090 A1 | 1/2011 | Gordon |
| 2011/0029082 A1 | 2/2011 | Hall |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1 | 12/2011 | Glerum |
| 2012/0029636 A1 | 2/2012 | Ragab |
| 2012/0029645 A1 | 2/2012 | Fabian et al. |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0184822 A1 | 7/2013 | Kleiner |
| 2014/0039622 A1* | 2/2014 | Glerum ................ A61F 2/447 623/17.15 |
| 2014/0039625 A1 | 2/2014 | To |
| 2014/0243981 A1 | 8/2014 | Davenport et al. |
| 2015/0100128 A1 | 4/2015 | Glerum et al. |
| 2015/0148908 A1 | 5/2015 | Marino et al. |
| 2015/0190242 A1 | 7/2015 | Blain et al. |
| 2015/0374508 A1 | 12/2015 | Sandul |
| 2016/0015530 A1 | 1/2016 | To |
| 2016/0256291 A1 | 9/2016 | Miller |
| 2016/0317315 A1 | 11/2016 | Weiman |
| 2016/0338854 A1 | 11/2016 | Serhan et al. |
| 2017/0000622 A1* | 1/2017 | Thommen ............. A61F 2/4425 |
| 2017/0119540 A1 | 5/2017 | Greenhalgh |
| 2017/0209282 A1 | 7/2017 | Aghayev et al. |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0185163 A1 | 7/2018 | Weiman et al. |
| 2018/0193164 A1 | 7/2018 | Shoshtaev |
| 2018/0214221 A1 | 8/2018 | Crawford et al. |
| 2018/0256357 A1 | 9/2018 | To |
| 2018/0296361 A1 | 10/2018 | Butler et al. |
| 2018/0303626 A1 | 10/2018 | Rogers et al. |
| 2018/0360489 A1 | 12/2018 | Geist |
| 2018/0360617 A1 | 12/2018 | Fabian et al. |
| 2019/0053913 A1 | 2/2019 | To |
| 2019/0060085 A1 | 2/2019 | Geist |
| 2019/0076263 A1 | 3/2019 | Emstad |
| 2019/0091033 A1 | 3/2019 | Dewey et al. |
| 2019/0099278 A1 | 4/2019 | Farris et al. |
| 2019/0110900 A1 | 4/2019 | Suddaby |
| 2019/0110902 A1 | 4/2019 | Vigliotti et al. |
| 2019/0117409 A1 | 4/2019 | Shoshtaev |
| 2019/0117827 A1 | 4/2019 | Roth |
| 2019/0201209 A1 | 7/2019 | Branch et al. |
| 2019/0209339 A1 | 7/2019 | To |
| 2019/0240039 A1 | 8/2019 | Walker et al. |
| 2019/0254836 A1 | 8/2019 | Cowan et al. |
| 2019/0254841 A1 | 8/2019 | To |
| 2019/0269521 A1 | 9/2019 | Shoshtaev |
| 2019/0290448 A1 | 9/2019 | Predick et al. |
| 2019/0307573 A1 | 10/2019 | Sicotte et al. |
| 2019/0328544 A1 | 10/2019 | Ashley et al. |
| 2019/0336299 A1 | 11/2019 | Bernard et al. |
| 2020/0000607 A1 | 1/2020 | To |
| 2020/0015985 A1 | 1/2020 | Rogers et al. |
| 2020/0030110 A1 | 1/2020 | Sharabani et al. |
| 2020/0093609 A1 | 3/2020 | Shoshtaev |
| 2020/0113706 A1 | 4/2020 | Robinson |
| 2020/0129307 A1 | 4/2020 | Hunziker et al. |
| 2020/0229939 A1 | 7/2020 | To |
| 2020/0352732 A1 | 11/2020 | To |
| 2021/0045893 A1 | 2/2021 | To |
| 2021/0137695 A1* | 5/2021 | Huang ................ A61F 2/4455 |

(56) References Cited

U.S. PATENT DOCUMENTS

| | | |
|---|---|---|
| 2021/0196470 A1 | 7/2021 | Shoshtaev |
| 2021/0330472 A1 | 10/2021 | Shoshtaev |

FOREIGN PATENT DOCUMENTS

| | | |
|---|---|---|
| EP | 1011503 | 2/1998 |
| EP | 1233732 | 2/2001 |
| EP | 2327377 | 3/2002 |
| EP | 1532949 | 11/2003 |
| EP | 2237748 | 1/2009 |
| JP | 2009/505686 | 7/2005 |
| WO | WO 1996/040015 | 6/1996 |
| WO | WO 2000/044319 | 1/2000 |
| WO | WO 2001/066047 | 7/2001 |
| WO | WO 2005/112834 | 12/2005 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | PCT/US2013/052799 | 7/2012 |
| WO | WO 2012/135764 | 10/2012 |
| WO | WO 2013/148176 | 10/2013 |
| WO | PCT/US2014/054437 | 2/2014 |
| WO | WO 2014/164625 | 10/2014 |
| WO | PCT/US2016/014100 | 12/2015 |
| WO | WO 2016/019241 | 2/2016 |
| WO | WO 2017/004503 | 1/2017 |
| WO | WO 2017/035155 | 3/2017 |
| WO | PCT/US2017/52708 | 9/2017 |
| WO | PCT/US2019/20354 | 3/2018 |
| WO | PCT/US2018/43517 | 7/2018 |
| WO | PCT/US2021/42392 | 7/2020 |

OTHER PUBLICATIONS

U.S. Appl. No. 17/553,136, filed Dec. 13, 2012, To—owned by Applicant.
U.S. Appl. No. 60/666,945 (priority for U.S. Pat. No. 7,731,751, cited herein), filed Mar. 31, 2005, Butler, et al.
U.S. Appl. No. 61/585,724 (priority for U.S. Pat. No. 9,463,052, cited herein), filed Jan. 12, 2012, Geist—owned by Applicant.
U.S. Appl. No. 61/737,054 (priority for U.S. Pat. No. 8,663,332, cited herein), filed Dec. 15, 2013, To—owned by Applicant.
U.S. Appl. No. 61/875,688 (priority for U.S. Pat. No. 9,186,259, cited herein), filed Oct. 4, 2013, To—owned by Applicant.
U.S. Appl. No. 62/232,021 (priority for U.S. Pat. No. 10,058,350, cited herein), filed Sep. 24, 2015, Geist—owned by Applicant.
U.S. Appl. No. 62/444,663 (priority for U.S. 2018/0193164, cited herein), filed Jan. 10, 2017, Shoshtaev—owned by Applicant.
U.S. Appl. No. 62/471,206 (priority for U.S. 2018/0193164, cited herein), filed Jan. 10, 2017, Shoshtaev—owned by Applicant.
U.S. Appl. No. 62/481,565 (priority for U.S. 2018/0193164, cited herein), filed Jan. 10, 2017, Shoshtaev—owned by Applicant.
U.S. Appl. No. 62/536,335 (priority for PCT/US2018/43517, cited herein), filed Jul. 24, 2017, To—owned by Applicant.
U.S. Appl. No. 62/550,557 (priority for U.S. Appl. No. 16/113,040, cited herein), filed Aug. 25, 2017, Geist—owned by Applicant.
U.S. Appl. No. 62/637,306 (priority for U.S. Appl. No. 16/290,428, cited herein), filed Mar. 1, 2018, Shoshtaev—owned by Applicant.
U.S. Appl. No. 63/054,229 (priority for U.S. Appl. No. 17/380,897, cited herein), filed Jul. 20, 2020, Shoshtaev—owned by Applicant.
Written opinion and search report for PCT/US2013/052799, To—owned by Applicant, Dec. 2, 2012.
PCT/US2013/073435 Published as WO 2014/093136, To—owned by Applicant, Dec. 5, 2013.
Written opinion and search report for PCT/US2013/073435, To—owned by Applicant, Apr. 30, 2012.
Written opinion and search report for PCT/US2014/054437, To—owned by Applicant, Jan. 6, 2015.
Written opinion and search report for PCT/US2016/014100, To—owned by Applicant, Jan. 6, 2015.
Written opinion and search report for PCT/US2017/52708, To—owned by Applicant, Sep. 21, 2017.
PCT/US2016/053467 Published as WO 2017/053813, Geist—owned by Applicant, Sep. 24, 2015.
Written opinion and search report for PCT/US2016/053467, Geist—owned by Applicant, Sep. 24, 2015.
PCT/US2018/13207 Published as WO 2018/132502, Shoshtaev—owned by Applicant, Jan. 10, 2018.
Written opinion and search report for PCT/US2018/13207, Shoshtaev—owned by Applicant, Jan. 10, 2018.
Written opinion and search report for PCT/US2018/43517, To—owned by Applicant, Jul. 24, 2018.
Written opinion and search report for PCT/US2019/20354, Shoshtaev—owned by Applicant, Mar. 1, 2018.
Written opinion and search report for PCT/US2021/42392, Shoshtaev—owned by Applicant, Jul. 20, 2020.
European search report for EP 13862126, Dec. 5, 2013, To—owned by Applicant.
European search report for EP 14842880, Jun. 22, 2016, To—owned by Applicant.
European search report for EP 16740662, Nov. 29, 2017, To—owned by Applicant.
European search report for EP 17853887.2, Jul. 31, 2019, To—owned by Applicant.
European search report for EP 18738659.5, Jan. 10, 2018, Shoshtaev—owned by Applicant.
European search report for EP 19162909.6, Dec. 5, 2013, To—owned by Applicant.
European search report for EP 19760773.2, Dec. 2, 2020, Shoshtaev—owned by Applicant.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
Capstone® Peek spinal system PLIF anf TLIF surgical technique. Medtronic Sofamor Danek 1-36 (2009).
Coalign. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage_Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).

(56) References Cited

OTHER PUBLICATIONS

Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].

PowerBuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].

PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].

Sasani, M. et al. Single-stage posterior corpectomy and expandable cage placement for treatment of thoracic or lumbar burst fractures. Spine 34(1): E33-E40 (Jan. 1, 2009).

Spineology. OptiMesh 1500E deploying grafting system. [online] URL: http://www.spineology.com/fb/intl/products/products/optimesh1500e.html (retrieved Jun. 3, 2013).

Staxx XD, www.spinewave.com. [online] URL: http://www.spinewave.com/products/xd_us.html [retrieved on Jan. 27, 2013].

Synfix-LR System. Instruments and implants for stand-alone anterior lumbar interbody fusion (ALIF). Synthes SynFix-LR system technique guide 52 pages (2010).

Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].

Uchida, K. et al. Anterior expandable strut cage replacement for osteoporotic thoracolumbar vertebral collapse. J Neurosurg Spine 4(6): 454-462 (Jun. 2006).

Xenos. Cage mesh system for spine. Biotek Chetan Meditech Pvt. Ltd. [online] URL: http://www.biotekortho.net/spine-treatment.html [retrieved on Feb. 13, 2013].

Zeus-O, [online] URL: http://www.amendia.com/zeuso.html [retrieved on Jan. 27, 2013].

* cited by examiner

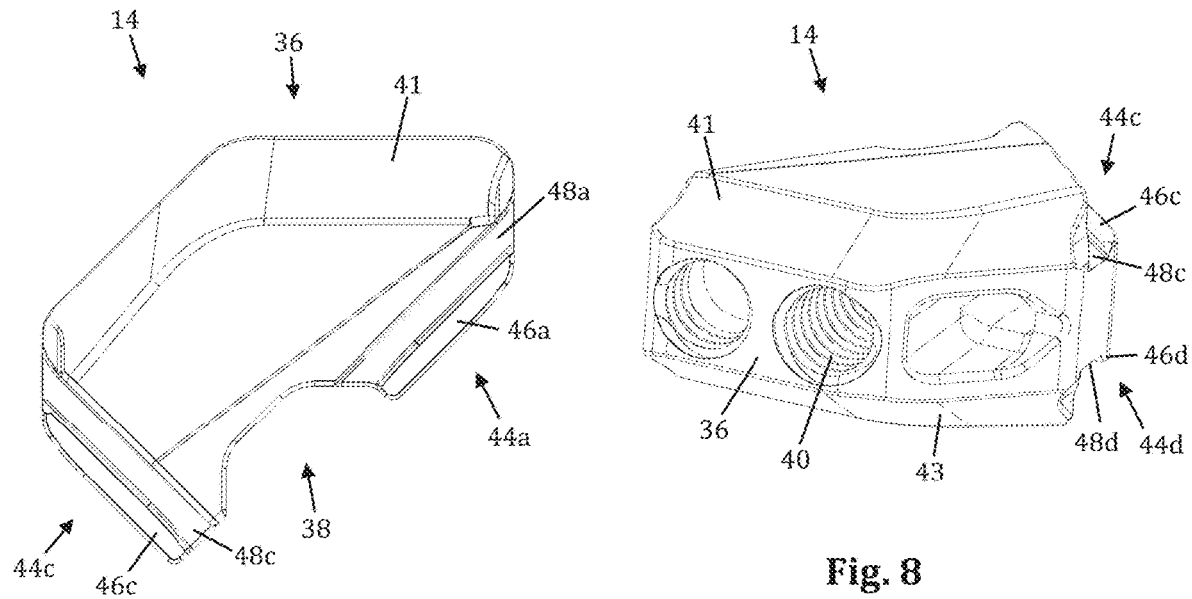
Fig. 7
Fig. 8
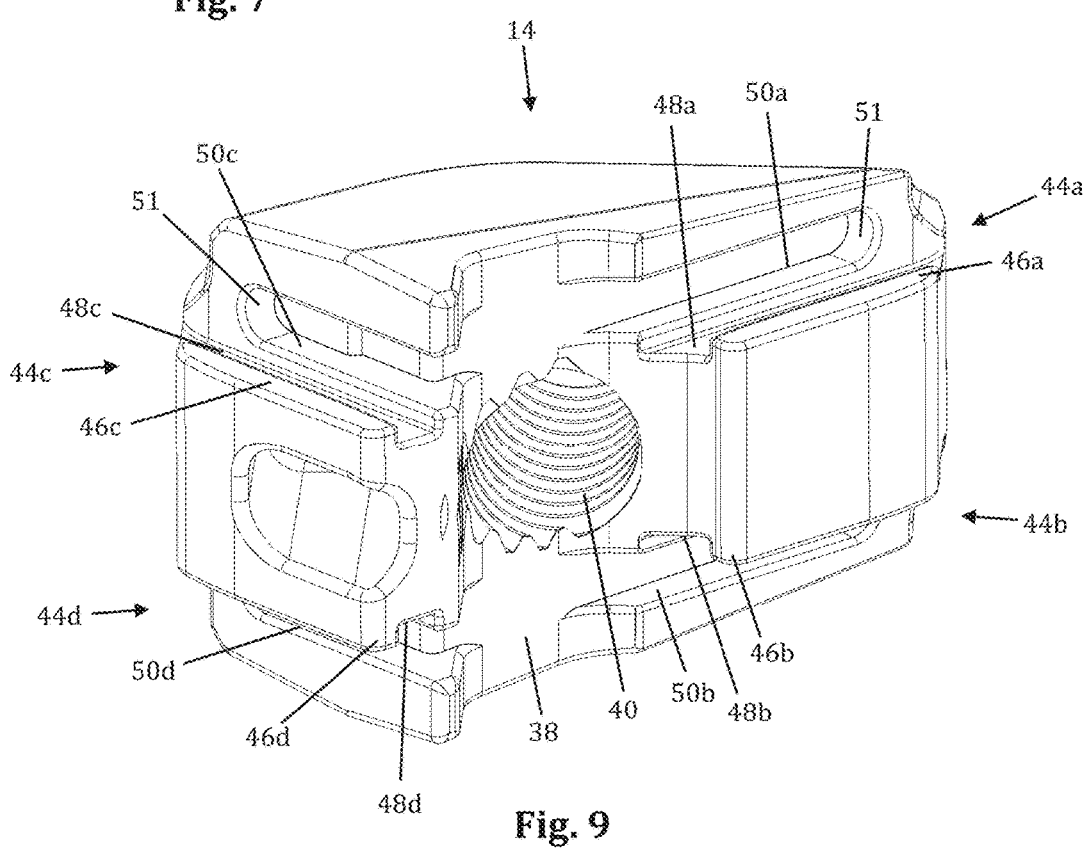
Fig. 9

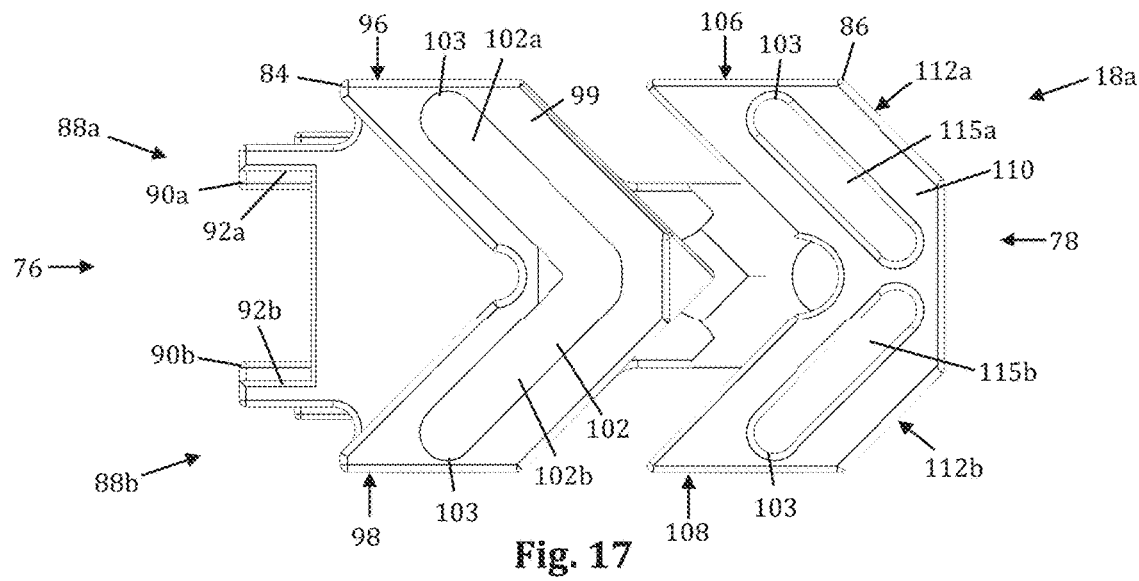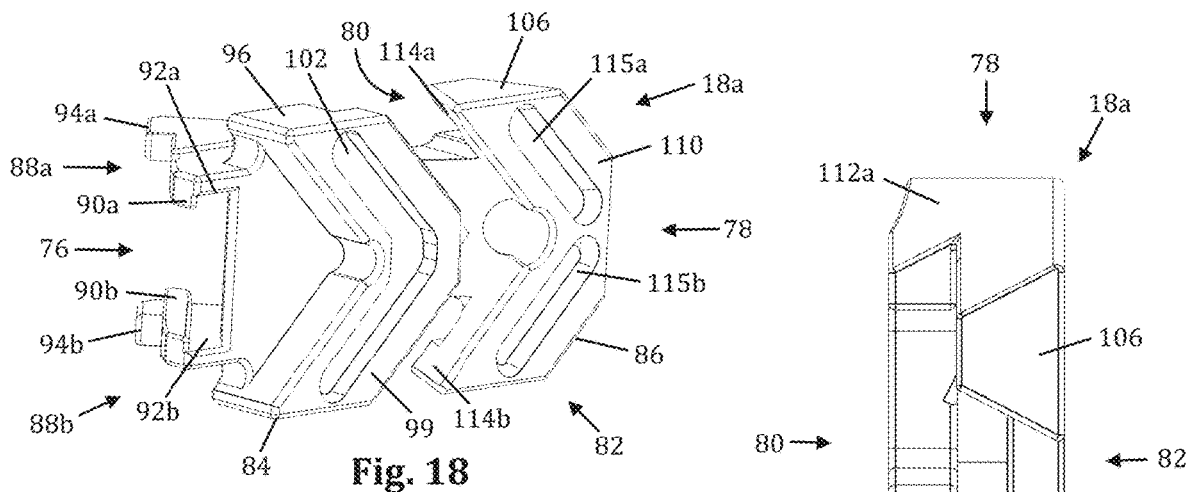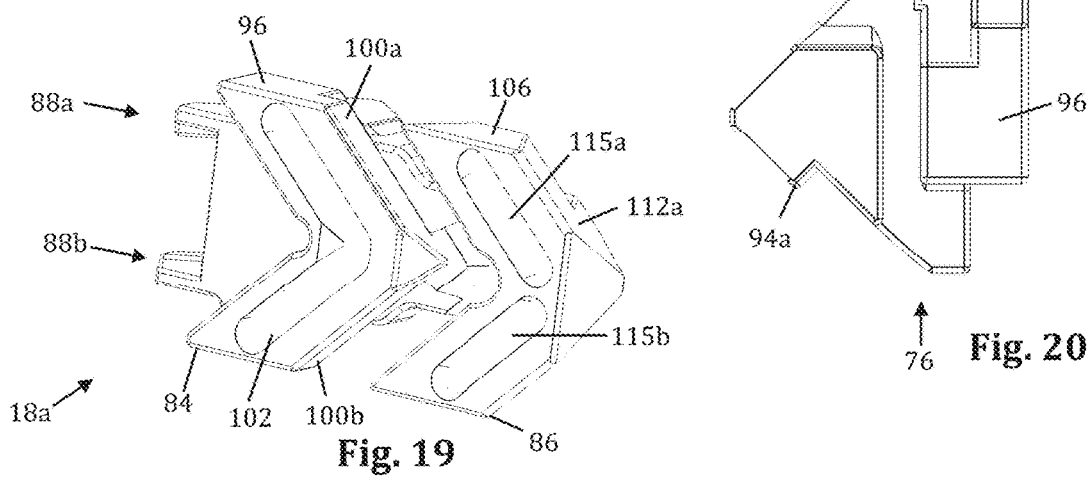

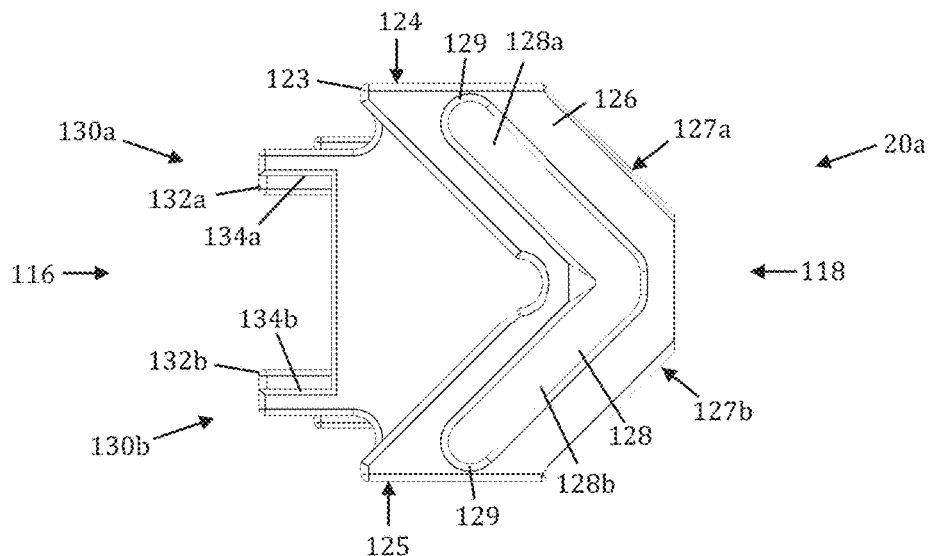
Fig. 21
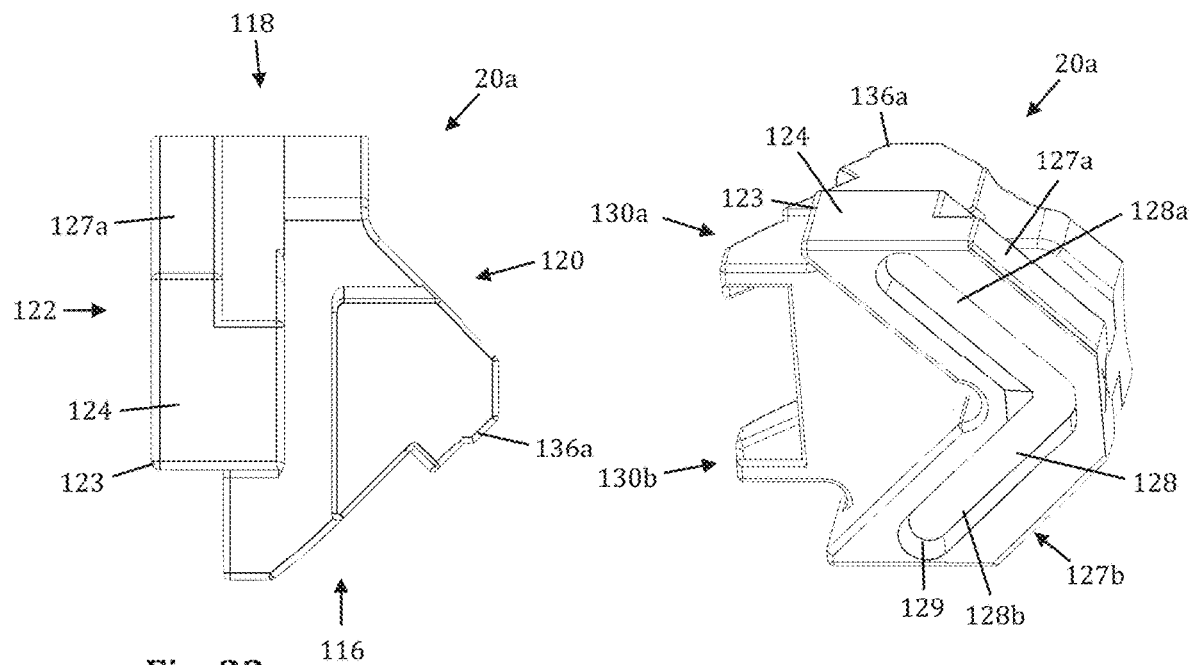
Fig. 22
Fig. 23

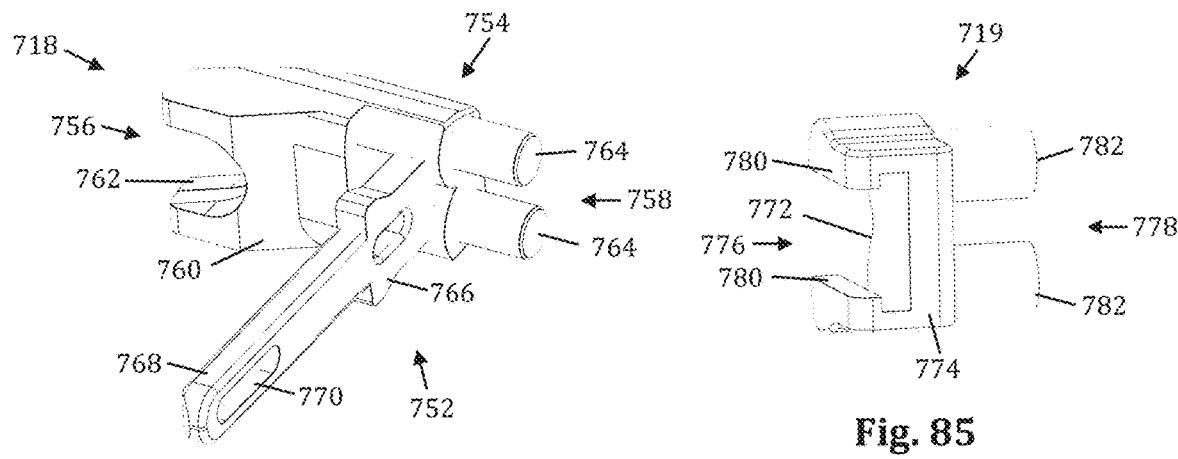
Fig. 84
Fig. 85
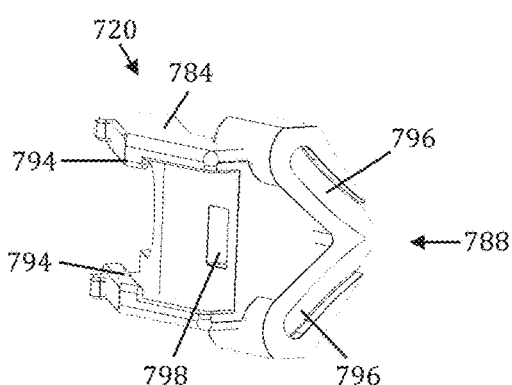
Fig. 86
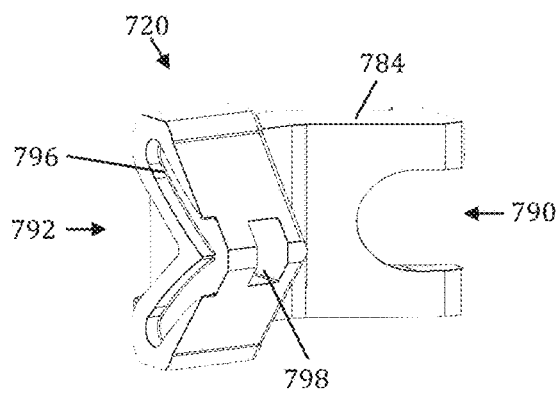
Fig. 87
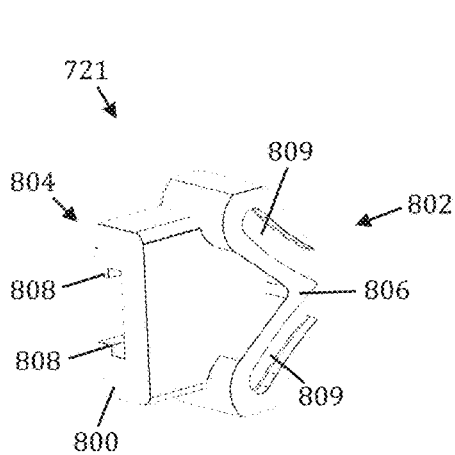
Fig. 88
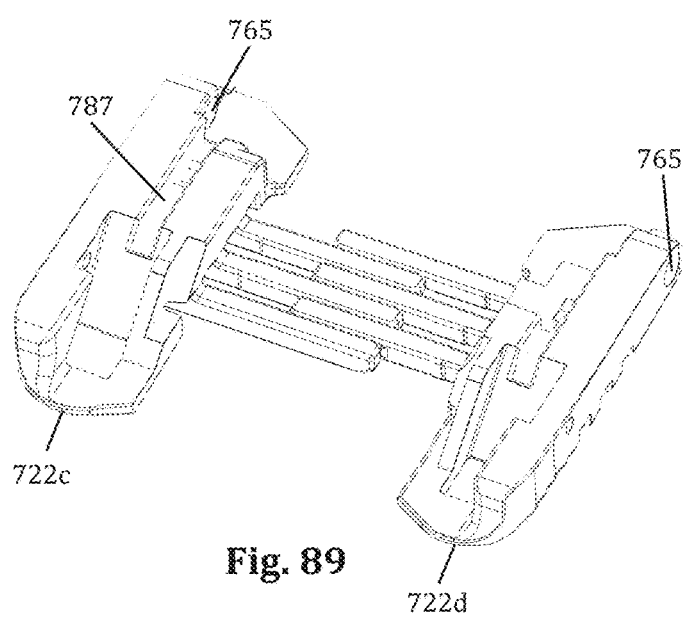
Fig. 89

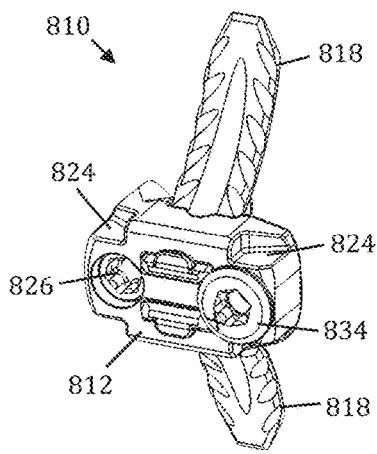
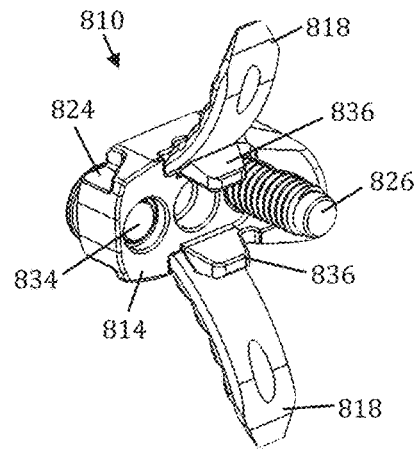
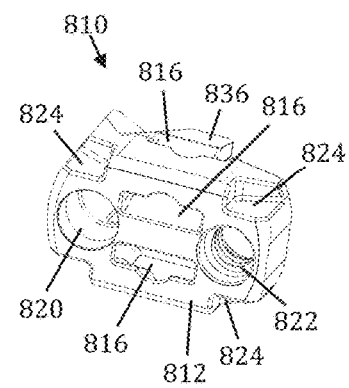
Fig. 90    Fig. 91    Fig. 92
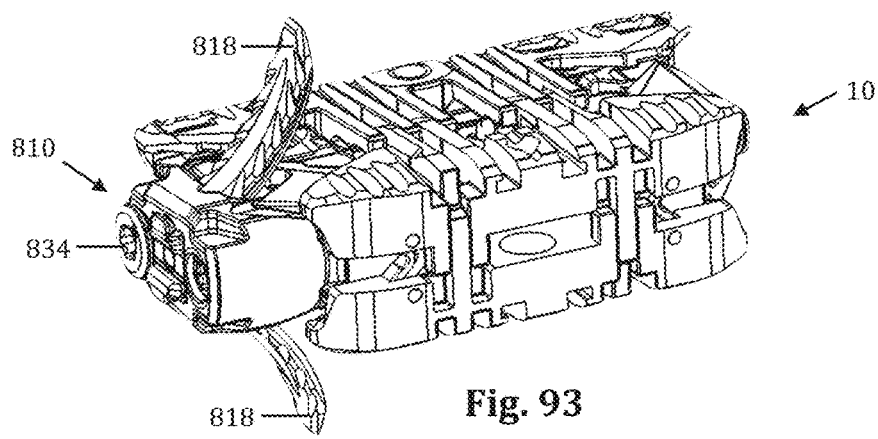
Fig. 93
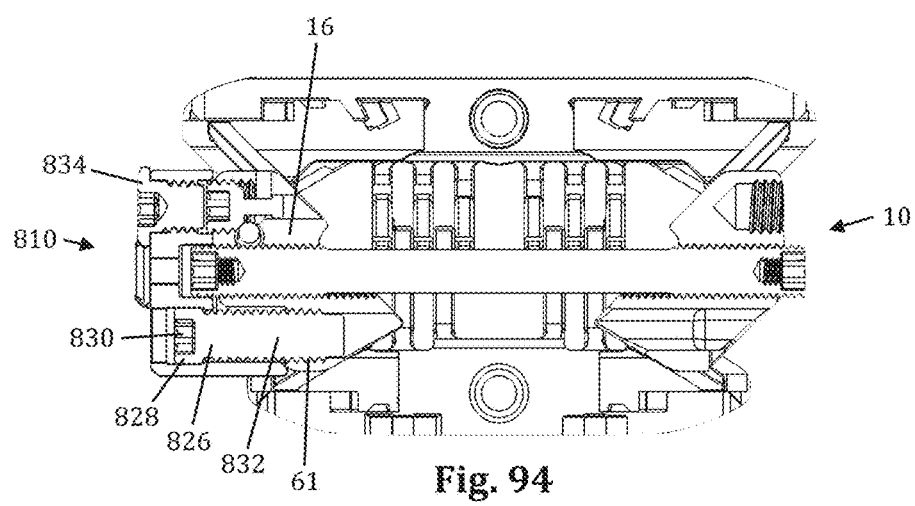
Fig. 94

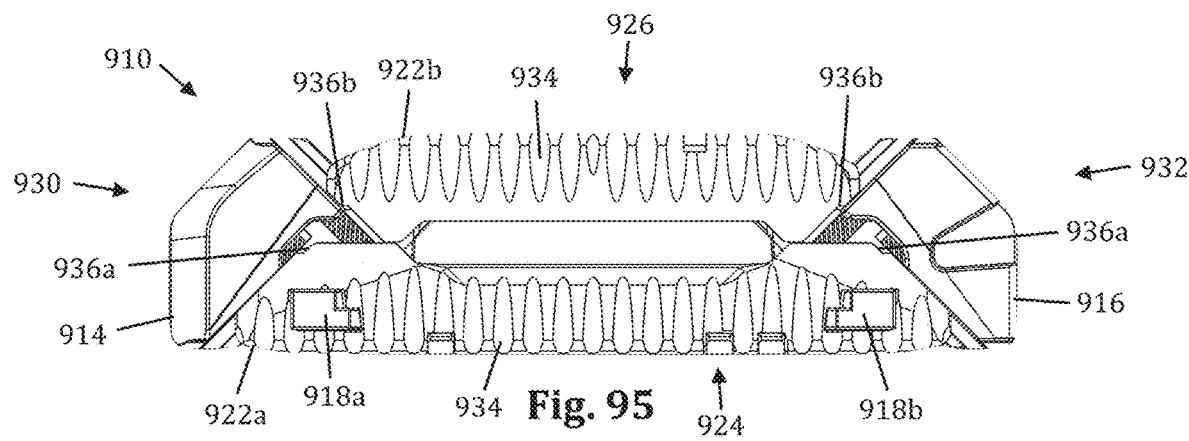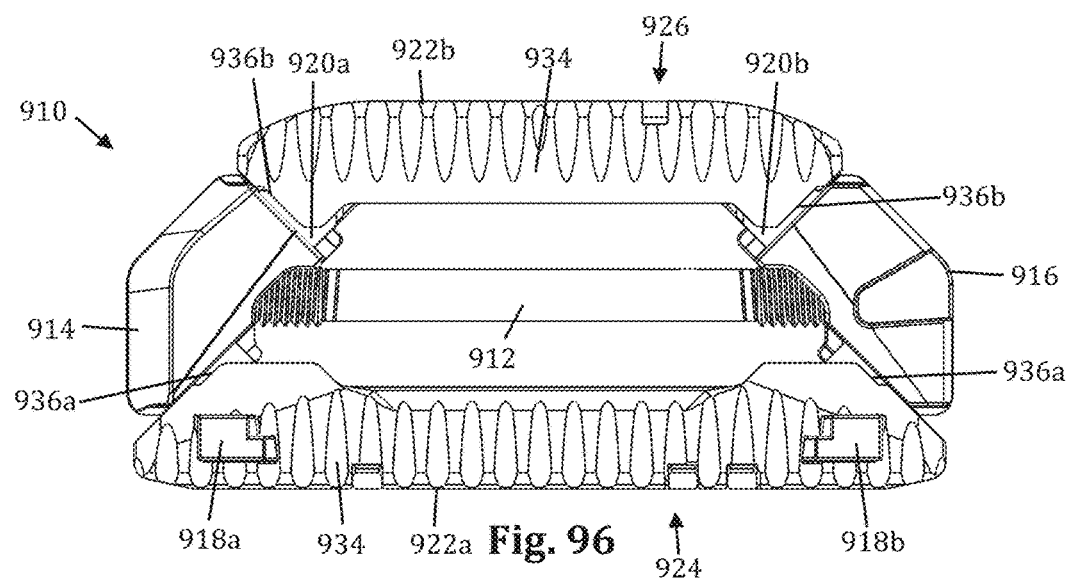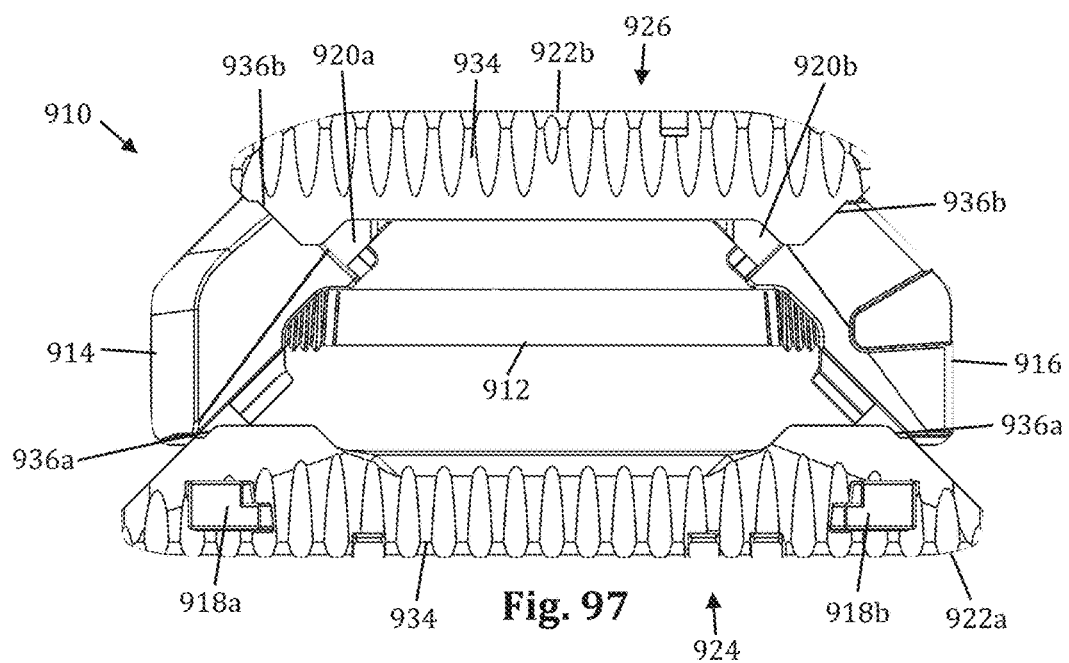

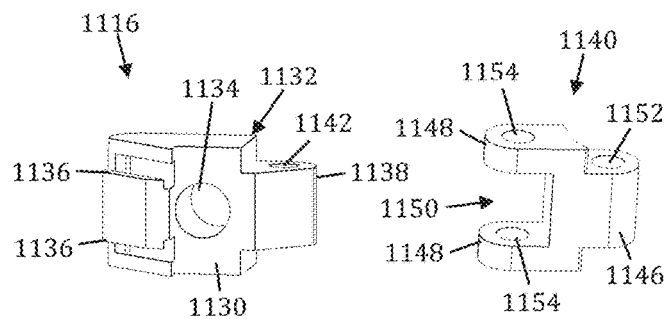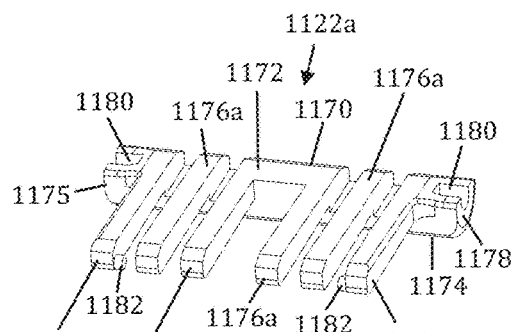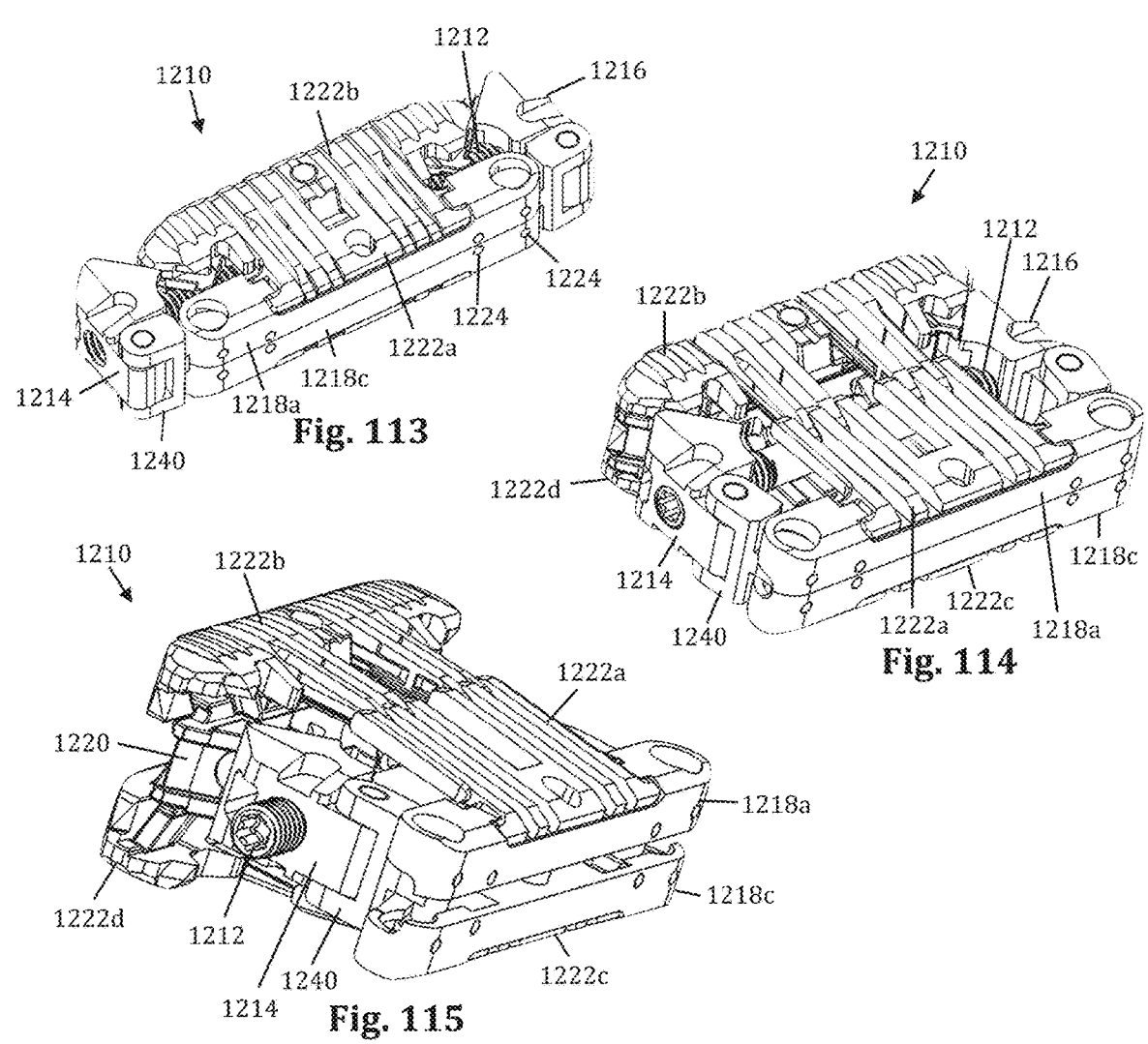

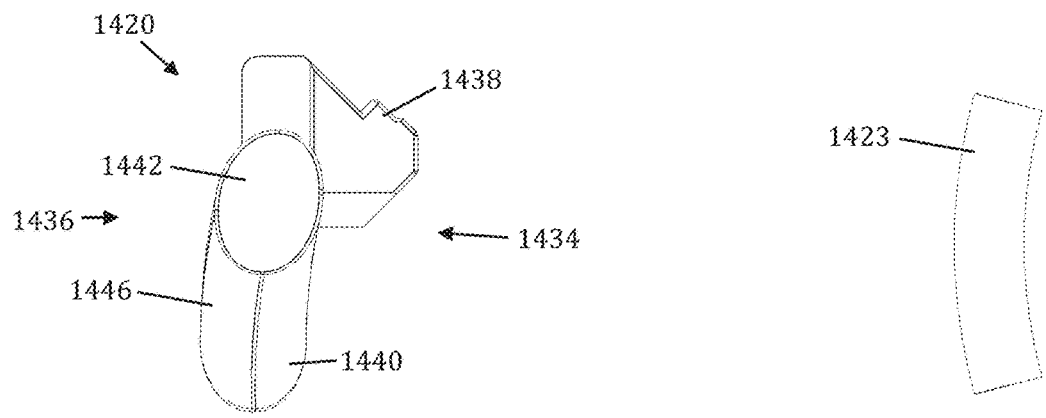
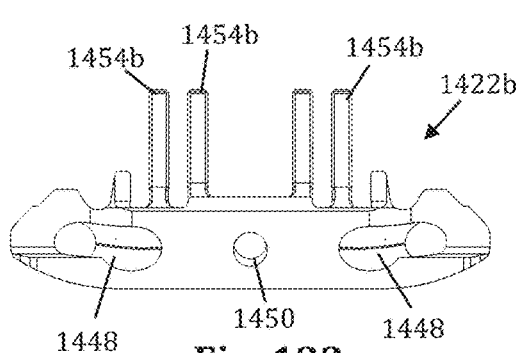
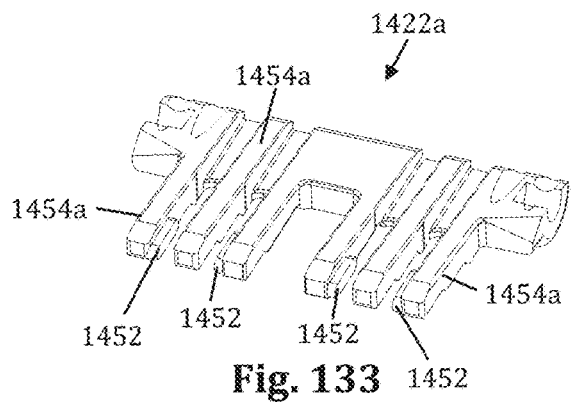
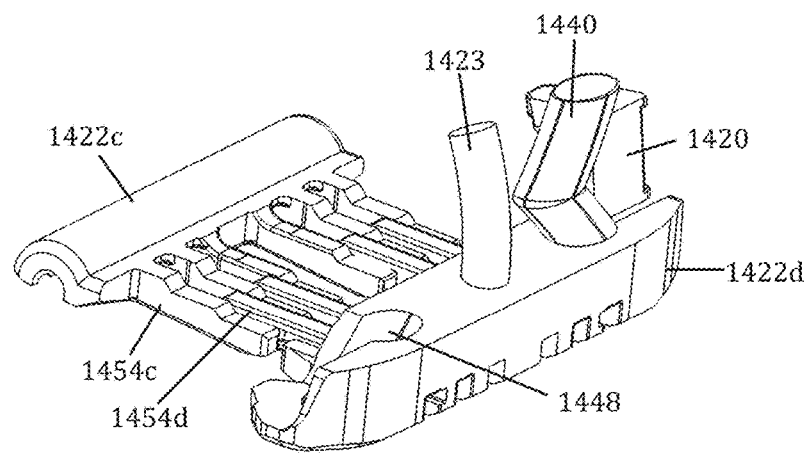

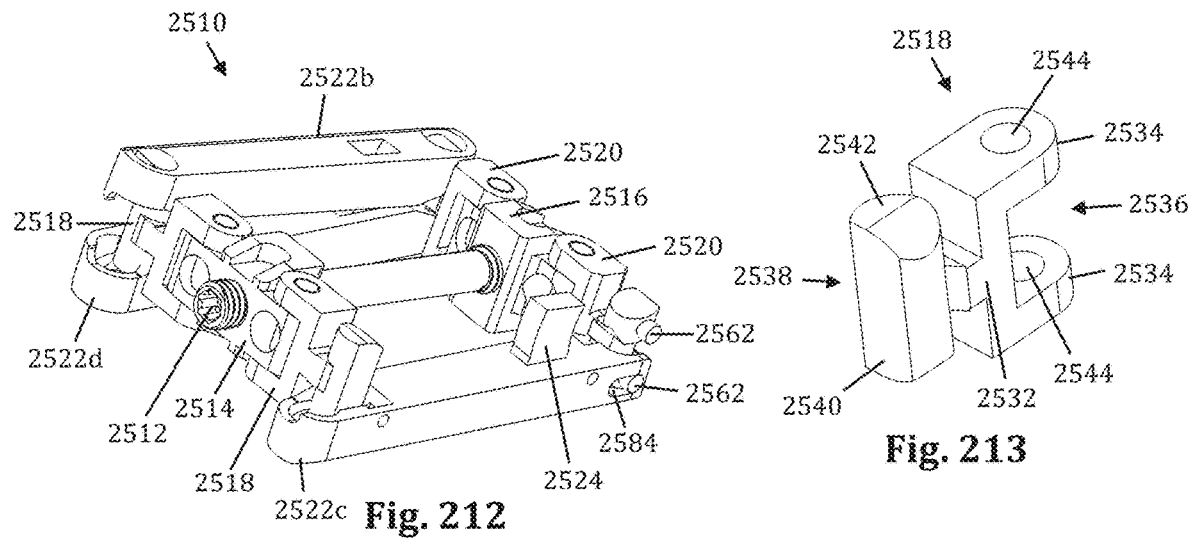
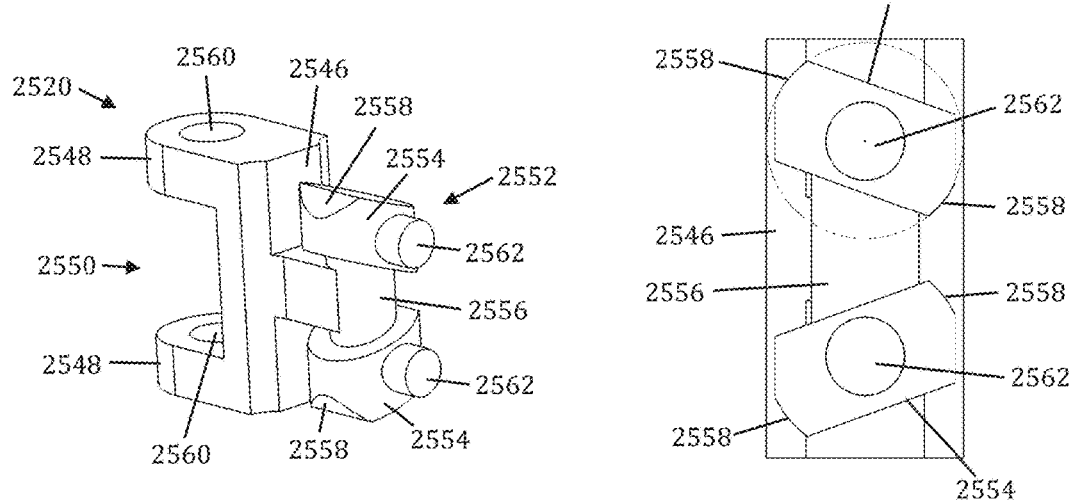
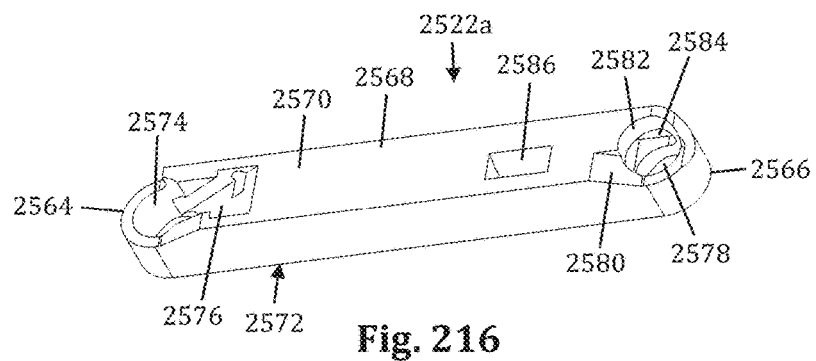

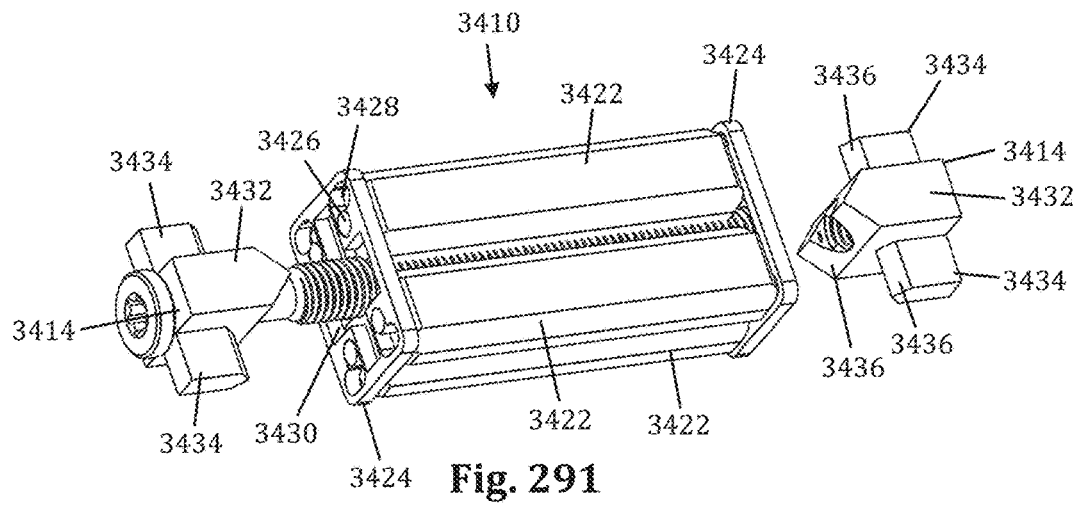
Fig. 291
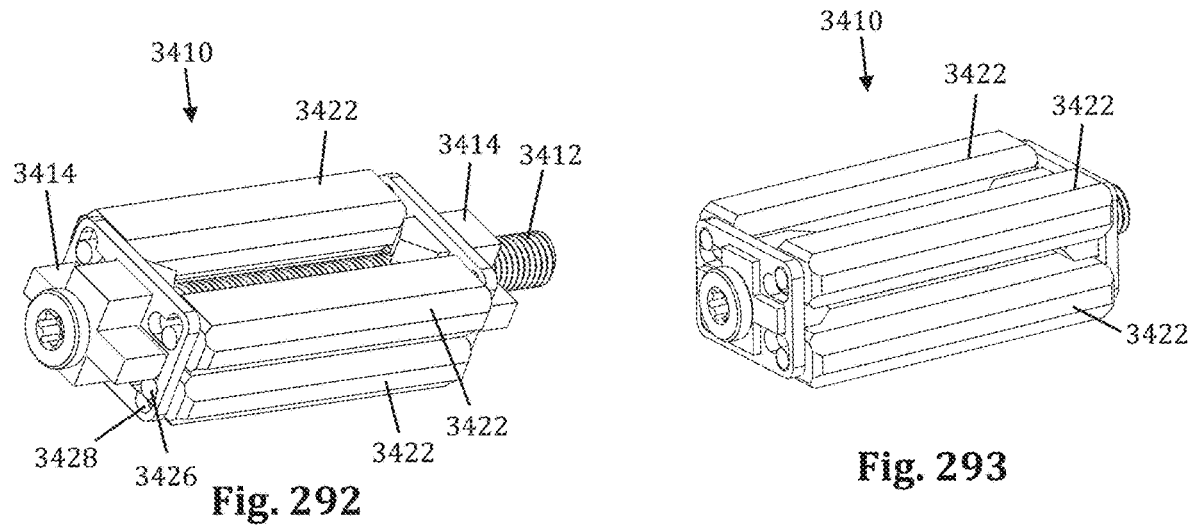
Fig. 292
Fig. 293
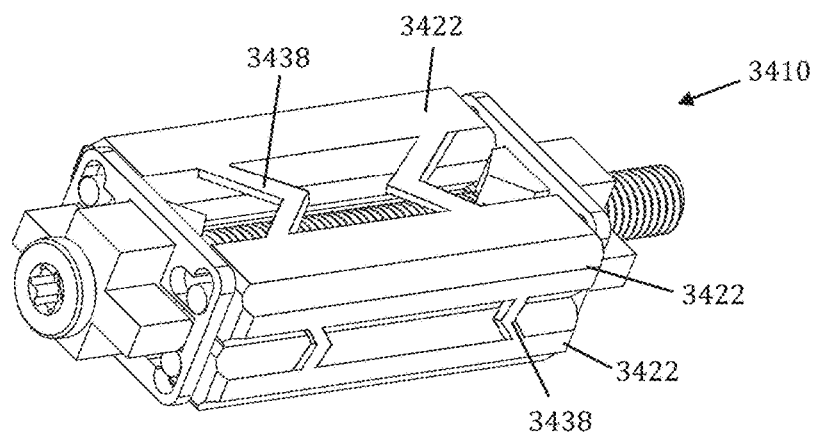
Fig. 294

EXPANDABLE FUSION DEVICE WITH INDEPENDENT EXPANSION SYSTEMS

CROSS REFERENCES TO RELATED APPLICATIONS

This application claims priority to U.S. Provisional Application No. 63/054,229, filed Jul. 20, 2020, which is hereby incorporated herein by reference in its entirety.

BACKGROUND

Field of the Invention

The teachings herein are directed generally to medical devices and methods, including devices and methods for promoting an intervertebral fusion, such as devices that can be inserted in a subject in a collapsed state through a small surgical corridor, and the expand cephalocaudal only, transverse only, or in both directions, in which direction of expansion can also be obtained independently, if desired, after the insertion.

Description of the Related Art

The teachings provided herein include methods, devices, and systems for performing a spinal implant procedure on a subject. A spinal fusion is typically employed to eliminate pain caused by the motion of degenerated disk material. Upon successful fusion, a fusion device becomes permanently fixed within the intervertebral disc space. A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are challenges associated with the known conventional fusion devices and methodologies. For example, present methods for installing a conventional fusion device may require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height may make it difficult for a surgeon to install the fusion device in the distracted intervertebral space.

As such, there exists a need for a fusion device capable of being installed inside an intervertebral disc space at a minimum to no distraction height and for a fusion device capable of maintaining a normal distance between adjacent vertebral bodies when implanted.

One of the most common post-operative complications of intervertebral fusion surgery is intervertebral graft or cage subsidence which are minimized or mitigated by using an intervertebral cage or graft of a larger footprint. This is often difficult because to minimize the trauma and morbidity associated with spine surgery, it is often advantageous to utilize the smallest surgical access corridor possible to achieve the goals of surgery. As such there exists a need for a fusion device capable of being inserted through a relatively small surgical corridor and capable to then be expanded to a larger footprint suitable to resist subsidence.

It should be appreciated that a spinal fusion, for example, is a procedure that can be used to eliminate pain. This pain, for example, can be caused by the motion of degenerated disk material. Upon a successful fusion, a fusion device becomes permanently fixed within the intervertebral disc space. Unfortunately, the devices and procedures used in the art still suffer several problems, including those discussed above. One of skill will understand that the inventions described herein, however, address several of these problems including at least, for example, (i) a reduced surgical complexity and risk in an insertion of the device through the use of a minimum to minimal, or perhaps no, intervertebral distraction; (ii) a reduced surgical complexity and risk in an insertion of the device through a small surgical corridor; (iii) a desired width control in the expansion of the device through a variable transverse expansion system in a single device which provides for selection of a desirable footprint, which can be a larger, or perhaps biased, footprint for achieving a desired alignment, or perhaps for avoiding subsidence of the device during use, the width control offering an ability to increase width in one end of the cage relative to another; (iv) a desired control of height expansion through a gradual cephalocaudal expansion of the device, gradually increased at a desired amount and offering an ability to increase height in a portion of the cage relative to another, to obtain a desirable intervertebral height and/or pressure which may, for example, controllably decompress the neural elements and reach the desired the intervertebral height with increased safety due to the incremental control of the speed, amount, and pressure of expansion applied to the surrounding tissue; (v) a desired control of the alignment of the adjacent vertebral bodies through a control that is provided by a design that provides freedom to choose any expansion width desired, and obtaining that desired width independent of the gradual height control; and, (vi) a desired control of the contact area desired between the device and the upper and lower vertebral endplates achieved, for example, using an interdigitated endplate system that can slide to distribute forces as desired over a larger area on an endplate.

SUMMARY

A variety of expandable cages are provided. In some embodiments the cages have a width expansion assembly that operates independently of a height expansion assembly and, in some embodiments, the wedges and ramps do not make contact with each other. In some embodiments, movable spacers are used with pivotal link connections and, in some embodiments, any portion of the cage can be expanded in width or in height in an amount that differs from other portions of the cage to provide any of a multitude of desired cage shapes.

In some embodiments, a cage with independent width and height expansion is provided, the cage can comprise, for example, a beam assembly having a proximal end, a distal end, and a long axis disposed between the proximal end and the distal end; a first beam with a proximal end and a distal end, a second beam with a proximal end and a distal end, and a third beam with a proximal end and a distal end; and, a collapsed state and an expanded state; a wedge assembly having a first wedge and a second wedge, the first wedge movably connected to a first guide and configured for increasing the width of the cage when the first wedge is moved in the direction of the long axis relative to the beam assembly; wherein, the first wedge is positioned between the first beam and the third beam; and, the first guide (i) is movably positioned between the first beam and the second beam, and, (ii) does not provide an expansion in height by being moved in the direction of the long axis relative to the beam assembly; and, a ramp assembly having a ramp movably positioned between the first beam and the second beam and configured for increasing the height of the cage with a movement of the ramp in the direction of the long axis relative to the beam assembly; wherein, the translation of the wedge increases the width of the cage without increasing the height of the cage; the translation of the ramp increases the height of the cage without increasing the width of the cage; and, the ramp is configured to translate independently of the wedge assembly in the direction of the long axis.

The cages taught herein can have ramp assemblies and wedge assemblies. In some embodiments, the ramp is not in contact with the wedge through at least a first distance moved by the wedge. In some embodiments, the ramp is not in contact with the wedge through at least a final distance moved by the wedge. In some embodiments, the ramp is not in contact with the wedge through the entirety of the distance moved by the wedge.

In some embodiments, the wedge assembly is configured to retain the first beam, the second beam, and the third beam from expanding beyond a desired width in the expanded state; the wedge is configured with a retaining mechanism to retain the first guide from separating from the wedge in the expanded state; the first guide is configured with a retaining mechanism to retain the first beam and the second beam from separating from the first guide in the expanded state; and, the wedge assembly is configured with a retaining mechanism to retain the third beam from separating from the wedge assembly in the expanded state.

In some embodiments, the wedge assembly is configured to retain the first beam, the second beam, and the third beam from expanding beyond a desired width in the expanded state; the wedge is configured with a first retaining mechanism to retain the first guide from separating from the wedge in the expanded state; the wedge is configured with a second retaining mechanism to retain the second guide from separating from the wedge in the expanded state; the first guide is configured with a retaining mechanism to retain the first beam and the second beam from separating from the first guide in the expanded state; and, the second guide is configured with a retaining mechanism to retain the second side from separating from the second guide in the expanded state.

In some embodiments, the beam assembly further comprises a fourth beam; and, the wedge assembly has a second guide that is (i) movably positioned between the third beam and the fourth beam, and, (ii) does not provide an expansion in height by being moved in the direction of the long axis relative to the beam assembly;

In some embodiments, the wedge assembly expands the distal end more than the proximal end. In some embodiments, the wedge assembly expands the proximal end more than the distal end. In some embodiments, the wedge assembly expands the first beam away from the third beam more than the second beam away from the fourth beam. In some embodiments, the wedge assembly expands the second beam away from the fourth beam more than the first beam away from the third beam.

In some embodiments, the devices include a 3-beam cage. These devices can provide asymmetric vertical expansion. In some embodiments, the cage can comprise a beam assembly having a first end, a second end, a first beam, a second beam, a spanning beam, and a long axis; a width expansion assembly positioned between the first beam and the spanning beam and having a first spacer rotatably connected to a first pivotal link, the first pivotal link rotatably connected to the spanning beam at the first end of the cage; and, a second spacer rotatably connected to a second pivotal link, the second pivotal link rotatably connected to the spanning beam at the second end of the cage; wherein a first movement of the first spacer in the direction of the long axis rotates the first pivotal link to expand the width of the first end of the cage, and a first movement of the second spacer in the direction of the long axis rotates the second pivotal link to expand the width of the second end of the cage; and, a height expansion assembly positioned between the first beam and the second beam and having a ramp movably connected to the first beam and the second beam, wherein a movement of the ramp in the direction of the long axis expands the height of the cage only at the first beam and the second beam.

In some embodiments, the 3-beam cage can further comprise a pivotal endplate in a pivotal connection with the spanning beam; a first set of interdigitating fingers attached to the first beam; and, a second set of interdigitating fingers attached to the spanning beam; wherein, the first set of interdigitating fingers are slidably and pivotably attached to the second set of interdigitating fingers for sliding during the width expansion and pivoting during the height expansion.

In some embodiments, the devices include a 4-beam cage. In some embodiments, the 4-beam cage can provide asymmetric vertical expansion. In some embodiments, the cage comprises a beam assembly having a first end, a second end, a first beam, a second beam, a third beam, a fourth beam, and a long axis; a width expansion assembly positioned between the first beam and the third beam and having a first spacer rotatably connected to a first pivotal link and a second pivotal link; a second spacer rotatably connected to third pivotal link and a fourth pivotal link; the first pivotal link rotatably connected at the first end to the first beam and the third beam; the second pivotal link rotatably connected at the first end to the second beam and the fourth beam; the third pivotal link rotatably connected at the second end to the first beam and the third beam; the fourth pivotal link rotatably connected at the second end to the second beam and the fourth beam; wherein a first movement of the first spacer in the direction of the long axis rotates the first pivotal link and the second pivotal link to expand the first end of the cage, and a first movement of the second spacer in the direction of the long axis rotates the third pivotal link and the fourth pivotal link to expand the second end of the cage; and, a height expansion assembly positioned (i) between the first beam and the third beam, and (ii) between the second beam and the fourth beam; wherein, the height expansion assembly has a first ramp connected to the first pivotal link; a second ramp connected to the second pivotal link; a first post connected to the third pivotal link; and a second post connected to the fourth pivotal link; wherein, a second movement of the first spacer in the direction of the long axis moves the first pivotal link and the second pivotal link to expand the first end of the cage; the second spacer does not have a second movement in the direction of the long axis and the first post and the second post do not expand the second end of the cage.

Methods of treating subjects are also provided. In some embodiments, the method of treating the subject includes inserting the cage into an intervertebral space and placing bone graft material into void spaces in and around the cage. The bone graft material can be inserted in any way known to those of skill, including injecting through a port in the device, injecting the graft material around the device, and the like. In some embodiments, the method is directed to fusing an intervertebral space of a subject. The method can comprise, for example, inserting the device into an intervertebral space of the subject; and, performing cephalocaudal expansion and/or transverse expansion of the device by (i) moving the first wedge or spacer in the direction of the long axis relative to the beam assembly; and (ii) moving the ramp in the direction of the long axis relative to the beam assembly. It should be appreciated that, in some embodiments, the method includes operating the wedge assembly using one mechanism and operating the ramp assembly using a different mechanism. In some embodiments, the performing of the expansion using the wedge assembly is done independent of the expansion using the ramp assembly. And, in some embodiments, the method further comprising performing the transverse expansion before performing the cephalocaudal expansion. In some embodiments, the method includes expanding the width without expanding the height, followed by expanding the height without expanding the width.

In some embodiments, the device has a wedge assembly and a ramp assembly. For example, the wedge assembly can provide the width expansion, and the ramp assembly can provide the height expansion. The width expansion can be referred to as transverse expansion in some embodiments, and the height expansion can be referred to as vertical expansion or cephalocaudal expansion in some embodiments. Likewise, the width or transverse expansion can be referred to as increasing the width and, the height, vertical, or cephalocaudal expansion can be referred to as increasing the height.

Further areas of applicability of the present disclosure will become apparent from the detailed description provided hereinafter. It should be understood that the detailed description and specific examples, while indicating the preferred or exemplary embodiments of the disclosure, are intended for purposes of illustration only and are not intended to limit the scope of the disclosure.

BRIEF DESCRIPTION OF THE DRAWINGS

Patentable features are set forth with particularity in the appended claims. A better understanding of the features and advantages of the inventions taught herein, however, can be obtained by reference to the following detailed description that sets forth illustrative embodiments, in which the principles of the disclosure are utilized in the following drawings:

FIG. 7 is a top plan view of an example of a distal wedge forming part of the expandable fusion device of FIG. 3, according to some embodiments;

FIG. 8 is a perspective view of the distal wedge of FIG. 7, according to some embodiments;

FIG. 9 is another perspective view of the distal wedge of FIG. 7, according to some embodiments;

FIG. 17 is side plan view of an example of a posterior ramp forming part of the expandable fusion device of FIG. 3, according to some embodiments;

FIGS. 18-19 are perspective views of the posterior ramp of FIG. 17, according to some embodiments;

FIG. 20 is a top plan view of the posterior ramp of FIG. 17, according to some embodiments;

FIG. 21 is a side plan view of an example of an anterior ramp forming part of the expandable fusion device of FIG. 3, according to some embodiments;

FIG. 22 is a top plan view of the anterior ramp of FIG. 21, according to some embodiments;

FIG. 23 is a perspective view of the anterior ramp of FIG. 21, according to some embodiments;

FIG. 84 is a perspective view of an example of a first distal ramp forming part of the expandable fusion device of FIG. 76, according to some embodiments;

FIG. 85 is a perspective view of an example of a second distal ramp forming part of the expandable fusion device of FIG. 76, according to some embodiments;

FIGS. 86-87 are perspective views of an example of a first proximal ramp forming part of the expandable fusion device of FIG. 76, according to some embodiments;

FIG. 88 is a perspective view of an example of a second proximal ramp forming part of the expandable fusion device of FIG. 76, according to some embodiments;

FIG. 89 is a perspective view of an example of a lower endplate assembly forming part of the expandable fusion device of FIG. 76, according to some embodiments;

FIGS. 90-92 are perspective views of an example of a modular fixation plate configured for use with an expandable fusion device, according to some embodiments;

FIG. 93 is a perspective view of the modular fixation plate of FIG. 90 coupled with an expandable fusion device of FIG. 3, according to some embodiments;

FIG. 94 is a sectional view of the modular fixation plate of FIG. 90 coupled with an expandable fusion device of FIG. 3, according to some embodiments;

FIG. 95 is a top plan view of another example of an expandable fusion device in a collapsed position, according to some embodiments;

FIG. 96 is a top plan view of the expandable fusion device of FIG. 95, in a first width expanded position, according to some embodiments;

FIG. 97 is a top plan view of the expandable fusion device of FIG. 95 in a second width expanded position, according to some embodiments;

FIG. 111 is a perspective view of an example of a proximal wedge forming part of the expandable fusion device of FIG. 107, according to some embodiments;

FIG. 111A is a perspective view of an example of a link element forming part of the expandable fusion device of FIG. 107, according to some embodiments;

FIG. 112 is a perspective view of an example of a posterior endplate forming part of the expandable fusion device of FIG. 107, according to some embodiments;

FIG. 113 is a perspective view of another example of an expandable fusion device in a collapsed position, according to some embodiments;

FIG. 114 is a perspective view of the expandable fusion device of FIG. 113 in a width expanded position, according to some embodiments;

FIG. 115 is a perspective view of the expandable fusion device of FIG. 113 in a fully expanded position, according to some embodiments;

FIGS. 130A-130C are perspective, side plan, and top plan views, respectively, of an example of a proximal ramp forming part of the expandable fusion device of FIG. 126, according to some embodiments;

FIG. 131 is a perspective view of an example of a stabilization post forming part of the expandable fusion device of FIG. 126, according to some embodiments;

FIG. 132 is a plan view of an example of an anterior endplate forming part of the expandable fusion device of FIG. 126, according to some embodiments;

FIG. 133 is a perspective view of an example of a posterior endplate forming part of the expandable fusion device of FIG. 126, according to some embodiments;

FIG. 134 is a perspective view of an example of a lower endplate assembly forming part of the expandable fusion device of FIG. 126, according to some embodiments;

FIG. 135 is a plan view of another example of an expandable fusion device in a fully expanded position, according to some embodiments;

FIG. 136A is a perspective view of an example of a posterior ramp forming part of the expandable fusion device of FIG. 135, according to some embodiments;

FIG. 136B is a plan view of an example of a posterior endplate forming part of the expandable fusion device of FIG. 135, according to some embodiments;

FIG. 137A is a perspective view of the expandable fusion device of FIG. 135 with the lower endplate assembly removed, according to some embodiments;

FIG. 137B is a plan view of the expandable fusion device of FIG. 135 with the upper endplate assembly removed, according to some embodiments;

FIG. 138 is a perspective view of another example of an expandable fusion device in a width expanded position, according to some embodiments;

FIG. 139 is a perspective view of the expandable fusion device of FIG. 138 in a fully expanded position, according to some embodiments;

FIG. 140 is a sectional view of the expandable fusion device of FIG. 138 in a collapsed position, according to some embodiments;

Figure 3:
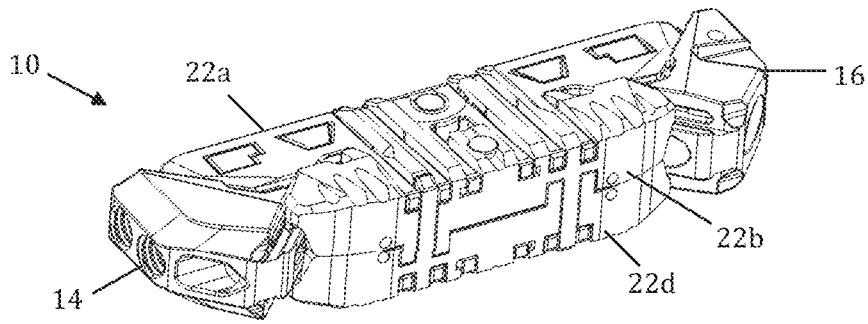
FIG. 3 is a perspective view of an example of an expandable fusion device in a collapsed state, according to some embodiments.
Figure 138:
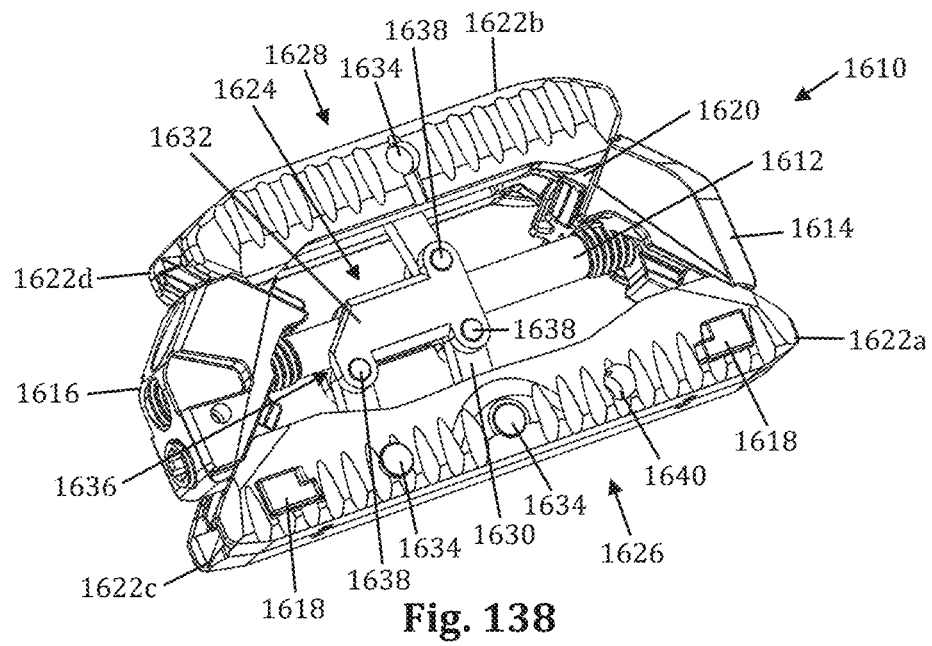
Figure 139:
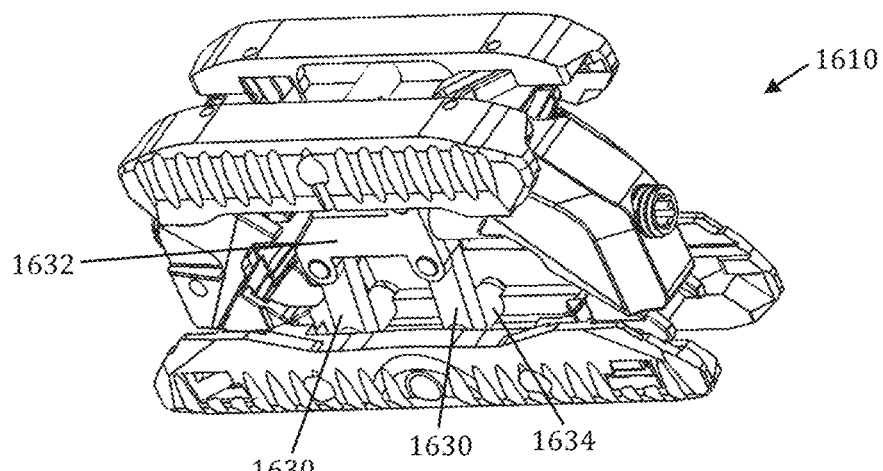
Figure 141:
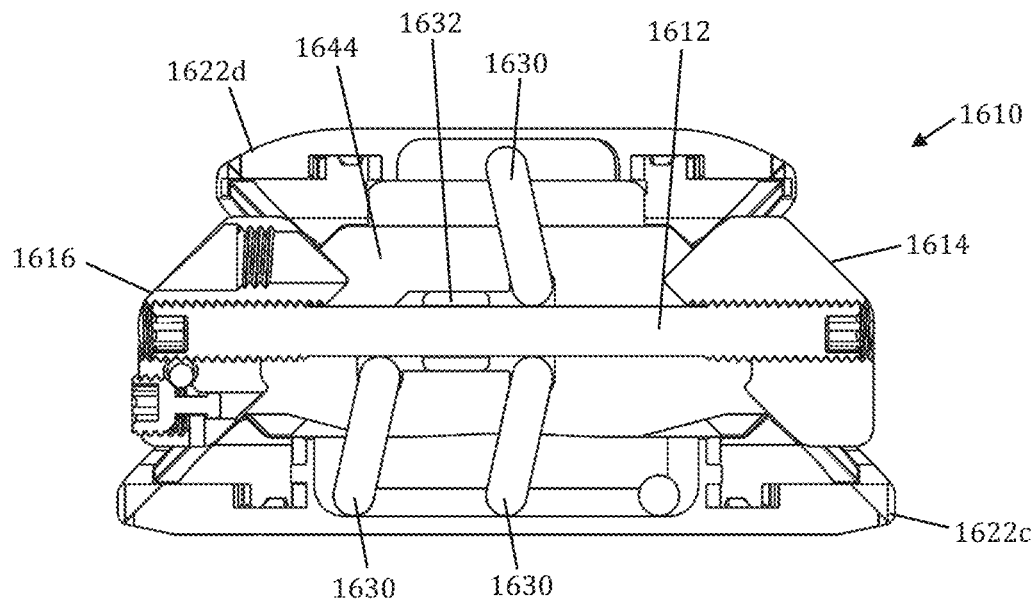
Figure 142:
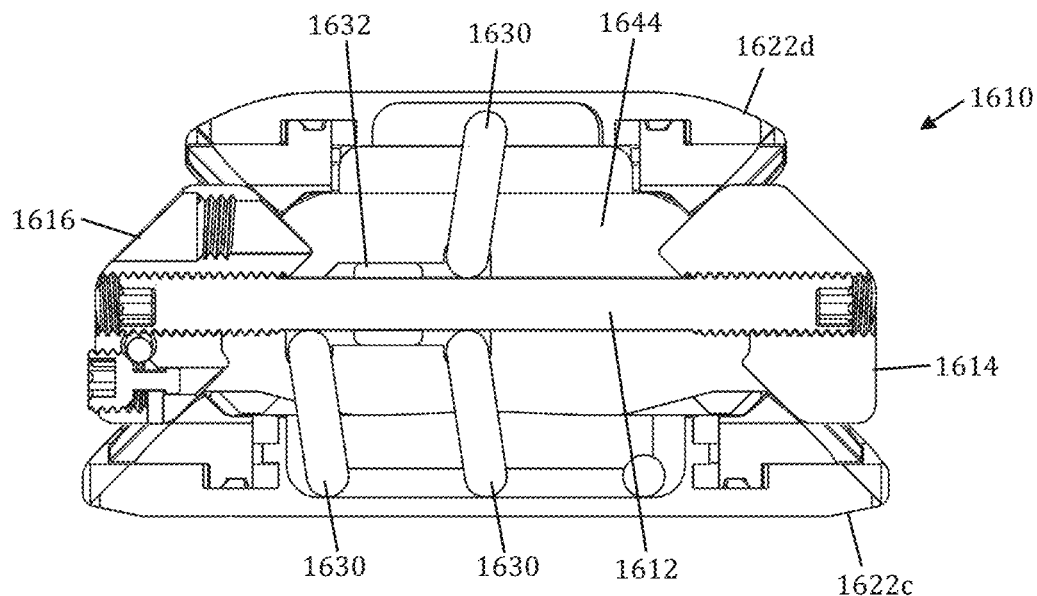
Figure 143:
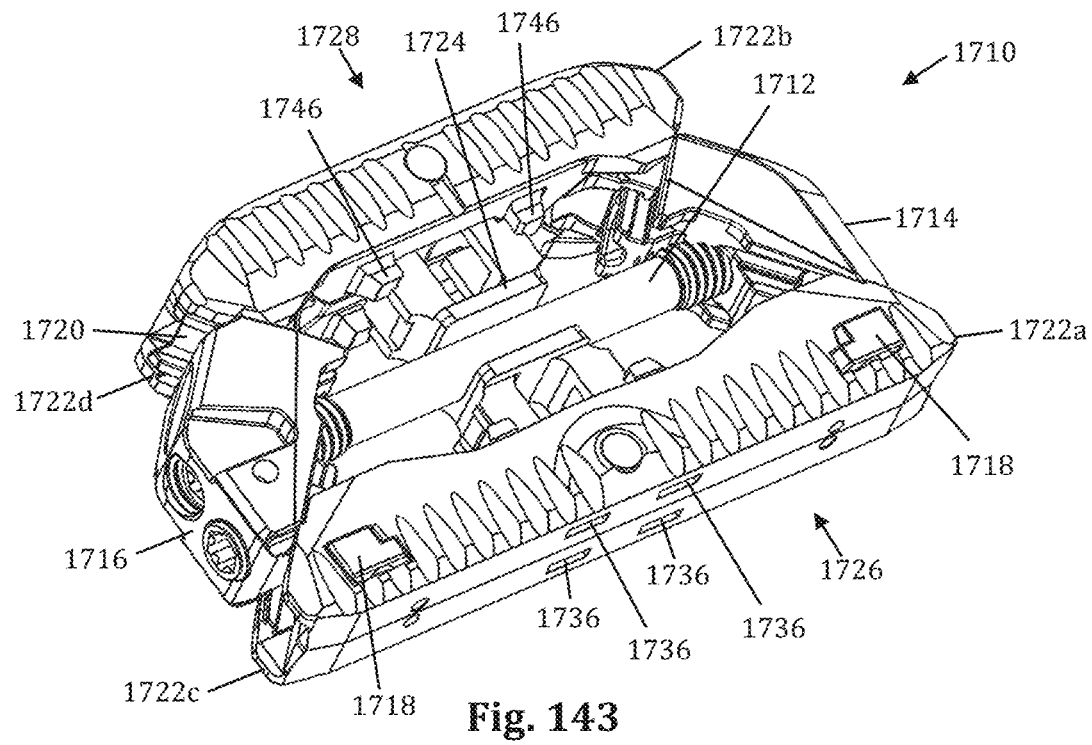
Figure 144:
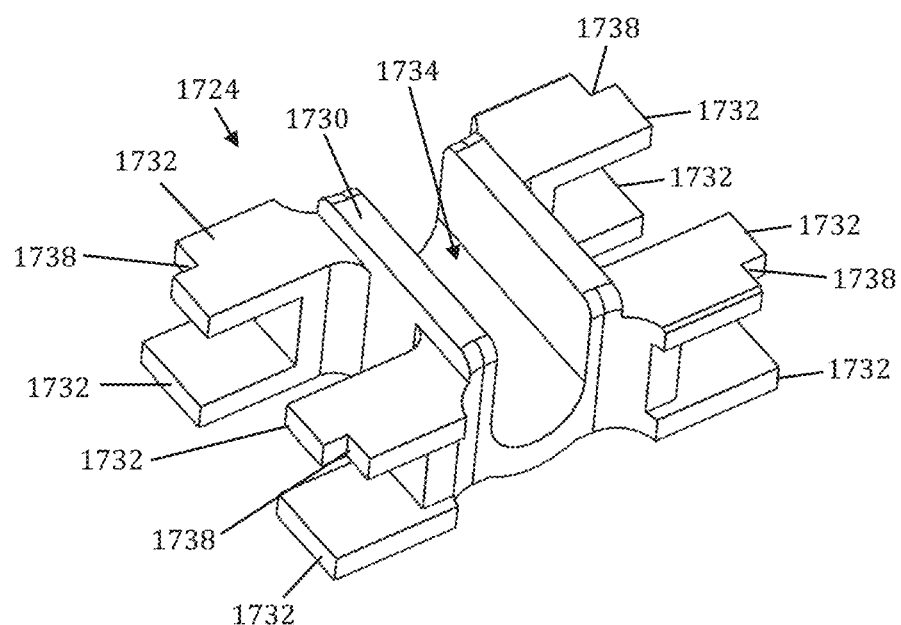
Figure 145:
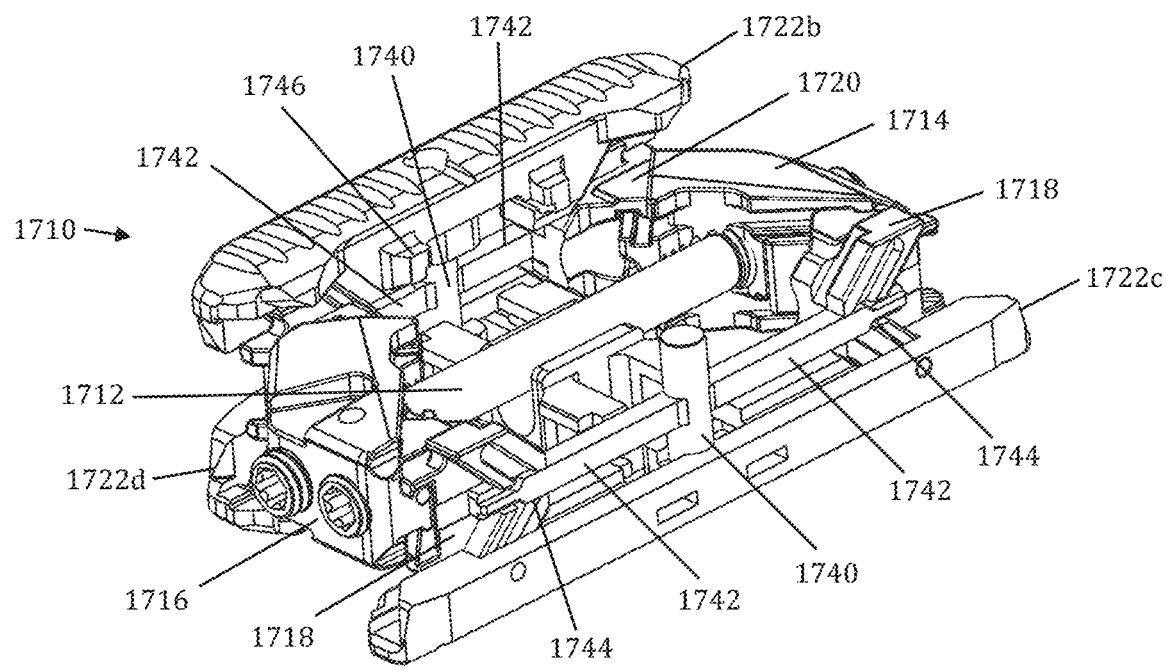
Figure 146:
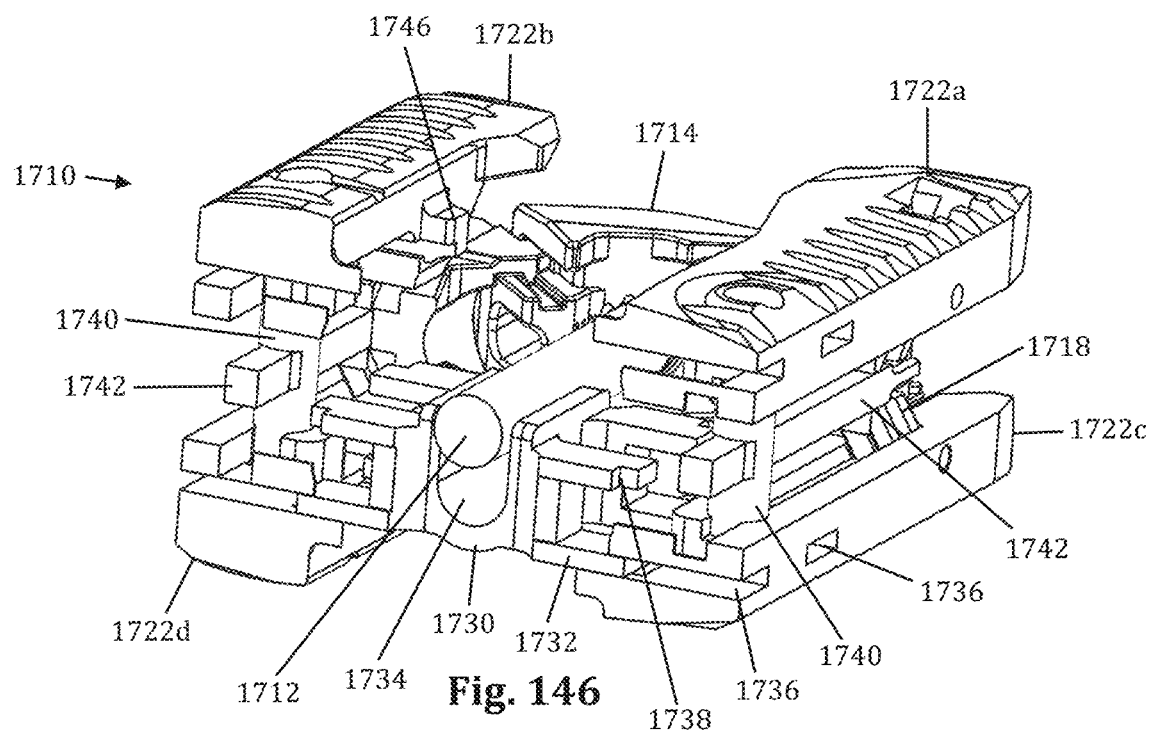
Figure 147:
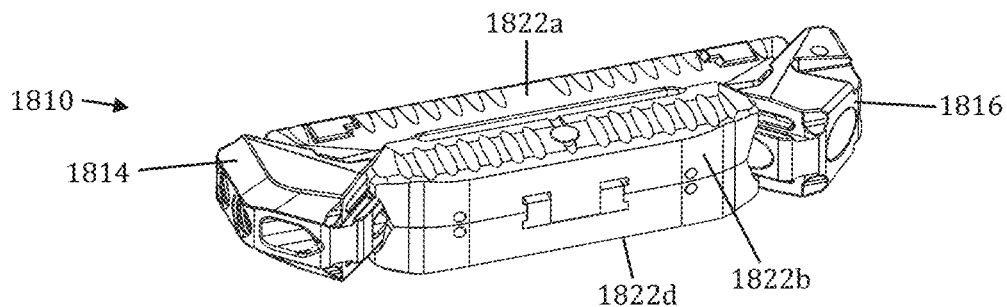
Figure 148:
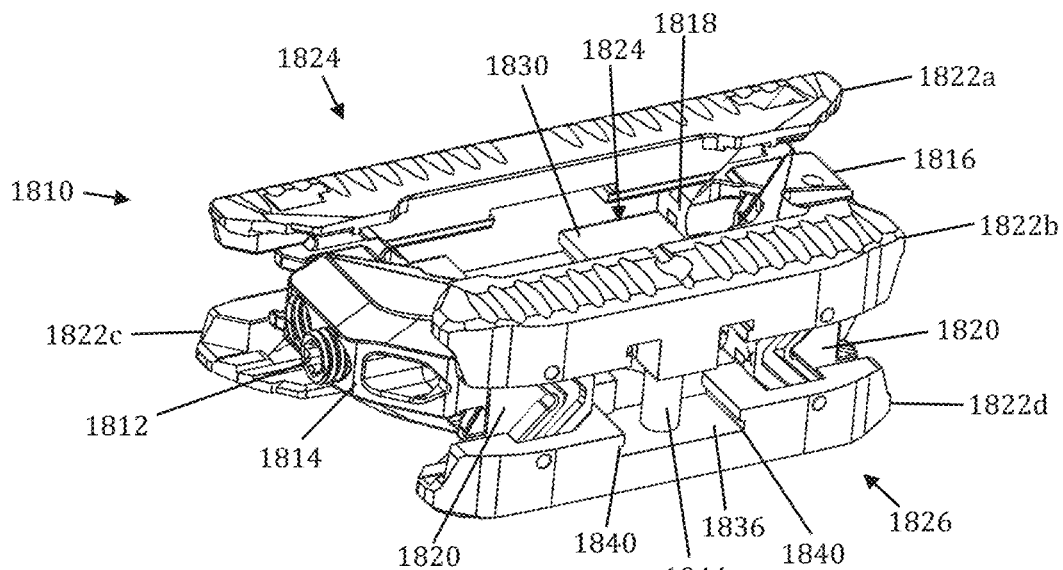
Figure 149:
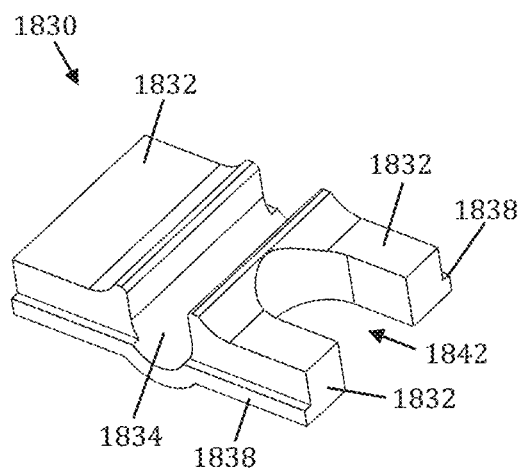
Figure 150:
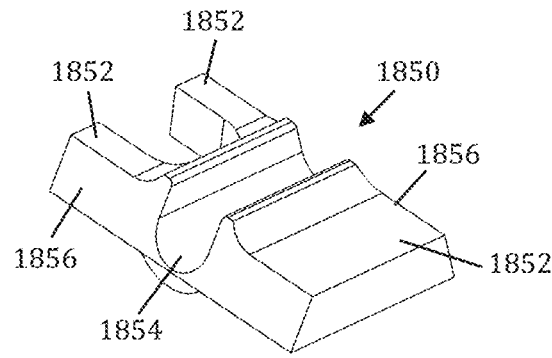
Figure 151:
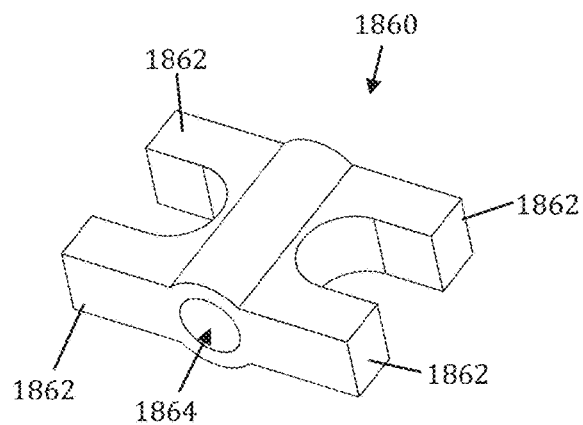
Figure 152:
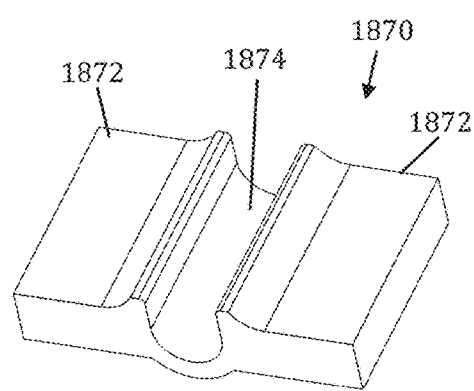
Figure 153:
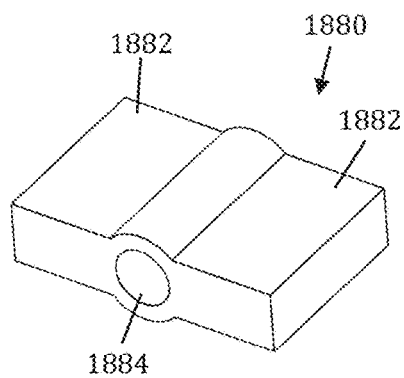
Figure 154:
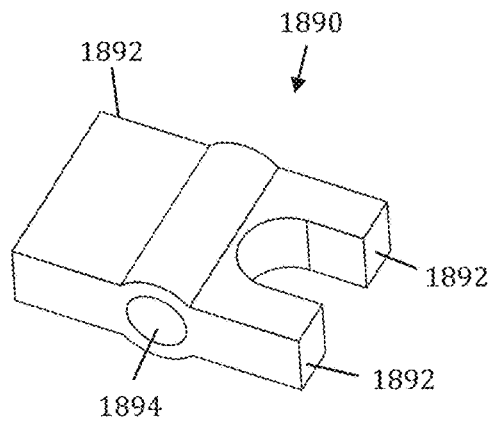
Figure 155:
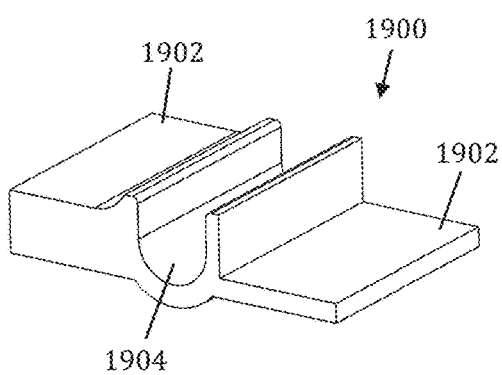
Figure 156:
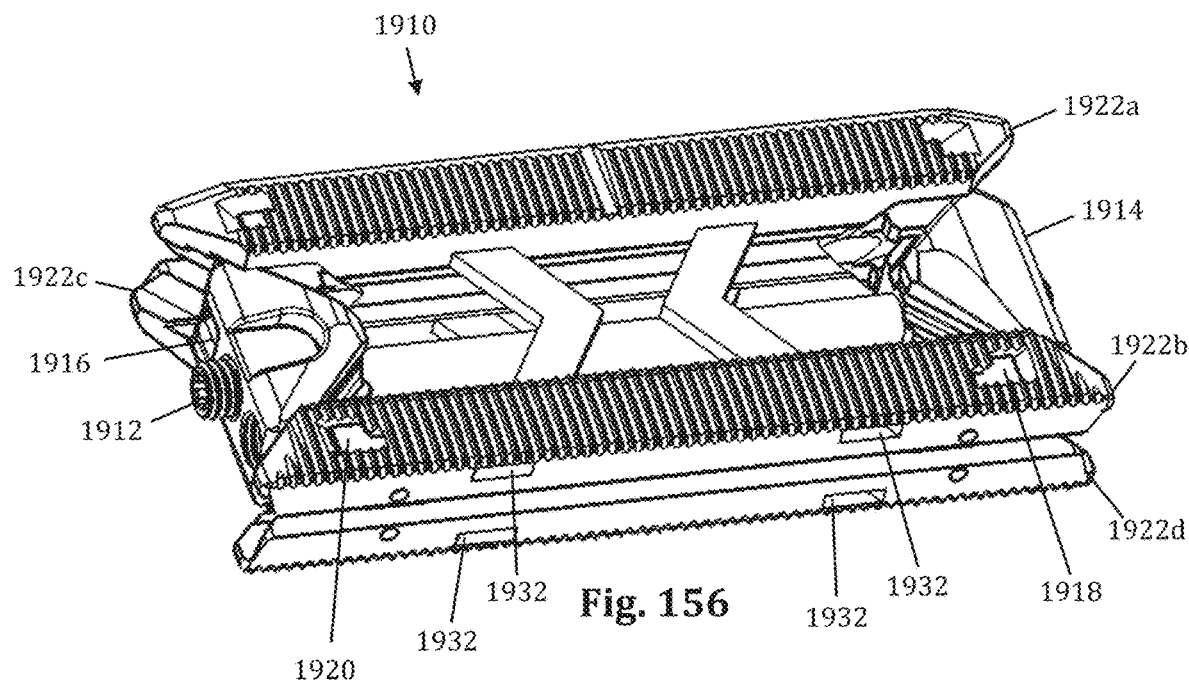
Figure 157:
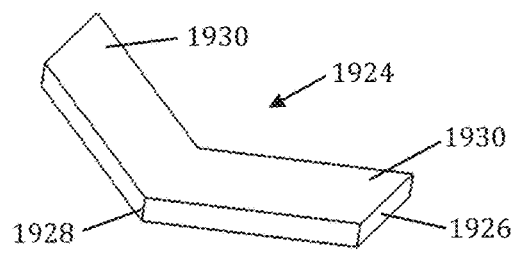
Figure 158:
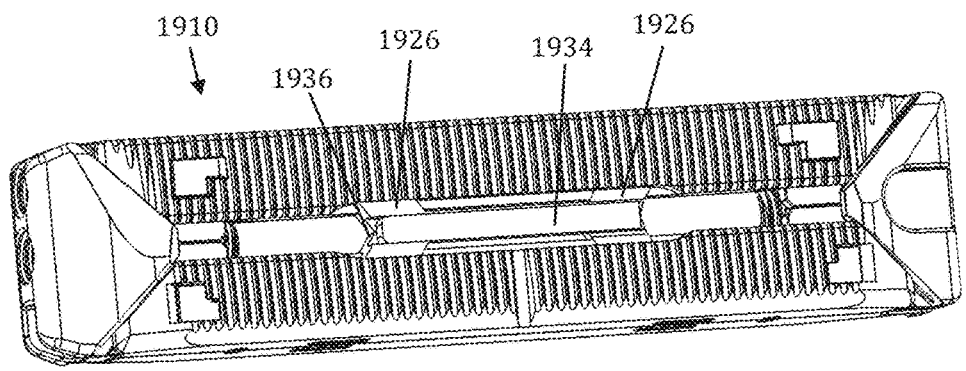
Figure 159:
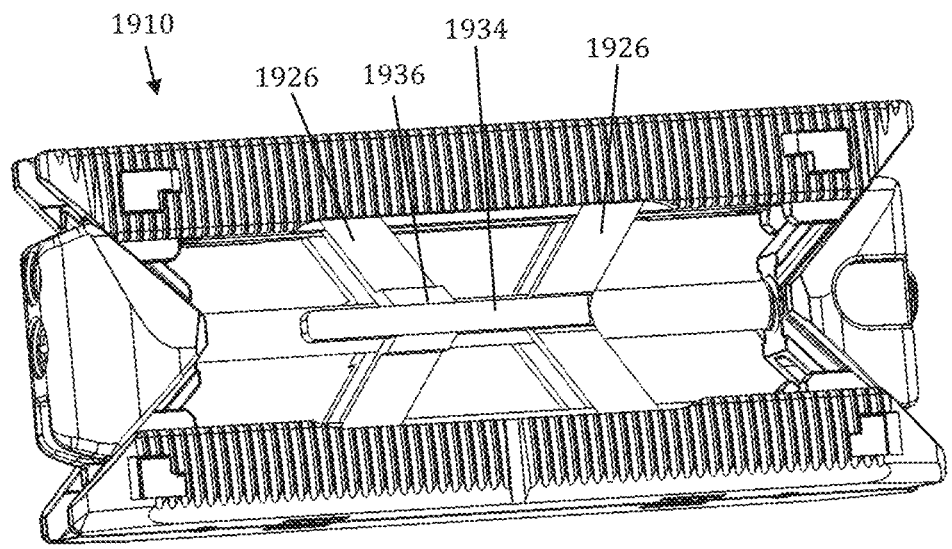
Figure 160:
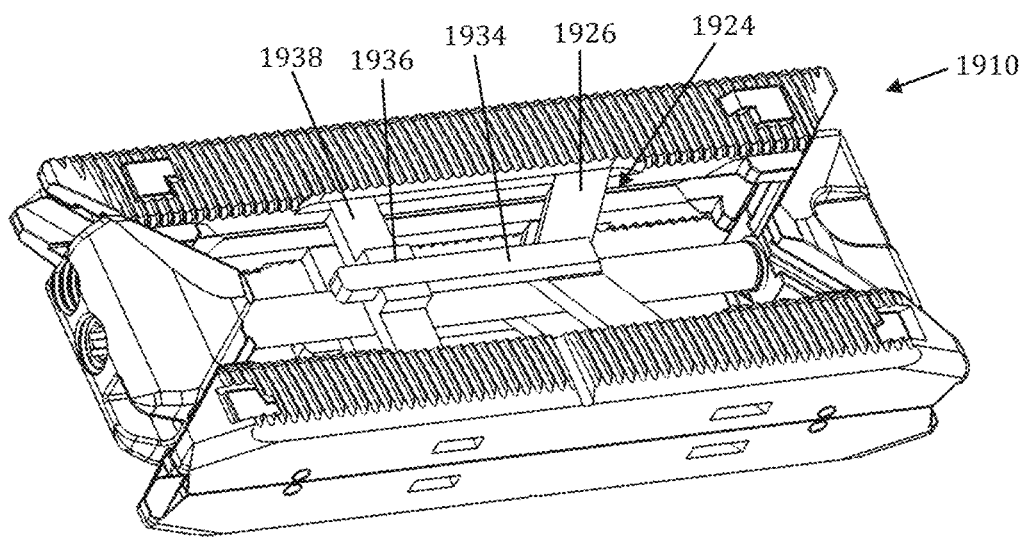
Figure 161:
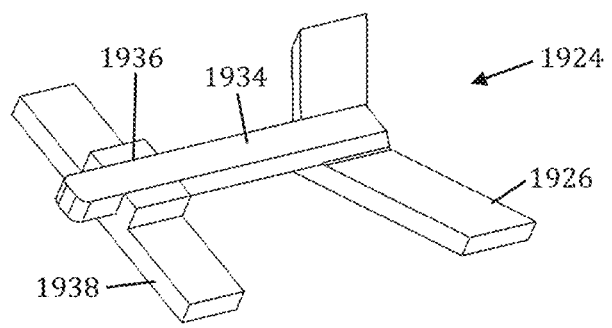
Figure 162:
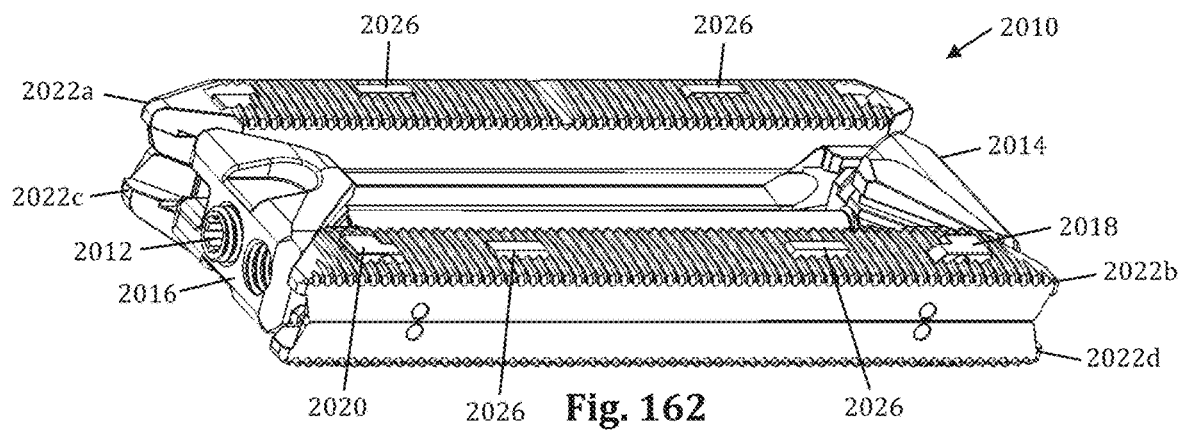
Figure 163:
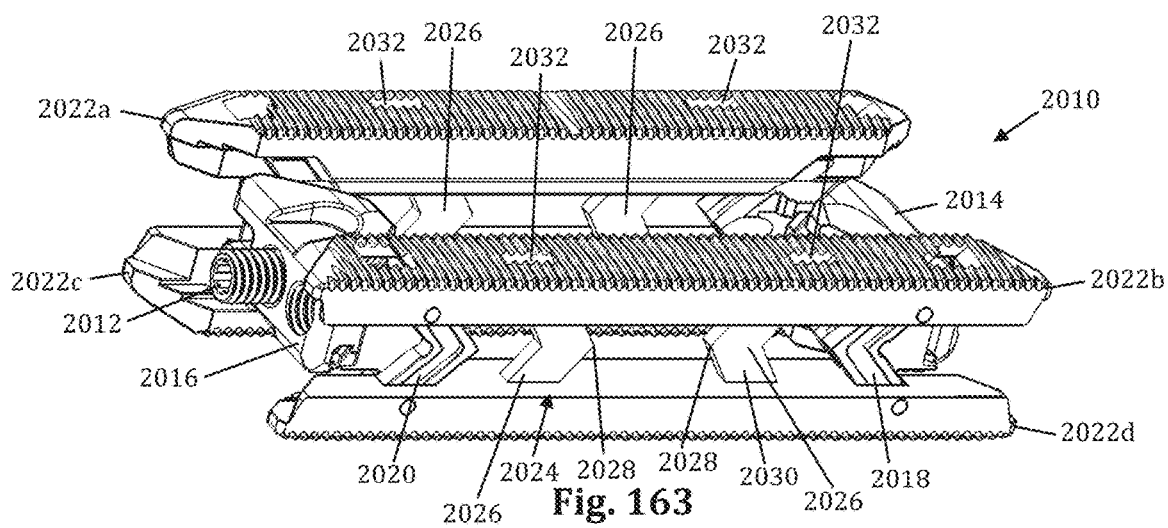
Figure 164:
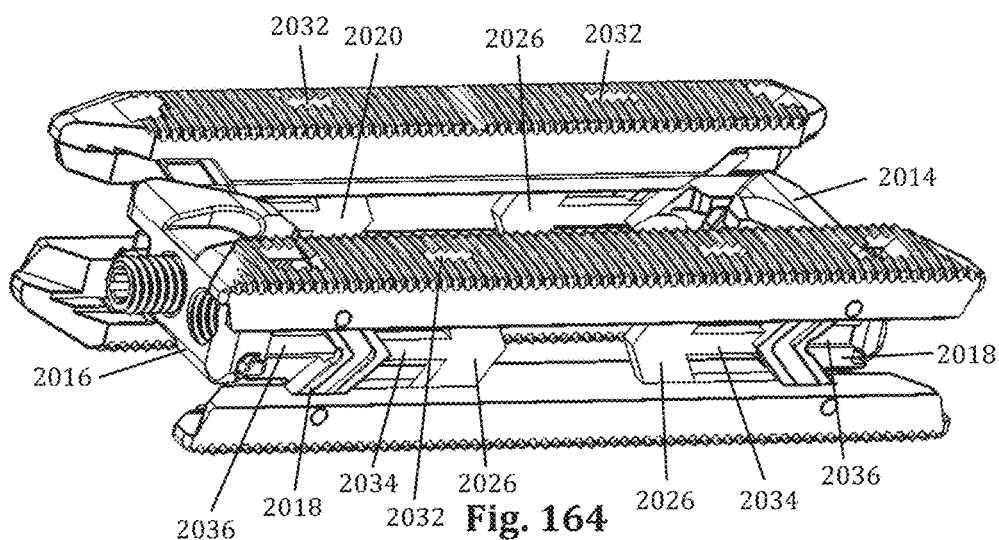
Figure 165:
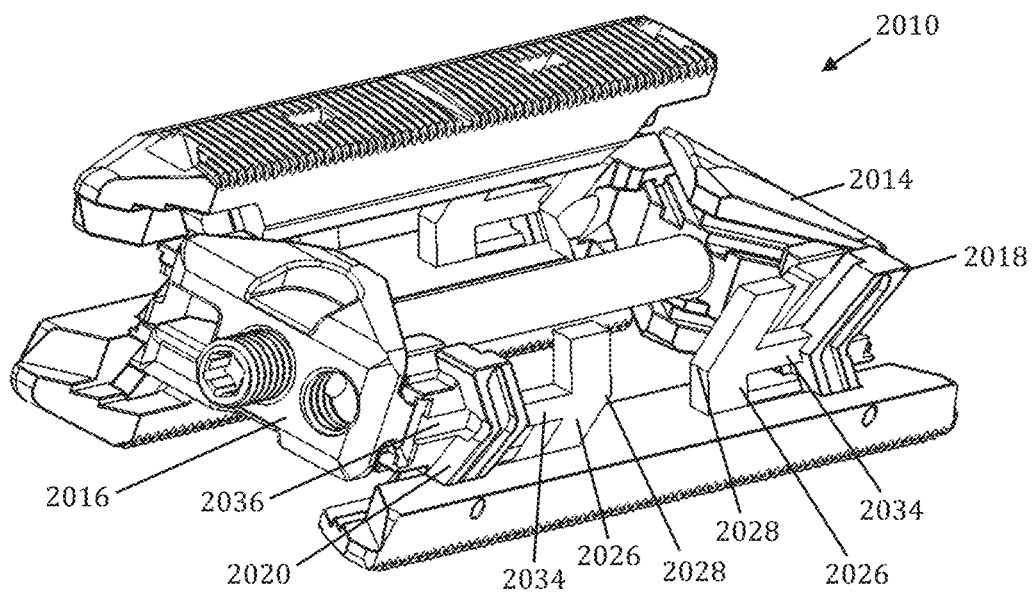
Figure 166:
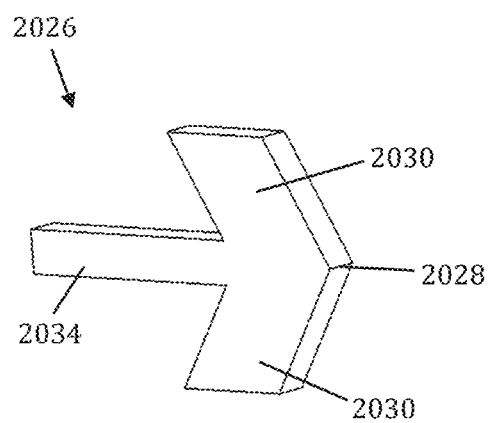
Figure 167:
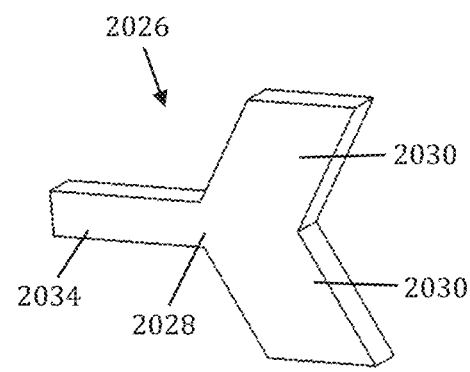
Figure 168:
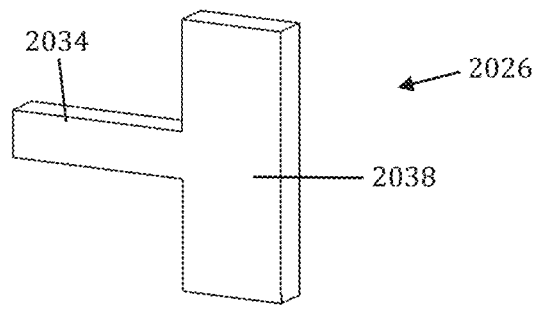
Figure 169:
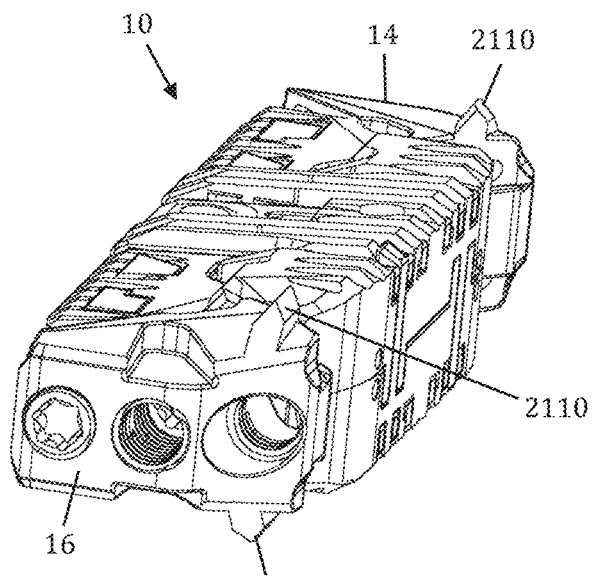
Figure 170:
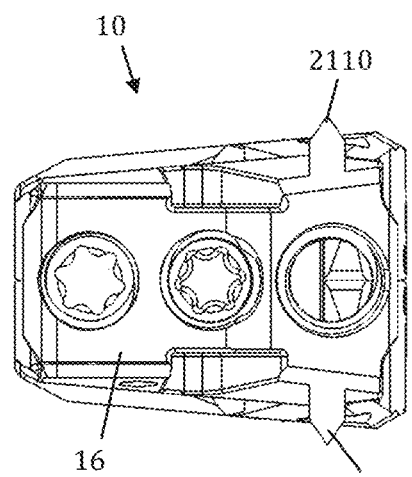
Figure 171:
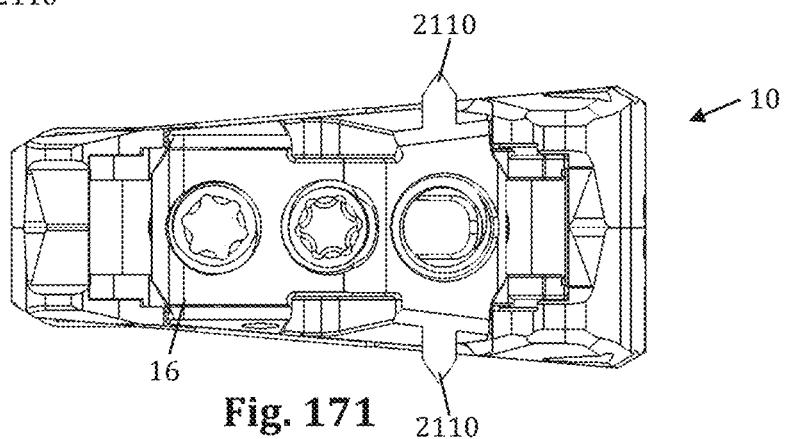
Figure 172:
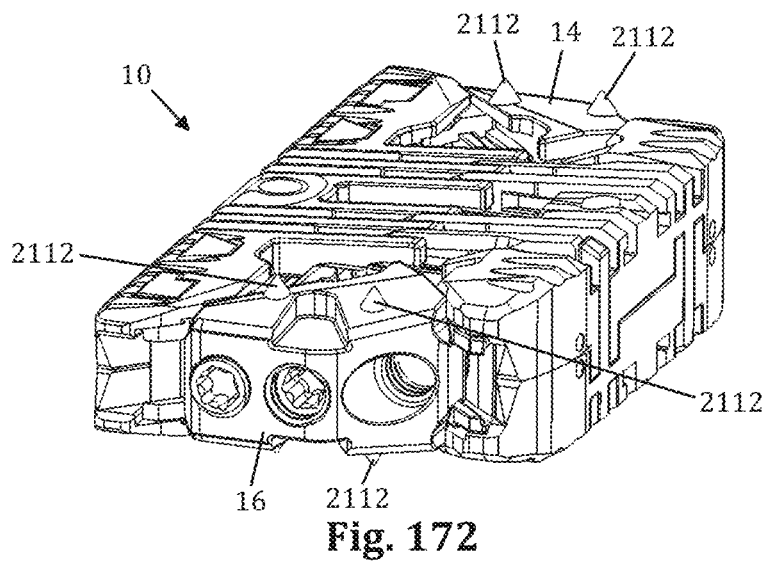
Figure 173:
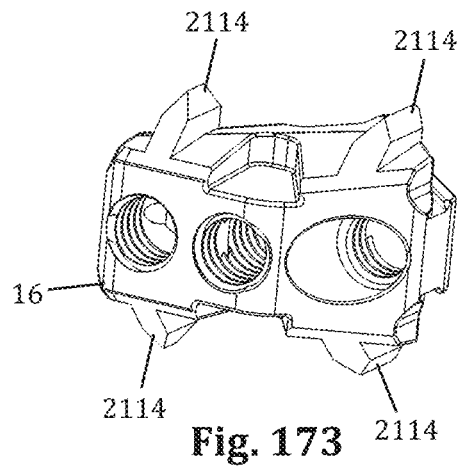
Figure 174:
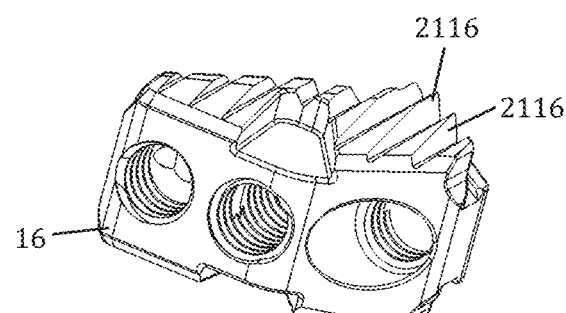
Figure 175:
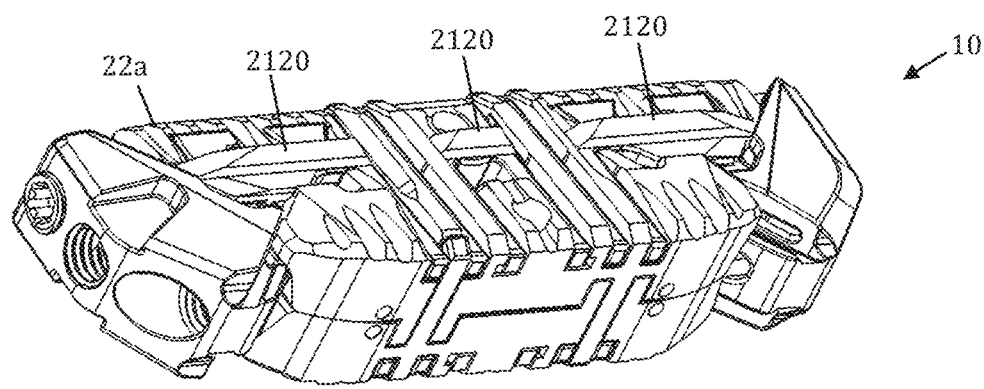
Figure 176:
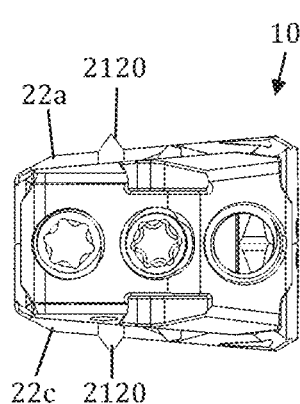
Figure 177:
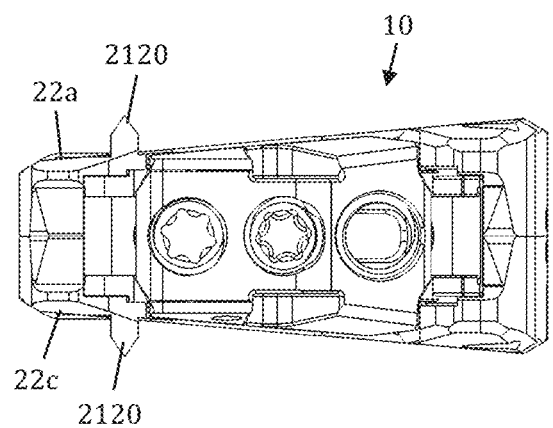
Figure 178:
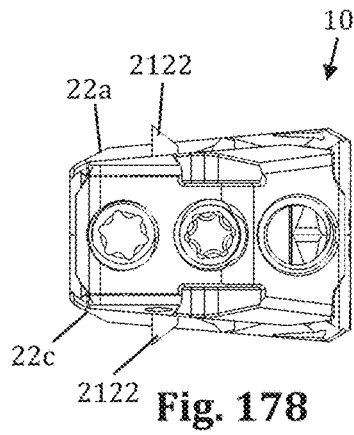
Figure 179:
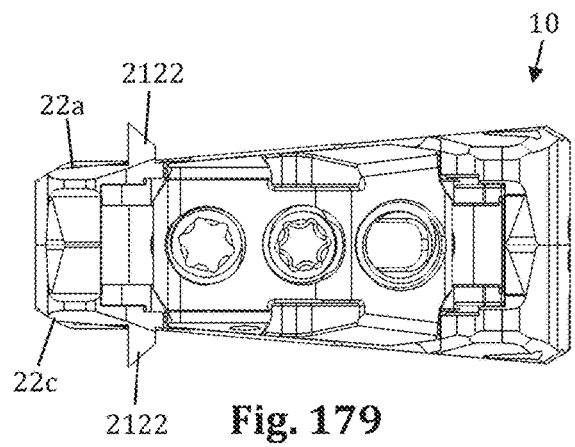
Figure 180:
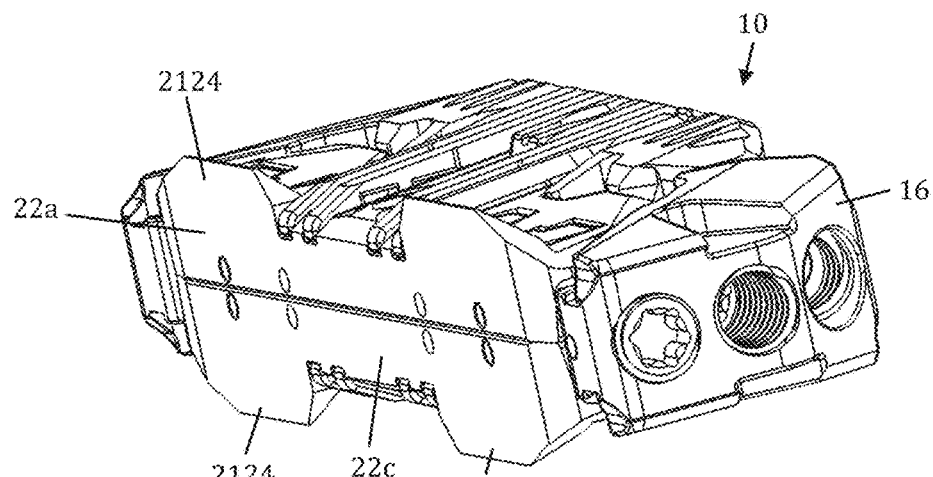
Figure 181:
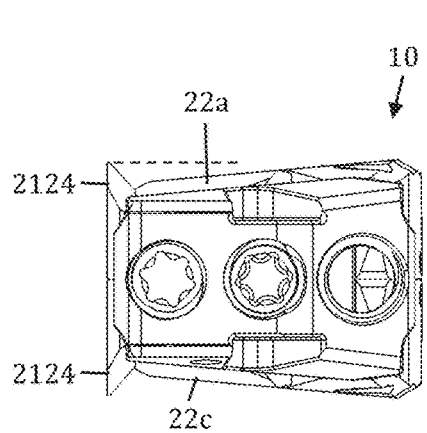
Figure 182:
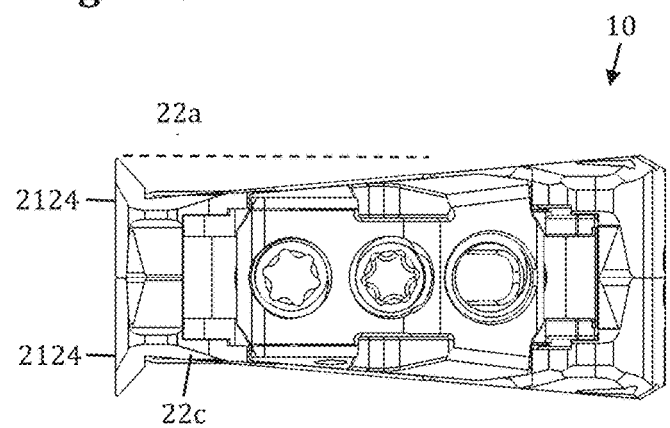
Figure 183:
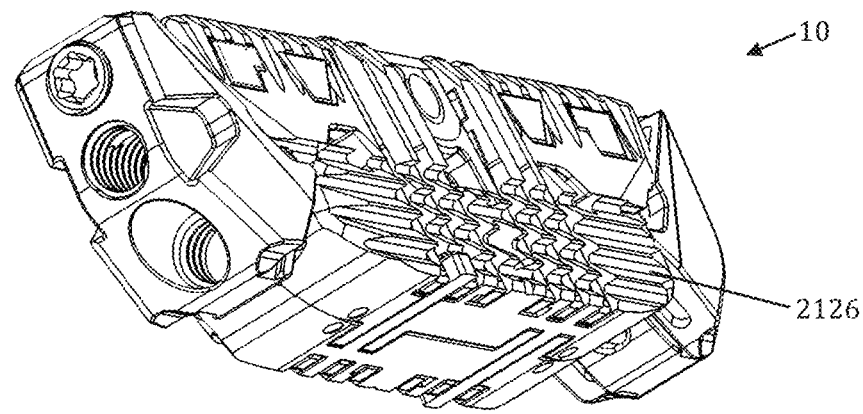
Figure 184:
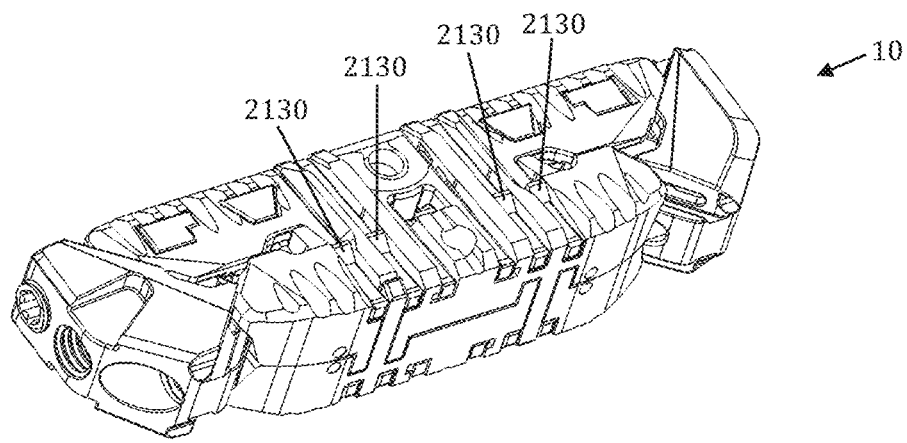
Figure 185:
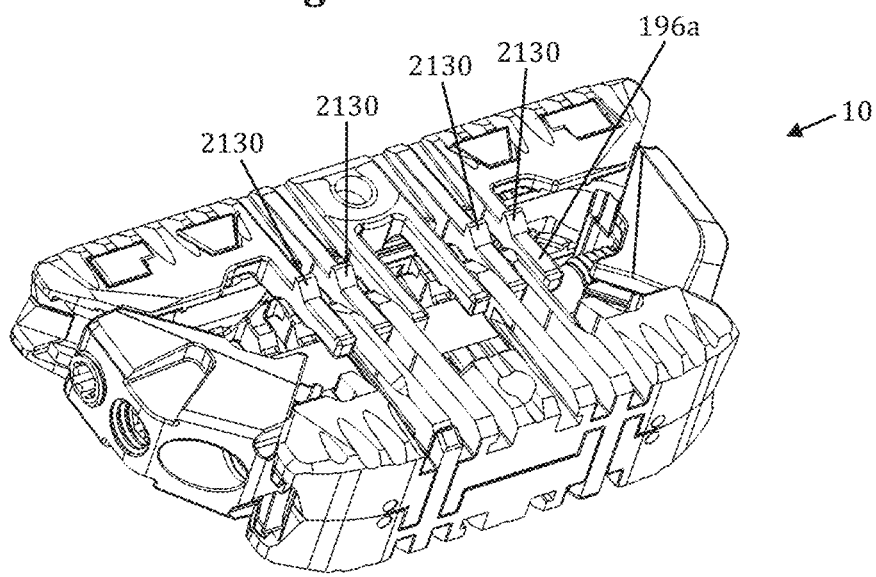
Figure 186:
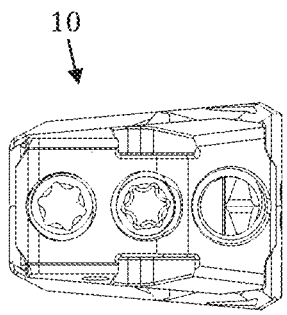
Figure 187:
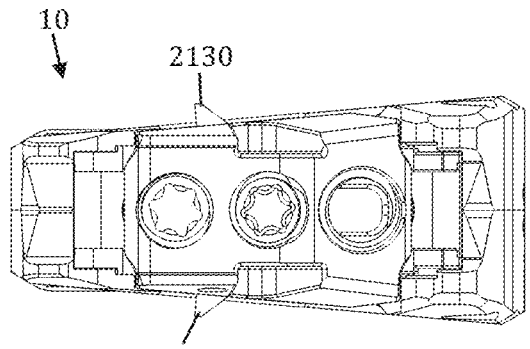
Figure 188:
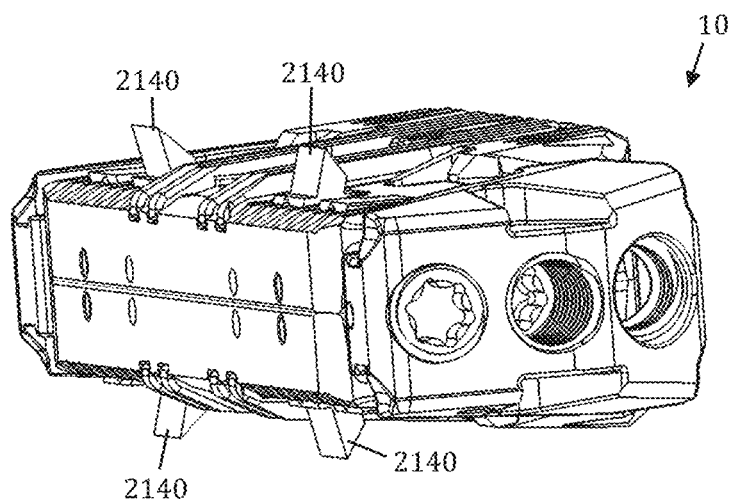
Figure 189:
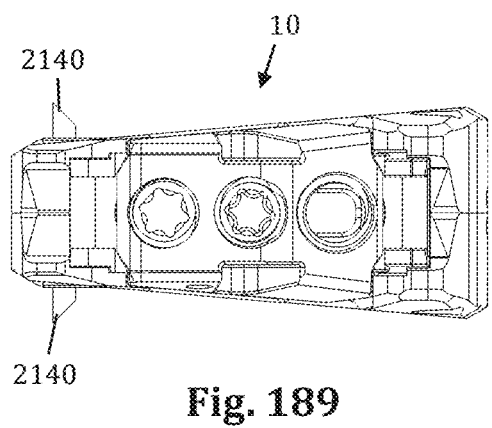
Figure 190:
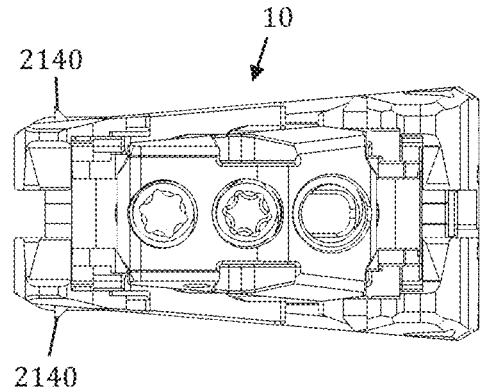
Figure 191:
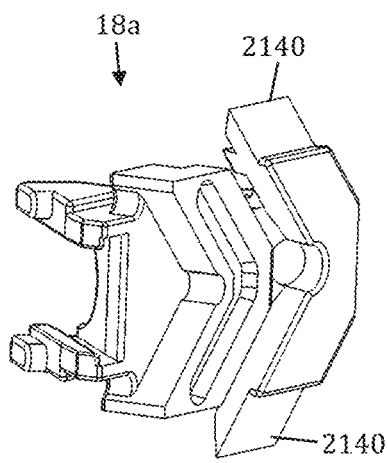
Figure 192:
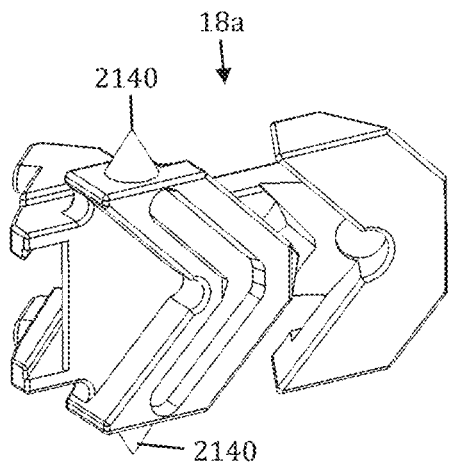
Figure 193:
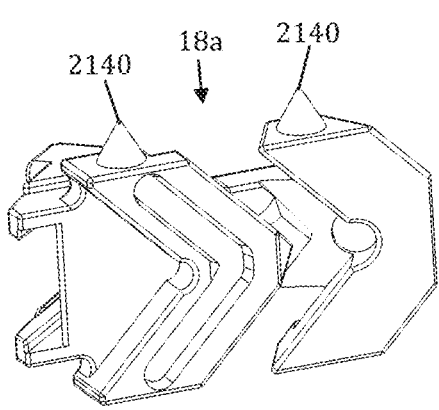
Figure 194:
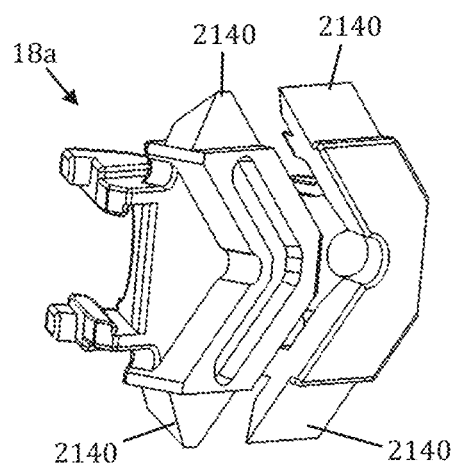
Figure 195:
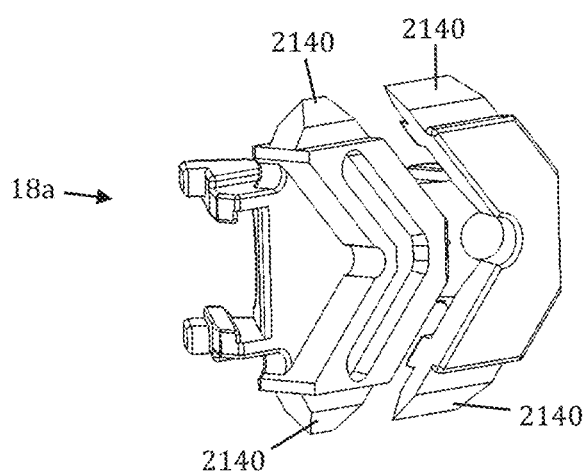
Figure 196:
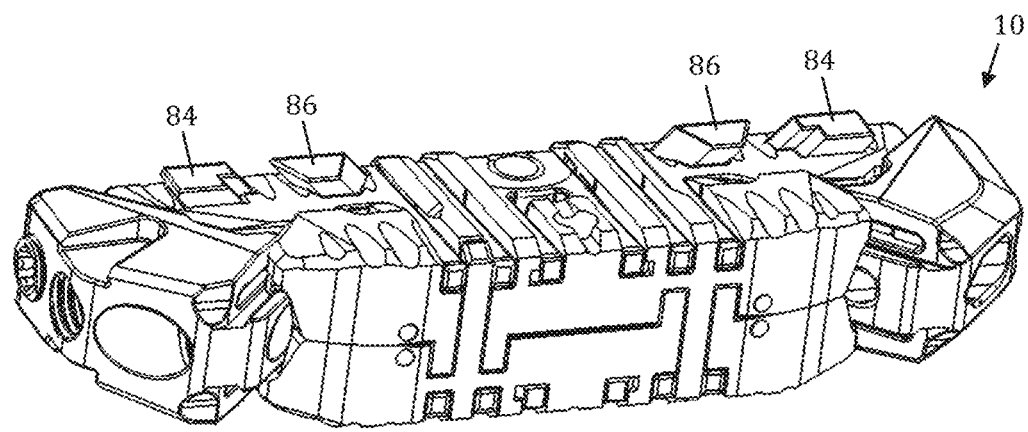
Figure 197:
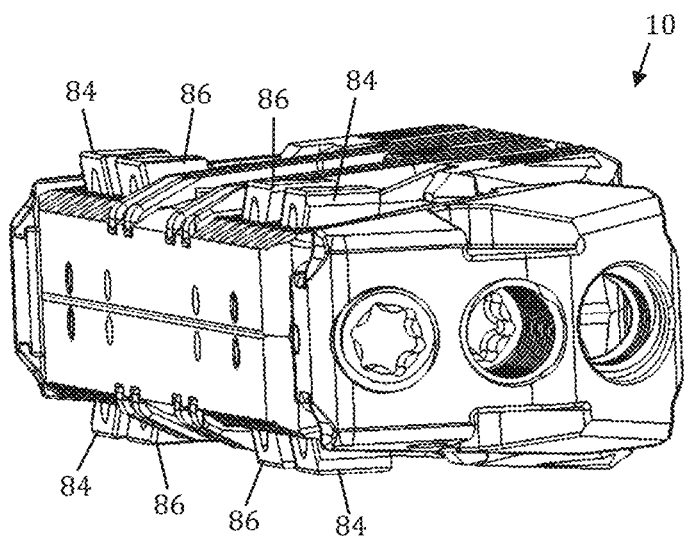
Figure 198:
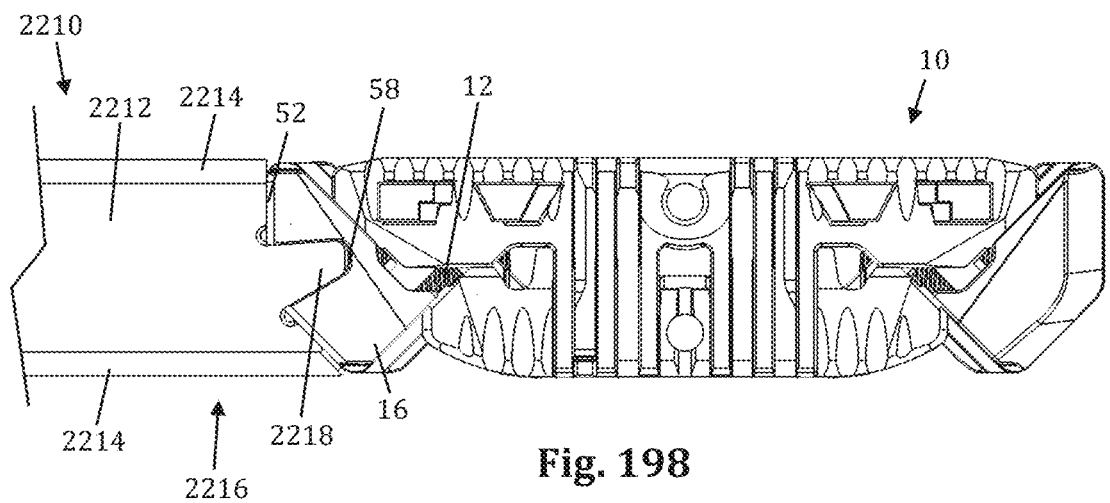
Figure 199:
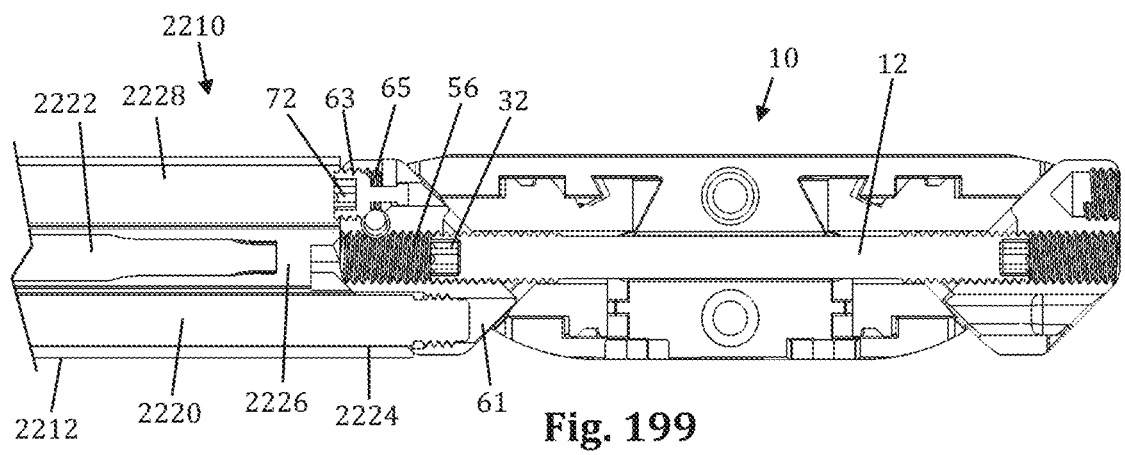
Figure 200:
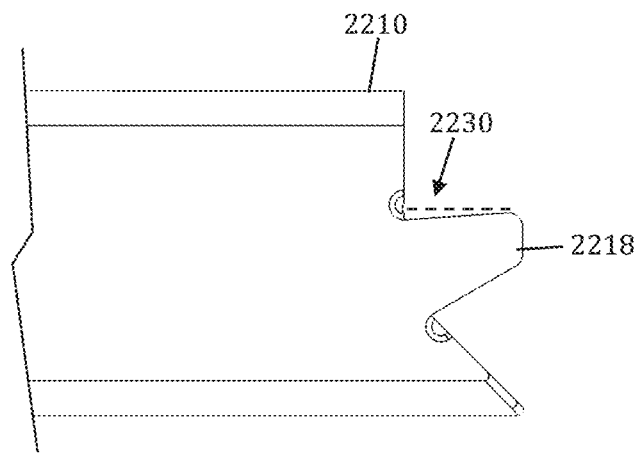
Figure 201:
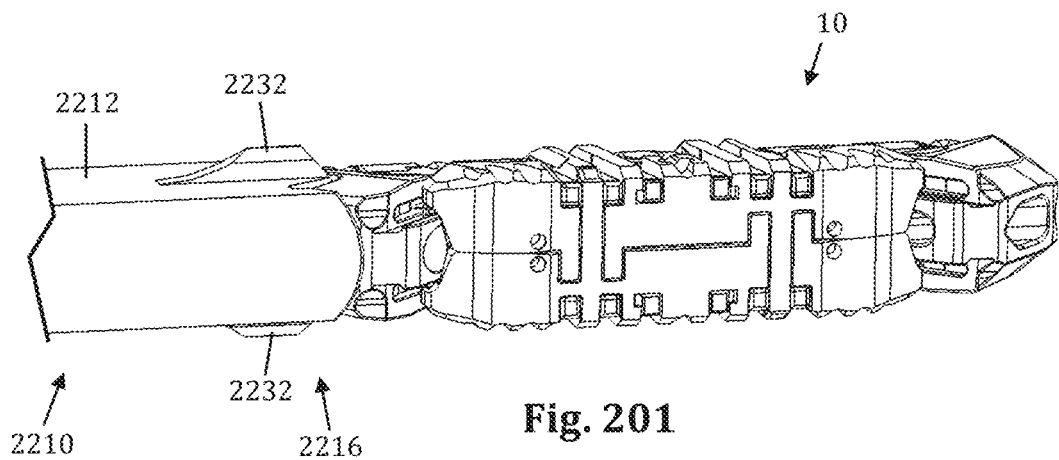
Figure 202:
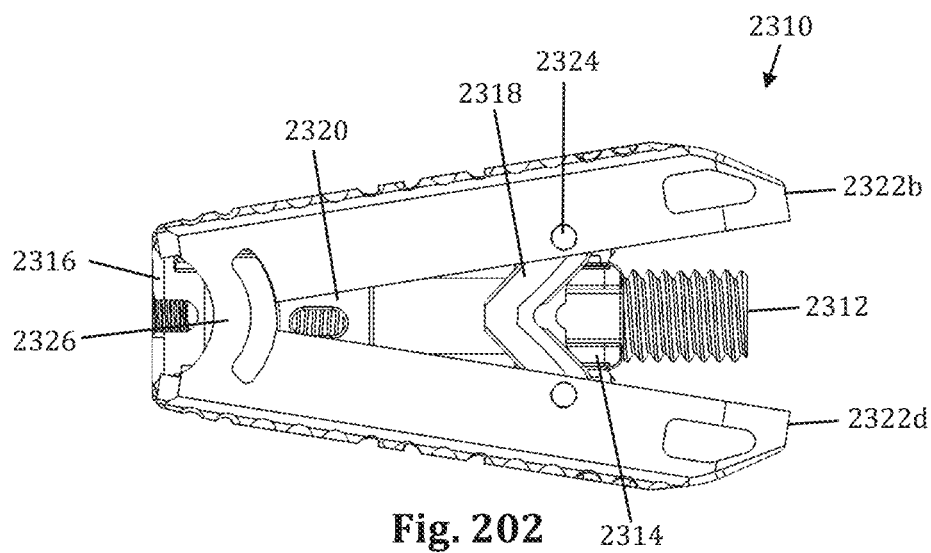
Figure 203:
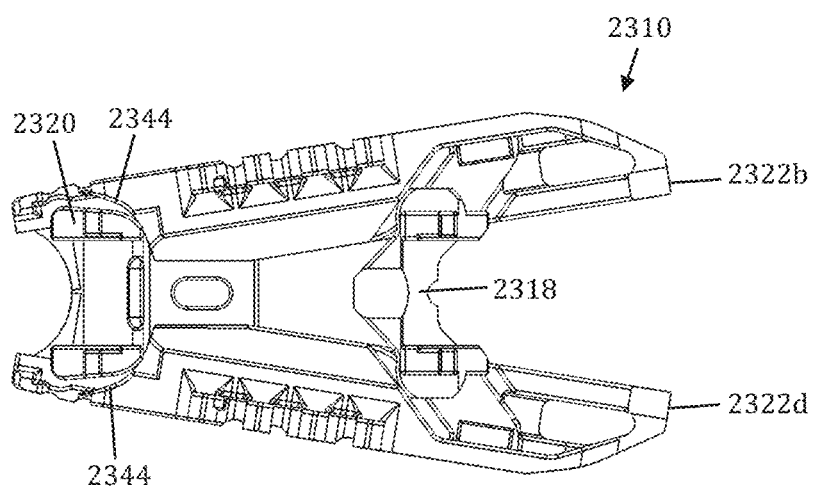
Figure 204:
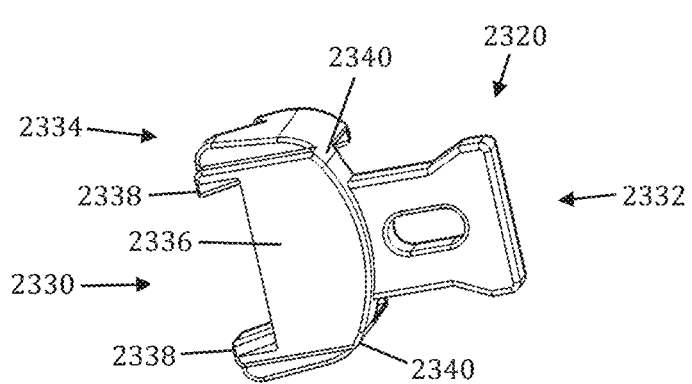
Figure 205:
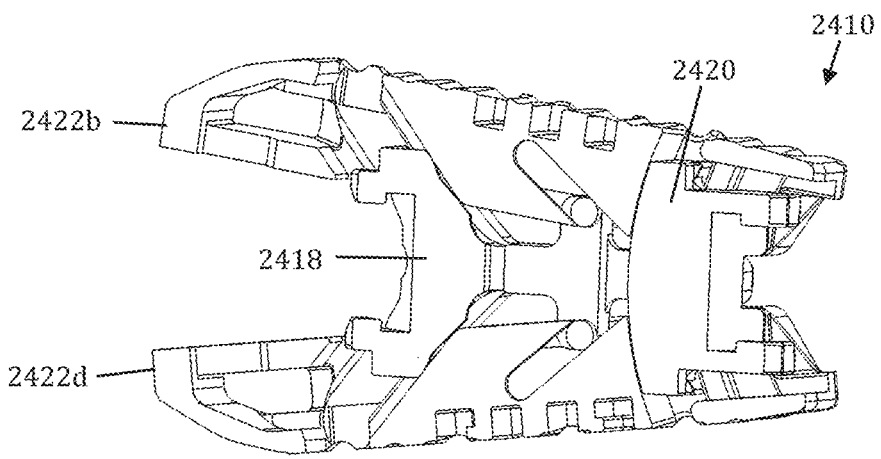
Figure 206:
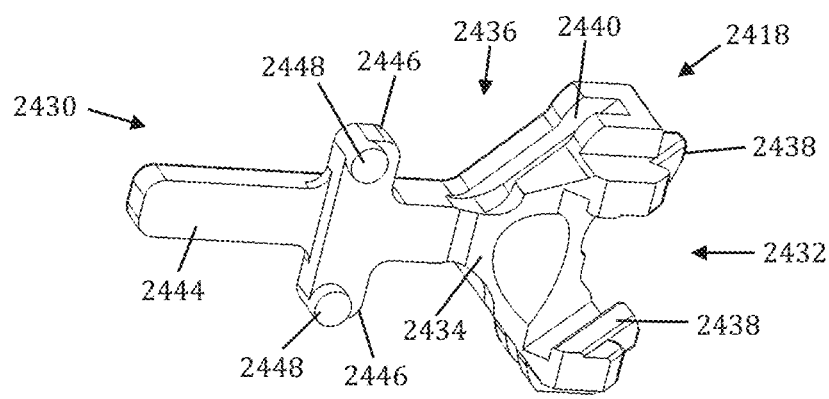
Figure 207:
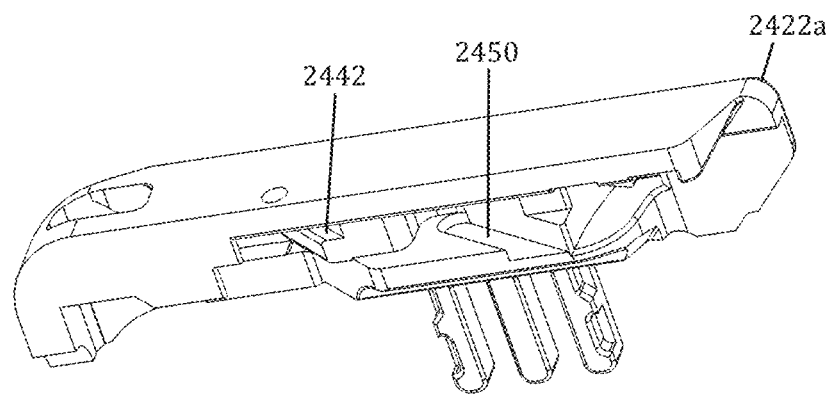
Figure 208:
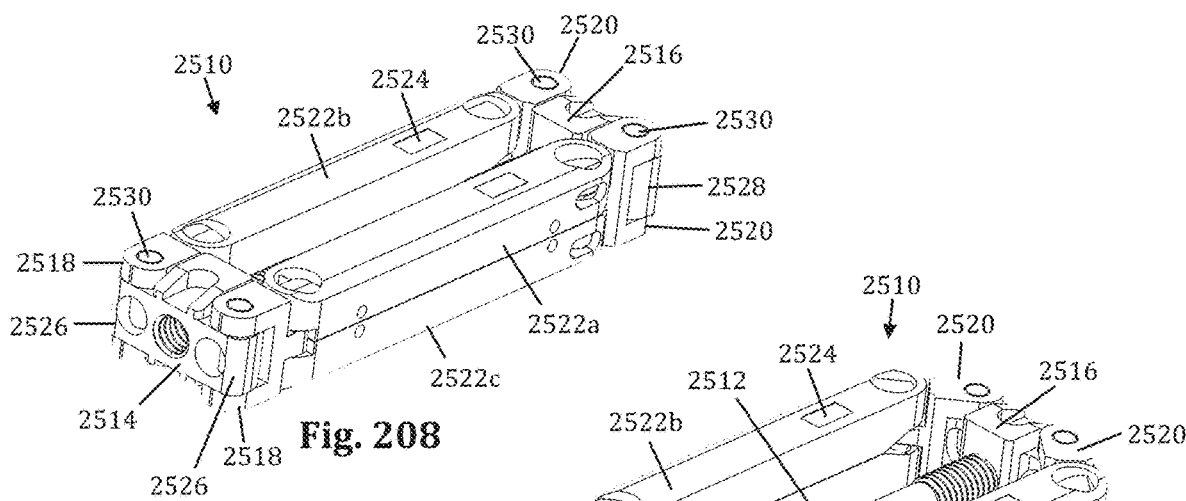
Figure 209:
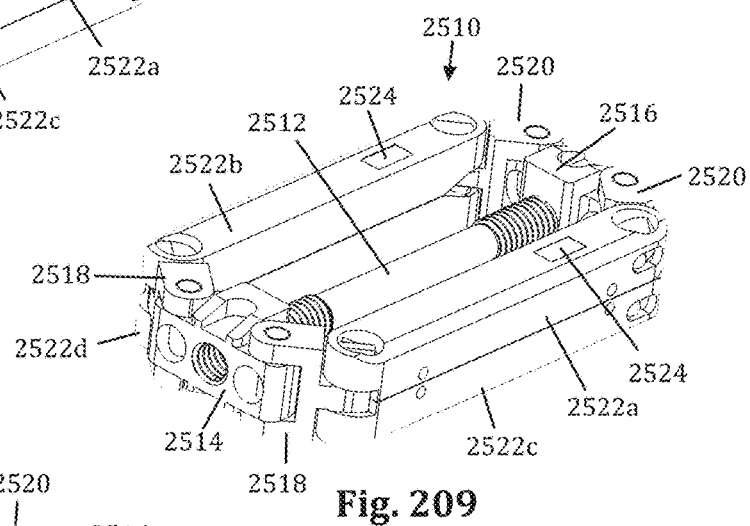
Figure 210:
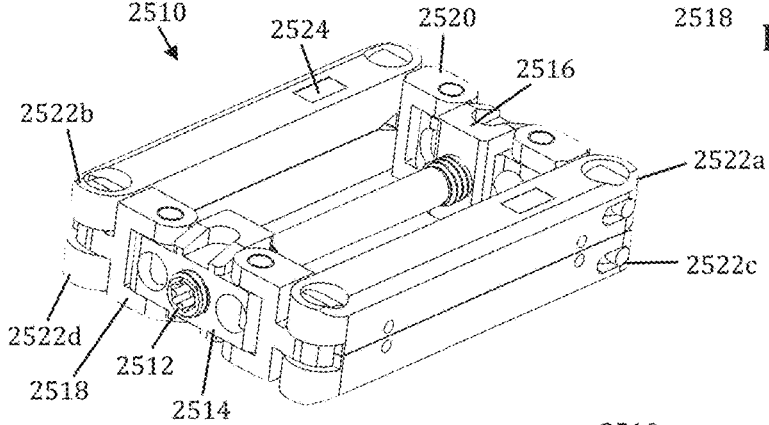
Figure 211:
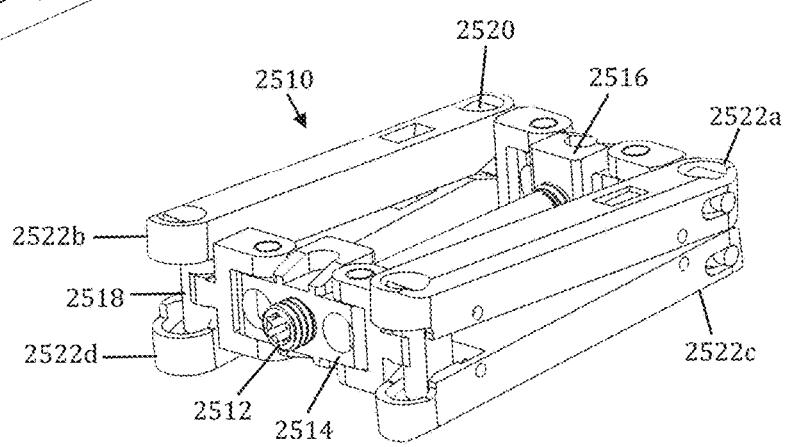
Figure 217:
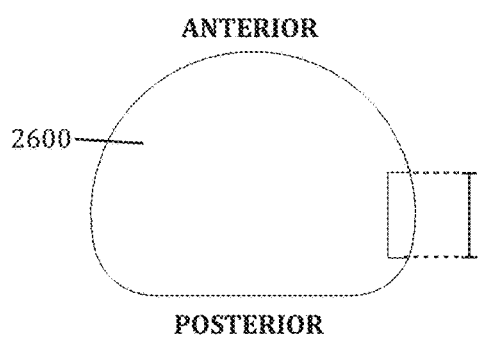
Figure 218:
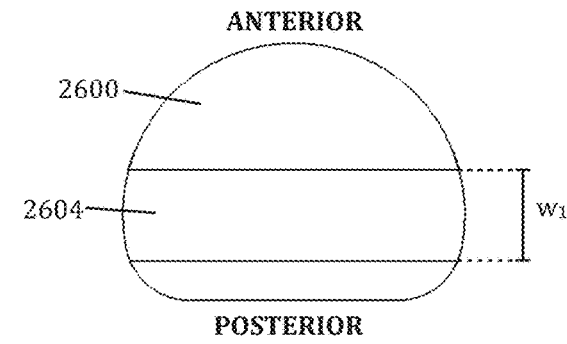
Figure 219:
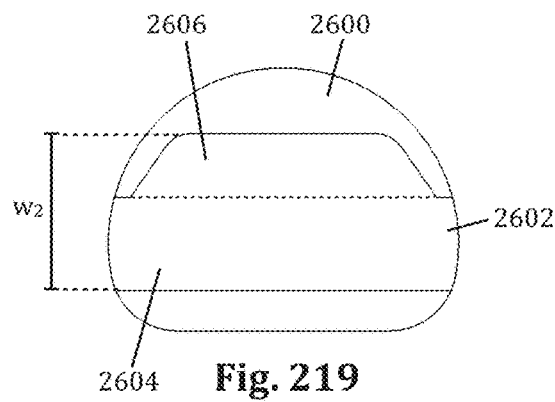
Figure 220:
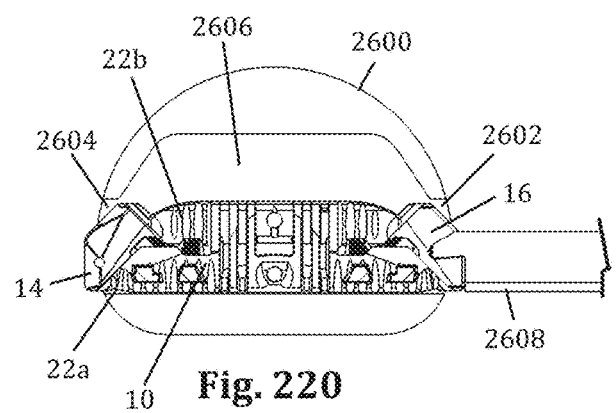
Figure 221:
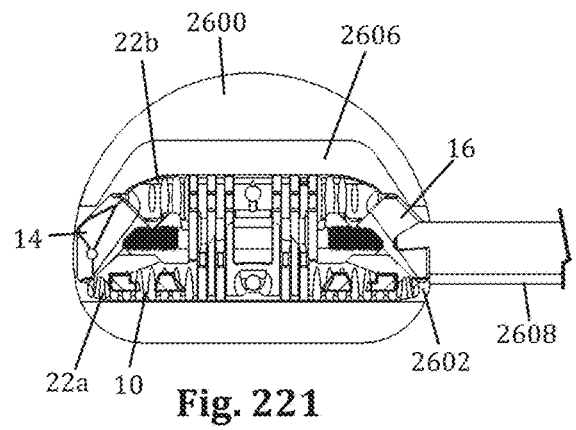
Figure 222:
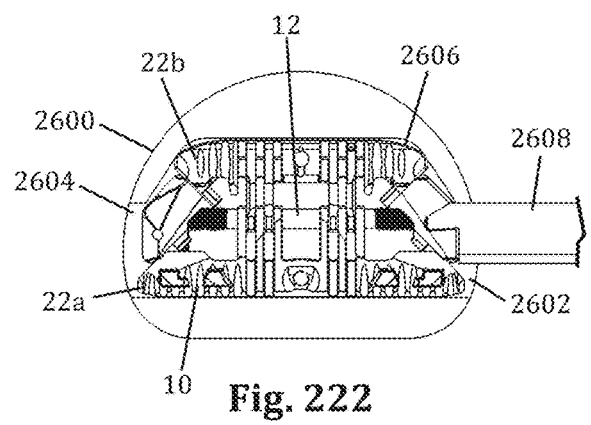
Figure 223:
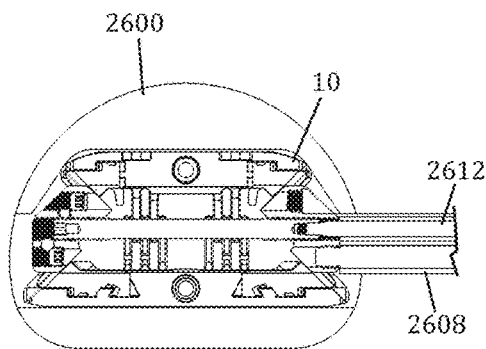
Figure 224:
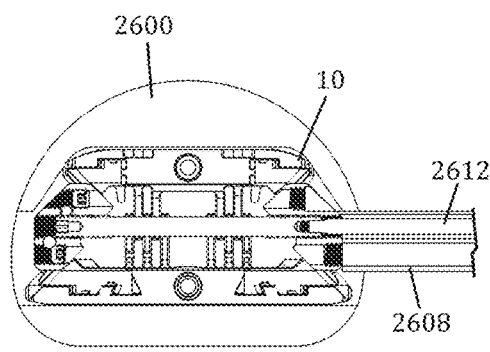
Figure 225:
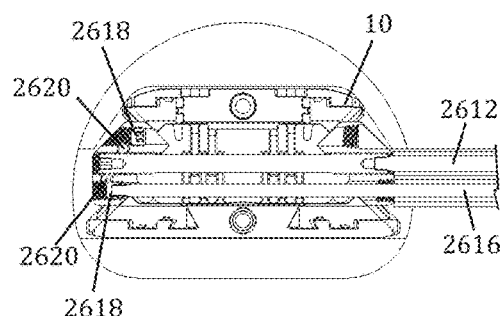
Figure 226:
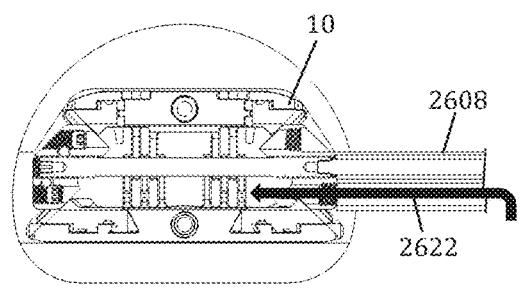
Figure 227:
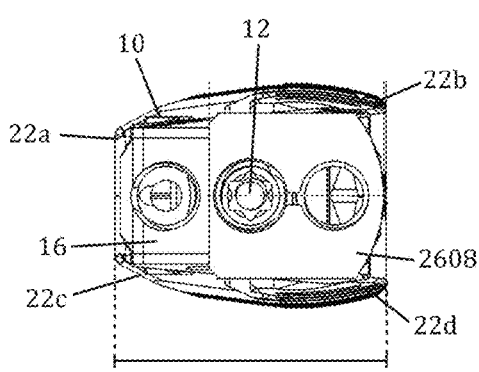
Figure 228:
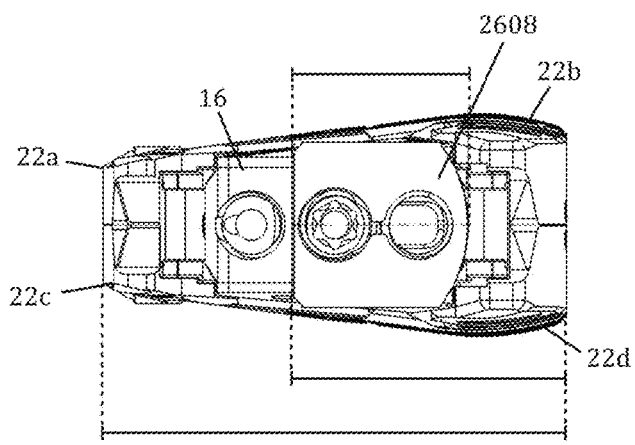
Figure 229:
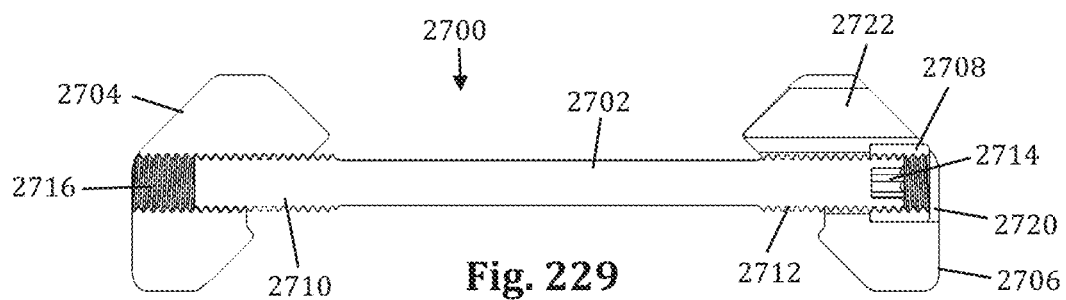
Figure 230:
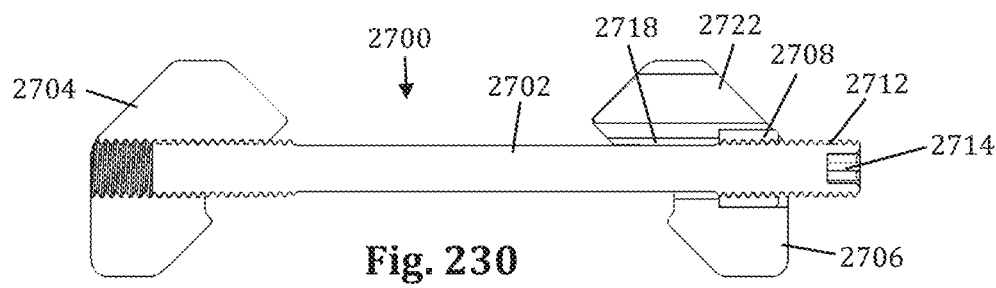
Figure 231:
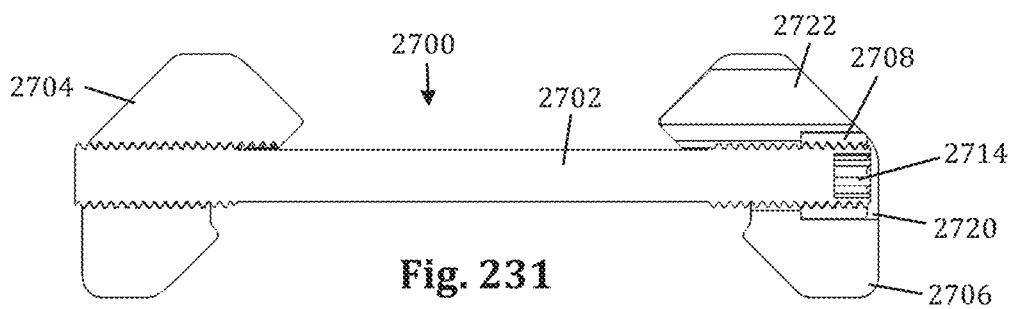
Figure 232:
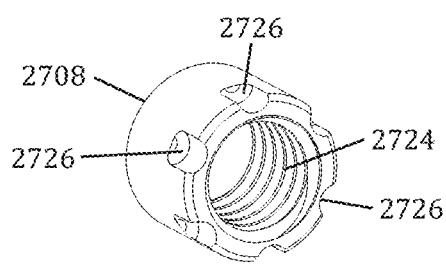
Figure 233:
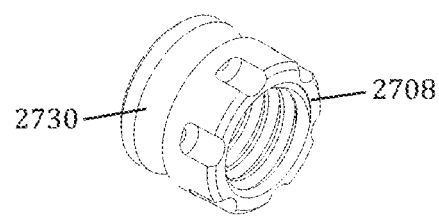
Figure 234:
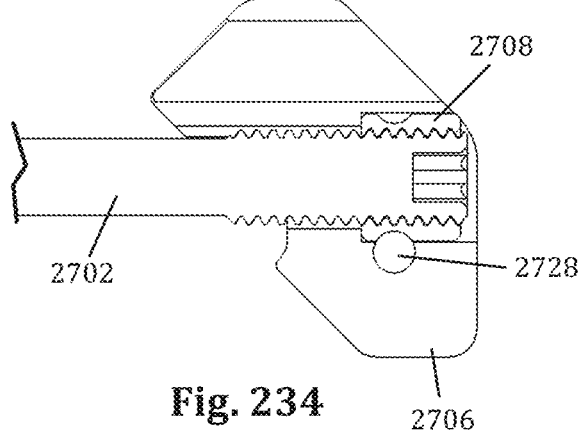
Figure 241:
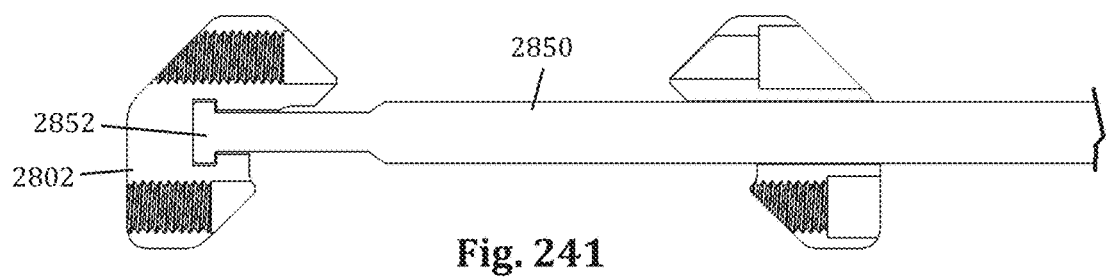
Figure 242:
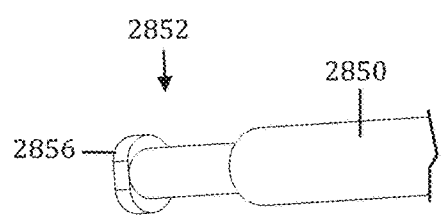
Figure 243:
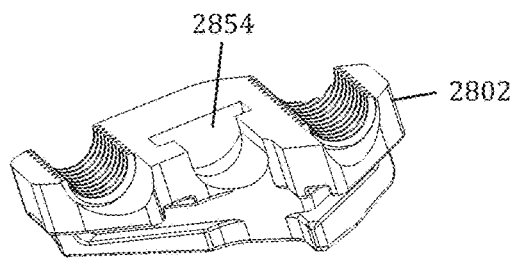
Figure 244:
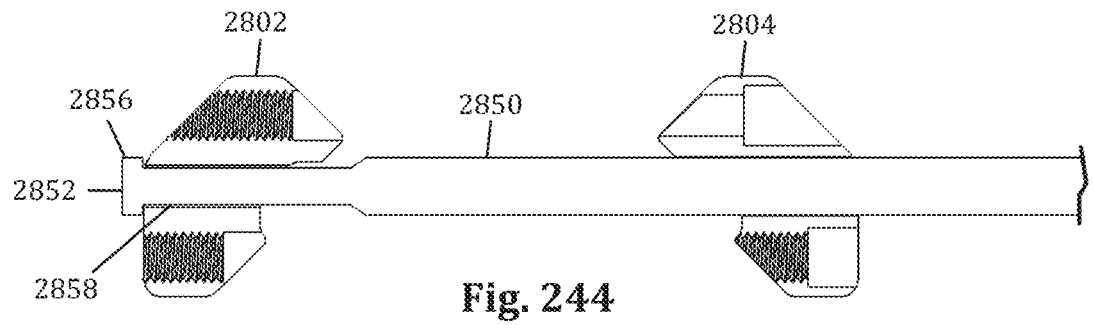
Figure 245:
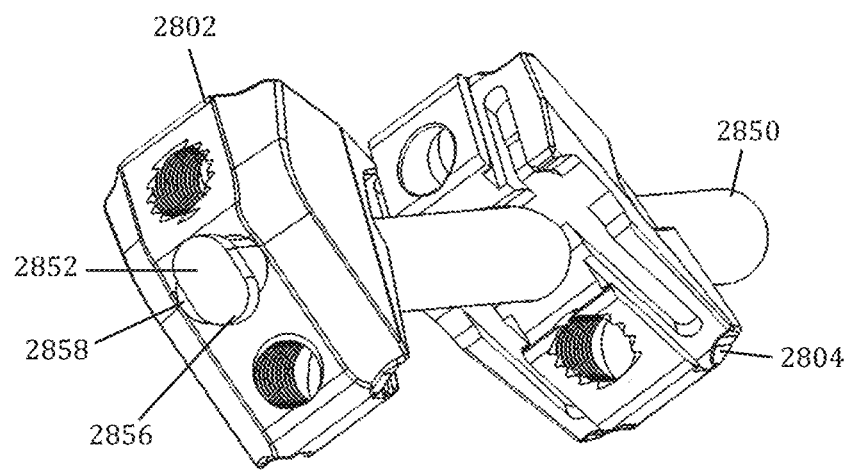
Figure 249:
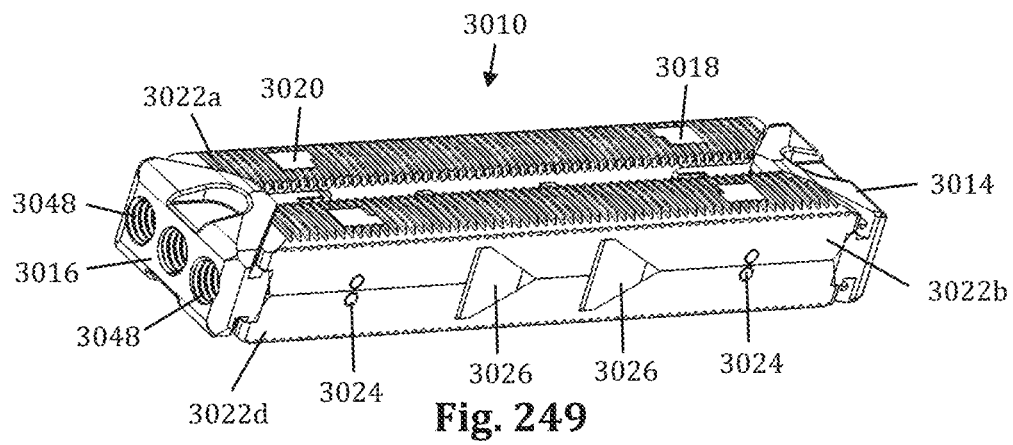
Figure 250:
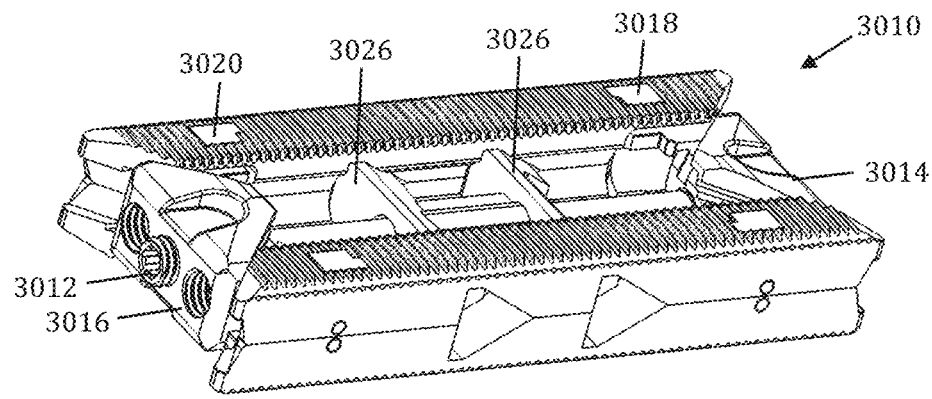
Figure 251:
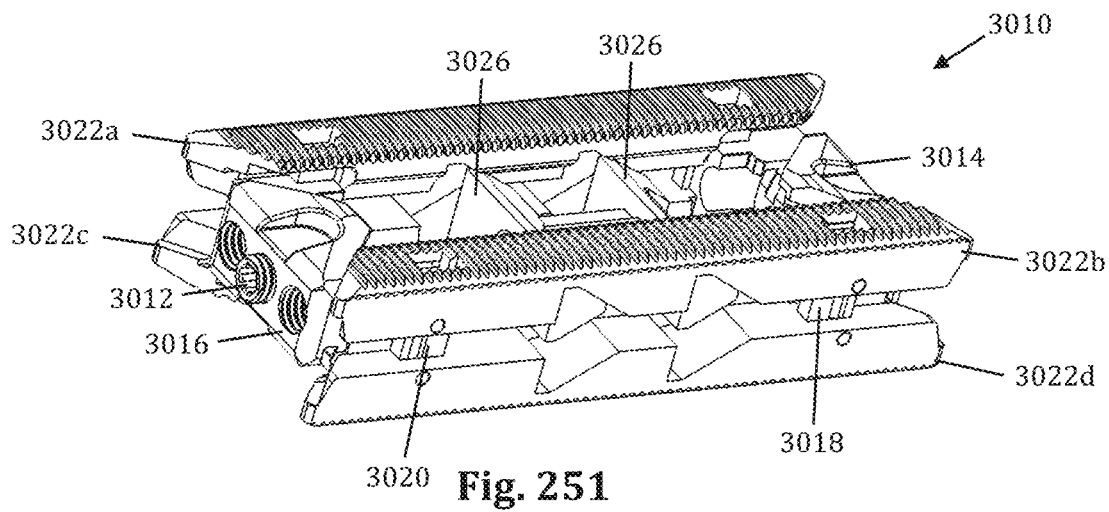
Figure 252:
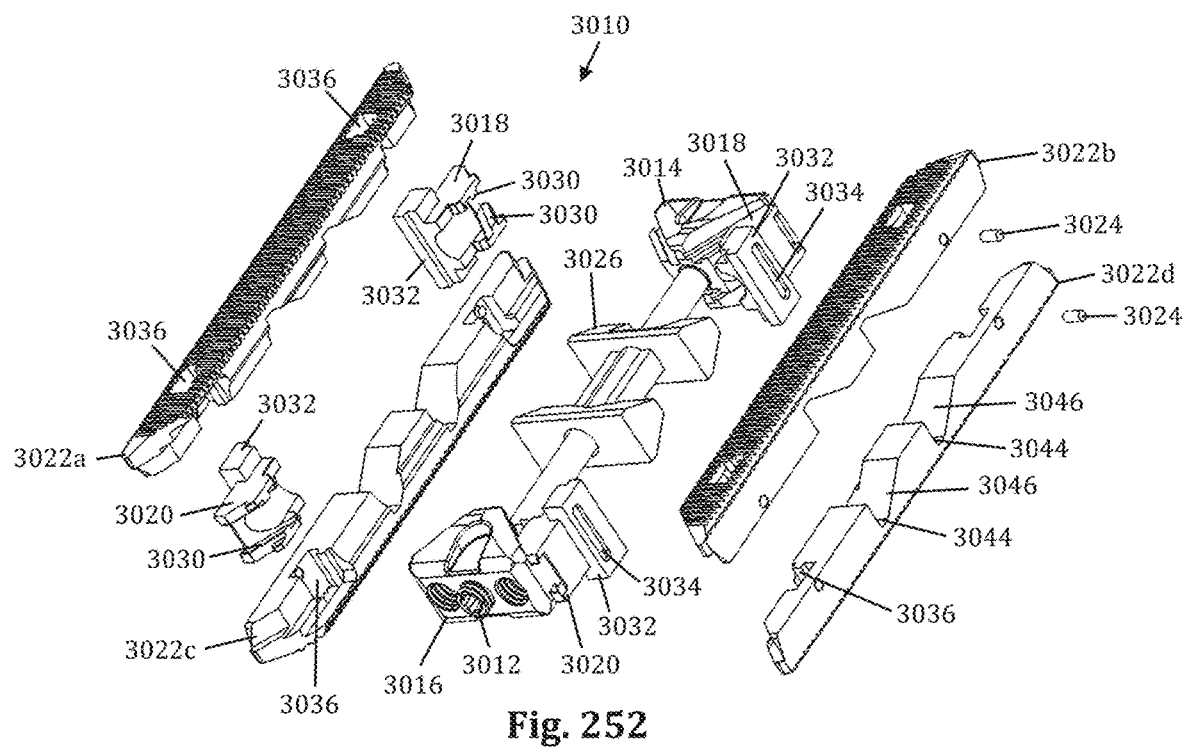
Figure 268:
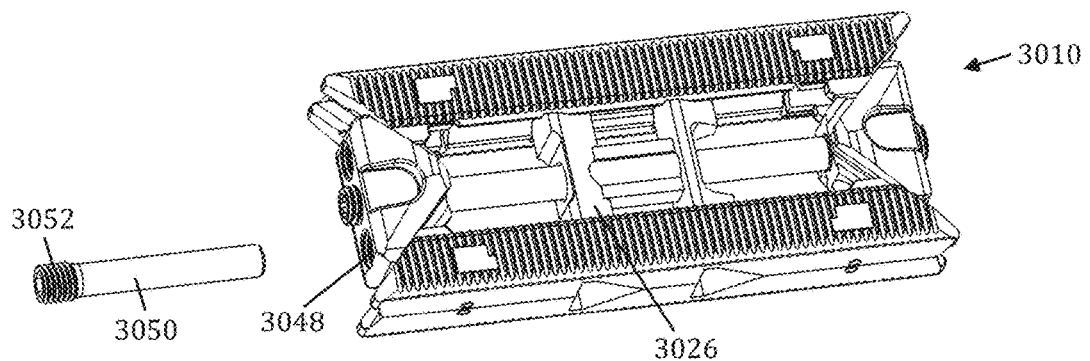
Figure 269:
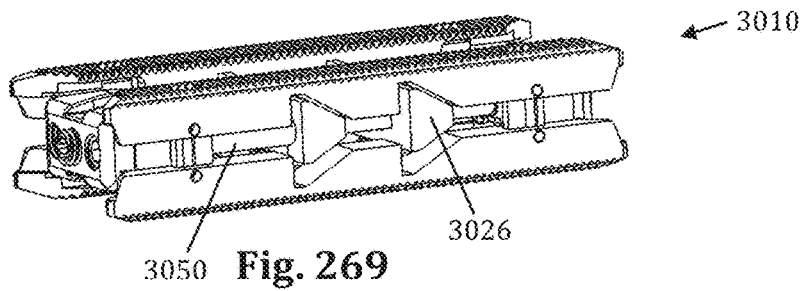
Figure 270:
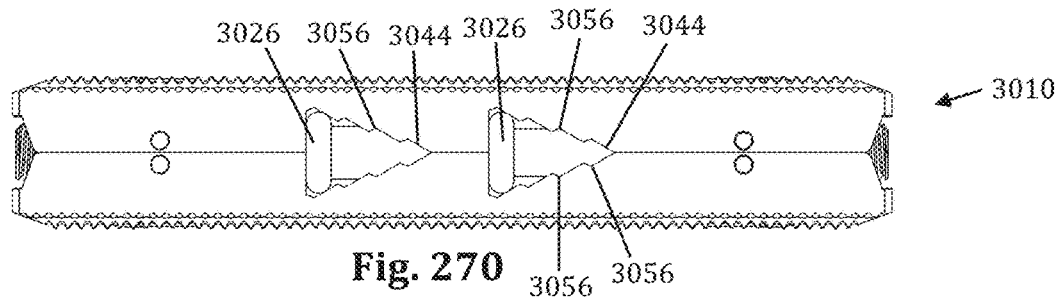
Figure 271:
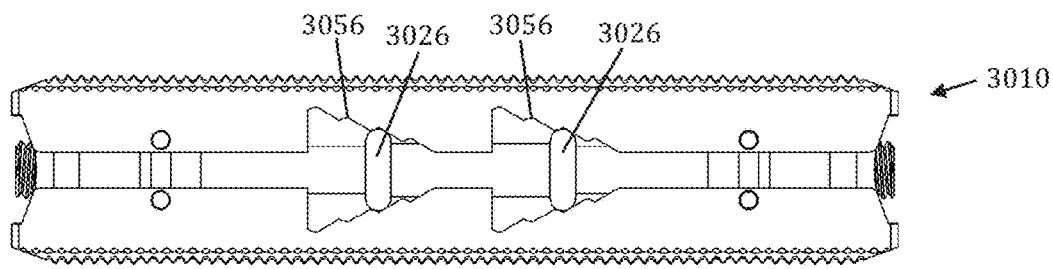
Figure 272:
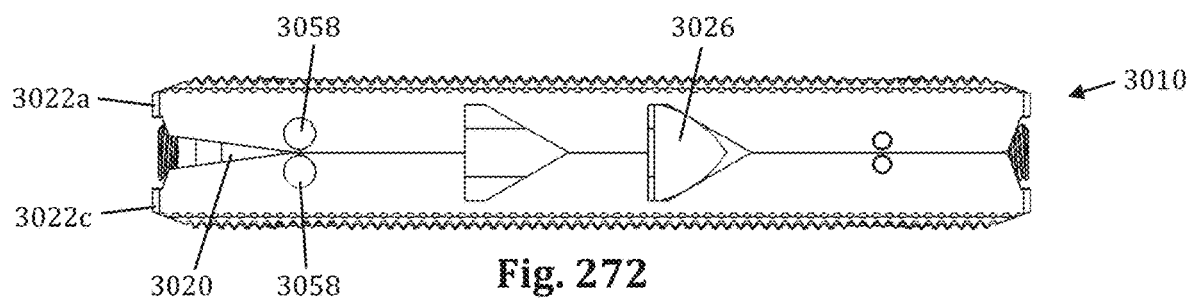
Figure 273:
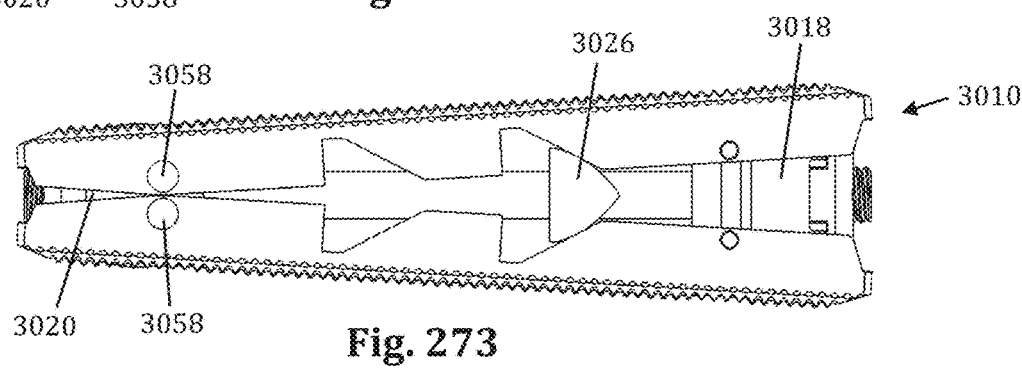
Figure 274:
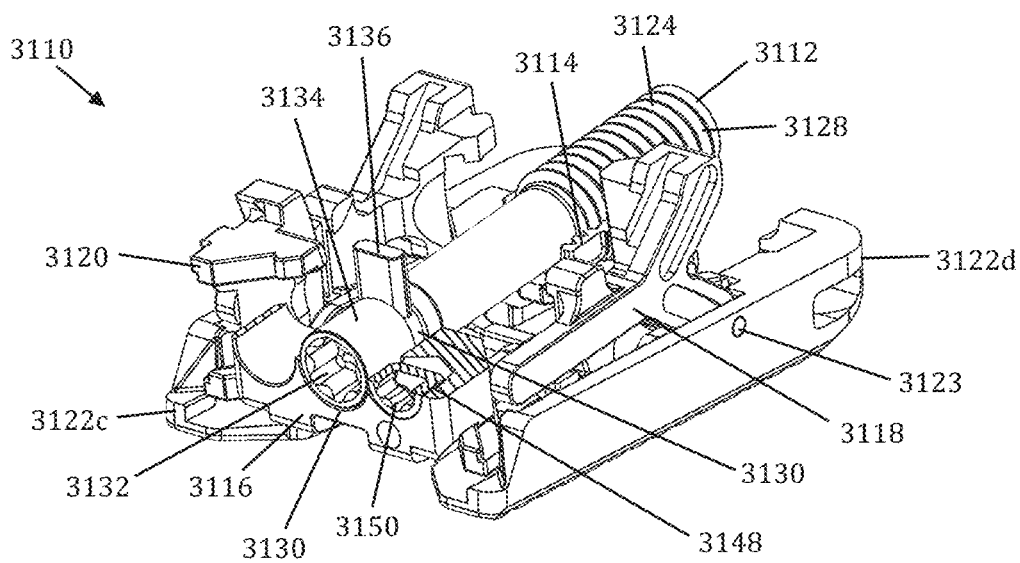
Figure 275:
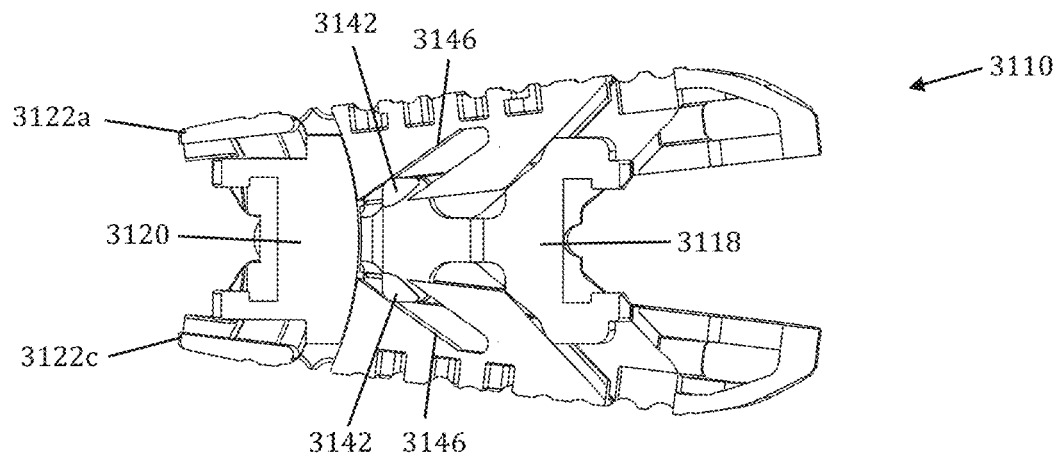
Figure 276:
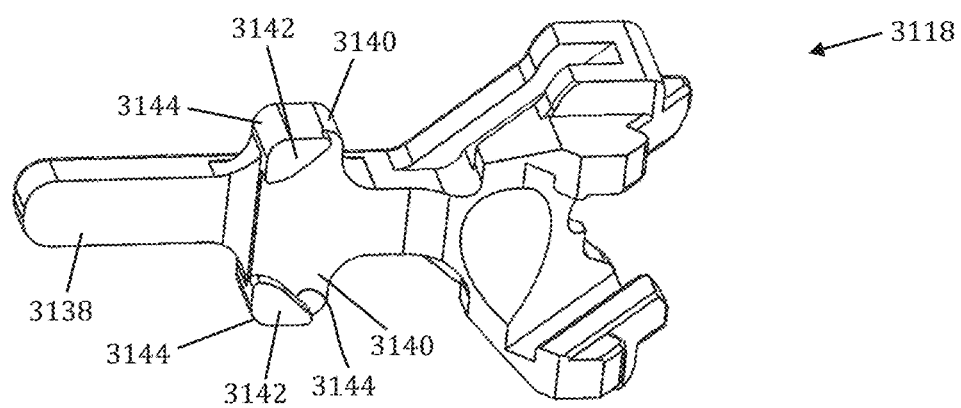
Figure 277:
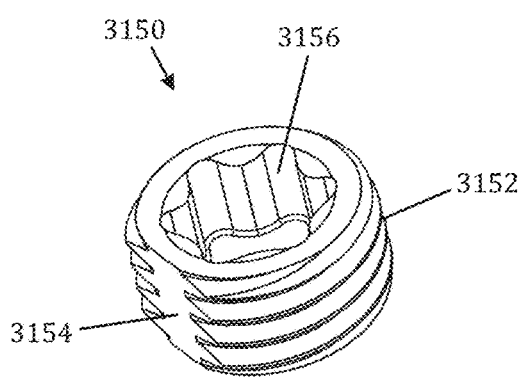
Figure 278:
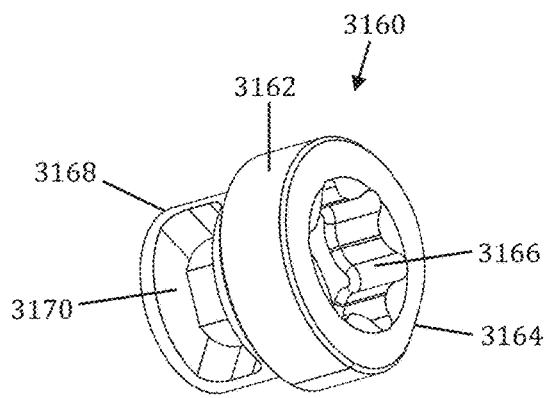
Figure 279:
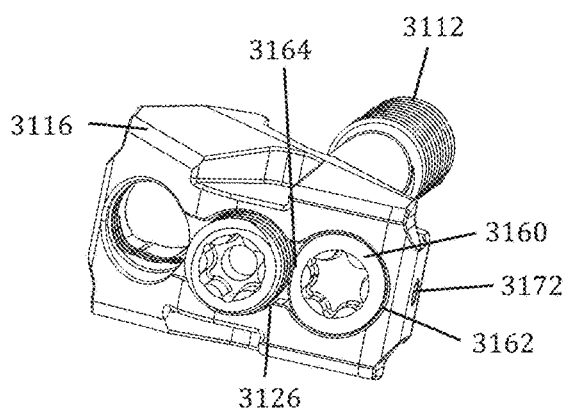
Figure 280:
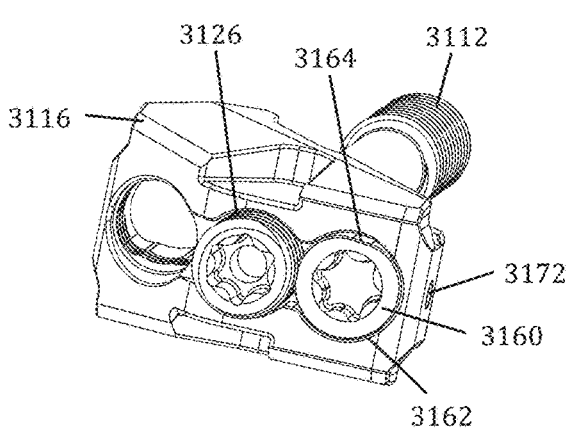
Figure 281:
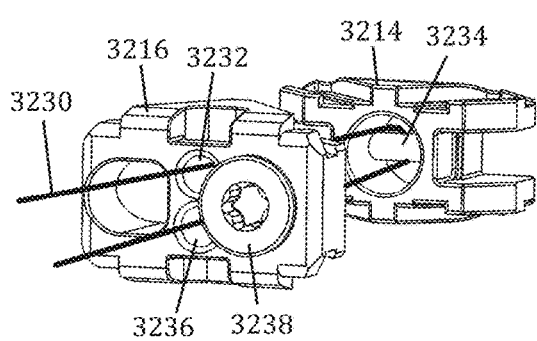
Figure 282:
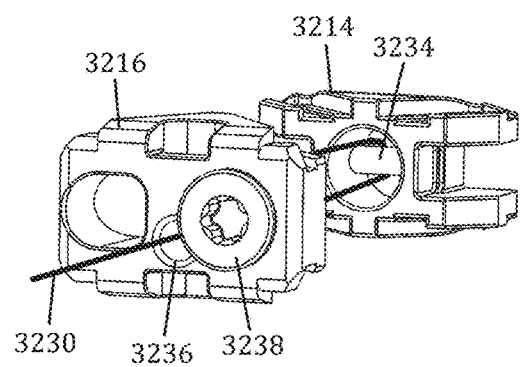
Figure 283:
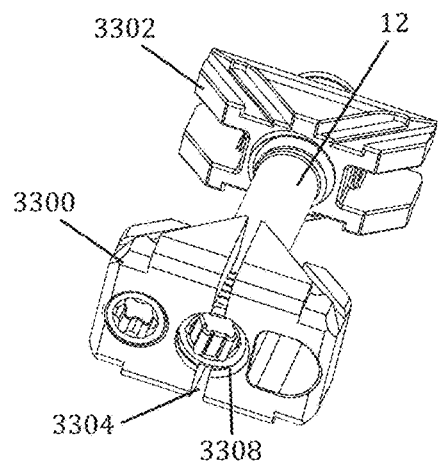
Figure 284:
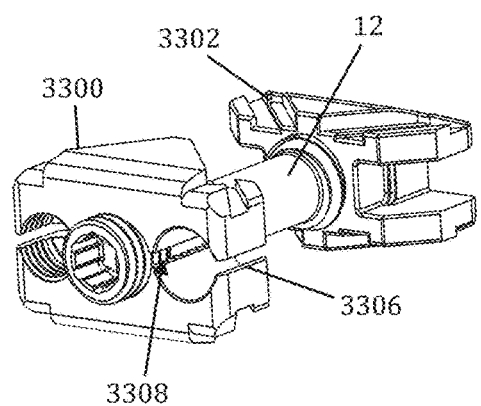
Figure 285:
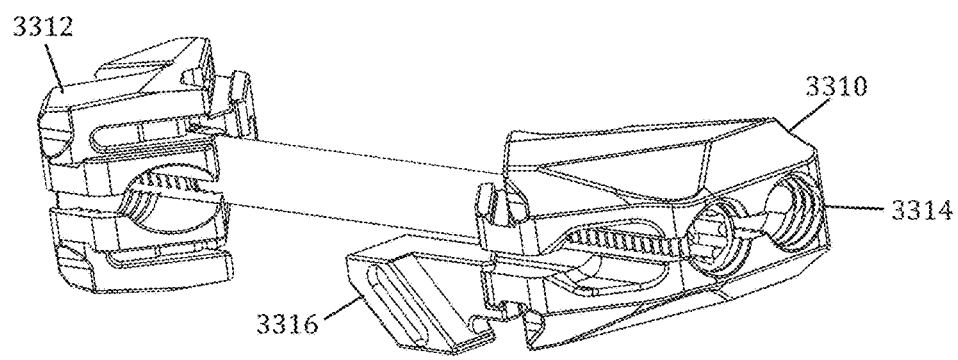
Figure 286:
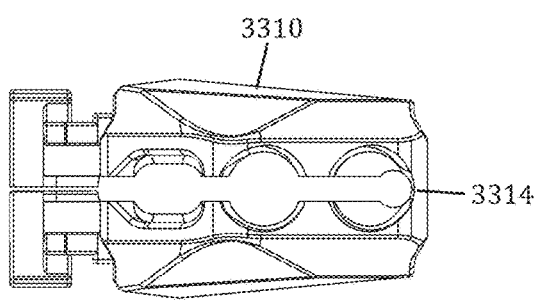
Figure 287:
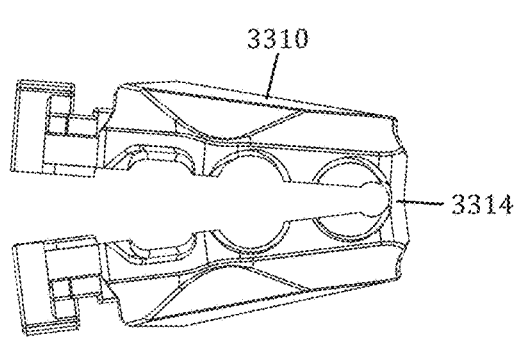
Figure 288:
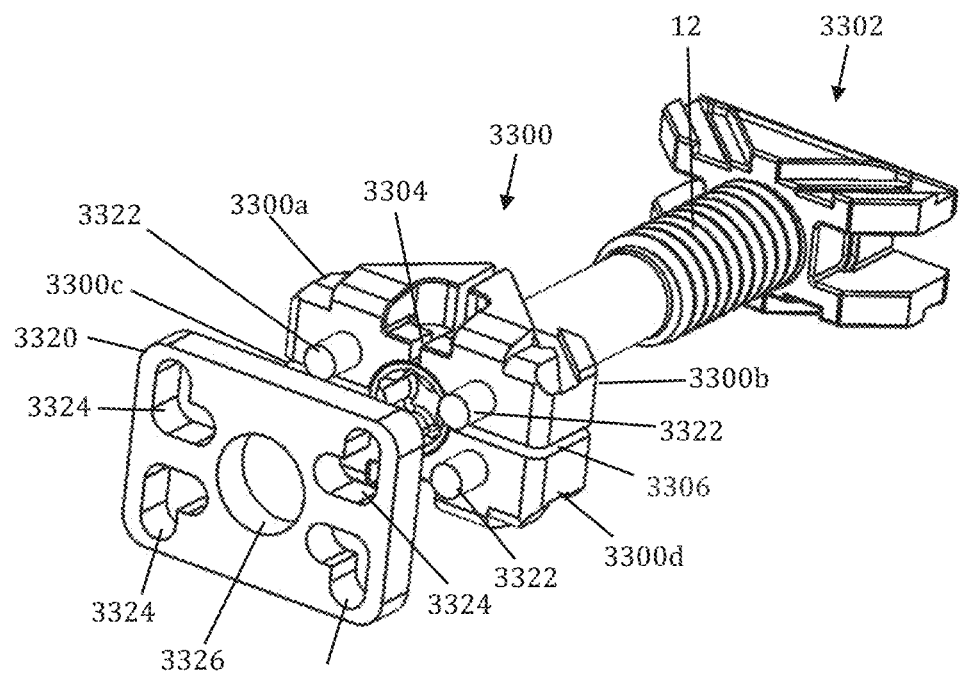
Figure 289:
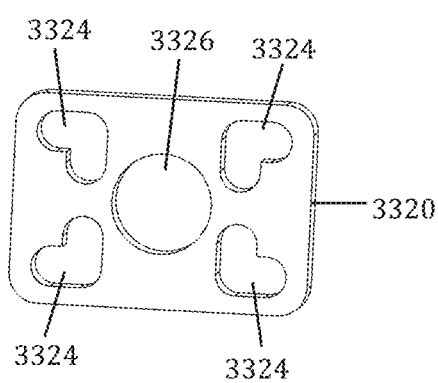
Figure 290:
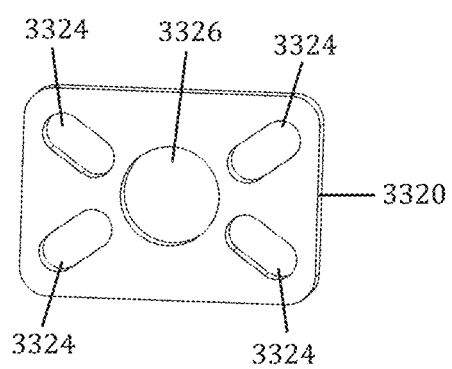
Figure 295:
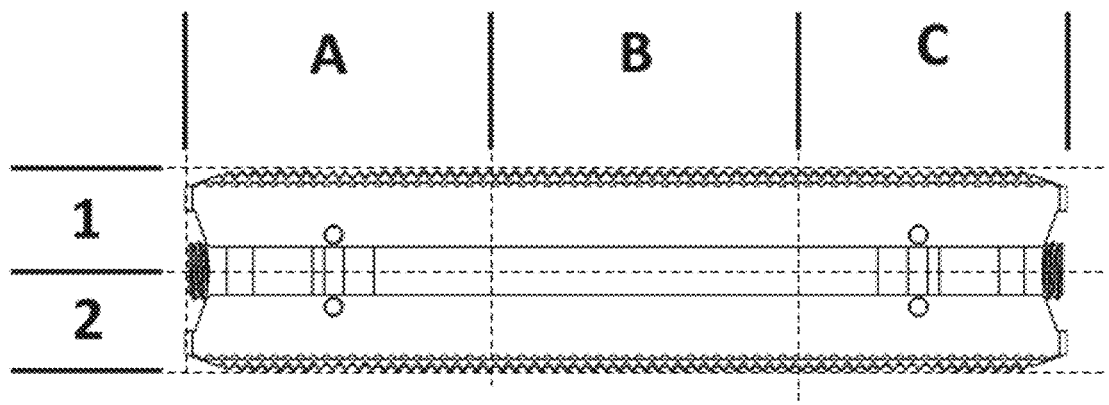
Figure 296:
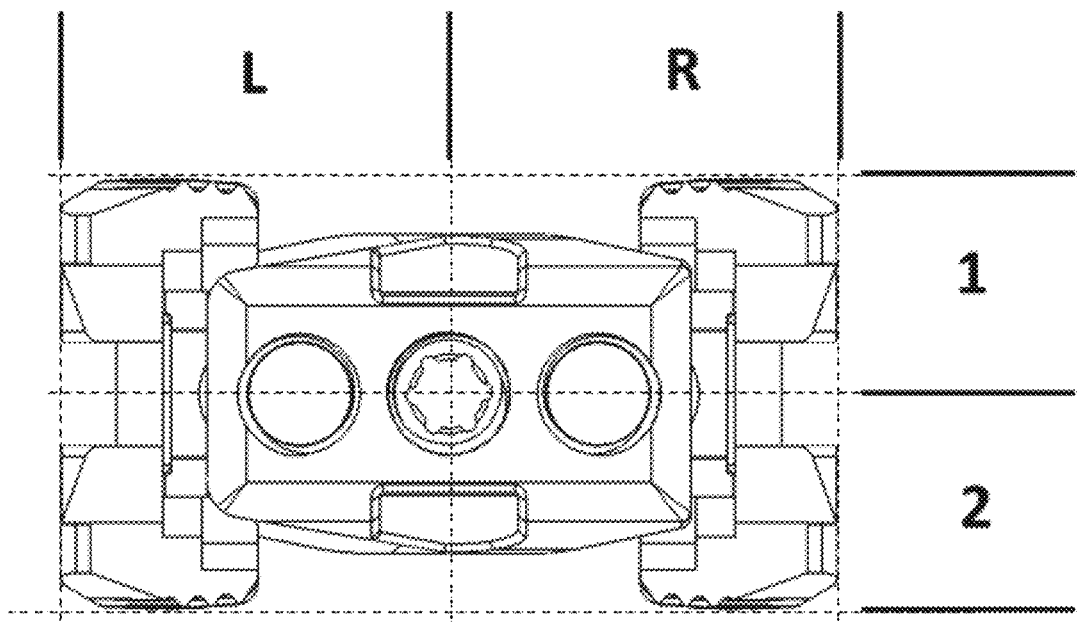

FIG. 141 is a sectional view of the expandable fusion device of FIG. 138 in a width expanded position, according to some embodiments;

FIG. 142 is a sectional view of the expandable fusion device of FIG. 138 in a fully expanded position, according to some embodiments;

FIG. 143 is a perspective view of another example of an expandable fusion device in a width expanded position, according to some embodiments;

FIG. 144 is a perspective view of an example of a carriage forming part of the expandable fusion device of FIG. 143, according to some embodiments;

FIG. 145 is a perspective view of the expandable fusion device of FIG. 143 in a fully expanded position with an endplate removed, according to some embodiments;

FIG. 146 is a sectional view of the expandable fusion device of FIG. 143, according to some embodiments;

FIG. 147 is a perspective view of another example of a expandable fusion device in a collapsed position, according to some embodiments;

FIG. 148 is a perspective view of the expandable fusion device of FIG. 147 in a fully expanded position, according to some embodiments;

FIG. 149 is a perspective view of an example of a carriage forming part of the expandable fusion device of FIG. 147, according to some embodiments;

FIGS. 150-155 are perspective views of examples of alternative carriages forming part of the the expandable fusion device of FIG. 147, according to some embodiments;

FIG. 156 is a perspective view of another example of an expandable fusion device in a width expanded position, according to some embodiments;

FIG. 157 is a perspective view of an example of a width stabilizer forming part of the expandable fusion device of FIG. 156, according to some embodiments;

FIGS. 158-160 are perspective views of the expandable fusion device of FIG. 156, according to some embodiments;

FIG. 161 is a perspective view of an example of another width stabilizer forming part of the expandable fusion device of FIG. 156, according to some embodiments;

FIG. 162 is a perspective view of another example of an expandable fusion device in a width expanded position, according to some embodiments;

FIGS. 163-164 are a perspective views of the expandable fusion device of FIG. 162 in a height expanded position, according to some embodiments;

FIG. 165 is a perspective view of the expandable fusion device of FIG. 162 in a height expanded position with an endplate removed, according to some embodiments;

FIGS. 166-168 are perspective views of various examples of height stabilizers forming part of the expandable fusion device of FIG. 162, according to some embodiments;

FIG. 169 is a perspective view of the expandable fusion device of FIG. 3 in a fully collapsed position with examples of wedges having anti-migration features, according to some embodiments;

FIG. 170 is an end plan view of the expandable fusion device of FIG. 169, according to some embodiments;

FIG. 171 is an end plan view of the expandable fusion device of FIG. 169 in a width expanded position, according to some embodiments;

FIG. 172 is a perspective view of the expandable fusion device of FIG. 169 in a width expanded position with an alternative example of wedges having anti-migration features, according to some embodiments;

FIGS. 173-174 are perspective views of alternative examples of proximal wedges with anti-migration features forming part of the expandable fusion device of FIG. 169, according to some embodiments;

FIG. 175 is a perspective view of the expandable fusion device of FIG. 3 in a collapsed position with examples of endplates having anti-migration features, according to some embodiments;

FIG. 176 is an end plan view of the expandable fusion device of FIG. 175, according to some embodiments;

FIG. 177 is an end plan view of the expandable fusion device of FIG. 175 in a width expanded position, according to some embodiments;

FIG. 178 is an end plan view of the expandable fusion device of FIG. 175, with an alternative example of an anti-migration feature on the endplate, according to some embodiments;

FIG. 177 is an end plan view of the expandable fusion device of FIG. 178 in a width expanded position, according to some embodiments;

FIG. 180 is a perspective view of the expandable fusion device of FIG. 175 with an alternative example of an anti-migration feature on the endplate, according to some embodiments;

FIG. 181 is an end plan view of the expandable fusion device of FIG. 180, according to some embodiments;

FIG. 182 is an end plan view of the expandable fusion device of FIG. 180 in a width expanded position, according to some embodiments;

FIG. 183 is a perspective view of the expandable fusion device of FIG. 175 with an alternative example of an anti-migration feature on the endplate, according to some embodiments;

FIG. 184 is a perspective view of the expandable fusion device of FIG. 3 in a collapsed position with examples of medial flanges having anti-migration features, according to some embodiments;

FIG. 185 is a perspective view of the expandable fusion device of FIG. 184 in a width expanded position, according to some embodiments;

FIG. 186 is an end plan view of the expandable fusion device of FIG. 184, according to some embodiments;

FIG. 187 is an end plan view of the expandable fusion device of FIG. 184 in a width expanded position, according to some embodiments;

FIG. 188 is a perspective view of the expandable fusion device of FIG. 3 in a collapsed position with examples of posterior ramps having anti-migration features, according to some embodiments;

FIG. 189 is an end plan view of the expandable fusion device of FIG. 188 in a width expanded position, according to some embodiments;

FIG. 190 is an end plan view of the expandable fusion device of FIG. 188 in a width and height expanded position, according to some embodiments;

FIGS. 191-195 are perspective views of various example configurations of a posterior ramp with anti-migration features forming part of the expandable fusion device of FIG. 188, according to some embodiments;

FIGS. 196-197 are perspective views of the expandable fusion device of FIG. 3 having prominent posterior ramps, according to some embodiments;

FIG. 198 is a plan view of the distal end of an example of an insertion instrument coupled to the expandable fusion device of FIG. 3, according to some embodiments;

FIG. 199 is a sectional view of the insertion instrument and device coupling of FIG. 198, according to some embodiments;

FIG. 200 is a plan view of the distal end of the insertion instrument of FIG. 198, according to some embodiments;

FIG. 201 is a perspective view of the insertion instrument and device coupling of FIG. 198, showing an insertion instrument with anti-migration features, according to some embodiments;

FIG. 202 is a side plan view of another example of an expandable fusion device in a fully expanded position, according to some embodiments;

FIG. 203 is a side sectional view of the expandable fusion device of FIG. 202, according to some embodiments;

FIG. 204 is a perspective view of an example of a proximal ramp forming part of the expandable fusion device of FIG. 202, according to some embodiments;

FIG. 205 is a side sectional view of another example of an expandable fusion device in a fully expanded position, according to some embodiments;

FIG. 206 is a perspective view of an example of a distal ramp forming part of the expandable fusion device of FIG. 205, according to some embodiments;

FIG. 207 is a perspective view of an example of an endplate component forming part of the expandable fusion device of FIG. 205, according to some embodiments;

FIG. 208 is a perspective view of another example of an expandable fusion device in a fully collapsed position, according to some embodiments;

FIG. 209 is a perspective view of the expandable fusion device of FIG. 208 in a partial width-expanded position, according to some embodiments;

FIG. 210 is a perspective view of the expandable fusion device of FIG. 208 in a fully width-expanded position, according to some embodiments;

FIG. 211 is a perspective view of the expandable fusion device of FIG. 208 in a fully expanded position, according to some embodiments;

FIG. 212 is a perspective view of the expandable fusion device of FIG. 208 in a fully expanded position with one endplate removed, according to some embodiments;

FIG. 213 is a perspective view of an example of a distal link element forming part of the expandable fusion device of FIG. 208, according to some embodiments;

FIG. 214 is a perspective view of an example of a proximal link element forming part of the expandable fusion device of FIG. 208, according to some embodiments;

FIG. 215 is a side plan view of the proximal link element of FIG. 214, according to some embodiments;

FIG. 216 is a perspective view of an example of an endplate component forming part of the expandable fusion device of FIG. 208, according to some embodiments;

FIG. 217 is an axial section view of an intervertebral disc with an annulotomy opening formed therein, according to some embodiments;

FIG. 218 is an axial section view of the intervertebral disc of FIG. 217 with a discectomy channel formed therein, according to some embodiments;

FIG. 219 is an axial section view of the intervertebral disc of FIG. 217 with a discectomy channel with directional discectomy void formed therein, according to some embodiments;

FIG. 220 is an axial section view of the intervertebral disc of FIG. 219 with an expandable fusion device of FIG. 3 inserted therein in a collapsed state, according to some embodiments;

FIG. 221 is an axial section view of the intervertebral disc of FIG. 219 with an expandable fusion device of FIG. 3 inserted therein in a partial width expanded state, according to some embodiments;

FIG. 222 is an axial section view of the intervertebral disc of FIG. 219 with an expandable fusion device of FIG. 3 inserted therein in a fully width expanded state, according to some embodiments;

FIG. 223 is an axial section view of the intervertebral disc of FIG. 219 with an expandable fusion device of FIG. 3 inserted therein in a fully width expanded state, illustrating in particular the engagement of the inserter and driver instruments with the expandable fusion device, according to some embodiments;

FIG. 224 is an axial section view of the intervertebral disc of FIG. 223 with an expandable fusion device of FIG. 3 inserted therein in a fully width expanded state, illustrating in particular the removal of the inserter from the expandable fusion device, according to some embodiments;

FIG. 225 is an axial section view of the intervertebral disc of FIG. 224 with an expandable fusion device of FIG. 3 inserted therein in a fully width expanded state, illustrating in particular the insertion of a locking driver instrument within the expandable fusion device, according to some embodiments;

FIG. 226 is an axial section view of the intervertebral disc of FIG. 225 with an expandable fusion device of FIG. 3 inserted therein in a fully width expanded state, illustrating in particular the delivery of fusion-promoting material into the expandable fusion device, according to some embodiments;

FIG. 227 is an axial plan view of an expandable fusion device of FIG. 3 in a fully collapsed state and coupled with an inserter, according to some embodiments;

FIG. 228 is an axial plan view of the expandable fusion device of FIG. 227, illustrating in particular a biased posterior expansion, according to some embodiments;

FIGS. 229-231 are plan views of an example of an actuation mechanism forming part of the expandable fusion device of FIG. 3, according to some embodiments;

FIG. 232 is an example of an actuation nut forming part of the actuation mechanism of FIG. 229, according to some embodiments;

FIG. 233 is another example of an actuation nut forming part of the actuation mechanism of FIG. 229, according to some embodiments;

FIG. 234 is an example of a wedge component forming part of the actuation mechanism of FIG. 229, according to some embodiments;

FIGS. 235-240 are sectional plan views of another example of an expansion mechanism forming part of the expandable fusion device of FIG. 3, according to some embodiments;

FIG. 241 is a plan view of another example of an expansion mechanism forming part of the expandable fusion device of FIG. 3, according to some embodiments;

FIG. 242 is a perspective view of a distal end of an expansion instrument forming part of the expansion mechanism of FIG. 241, according to some embodiments;

FIG. 243 is a perspective sectional view of a distal wedge component forming part of the expansion mechanism of FIG. 241, according to some embodiments;

FIGS. 244-245 are sectional and perspective views, respectively, of another example of an expansion mechanism forming part of the expandable fusion device of FIG. 3, according to some embodiments;

FIGS. 245-248 are sectional plan views of another example of an expansion mechanism forming part of the expandable fusion device of FIG. 3, according to some embodiments;

FIG. 249 is a perspective view of another example of an expandable fusion device in a collapsed position, according to some embodiments;

FIG. 250 is a perspective view of the expandable fusion device of FIG. 249 in a width expanded position, according to some embodiments;

FIG. 251 is a perspective view of the expandable fusion device of FIG. 249 in a fully expanded position, according to some embodiments;

FIG. 252 is an exploded view of the expandable fusion device of FIG. 249 in a fully expanded position, according to some embodiments;

FIGS. 253-267 are perspective views of various examples of height expansion cores forming part of the expandable fusion device of FIG. 249, according to some embodiments;

FIGS. 268-269 are perspective views of the expandable fusion device of FIG. 249 in association with an implantable height expansion element, according to some embodiments;

FIGS. 270-271 are perspective views of the expandable fusion device of FIG. 249 in collapsed and height-expanded form, respectively, adapted for use with a removable height expansion element, according to some embodiments;

FIGS. 272-273 are perspective views of the expandable fusion device of FIG. 249 in collapsed and lordotic-expanded form, respectively, according to some embodiments; and FIG. 274 is a perspective view of another example of an expandable fusion device in an expanded position with the top endplates removed, according to some embodiments;

FIG. 275 is a sectional view of the expandable fusion device of FIG. 274, according to some embodiments;

FIG. 276 is a perspective view of an example of a distal ramp forming part of the expandable fusion device of FIG. 274, according to some embodiments;

FIG. 277 is a perspective view of one example of a locking element forming part of the expandable fusion device of FIG. 274, according to some embodiments;

FIG. 278 is a perspective view of another example of a locking element forming part of the expandable fusion device of FIG. 274, according to some embodiments;

FIGS. 279-280 are perspective views of a proximal wedge and actuator forming part of the expandable fusion device of FIG. 274, with a locking element of FIG. 278 engaged therein, according to some embodiments;

FIG. 281 is a perspective view of an example of a pair of wedge elements connected by a flexible actuator member, according to some embodiments;

FIG. 282 is a perspective view of another example of a pair of wedge elements connected by a flexible actuator member, according to some embodiments;

FIG. 283 is a perspective view of another example of a pair of wedge elements connected by an actuator, wherein at least one of the wedge elements is split in half vertically, according to some embodiments;

FIG. 284 is a perspective view of another example of a pair of wedge elements connected by an actuator, wherein at least one of the wedge elements is split in half horizontally, according to some embodiments;

FIG. 285 is a perspective view of another example of a pair of wedge elements connected by an actuator, wherein at least one of the wedge elements is substantially split in half horizontally, according to some embodiments;

FIGS. 286-287 are plan views of a wedge element of FIG. 285, according to some embodiments;

FIG. 288 is a perspective view of another example of a pair of wedge elements connected by an actuator, wherein at least one of the wedge elements is split into multiple parts that are held in place by a control panel, according to some embodiments;

FIGS. 289-290 are perspective views of alternative examples of the control panel of FIG. 288, according to some embodiments;

FIGS. 291-294 are perspective views of another example of an expandable fusion implant illustrating staged expansion, according to some embodiments; and FIGS. 295-296 are side plan and end plan views, respectively, of an example of an expandable fusion device in fully expanded form, illustrating in particular the divisibility of the implant into interchangeable sectors, according to some embodiments.

DETAILED DESCRIPTION

Expandable spinal fusion devices, systems, and methods of using them are provided and reduce surgical complexity and risk through the use of a minimum to minimal, or perhaps no, intervertebral distraction and use of a small surgical corridor. The devices, systems, and methods allow for a desired width control in the expansion of the device through a variable transverse expansion system in a single device which provides for selection of a desirable footprint, which can be a larger, or perhaps biased, footprint for achieving a desired alignment, or perhaps for avoiding subsidence of the device during use. They also allow for a desired control of height expansion through a gradual cephalocaudal expansion of the device, gradually increased at a desired amount, to obtain a desirable intervertebral height and/or pressure, for controllably decompressing the neural elements and reaching the desired the intervertebral height with increased safety due to the incremental control of the speed, amount, and pressure of expansion applied to the surrounding tissue. A desired control of the alignment of the adjacent vertebral bodies is offered through a design that gives a surgeon the freedom to choose any expansion width desired, uniform or variable, and obtaining that desired width independent of the gradual height control, which can also be any expansion height desired, uniform or variable.

Devices, systems, and methods are also offered that allow for a desired control of the stress distribution over a contact area desired between the device and the upper and lower vertebral endplates achieved, for example, using an inter-digitated endplate system that expand, pivot, or both.

The devices taught herein can be referred to as a "cage", a "device", an "implant", and the like. The cages taught herein can have ramp assemblies and wedge assemblies. In some embodiments, the ramp is not in contact with the wedge through at least a first distance moved by the wedge. In some embodiments, the ramp is not in contact with the wedge through at least a final distance moved by the wedge. In some embodiments, the ramp is not in contact with the wedge through the entirety of the distance moved by the wedge.

The fusion devices taught herein can include a proximal wedge, a distal wedge, a first ramp, a second ramp, a third ramp, a fourth ramp, a first endplate, a second endplate, a third endplate, a fourth endplate, an actuator, and/or a retention member designed to constrain the linear motion of the actuator relative to the proximal wedge. The proximal wedge and the distal wedge can be moved together or apart from each other, forcing the first ramp away from the fourth ramp and forcing the second ramp away from the third ramp and also forcing the first ramp away from or toward the second ramp and forcing the third ramp away from or toward the fourth ramp, to result in moving the first endplate, the second endplate, the third endplate and the fourth endplate outwardly from each other and into an expanded configuration. In some embodiments, the ramps can move together along the long axis of a device in series at the same or a different rate of speed to provide different heights at end of the cage over the other, or one side of the cage over the other, or one corner of the cage over the others. And, in some embodiments, the rate of incline of one ramp can be different than the rate of incline of another ramp to provide different heights at end of the cage over the other.

The device can have a width comprising an external width of at least one of the upper endplate assembly and the lower endplate assembly. Likewise, the device can have a height comprising an external distance between the upper endplate assembly and the lower endplate assembly.

In some embodiments, actuation can be a step used that results in movement of a wedge or ramp. In some embodiments, the movement is from actuation of a drive feature. The actuation step can include the use of any mechanism known to one of skill including, but not limited to, actuating any drive feature that is a part of the cage, or a part of a tool that is used in the actuating of the cage and then removed. In some embodiments, an actuator can be introduced to the cage after inserting the cage and then left in the cage after the actuating. In some embodiments, an actuator can be introduced to the cage and then removed after the actuating. The actuation or drive feature might be a thread on a shaft, perhaps, a rod, or features on a rod, and the like. As such, actuation might include turning a threaded shaft, pushing a rod, and the like. For example, actuation by a first number of actuations in a first actuation direction can increase the width without increasing the height. Likewise, actuation by a second number of actuations beyond the first number of actuations in the first actuation direction can increase at least one of the height and the width. In the embodiments taught herein, actuation can be done to move a wedge, move a ramp, pivot a linkage, and the like. For example, the wedge and/or ramp may be moved a first distance, a second distance, a third distance, etc. Wedges and ramps can be moved independently. Likewise, a first wedge may be moved independent of a second wedge, and a first ramp may be moved independent of a second ramp. The term "move" can be used to refer to "sliding", "translation", "rotation", or a combination thereof, in some embodiments. An actuator can be an integrated part of a cage taught herein, or it can be merely a tool that is used and removed outside of the cage. As such, any system provided herein may or may not include an actuator. In some embodiments, the term "wedge" may or may not refer a component that moves to provide a width expansion. For example, the term "spacer" may be used, in some embodiments. The term "endplate" or "beam" can be used interchangeably in some embodiments.

One of skill will appreciate the range of expansions available, as well as the improved, and independent, control of both cephalocaudal and transverse expansions that is offered to the art by the devices presented herein. In some embodiments, the width (dimension in which the device expands in the transverse direction in vivo) of the device can range from about 5 mm to about 30 mm in the collapsed state, and any amount or range therein in increments of 1 mm; and, from about 10 mm to about 60 mm in the expanded state, and any amount or range therein in increments of 1 mm. In some embodiments, the height (dimension in which the device expands in the cephalocaudal direction in vivo) of the device can range from about 5 mm to about 20 mm in the collapsed state, and from about 10 mm to about 40 mm in the expanded state. The percent expansion in either direction can range from about 1% to about 100%, and any percent therein in increments of 1%, in some embodiments. As such, in the collapsed state, the width of the device can be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, or any amount or range therein in increments of 0.1 mm; and, the height can be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or any amount or range therein in increments of 0.1 mm. Likewise, in the expanded state, the width of the device can be about 10 mm, about 12 mm, about 14 mm, about 16 mm, about 18 mm, about 20 mm, about 24 mm, about 24 mm, about 26 mm, about 28 mm, about 30 mm, about 32 mm, about 34 mm, about 36 mm, about 38 mm, about 40 mm, about 42 mm, about 44 mm, about 46 mm, about 48 mm, about 50 mm, about 52 mm, about 54 mm, about 56 mm, about 58 mm, about 60 mm, or any amount or range therein in increments of 0.1 mm; and, the height can be about 10 mm, about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, or any amount or range therein in increments of 0.1 mm. Any combination, or combination of ranges, of the above height and width dimensions can be used together, in some embodiments. In some embodiments, for example, a device can have a height ranging from about 7-8 mm when collapsed, whereas the height ranges from about 12-14 mm when expanded in vivo; and, it can have a width a ranging from about 7-20 mm when collapsed, whereas the width ranges from about 14-40 mm when expanded in vivo. In some embodiments, for example, a device can have a height ranging from about 6-10 mm when collapsed, whereas the height ranges from about 12-20 mm when expanded in vivo; and, it can have a width a ranging from about 6-24 mm when collapsed, whereas the width ranges from about 12-48 mm when expanded in vivo.

Figure 1:
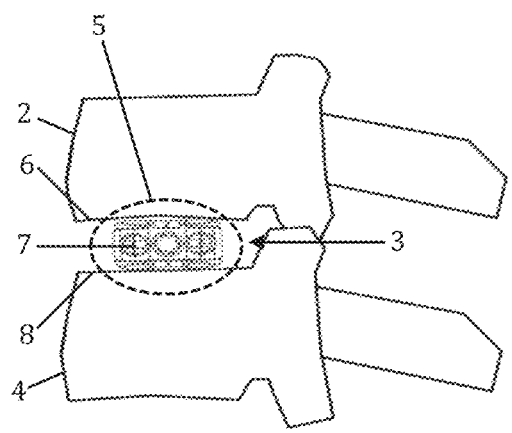
FIG. 1 depicts an example of an expandable fusion device implanted between two vertebral bodies in an initial collapsed state, according to some embodiments.
Figure 2:
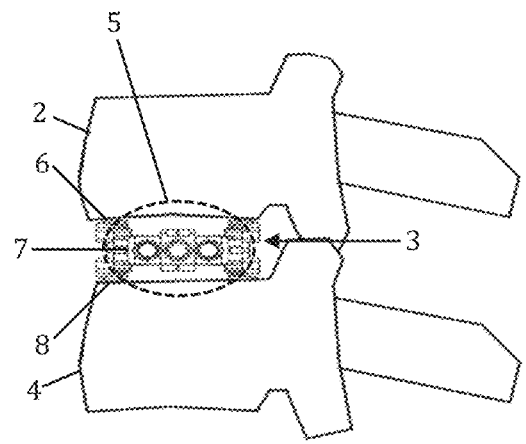
FIG. 2 depicts the expandable fusion device of FIG. 1 implanted between two vertebral bodies in a fully expanded state, according to some embodiments.

FIGS. 1-2 illustrate an example of one embodiment of an expandable fusion device 7 of the type disclosed herein, and is a representative example of the type of expansion common to each embodiment described by way of example below. By way of example, FIG. 1 illustrates the expandable fusion device 7 in an initial collapsed state positioned within an intervertebral space 3 between adjacent vertebral bodies 2, 4 having endplates 6, 8, respectively, by way of surgical access corridor 5. Implanting the expandable fusion device 7 in an initial collapsed state reduces the impaction force and the size of the surgical corridor 5 required for implantation. FIG. 2 illustrates the expandable fusion device 7 in an expanded state (expanded in both width and height) engaging vertebral endplates 6, 8 of adjacent vertebral bodies 2, 4, respectively. The expandable fusion device 7 may be longer than it is wide in its initial collapsed state and the endplates may also be longer than they are wide. Expanding the fusion device 7 while positioned between the vertebral bodies 2, 4 (e.g. "intraoperative expansion") allows an increase in the width of the fusion device 7 and correspondingly the spacing or contact area (or foot-print) between the fusion device 7 and the endplates 6, 8 beyond that which would otherwise be allowed by the surgical corridor 5. Additionally, intraoperative expansion of the expandable fusion device 7 facilitates the application of distraction forces to the endplates 6, 8 in order to increase and maintain the distance and/or angle between the vertebral bodies 2, 4, by increasing and maintaining the height of the implant and/or the angular orientation of its components.

Preferably, the various components of the fusion device 7 (and further embodiments) described herein are manufactured out of a Titanium alloy (including but not limited to Ti-6Al-4V alloys) or a Cobalt alloy including but not limited to CoCrMo alloys. Moreover, manufacturing some of the threaded components of the fusion device 7 out of a CoCr-based alloy allows for increased strength, reduced size, and other performance considerations. However, it should be understood that the various components of the expandable fusion device 7 (and/or any embodiment described herein) may be made out of a variety of materials including but not limited to metals and alloys (e.g. Commercially Pure Titanium, Titanium alloys including Ti-6A1-4V based alloys, Cobalt alloys including CoCrMo alloys, Stainless steel, Tantalum and its alloys, Platinum and its alloys, etc.), polymers (e.g. PEEK, PEKK, PEKEK, PEI, PET, PETG, UHMWPE, PPSU, Acetal, Polyacetal, etc. including carbon fiber reinforced varieties and other varieties filled, for example, with Carbon Fiber, Carbon nano-tubes, Graphene, Barium Sulfate or Hydroxyapatite), ceramics (e.g. Aluminum Oxide, Zirconium oxide, Silicon nitride, diamond-like carbon, etc. as well as various metalized ceramics an metal-ceramic composites).

As such, in any embodiments, at least one of the actuator, the wedge assembly, the ramp assembly, the upper endplate assembly, and the lower endplate assembly can comprise titanium, cobalt, stainless steel, tantalum, platinum, PEEK, PEKK, carbon fiber, barium sulfate, hydroxyapatite, a ceramic, zirconium oxide, silicon nitride, carbon, bone graft, demineralized bone matrix product, synthetic bone substitute, a bone morphogenic agent, a bone growth inducing material, or any combination thereof.

Optionally, in any embodiment, bone allograft, bone autograft, xenograft, demineralized bone matrix product, synthetic bone substitute, bone morphogenic agents, or other bone growth inducing material are introduced within and/or around the fusion device 7 to further promote and facilitate the intervertebral fusion. In one embodiment, the fusion device 7 may be preferably packed or injected with bone graft, demineralized bone matrix product, synthetic bone substitute, bone morphogenic agents, or other bone growth inducing material after it has been expanded, but in other embodiments, the graft material may also be introduced into the intervertebral space 3 within or around the fusion device 7 prior to implantation or after the implantation but prior to expansion.

Optionally, in any embodiment, the device can further comprise one or more pins. Optionally, in any embodiment, at least one of the first endplate, the second endplate, the third endplate, and the fourth endplate, can comprise a bone-facing surface that does not contain any through-holes. Optionally, in any embodiment, at least two of the first endplate, the second endplate, the third endplate, and the fourth endplate can be equivalent. Optionally, in any embodiment, at least two of the first endplate, the second endplate, the third endplate, and the fourth endplate can have mirrored symmetry.

Figure 4:
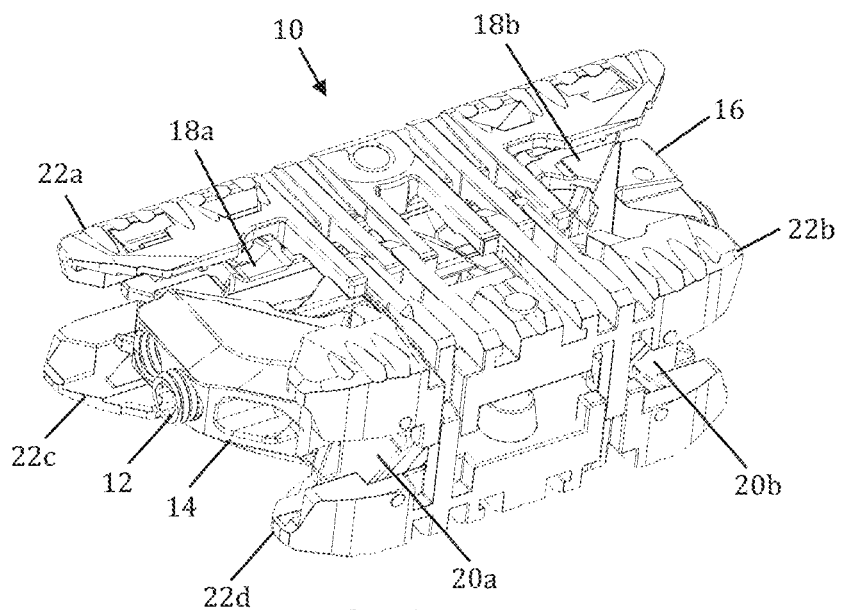
FIG. 4 is a perspective view of the expandable fusion device of FIG. 3 in a fully expanded state, according to some embodiments.
Figure 5:
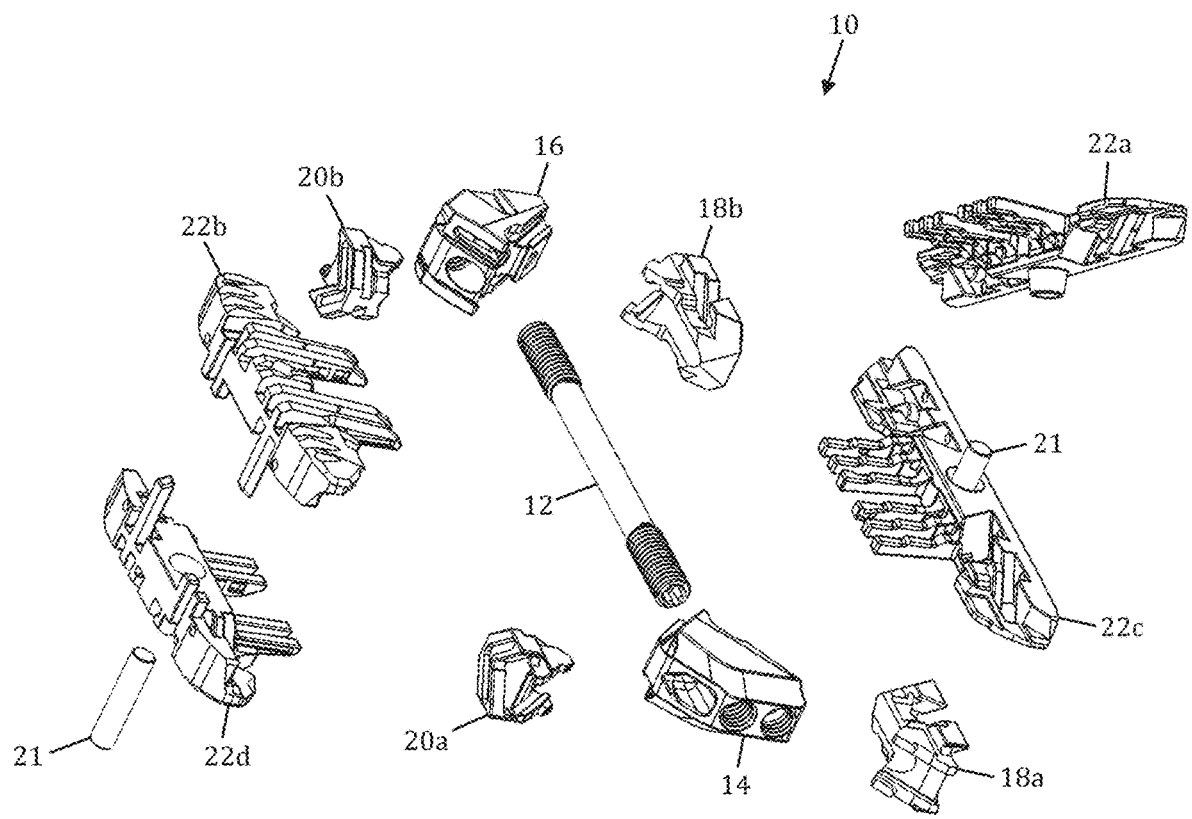
FIG. 5 is an exploded perspective view of the expandable fusion device of FIG. 3, according to some embodiments.

FIGS. 3-33 illustrate an example of an expandable fusion device 10 for implantation between two adjacent vertebrae according to some embodiments. By way of example only, the expandable fusion device 10 of the present embodiment is configured for lateral insertion into a target disc space, and is described as having an anterior side (e.g. configured for positioning within an anterior aspect of the target disc space) and a posterior side (e.g. configured for positioning within a posterior aspect of the target disc space). Referring first to FIGS. 3-5, and by way of example only, the expandable fusion device 10 of the present embodiment includes an actuator 12, a distal wedge 14, a proximal wedge 16, a pair of posterior ramps 18a, 18b (e.g., distal posterior ramp 18a and proximal posterior ramp 18b), a pair of anterior ramps 20a, 20b, (e.g., distal anterior ramp 20a and proximal anterior ramp 20b), a plurality of endplates 22a-22d (e.g., first or upper posterior endplate 22a, first or upper anterior endplate 22b, second or lower posterior endplate 22c, and second or lower anterior endplate 22d), a plurality of stabilization posts 21, and a plurality of guide pins 23. As will be described in greater detail below, the distal and proximal wedges 14, 16 are coupled with the actuator 12. The distal ramps 18a, 20a are slideably coupled with the distal wedge 14. The proximal ramps 18b, 20b are slideably coupled with the proximal wedge 16. The plurality of endplates 22a-22d are slideably coupled with the ramps 18a, 18b, 20a, 20b. More specifically, the first endplate 22a comprises a first or upper posterior endplate slideably associated with the distal posterior ramp 18a and the proximal posterior ramp 18b, the second endplate 22b comprises a first or upper anterior endplate slideably associated with the distal anterior ramp 20a and the proximal anterior ramp 20b, the third endplate 22c comprises a second or lower posterior endplate slideably associated with the distal posterior ramp 18a and the proximal posterior ramp 18b, and the fourth endplate 22d comprises a second or lower anterior endplate slideably associated with the distal anterior ramp 20a and the proximal anterior ramp 20b. In the exemplary embodiment, the endplates 22a-22d may also be in sliding contact with the wedges 14 and 16 when the device is in an initial collapsed state.

Figure 6:
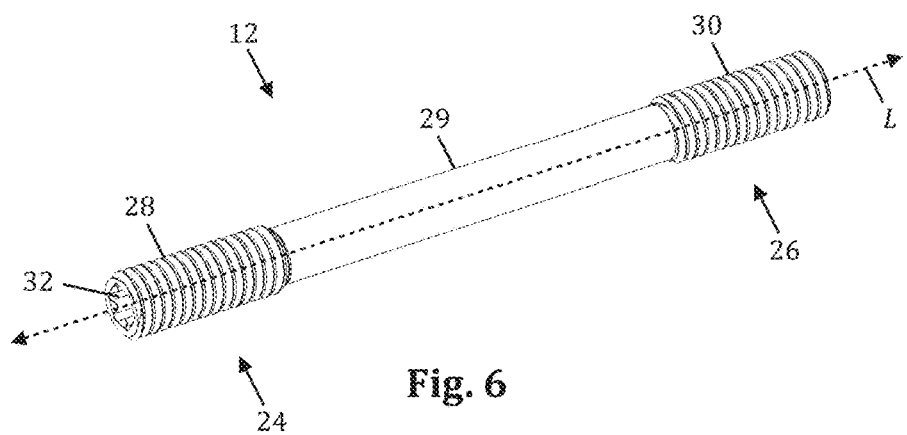
FIG. 6 is a perspective view of an example of an actuator forming part of the expandable fusion device of FIG. 3, according to some embodiments.

FIG. 6 illustrates an example of an actuator 12 forming part of the expandable fusion device 10 of the present embodiment. By way of example only, the actuator 12 comprises a cylindrically shaped elongate shaft having a distal end 24, a proximal end 26, and a longitudinal axis L. At least a portion of the distal end 24 includes a first thread feature 28. Similarly, at least a portion of the proximal end 26 includes a second thread feature 30. The first and second thread features 28, 30 may be separated by a non-threaded segment 29 disposed between the first thread feature 28 and the second thread feature 30. At least one of the distal and proximal ends 24, 26 includes a drive feature 32 coincident with the longitudinal axis L and configured to engage with a driver instrument (not shown) to operate the actuator. The first and second thread features 28, 30 each comprise a thread disposed externally around the shaft of the actuator 12. By way of example, the first thread feature 28 and the second thread feature 30 may have opposing threading directions. Alternatively, the first and second thread features 28, 30 may have the same threading direction. For example, at least one of the first and second thread features 28, 30 may comprise a right-handed threading. Alternatively (or additionally), at least one of the first and second thread features 28, 30 may comprise a left-handed threading. The drive feature 32 comprises a recessed region configured to receive a driving instrument. The recessed region may comprise any shape capable of engaging a corresponding drive element of driving instrument, including but not limited to (and by way of example only) a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess or any other shaped recess. Alternatively, the drive feature 32 may comprise a protuberance (for example a hex, a hexalobular, or a square protuberance or any other shaped protuberance) extending longitudinally from the proximal and/or distal end and configured to be coupled to a driving instrument.

In some embodiments, the cage does not include an actuator. Optionally, in any embodiment, the actuator, whether included with the cage or implement after insertion of the cage, can have a distal end and a proximal end. Optionally, in any embodiment, at least a portion of the distal end can comprise a first thread feature. Optionally, in any embodiment, at least a portion of the proximal end can comprise a second thread feature. Optionally, in any embodiment, the proximal end can comprise the drive feature. Optionally, in any embodiment, at least one of the first thread feature and the second thread feature can comprise a thread disposed externally around the actuator. Optionally, in any embodiment, at least one of the first thread feature and the second thread feature can have an opposite threading direction.

Optionally, in any embodiment, the wedge assembly can comprise a distal wedge and a proximal wedge. Optionally, in any embodiment, actuation of the drive feature in the first direction can converge the distal wedge and the proximal wedge toward one another. Optionally, in any embodiment, the distal wedge can comprise a third thread feature, wherein the third thread feature can be threadably coupled to the first thread feature. Optionally, in any embodiment, the proximal wedge can comprise a fourth thread feature, wherein the fourth thread feature can be threadably coupled to the second thread feature. Optionally, in any embodiment, the third thread feature can comprise a thread disposed internally within the distal wedge. Optionally, in any embodiment, the fourth thread feature can comprise a thread disposed internally within the proximal wedge.

FIGS. 7-9 illustrate an example of a distal wedge 14 according to some embodiments. By way of example, the distal wedge 14 comprises a distal side 36, a proximal side 38, and a threaded bore 40 extending axially therethrough between the distal and proximal sides 36, 38. The distal wedge 14 includes distally tapered top and bottom surfaces 41, 43 that aid in the insertion process. The threaded bore 40 comprises an internal thread configured for threaded coupling with the first and/or second thread feature 28, 30 of the actuator 12. The distal wedge 14 may be configured for slideable coupling with the distal ramps 18a, 20a and/or the endplates 22a, 22b, 22c, 22d. To facilitate slideable coupling with the distal ramps 18a, 20a, the distal wedge 14 comprises a plurality of tongue and groove connectors 44a-44d, each comprising a ridge or tongue (e.g. ridge 46a-46d) and a slot or groove (e.g. slot 48a-48d), and a plurality of control slots 50a-50d. By way of example only, the tongue and groove connectors 44a, 44b may slideably mate with tongue and groove connectors 88a, 88b on the distal posterior ramp 18a, tongue and groove connectors 44c, 44d may slideably mate with tongue and groove connectors 130a, 130b on the distal anterior ramp 20a, control slots 50a, 50b may slideably receive the protrusions 94a, 94b on the distal posterior ramp 18a, and the control slots 50c, 50d may slideably receive the protrusions 136a, 136b on the distal anterior ramp 20a. By way of example, the tongue and groove connector 44a comprises an upper right tongue and groove connector 44a (when viewing the proximal side 38 of the distal wedge 14 (as shown in FIG. 9)), the tongue and groove connector 44b comprises a lower right tongue and groove connector 44b, the tongue and groove connector 44c comprises an upper left tongue and groove connector 44c, and the tongue and groove connector 44d comprises a lower left tongue and groove connector 44d. By way of example, the upper right tongue and groove connector 44a and the lower right tongue and groove connector 44b, and the upper left tongue and groove connector 44c and the lower left tongue and groove connector 44d have mirrored symmetry about a transverse plane of the distal wedge 14. By way of example, the medial plane of each of the tongue and groove connectors 44a-44d is oriented at a transverse angle from the sagittal plane of the distal wedge 14.

Optionally, in any embodiment, the ramp assembly can comprise a first or posterior distal ramp, a second or anterior distal ramp, a first or posterior proximal ramp, and a second or anterior proximal ramp. Optionally, in any embodiment, the slideable coupling between at least one of the wedge assembly and the ramp assembly, the ramp assembly and the upper endplate assembly, and the ramp assembly and the lower endplate assembly can be at a transverse angle from the longitudinal axis. The transverse angle can be, for example, in a range that includes about 0 degrees to about 90 degrees. Accordingly, in any embodiment, the transverse angle can be at least about 0 degrees.

Optionally, in any embodiment, the slideable coupling between at least one of the wedge assembly and the ramp assembly, the ramp assembly and the upper endplate assembly, and the ramp assembly and the lower endplate assembly can comprise a protrusion and a slot. Optionally, in any embodiment, the protrusion can extend from at least one of the wedge assembly, the ramp assembly, the upper endplate assembly, and the lower endplate assembly, wherein the slot is disposed in at least one of the upper endplate assembly, and the lower endplate assembly. Optionally, in any embodiment, the protrusion can comprise a pin, a ridge, a dimple, a bolt, a screw, a bearing, or any combination thereof. Optionally, in any embodiment, the slot can comprise a through slot, a blind slot, a t-slot, a v-slot, a groove, or any combination thereof.

By way of example only, the control slot 50a comprises an upper right control slot 50a (when viewing the proximal side 38 of the distal wedge 14 (as shown in FIG. 9)), the control slot 50b comprises a lower right control slot 50b, the control slot 50c comprises an upper left control slot 50c, and the control slot 50d comprises a lower left control slot 50d. By way of example, the upper right control slot 50a and the lower right control slot 50b, and the upper left control slot 50c and a lower left control slot 50d have mirrored symmetry about a transverse plane of the distal wedge 14. By way of example, the medial plane of each of the control slots 50a-50d are oriented at a transverse angle from the sagittal plane of the distal wedge 14. Each of the control slots 50a-50d includes a translation stop 51 at the distal-lateral terminus of the respective control slot. The translation stop 51 blocks further distal-lateral translation of the protrusions 94a, 94b on the distal posterior ramp 18a, and protrusions 136a, 136b of the distal anterior ramp 20a, which stops outward movement of the distal ramps 18a, 20a and thus stops width expansion of the expandable fusion device 10.

Figure 10:
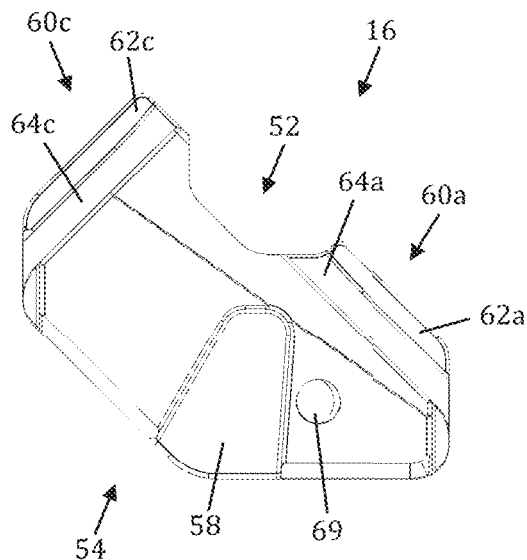
FIG. 10 is a top plan view of an example of a proximal wedge forming part of the expandable fusion device of FIG. 3, according to some embodiments.
Figure 11:
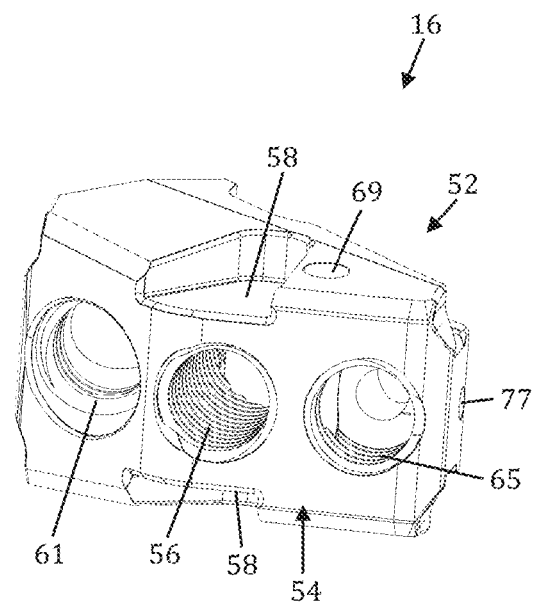
FIG. 11 is a perspective view of the proximal wedge of FIG. 10, according to some embodiments.
Figure 12:
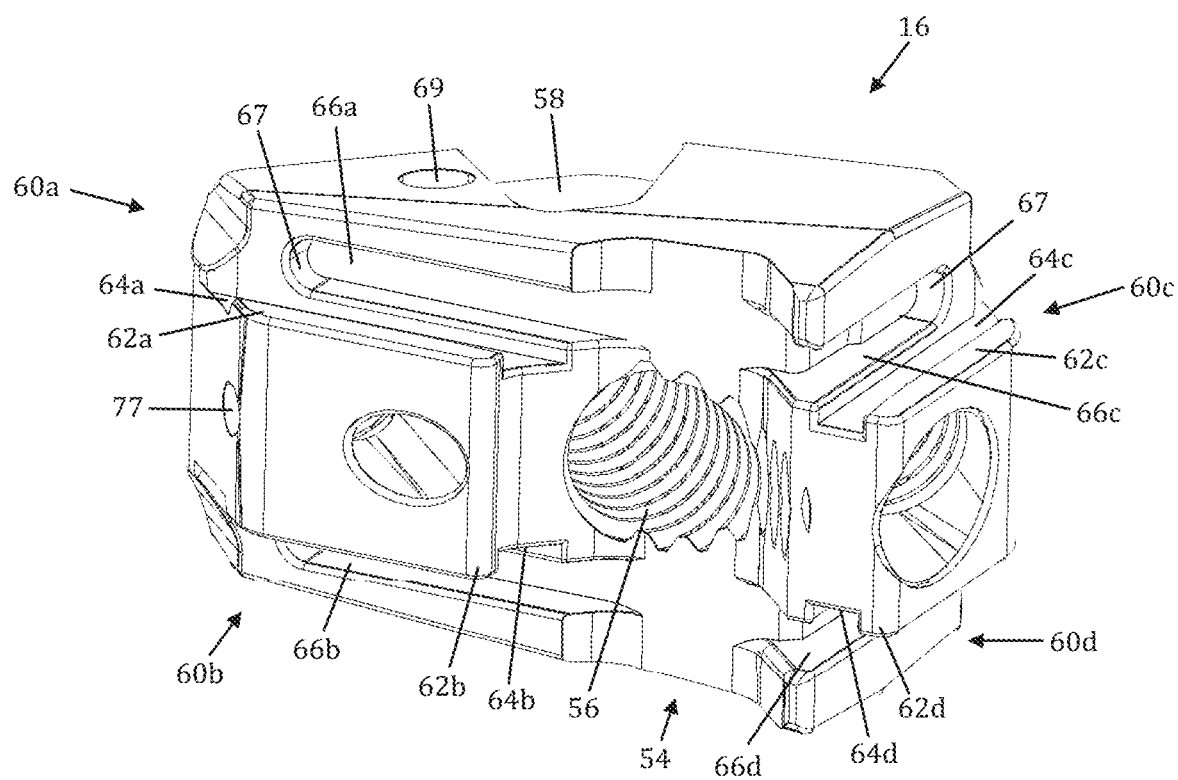
FIG. 12 is another perspective view of the proximal wedge of FIG. 10, according to some embodiments.
Figure 13:
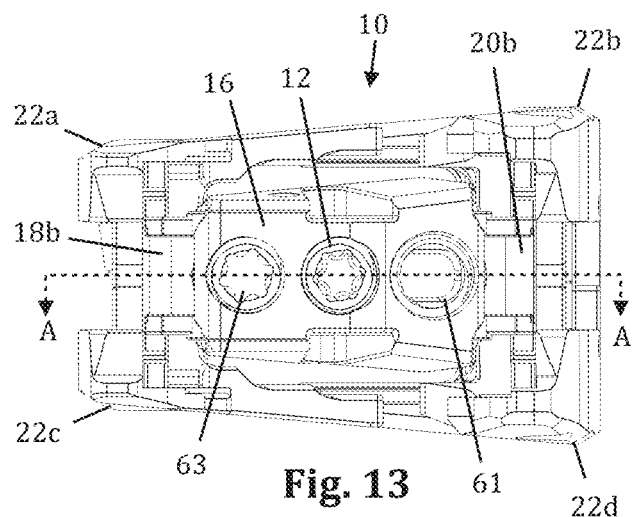
FIG. 13 is a end plan view of the expandable fusion device of FIG. 4, according to some embodiments.
Figure 14:
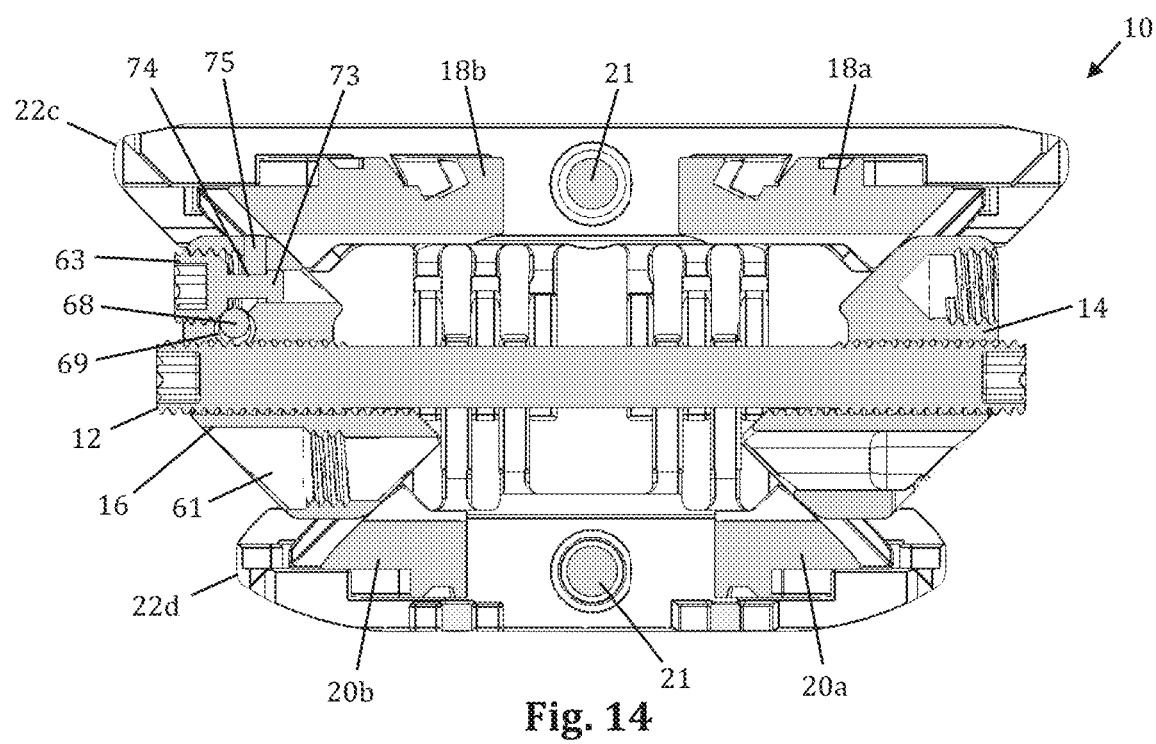
FIG. 14 is a sectional view of the expandable fusion device of FIG. 4, taken along line A-A of FIG. 13, according to some embodiments.
Figures 15, 16:
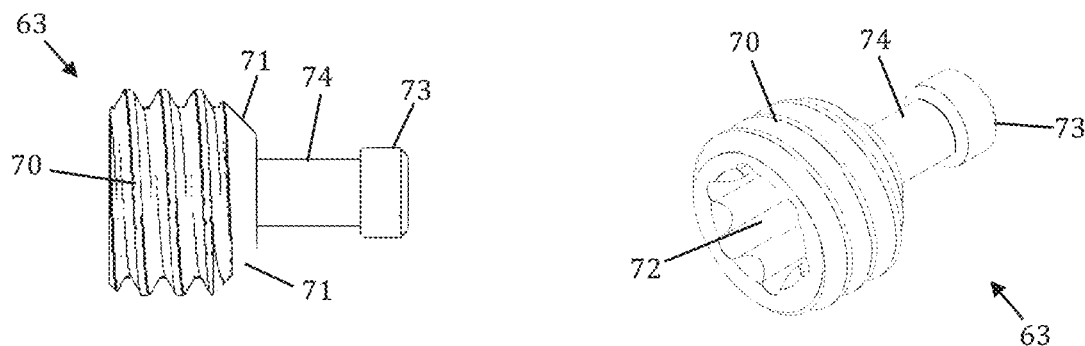
FIGS. 15-16 are side plan and perspective views, respectively, of a locking set screw forming part of the expandable fusion device of FIG. 3, according to some embodiments.

FIGS. 10-12 illustrate an example of a proximal wedge 16, according to some embodiments. By way of example, the proximal wedge 16 has a distal side 52, a proximal side 54, and a threaded bore 56 extending axially therethrough between the distal and proximal sides 52, 54. The proximal wedge 16 further comprises one or more engagement features 58 configured for temporary attachment to an inserter tool, for example one or more recesses 58 on the top and/or bottom sides of the distal wedge 16. The threaded bore 56 comprises an internal thread configured for threaded coupling with the first and/or second thread feature 28, 30 of the actuator 12. The proximal wedge 16 may further comprise an auxiliary aperture 61 positioned on one side of the threaded bore 56 and a lock screw aperture 65 on the other side of the threaded bore 56. By way of example, the auxiliary aperture 61 may be threaded or unthreaded, and configured to engage a variety of instruments and/or attachments, for example including but not limited to a modular fixation plate 810 of FIG. 90 (described below).

The proximal wedge 16 may be configured for slideable coupling with the proximal ramps 18b, 20b and/or the endplates 22a, 22b, 22c, 22d. To facilitate slideable coupling, the proximal wedge 16 comprises a plurality of tongue and groove connectors 60a-60d, each comprising a ridge or tongue (e.g. ridge 62a-62d) and a slot or groove (e.g. slot 64a-64d), and a plurality of control slots 66a-66d. By way of example, the tongue and groove connectors 60a, 60b may slideably mate with tongue and groove connectors 88a, 88b on proximal posterior ramp 18b, tongue and groove connectors 60c, 60d may slideably mate with tongue and groove connectors 130a, 130b on proximal anterior ramp 20b, control slots 66a, 66b slideably receive the protrusions 94a, 94b of posterior ramp 18b, and control slots 66c, 66d slideably receive the protrusions 136a, 136b on the anterior ramp 20b. By way of example, the tongue and groove connector 60a comprises an upper left tongue and groove connector 60a (when viewing the distal face 54 of the proximal wedge 16 (as shown in FIG. 12), the tongue and groove connector 60b comprises a lower left tongue and groove connector 60b, the tongue and groove connector 60c comprises an upper right tongue and groove connector 60c, and the tongue and groove connector 60d comprises a lower right tongue and groove connector 60d. By way of example, the upper left tongue and groove connector 60a and the lower left tongue and groove connector 60b, and the upper right tongue and groove connector 60c and the lower right tongue and groove connector 60d have mirrored symmetry about a transverse plane of the proximal wedge 16. By way of example, the medial plane of each of the tongue and groove connectors 60a-60d is oriented at a transverse angle from the sagittal plane of the proximal wedge 16.

By way of example only, the control slot 66a comprises an upper left control slot 66a (when viewing the distal side 54 of the proximal wedge 16 (as shown in FIG. 12)), the control slot 66b comprises a lower left control slot 66b, the control slot 66c comprises an upper right control slot 66c, and the control slot 66d comprises a lower right control slot 66d. By way of example, the upper left control slot 66a and the lower left control slot 66b, and the upper right control slot 66c and a lower right control slot 66d have mirrored symmetry about a transverse plane of the proximal wedge 16. By way of example, the medial plane of each of the control slots 66a-66d are oriented at a transverse angle from the sagittal plane of the proximal wedge 16. Each of the control slots 66a-66d includes a translation stop 67 at the proximal-lateral terminus of the respective control slot. The translation stop 67 blocks further proximal-lateral translation of the protrusions 94a, 94b on the posterior ramp 18b and protrusions 136a-136b on the anterior ramp 20b, which stops outward movement of the proximal ramps 18b, 20b and thus stops width expansion of the expandable fusion device 10.

With reference to FIGS. 13-16, in some embodiments, when the desired expansion has been achieved, the actuator 12 may be secured by a locking element (e.g. ball detent, pin detent, or other suitable feature capable of exerting immobilizing force upon the actuator shaft). To facilitate this, and by way of example only, the proximal wedge 16 may include a lock screw 63 positioned within the threaded lock screw aperture 65 positioned adjacent to the threaded bore 56 and a locking element 68 at least partially retained within a vertical lumen 69 positioned between the threaded bore 56 and the lock screw aperture 65. The vertical lumen 69 is configured to retain the locking element 68 therein while also enabling exposure to the threaded bore 56 for contacting the actuator 12 by way of a first side opening, and the lock screw aperture 65 for contacting the lock screw 63 by way of a second side opening (see, e.g. FIG. 14). Upon completion of the desired expansion, the lock screw 63 may be tightened within the lock screw aperture 65, which in turn may deflect the locking element 68 medially such that the locking element 68 forcibly contacts the actuator 12 to prevent translation of the actuator 12. By way of example, the lock screw 63 may have a threaded head 70 configured to mate with the threaded lock screw aperture 65. The threaded head 70 may include a distally tapered leading surface 71 that contacts and exerts force on the locking element 68, deflecting or biasing the locking element 68 in a medial direction. The threaded head 70 may further include a drive feature 72 on the trailing end comprise any shape capable of engaging a corresponding drive element of driving instrument, including but not limited to (and by way of example only) a slot, Phillips, pozidrive, frearson, robertson, 12-point flange, hex socket, security hex socket, star drive, security torx, ta, tri-point, tri-wing, spanner head, clutch, one-way, double-square, triple-square, polydrive, spline drive, double hex, bristol, or a pentalobe recess or any other shaped recess. Alternatively, the drive feature 72 may comprise a protuberance (for example a hex, a hexalobular, or a square protuberance or any other shaped protuberance) extending longitudinally from the proximal and/or distal end and configured to be coupled to a driving instrument. The lock screw 63 may further include a shaft 73 extending distally from the threaded head 70. By way of example, the shaft 73 may include a circumferential recess 74 configured to receive at least a portion of a retaining element 75 positioned within a lateral aperture 77 in the proximal wedge 16 and configured to retain the lock screw 63 within the lock screw aperture 65. By way of example, the actuator 12 may have a corresponding locking feature (e.g., groove, series of grooves, serrations, friction surface, etc.) configured to interact with the locking element 68 to improve resistance to slippage.

By way of example, the first and second posterior ramps 18a, 18b are identical to one another, and thus only the first distal ramp 18a is described in detail herein, however it should be understood that the features described with respect to the first or distal posterior ramp 18a also apply to the second or proximal posterior ramp 18b without reservation. Similarly, the first and second anterior ramps 20a, 20b are identical to one another, and thus only the first anterior ramp 20a will be described in detail herein, however it should be understood that the features described with respect to the first or distal anterior ramp 20a also apply to the second or proximal anterior ramp 20b without reservation.

FIGS. 17-20 illustrate an example of a posterior ramp 18a according to some embodiments. By way of example, the posterior ramp 18a has a first end 76 configured for engagement with the distal wedge 14 (or the proximal wedge 16, in the case of the posterior ramp 18b), a second end 78 oriented toward the center of the assembled expandable fusion device 10, a medial side 80 oriented toward the actuator 12 in the assembled expandable fusion device 10, and a lateral side 82 oriented away from the actuator 12 in the assembled expandable fusion device 10. Generally, the posterior ramp 18a comprises a rectangular prism divided into two lobes, a first lobe 84 and a second lobe 86, that facilitate height expansion of the expandable fusion device 10.

The posterior ramp 18a may be configured for slideable coupling with the distal wedge 14 and/or the endplates 22a, 22c (and correspondingly, the posterior ramp 18b may be configured for slideable coupling with the proximal wedge 16 and/or the endplates 22a, 22c). To facilitate slideable coupling, the first end 76 comprises a pair of tongue and groove connectors 88a, 88b, each comprising a ridge or tongue (e.g. ridge 90a, 90b) and a slot or groove (e.g. slot 92a, 92b), and a pair of protrusions 94a, 94b. The tongue and groove connectors 88a, 88b may slideably mate with tongue and groove connectors 44a, 44b on the distal wedge 14, and the protrusions 94a, 94b may slideably mate with the control slots 50a, 50b on the distal wedge 14. Although not shown, similar features on the posterior ramp 18b (e.g. tongue and groove connectors and protrusions) may mate with corresponding features on the proximal wedge 16 (e.g. tongue and groove connectors 60a, 60b and control slots 66a, 66b). By way of example, the tongue and groove connector 88a comprises an upper tongue and groove connector 88a (see, e.g., FIG. 18), the tongue and groove connector 88b comprises a lower tongue and groove connector 88b, the protrusion 94a comprises an upper protrusion 94a, and the protrusion 94b comprises a lower protrusion 94b. The upper and lower protrusions 94a, 94b are positioned on the respective medial distal corners of the posterior ramp 18a. The tongue and groove connectors 88a, 88b may be angled in a medial-lateral direction to correspond with the angle of the tongue and groove connectors 44a, 44b of the distal wedge 14.

The first lobe 84 comprises a chevron shape having an apex oriented away from the first end 76. The first lobe 84 includes a top surface 96, a bottom surface 98, a lateral surface 99, and angled proximal surfaces 100a, 100b. By way of example, the first lobe 84 has a generally L-shaped cross-sectional shape, however it should be noted that the first lobe 84 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). The angled proximal surface 100a slideably engages inclined surface 152 of the upper posterior endplate 22a and angled proximal surface 100b slideably engages the angled surface 152 of the lower posterior endplate 22c to facilitate height expansion. As shown by way of example in FIG. 19, upper and lower angled proximal surfaces 100a, 100b may have equivalent slopes. The equivalent slopes of the angled proximal surfaces 100a, 100b enable the upper endplate assembly and the lower endplate assembly to translate upwards and downwards, respectively, away from the actuator 12, at the same rate with respect to a rotation of the actuator 12. Alternatively, the angled proximal surfaces 100a, 100b may have inequivalent slopes. In such an arrangement, the inequivalent slopes of the proximal surfaces 100a, 100b enable the upper endplate assembly and the lower endplate assembly to translate upwards and downwards, respectively, away from the actuator 12, at different rates with respect to a rotation of the actuator 12. The first lobe 84 further includes a recessed slot 102 formed within the lateral surface 99 and configured to slideably receive one or more guide pins (not shown) therein to provide a hard stop 103 for height expansion.

By way of example, the recessed slot 102 comprises an upper slot 102a and a lower slot 102b. As shown by way of example in FIG. 17, upper and lower slots 102a, 102b may have equivalent slopes. In the instant embodiment, the purpose of the slots 102a, 102b may be to limit height expansion through interaction with guide pins, as such, an important feature of the slots 102a, 102b is how far they extend from the mid-line of the ramp 18a, The slots may have round, rectangular, triangular or any other cross-section and don't have to make contact with guide pins (not shown) until full height is achieved, when the contact between guide pins and slots results in limiting or stopping height expansion. In other embodiments, the slots may be configured to serve as ramped or curved pressure surfaces that the guide pins contact to facilitate expansion or collapsing of the device. Furthermore, as shown by way of example in FIG. 17, upper and lower slots 102a, 102b converge and intersect. In some embodiments, the slots 102a, 102b converge and do not intersect.

The second lobe 86 comprises a truncated chevron shape having a truncated apex oriented toward the second end 78. The second lobe 86 includes a top surface 106, a bottom surface 108, a lateral surface 110, and angled leading surfaces 112a, 112b, and angled trailing surfaces 114a, 114b. By way of example, the second lobe 86 has a generally trapezoidal cross-sectional shape (see, e.g., FIG. 20). The trapezoidal cross-section of the second lobe 86 is advantageous because having nonparallel leading contact surfaces of the dual chevron shape (e.g. angled surfaces 100a, 100b and angled surfaces 112a, 112b) increases the stability of the construct during height expansion. Furthermore, the trapezoidal shape of the second lobe 86 increases the surface area of the leading angled surfaces 112a, 112b and the trailing angled surfaces 114a, 114b, which increases the strength of the construct to resist compressive forces after height expansion has been completed. By way of example only the angled leading surface 112a is configured to slideably engage angled surface 156 of the upper posterior endplate 22a and angled leading surface 112b is configured to slideably engage the angled surface 156 of the lower posterior endplate 22c to facilitate height expansion. As shown by way of example in FIG. 19, upper and lower angled leading surfaces 112a, 112b may have equivalent slopes. The equivalent slopes of the angled leading surfaces 112a, 112b enable the upper endplate assembly and the lower endplate assembly to translate upwards and downwards, respectively, away from the actuator 12, at the same rate with respect to a rotation of the actuator 12. Alternatively, the angled leading surfaces 112a, 112b may have inequivalent slopes. In such an arrangement, the inequivalent slopes of the angled leading surfaces 112a, 112b enable the upper endplate assembly and the lower endplate assembly to translate upwards and downwards, respectively, away from the actuator 12, at different rates with respect to a rotation of the actuator 12. The second lobe 86 may further include recessed slots 115a, 115b formed within the lateral surface 110 and configured to slideably receive one or more guide pins (not shown) therein to provide a hard stop 103 for height expansion.

By way of example, the slots 115a, 115b comprises an upper slot 115a and a lower slot 115b. As shown by way of example in FIG. 17, upper and lower slots 115a, 115b may have equivalent slopes. In the instant embodiment, the purpose of the slots 115a, 115b may be to limit height expansion through interaction with guide pins, as such, an important feature of the slots 115a, 115b is how far they extend from the mid-line of the ramp 18a, The slots may have round, rectangular, triangular or any other cross-section and don't have to make contact with guide pins (not shown) until full height is achieved, when the contact between guide pins and slots results in limiting or stopping height expansion. In other embodiments, the slots may be configured to serve as ramped or curved pressure surfaces that the guide pins contact to facilitate expansion or collapsing of the device. Furthermore, as shown by way of example in FIG. 17, upper and lower slots 115a, 115b may converge but do not intersect. In some embodiments, the slots 115a, 115b may converge and intersect.

FIGS. 21-23 illustrate an example of a first or distal anterior ramp 20a according to some embodiments. By way of example, the first anterior ramp 20a has a first end 116 configured for engagement with the distal wedge 14 (or the proximal wedge 16, in the case of the anterior ramp 20b), a second end 118 oriented toward the center of the assembled expandable fusion device 10, a medial side 120 (e.g. oriented toward the actuator 12 in the assembled expandable fusion device 10), and a lateral side 122 (e.g. oriented away from the actuator 12 in the assembled expandable fusion device 10). By way of example only, the anterior ramps 20a, 20b of the present embodiment may be substantially similar to the first lobe 84 of the posterior ramp 18a.

The anterior ramp 20a may be configured for slideable coupling with the distal wedge 14 and/or the endplates 22b, 22d (and correspondingly, the anterior ramp 20b may be configured for slideable coupling with the proximal wedge 16 and/or the endplates 22b, 22d). To facilitate slideable coupling, the first end 116 comprises a pair of tongue and groove connectors 130a, 130b, each comprising a ridge or tongue (e.g. ridge 132a, 132b) and a slot or groove (e.g. slot 134a, 134b), and a pair of protrusions 136a, 136b. The tongue and groove connectors 130a, 130b may slideably mate with tongue and groove connectors 44c, 44d on the distal wedge 14, and the protrusions 136a, 136b may slideably mate with the control slots 50c, 50d on the distal wedge 14. Although not shown, similar features on the anterior ramp 20b (e.g. tongue and groove connectors and protrusions) may mate with corresponding features on the proximal wedge 16 (e.g. tongue and groove connectors 60c, 60d and control slots 66c, 66d). By way of example, the tongue and groove connector 130a comprises an upper tongue and groove connector 130a (see, e.g., FIG. 21), the tongue and groove connector 130b comprises a lower tongue and groove connector 130b, the protrusion 136a comprises an upper protrusion 136a, and the protrusion 136b comprises a lower protrusion 136b. The upper and lower protrusions 136a, 136b are positioned on the respective medial distal corners of the posterior ramp 18a. The tongue and groove connectors 130a, 130b may be angled in a medial-lateral direction to correspond with the angle of the tongue and groove connectors 44c, 44d of the distal wedge 14.

By way of example, the anterior ramp 20a includes an endplate engagement lobe 123 comprising a chevron shape having an apex oriented away from the first end 116. The endplate engagement lobe 123 includes a top surface 124, a bottom surface 125, a lateral surface 126, and angled translation surfaces 127a, 127b. By way of example, the engagement lobe 123 has a generally L-shaped cross-sectional shape, however it should be noted that the engagement lobe 123 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). By way of example, the angled translation surface 127a slideably engages inclined surface 178 of the upper anterior endplate 22b and angled translation surface 127b slideably engages the inclined surface 178 of the lower anterior endplate 22d to facilitate height expansion. The endplate engagement lobe 123 further includes a recessed slot 128 formed within the lateral surface 126 and configured to slideably receive one or more guide pins (not shown) therein to provide a hard stop 129 for height expansion.

By way of example, the slot 128 comprises an upper slot 128a and a ramp slot 128b. As shown by way of example in FIG. 21, upper and lower slots 128a, 128b may have equivalent slopes. In the instant embodiment, the purpose of the slots 128a, 128b may be to limit height expansion through interaction with guide pins, as such, an important feature of the slots 128a, 128b is how far they extend from the mid-line of the anterior ramp 20a, The slots may have round, rectangular, triangular or any other cross-section and don't have to make contact with guide pins (not shown) until full height is achieved, when the contact between guide pins and slots results in limiting or stopping height expansion. In other embodiments, the slots may be configured to serve as ramped or curved pressure surfaces that the guide pins contact to facilitate expansion or collapsing of the device. Furthermore, as shown by way of example in FIG. 21, upper and lower slots 128a, 128b converge and intersect. In some embodiments, the slots 128a, 128b converge and do not intersect.

Optionally, in any embodiment, the upper endplate assembly can comprise a first endplate and a second endplate, and wherein the lower endplate assembly can comprise a third endplate and a fourth endplate. Optionally, in any embodiment, at least one of the first posterior ramp and the second posterior ramp, and the first anterior ramp and the second anterior ramp can have mirrored equivalence. Optionally, in any embodiment, at least one of the second endplate and the fourth endplate can be larger than at least one of the first endplate and the third endplate. Optionally, in any embodiment, at least one of the exterior faces of the first end plate, the second endplate, the third endplate, and the fourth endplate can comprise a texture configured to grip the vertebrae.

By way of example, the posterior endplates 22a, 22c are identical to one another save for one feature described below, and thus only one of the posterior endplates needs to be described in further detail. By way of example only, the first or upper posterior endplate 22a is described in detail herein, however it should be understood that the features described with respect to the endplate 22a also apply to the second or lower posterior endplate 22c without reservation. Similarly, the anterior endplates 22b, 22d are identical to one another save for one feature described below, and thus only one of the anterior endplates needs to be described in further detail. By way of example only, the first or upper anterior endplate 22b is described in detail herein, however it should be understood that the features described with respect to the endplate 22b can also apply to the second or lower anterior endplate 22d.

Figure 24:
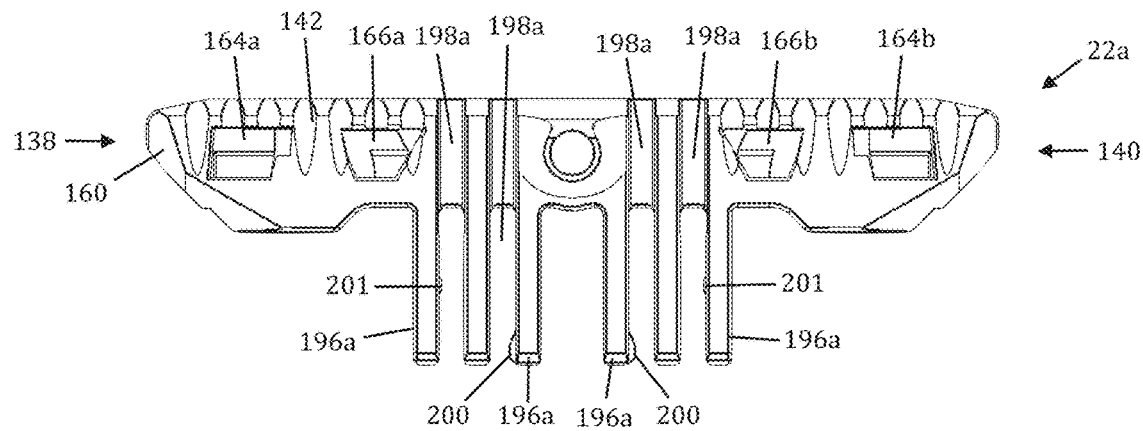
FIG. 24 is a top plan view of an example of a posterior endplate forming part of the expandable fusion device of FIG. 3, according to some embodiments.
Figure 25:
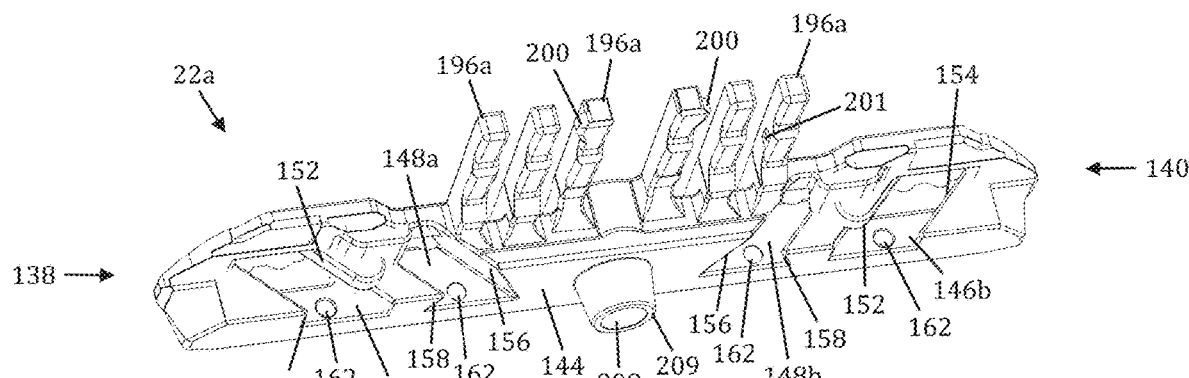
FIG. 25 is a perspective view of the posterior endplate of FIG. 24, according to some embodiments.

By way of example only, FIGS. 24-25 illustrate a first or upper posterior endplate 22a according to some embodiments. By way of example only, the endplate 22a has a first (e.g. distal) end 138 and a second (e.g. proximal) end 140. In the illustrated embodiment, the endplate 22a further comprises an outer vertebral contacting surface 142 connecting the first end 138 and the second end 140, and an inner-facing surface 144 connecting the first end 138 and the second end 140. The outer vertebral contacting surface 142 may comprise a texture configured to grip the vertebrae.

By way of example, the texturing may comprise at least one tooth, ridge, roughened area, metallic coating, ceramic coating, keel, spike, projection, groove, or any combination thereof. The inner-facing surface 144 is generally planar and smooth and may flushly abut a corresponding inner-facing surface on another endplate (e.g. endplate 22c) when the expandable fusion device 10 is fully contracted.

The first posterior endplate 22a further comprises a pair of outer inclined slots 146a, 146b proximate the distal and proximal ends 138, 140, respectively, each extending from the inner-facing surface 144 to the outer surface 142, and a pair of inner inclined slots 148a, 148b each extending from the inner-facing surface 144 to the outer surface 142. Optionally, in any embodiment, the slopes or shapes of the inclined slots 146a-146b and 148a-148b are equal or differ from each other.

By way of example, the outer inclined slots 146a, 146b may each have a generally L-shaped cross section, an inclined surface 152 generally transverse to the longitudinal axis of the implant, and an inclined surface 154 opposite of the inclined surface 152 and generally transverse to the longitudinal axis, wherein the inclined surfaces 152, 154 are parallel. The outer inclined slot 146a is sized and configured to slideably receive a portion (e.g. upper portion) of the first lobe 84 of the distal posterior ramp 18a such that the distal surface 100a of the first lobe 84 is slideably associated with the inclined surface 152. Similarly, the outer inclined slot 146b is sized and configured to slideably receive a portion (e.g. upper portion) of the first lobe 84 of the proximal posterior ramp 18b such that the distal surface 100a of the first lobe 84 is slideably associated with the inclined surface 152. Thus, after width expansion has completed, as the distal wedge 14 advances the distal posterior ramp 18a toward the proximal wedge 16 (and proximal posterior ramp 18b), the endplate 22a is vertically displaced in part due to the angular translation along the inclined surfaces 152 (resulting in height expansion).

By way of example, the inner inclined slots 148a, 148b may each have a generally trapezoidal cross section, an angled surface 156 generally transverse to the longitudinal axis of the implant, and an angled surface 158 opposite of the angled surface 156 and generally transverse to the longitudinal axis, wherein the angled surfaces 156 and 158 taper toward each other. The inner inclined slot 148a is sized and configured to slideably receive a portion (e.g. upper portion) of the second lobe 86 of the distal posterior ramp 18a such that the distal surface 112a of the second lobe 86 is slideably associated with the angled surface 156. Similarly, the inner inclined slot 148b is sized and configured to slideably receive a portion (e.g. upper portion) of the second lobe 86 of the proximal posterior ramp 18b such that the distal surface 112a of the second lobe 86 is slideably associated with the angled surface 156. Thus, after width expansion has completed, as the distal wedge 14 advances the distal posterior ramp 18a toward the proximal wedge 16 (and proximal posterior ramp 18b), the endplate 22a is vertically displaced in part due to the angular translation along the angled surface 156 (resulting in height expansion).

By way of example, the endplate 22a may further include a chamfer 160 proximate the first end 138 to help facilitate introduction of fusion device 10 between the adjacent vertebral bodies 2 and 4 by reducing the height of the endplate 22a at first end 138 thereby providing a tapered leading edge. The endplate 22a may further include a plurality of pin apertures 162 configured to hold the stabilizing guide pins (not shown). The outer contact surface 142 further includes a plurality of apertures corresponding to the inclined slots 146a, 146b, 148a, and 148b. By way of example, outer apertures 164a, 164b may be positioned proximate the first and second ends 138, 140, respectively, and correspond to the outer inclined slots 146a, 146b. As such, the outer apertures 164a, 164b each have a generally L-shaped cross-section. The outer apertures 164a, 164b are each sized and dimensioned to receive a portion of the first lobe 84 of the posterior ramps 18a, 18b (respectively) therethrough so that the top surfaces 96 of the first lobes 84 are generally level with the outer surface 142 when the expandable fusion device 10 is fully contracted. The inner apertures 166a, 166b are each located adjacent to the first apertures 164a, 164b and correspond to the inner inclined slots 148a, 148b, respectively. As such, the inner apertures 166a, 166b each have a generally trapezoidal cross-section. The inner apertures 166a, 166b are sized and dimensioned to receive a portion of the second lobe 86 of the posterior ramps 18a, 18b (respectively) therethrough so that the top surfaces 106 of the second lobes 86 are generally level with the outer surface 142 when the expandable fusion device 10 is fully contracted. This feature is beneficial in that allowing portions of the posterior ramps 18a, 18b to extend through the posterior endplate 22a to be level with the outer surface 142 thereof enables the expandable fusion device 10 to have a lower height h when in the fully contracted position.

Figure 26:
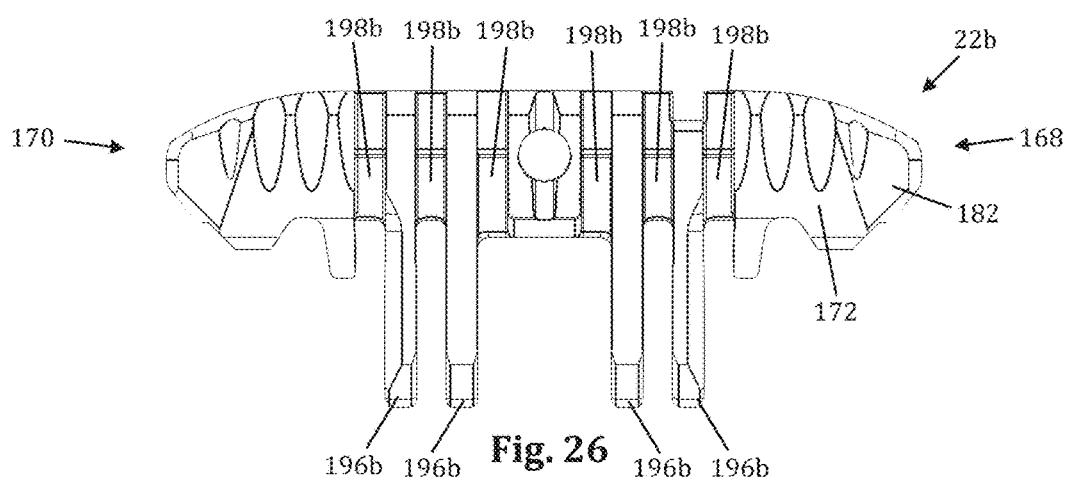
FIG. 26 is a top plan view of an example of an anterior endplate forming part of the expandable fusion device of FIG. 3, according to some embodiments.
Figure 27:
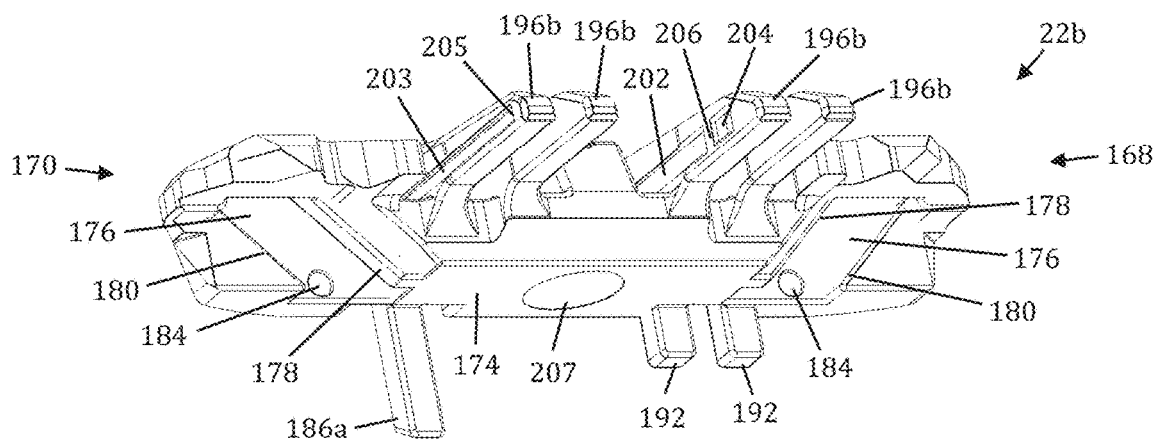
FIG. 27 is a perspective view of the anterior endplate of FIG. 26, according to some embodiments.
Figure 28:
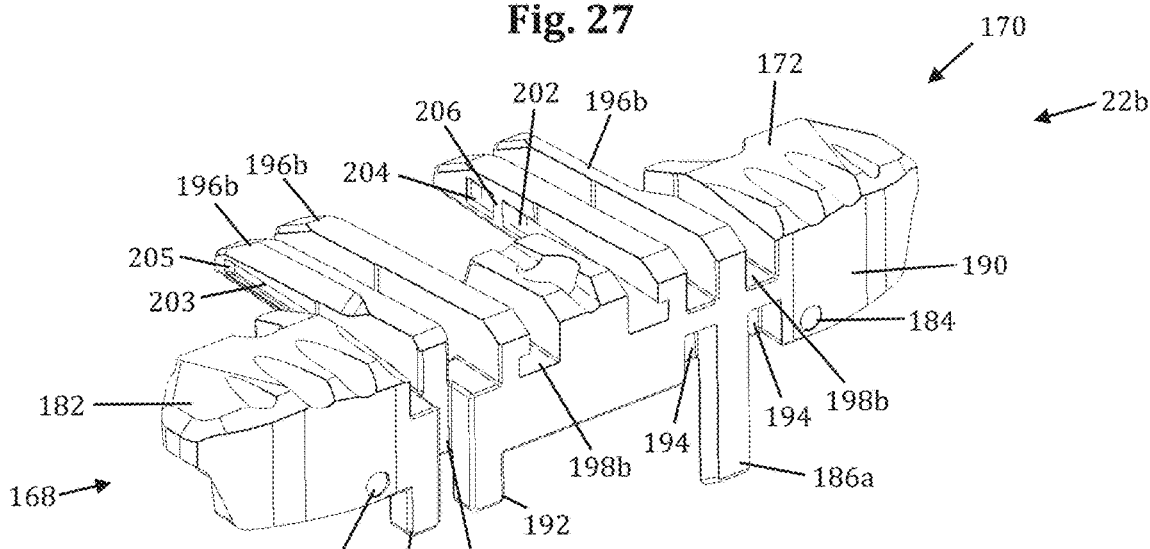
FIG. 28 is another perspective view of the anterior endplate of FIG. 26, according to some embodiments.

By way of example only, FIGS. 26-28 illustrate a first or upper anterior endplate 22b according to some embodiments. By way of example only, the endplate 22b has a first (e.g. distal) end 168 and a second (e.g. proximal) end 170. In the illustrated embodiment, the endplate 22b further comprises an outer vertebral contacting surface 172 connecting the first end 168 and the second end 170, and an inner-facing surface 174 connecting the first end 168 and the second end 170. The outer vertebral contacting surface 172 may comprise a texture configured to grip the vertebrae.

By way of example, the texturing may comprise at least one tooth, ridge, roughened area, metallic coating, ceramic coating, keel, spike, projection, groove, or any combination thereof. The inner-facing surface 174 is generally planar and smooth and may flushly abut a corresponding inner-facing surface on another endplate (e.g. endplate 22d) when the expandable fusion device 10 is fully contracted.

The first anterior endplate 22b further comprises a pair of inclined slots 176a, 176b proximate the distal and proximal ends 168, 170, respectively, each extending from the inner-facing surface 174 to the outer surface 172. Optionally, in any embodiment, the slopes or shapes of the inclined slots 176a, 176b are equal or differ from each other. By way of example, the inclined slots 176a, 176b may each have a generally L-shaped cross section, an inclined surface 178 generally transverse to the longitudinal axis of the implant, and an inclined surface 180 opposite of the inclined surface 178 and generally transverse to the longitudinal axis, wherein the inclined surfaces 178, 180 are parallel. The inclined slot 176a is sized and configured to slideably receive a portion (e.g. upper portion) of the endplate engagement lobe 123 of the distal anterior ramp 20a such that the angled surface 127a of the engagement lobe 123 is slideably associated with the inclined surface 178. Similarly, the inclined slot 176b is sized and configured to slideably receive a portion (e.g. upper portion) of the endplate engagement lobe 123 of the proximal anterior ramp 20b such that the distal surface 127a of the engagement lobe 84 is slideably associated with the inclined surface 178. Thus, after width expansion has completed, as the distal wedge 14 advances the distal anterior ramp 20a toward the proximal wedge 16 (and proximal anterior ramp 20b), the endplate 22b is vertically displaced in part due to the angular translation along the inclined surfaces 178 (resulting in height expansion).

By way of example, the endplate 22b may further include a chamfer 182 proximate the first end 168 to help facilitate introduction of fusion device 10 between the adjacent vertebral bodies 2 and 4 by reducing the height of the endplate 22b at first end 168 thereby providing a tapered leading edge. The endplate 22b may further include a plurality of pin apertures 184 configured to hold the stabilizing guide pins (not shown).

Figure 29:
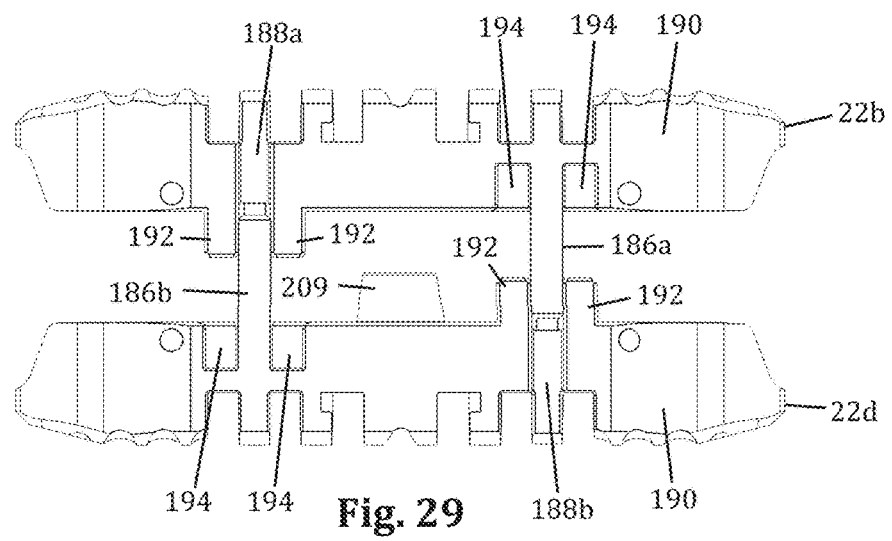
FIG. 29 is a side plan view of an anterior endplate assembly forming part of the expandable fusion device of FIG. 3, according to some embodiments.

With reference to FIGS. 28-29, the expandable fusion device 10 of the present example embodiment is illustrative of a height stabilizer that may be applied to any expandable fusion device examples described herein, according to some embodiments. By way of example only, the height stabilizer of the present example comprises a plurality of interdigitated vertical flanges 186 extending vertically from each anterior endplate to nest in slots 188 on the opposite endplate. For example, FIG. 29 illustrates the anterior endplates 22b, 22d only in an assembled, height-expanded configuration. By way of example only, the upper anterior endplate 22b may have a single flange 186a formed in the lateral surface 190 of the upper anterior endplate 22b and extending vertically toward the lower anterior endplate 22d. The single flange 186a is received within a complementary slot 188b formed in the lateral surface 190 of the lower anterior endplate 22d, enabling single-axis translation of the flange 186a within the slot 188b. Simultaneously, the lower anterior endplate 22d has a vertical flange 186b extending vertically toward the upper anterior endplate 22b. The vertical flange 186b is received within a complementary slot 188a formed in the lateral surface 190 of the upper anterior endplate 22b, enabling single-axis translation of the flange 186b within the slot 188a. One or more slot extenders 192 may be positioned on either side of the slots 188a, 188b and extend toward the opposing endplate. Complementary recesses 194 may be formed within the lateral surface 190 on either side of the flanges 186a, 186b and configured to receive the slot extenders 192 when the expandable fusion implant 10 is in a height-contracted configuration. The nesting of the flanges 186a, 186b within the slots 188a, 188b maintains the endplates 22b, 22d in vertical alignment during height expansion. Optionally, in any embodiment, the expandable fusion implant 10 may be provided with any number of interdigitated vertical flanges 186 without departing from the scope of the disclosure.

Figure 30:
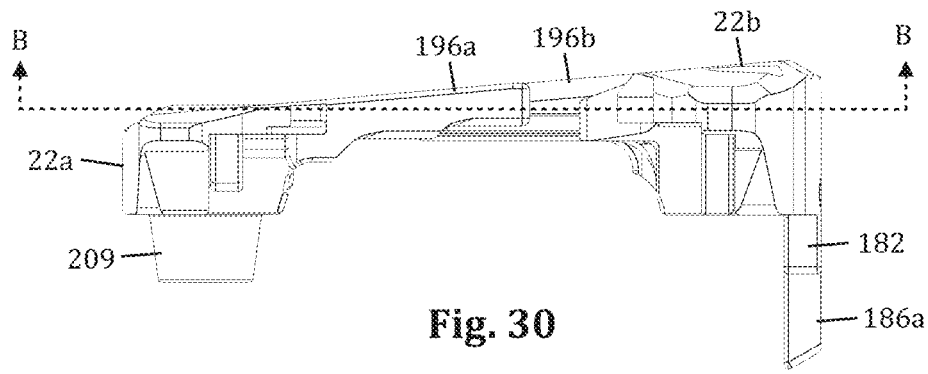
FIG. 30 is an end plan view of an upper endplate assembly forming part of the expandable fusion device of FIG. 3, according to some embodiments.
Figure 31:
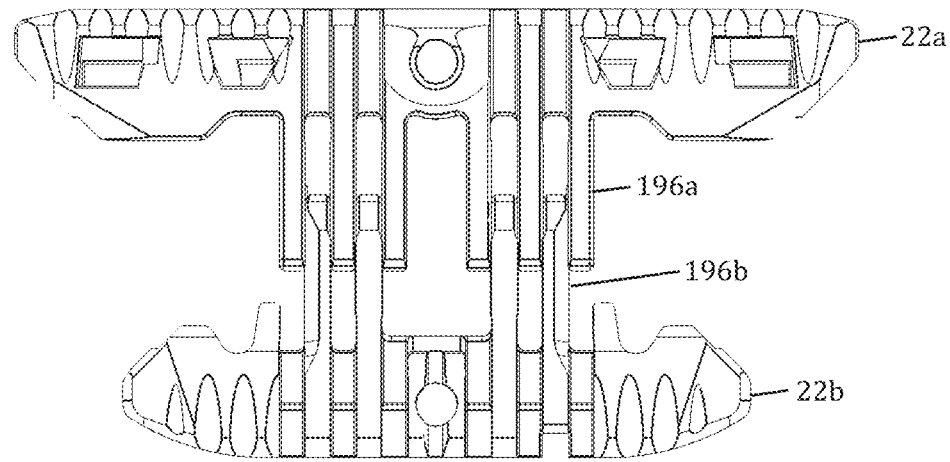
FIG. 31 is a top plan view of the upper endplate assembly of FIG. 30, according to some embodiments.
Figure 32:
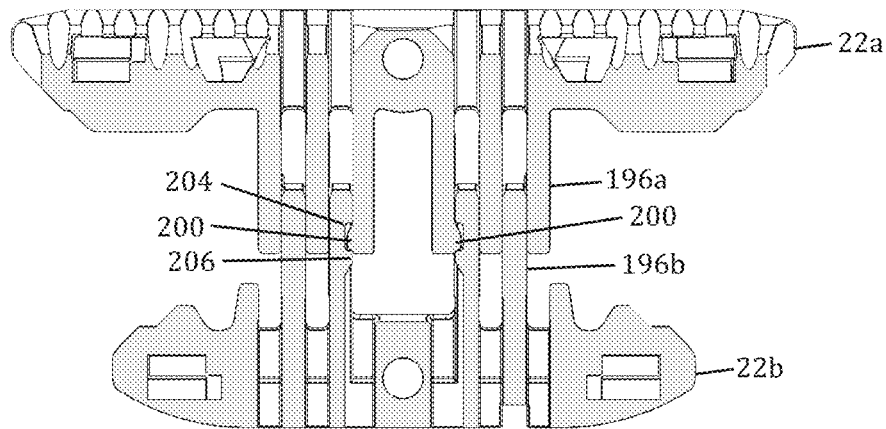
FIG. 32 is a sectional view of the upper endplate assembly of FIG. 30 taken along line B-B of FIG. 30, according to some embodiments.
Figure 33:
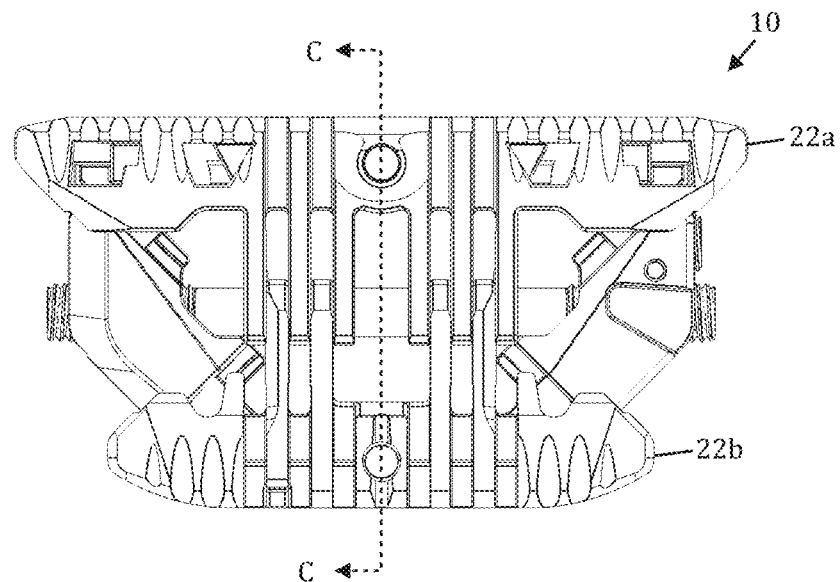
FIG. 33 is a top plan view of the expandable fusion device of FIG. 4, according to some embodiments.

With reference to FIGS. 24-32, the expandable fusion device 10 of the present example embodiment is illustrative of a width stabilizer that may be applied to any expandable fusion device examples described herein, according to some embodiments. By way of example only, the width stabilizer of the present example comprises a plurality of interdigitated medial flanges 196 extending medially from each endplate to nest in slots 198 on the opposite endplate. For example, FIGS. 30-32 illustrate the upper endplates 22a, 22b only in an assembled, width-expanded configuration. By way of example only, the upper posterior endplate 22a has a plurality of flanges 196a formed in the outer contact surface 142 of the upper posterior endplate 22a and extending medially toward the upper anterior endplate 22b. The flanges 196a are each configured to be received within a complementary slot 198b formed in the outer contact surface 172 of the upper anterior endplate 22b, enabling single-axis translation of the flanges 196a within the slots 198b. Similarly, the upper anterior endplate 22b has a plurality of flanges 196b formed in the outer contact surface 172 of the upper anterior endplate 22b and extending medially toward the upper posterior endplate 22a. The flanges 196b are configured to be received within complementary slots 198a formed in the outer contact surface 142 of the upper posterior endplate 22a (e.g. between each flange 196a extending therefrom), enabling single-axis translation of the flanges 196b within the slots 198a. The flanges 196a extend on either side of the flanges 196b and are in flush slideable contact with the flanges 196b. The nesting of the flanges 196a, 196b within the slots 198a, 198b as well as the flush contact between flanges maintains the endplates in a parallel orientation during width expansion. In some embodiments, the interdigitating flanges 196a, 196b and, optionally, the complementary slots 198a, 198b may be present only on one pair of endplates (the upper pair or the lower pair) and not the other in order to (among other things) maximize the volume of fusion mass. Optionally, in any embodiment, the expandable fusion implant 10 may be provided with any number of interdigitated flanges 196 without departing from the scope of the disclosure. By way of example, the interdigitated flanges 196 are each integral extensions of (as opposed to attachments to) the endplates 22a-22d. As a result, the endplates 22a and 22b overlap one another, and endplates 22c and 22d overlap one another. This helps provide stability with a lower profile, for example.

In some embodiments, the width stabilizer of the instant example may be provided with a width lock feature to (among other things and by way of example only) maintain the expanded width of the implant 10 while collapsing the height (e.g. in a revision procedure). According to one example of the width lock feature, one or more of the medial flanges 196a may include a lateral protrusion 200 positioned at the distal end of the flange 196a, and an opposing medial flange 196b adjacent the nesting slot 198b may include an elongated lateral recess 202 and a distal recess 204 that is separated from the elongated lateral recess 202 by a deflection element 206. By way of example, the lateral protrusion 200 is configured to translate within the elongated lateral recess 202 upon width expansion of the expandable fusion device 10. As the lateral protrusion 200 encounters the deflection element 206, the medial flange 196a deflects to enable the lateral protrusion 200 to fully traverse the deflection element 206. Once the lateral protrusion 200 has cleared the deflection element 206, the medial flange 196a snaps back to its normal (e.g. non-deflected) orientation and detains the lateral protrusion 200 within the distal recess 204. In some embodiments, the width stabilizer with or without the width lock feature described above may be used instead as a height stabilizer and a height lock feature by simply arranging the flanges to span the upper and lower endplates instead of the "left" and "right" endplates shown in FIG. 32.

According to another example of the width lock feature, one or more of the medial flanges 196a may include a lateral protrusion 201 positioned near the middle of the flange 196a, and an opposing medial flange 196b adjacent the nesting slot 198b may include an elongated lateral recess 203 having a deflection element 205 at the distal end. By way of example, the lateral protrusion 201 is configured to translate within the elongated lateral recess 203 upon width expansion of the expandable fusion device 10. As the lateral protrusion 201 encounters the deflection element 205, the medial flange 196a deflects to enable the lateral protrusion 201 to fully traverse the deflection element 205 and exit the elongated lateral recess 203. Once the lateral protrusion 201 has cleared the deflection element 205, the medial flange 196a snaps back to its normal (e.g. non-deflected) orientation and prevents the lateral protrusion 201 from reentering the elongated lateral slot 203 until a force sufficient to overcome the block is applied.

In either example, when the implant 10 is expanded in both width and height, to collapse it down to initial state, it is important that the device first collapses in height first and then in width (otherwise, the device may not be able to get back to initial state). The width lock of the medial flange 196a at full width provides resistance to collapsing width, so that upon actuation of the actuator 12 to collapse the implant 10, the implant 10 will first collapse in height (e.g. path of least resistance). Only when the height is fully collapsed will the actuator 12 apply enough force to overcome the resistance of the width lock to deflect the flange 196a again, unclick the width lock and collapse the implant 10 in width. By way of example only, the configuration of the width lock features (e.g. lateral protrusions 200, 201, and elongated lateral recesses 202, 203) described herein is not limited to the specific example shown, but rather may vary in number and/or placement without reservation.

As illustrated in FIGS. 24-29, the outer contact surfaces 142 of the posterior endplates 22a, 22c, and the outer contact surfaces 172 of the anterior endplates 22b, 22d are generally planar to enable the outer contact surfaces 142, 172 to engage with the adjacent vertebral bodies (e.g. vertebral bodies 2, 4 in FIG. 1). Alternatively, one or more of outer contact surfaces 142, 172 may be curved in one or more planes to allow for a greater degree of engagement with the adjacent vertebral bodies 2, 4. In another embodiment, one or more of the outer contact surfaces 142, 172 may be generally planar but include a generally straight ramped surface or a curved ramped surface. The ramped surface allows for engagement with the adjacent vertebral bodies 2, 4 in a lordotic fashion and/or for example in a coronally tapered fashion. Optionally, in any embodiment, an arrangement of non-ramped endplates of different heights as well as ramped and non-ramped endplates of different heights also results in a geometry suitable for lordotic engagement with the endplates. It is further contemplated that, in other embodiments, some or all of the endplates may have different lengths to better accommodate the target anatomy. Optionally, one or more of the endplates may be shorter, longer, narrower, or wider than others. It should be understood that although the various alternative geometries of the endplates are presented here as discrete embodiments, these alternative embodiments have optional features which may be substituted or mixed/matched with any other embodiment in the specification. It should also be understood that substituting any of the aforementioned optional alternative features in the endplate component may or will necessitate the mating components (e.g. the endplates, the ramps and the wedges) to use the inverse and/or complementary geometry of/to those features for proper contemplated engagement between the various components of the fusion device 10 and between those components and the surrounding anatomy and that the shape of that inverse and/or complementary geometry would follow inevitably from the optional alternative feature geometry described above.

Figure 34:
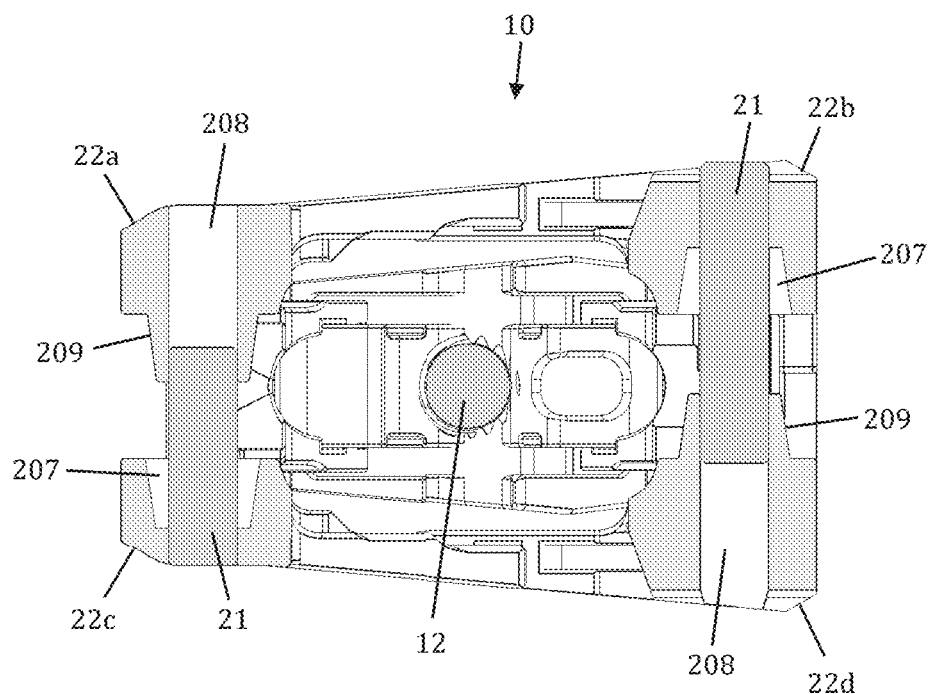
FIG. 34 is a sectional view of the expandable fusion device of FIG. 4 taken along line C-C of FIG. 33, according to some embodiments.

Due to the elongated nature of the endplates in a lateral expandable fusion device, such as the instant example embodiment of the expandable fusion implant 10, it may desirable to have a vertical stabilization feature extending between endplate pairs (e.g. posterior endplates 22a, 22c and/or anterior endplates 22b, 22d) to ensure the middle of the implant remains aligned during expansion. FIG. 34 illustrates one example of vertical stabilizers 21 for use with the expandable fusion device 10 of the present embodiment. By way of example, each vertical stabilizer 21 comprises a post 21 associated with one of the endplates of the endplate pair (e.g. "posted endplate", which in the example shown comprises the upper anterior endplate 22b and lower posterior endplate 22c) that extends vertically toward the other endplate of the endplate pair (e.g. "receiving endplate", which in the example shown comprises the lower anterior endplate 22d and upper posterior endplate 22a) such that each post 21 is received within a vertical channel 208 formed within the other endplate. By way of example only, the posts 21 are immovably associated with the posted endplates 22b, 22c (e.g. integrally formed, press-fit, or otherwise secured) within a mating recess 207 formed within the inner surfaces of the posted endplates (e.g. inner surface 144 of lower posterior endplate 22c and inner surface 174 of the upper anterior endplate 22b). The posts 21 are slideably received within vertical channels 208 formed within the inner surfaces of the receiving endplates (e.g. inner surface 144 of upper posterior endplate 22a and inner surface 174 of the lower anterior endplate 22d). The receiving endplates may also include boss members 209 protruding from the inner surfaces 144, 174 and surrounding the vertical channels 208 to function as channel extenders. The boss members 209 are sized and configured to nest within the mating recesses 207 on the posted endplates when the expandable fusion implant 10 is in a collapsed-height state. The post 21 and corresponding channel 208 may have any cross-sectional shape capable of maintaining alignment, including but not limited to circular, oval, elliptical, square, polygonal, irregular, etc. In some embodiments, the location of the post 21 and channel 208 may be reversed such that the posted endplates comprise the upper posterior endplate 22a and lower anterior endplate 22d, and the receiving endplates comprise the lower posterior endplate 22c and upper anterior endplate 22b. Furthermore, although shown as having one vertical stabilizer 21 on the each side, it should be understood that the expandable fusion device 10 may have any number of vertical stabilizers without departing from the scope of the disclosure.

Varying the slopes of the slots 146a, 146b, 148a, and 148b or limiting the allowable travel between the ramps and the slots 146a, 146b, 148a, and 148b within each of the posterior endplates 22a, 22c may result, but is not limited to the first ends 138 and the second ends 140 expanding evenly on both top and bottom of the fusion device 10, expanding unevenly on both top and bottom, expanding evenly on top and unevenly on bottom or expanding evenly on bottom and unevenly on top of the fusion device 10.

Optionally, in any embodiment, the first posterior endplate 22a and the second posterior endplate 22c, and the first anterior endplate 22b and the second anterior endplate 22d are substantially identical, but although each endplate pair has the same set of features, the specific size and angular orientation of these features do not have to be identical in all embodiments or within any particular embodiment. Similarly, the distal posterior ramp 18a and the proximal posterior ramp 18b are substantially identical to one another, and the distal anterior ramp 20a and proximal anterior ramp 20b are substantially identical to one another, but although each pair has the same set of features, the specific size and angular orientation of these features do not have to be identical in all embodiments or within any particular embodiment. It should be noted that the ramps, even while identical in an embodiment, may or need to be suitably rotated or mirrored to be assembled into arrangements shown by way of example herein.

In use, the actuator 12 functions to pull the distal wedge 14 and proximal wedge 16 together forcing the posterior endplates 22a, 22c away from the anterior endplates 22b, 22d which in turn forces the distal posterior ramp 18a away from the distal anterior ramp 20a and also forces the proximal posterior ramp 18b away from the proximal anterior ramp 20b (resulting in width expansion of the fusion device 10). It should be mentioned that in other embodiments the actuator 12 may function to pull the distal wedge 14 and proximal wedge 16 together, forcing the distal posterior ramp 18a away from the distal anterior ramp 20a and also forcing the proximal posterior ramp 18b away from the proximal anterior ramp 20b, which ramps further force the posterior endplates 22a, 22c away from the anterior endplates 22b, 22d (resulting in width expansion of the fusion device 10). Then, only after the width expansion is at least partially complete, posterior ramps 18a, 18b are pulled toward each other and the anterior ramps 20a, 20b are pulled toward each other. The movement of the posterior ramps 18a, 18b toward each other forces the upper posterior endplate 22a away from the lower posterior endplate 22c and the movement of the anterior ramps 20a, 20b toward each other forces the upper anterior endplate 22b away from the lower anterior endplate 22d (resulting in height expansion).

Optionally, in any embodiment, the posterior ramps 18a, 18b and the anterior ramps 20a, 20b only start moving toward each other after the width expansion has completely or substantially or at least partially taken place and the ramps 18a and 20a have substantially reached the limit of their travel relative to the distal wedge 14 and the ramps 18b and 20b have substantially reached the limit of their travel relative to the proximal wedge 16. Optionally, in any embodiment, this delay in height expansion may be achieved through the endplates 22a, 22b, 22c, 22d being slidably engaged with the distal wedge 14 and, optionally in some embodiments, the proximal wedge 16 through an initial portion of width expansion process (in some embodiments, said engagement between endplates and wedges may prevent or inhibit the distal and the proximal ramps from moving toward each other thus inhibiting height expansion). During the width expansion process, as the wedges 14 and 16 move toward each other, they eventually disengage from endplates 22a, 22b, 22c, 22d and allow them to expand in height. Optionally, the delay in height expansion may be further accomplished by means of an inserter instrument constraining the height expansion until the width expansion has substantially taken place.

Optionally, in any embodiment, a small gap may exist between the endplates and the wedges in the initial collapsed state. This results in the first number of actuations in a first actuation direction increasing both height and width, but not necessarily at the same time. For example, the device may first start expanding in height or in width depending on external loading conditions and/or inserter instrument configuration (e.g. an inserter may be configured to initially restrict height expansion, width expansion or neither). Actuation of the drive feature by a second number of actuations beyond the first number of actuations in the first actuation direction then increases at least one of the height and the width. In some embodiments, the first number of actuations of the actuator 12 may result in at least some height expansion (and in some embodiments—exclusively height expansion), whereas further rotation of the actuator 12 then increases at least one of width and height.

When fully assembled, the first expandable fusion device 10 is a stable assembly of components that are all detained within the assembly throughout its full range of motion by means of "tongue and groove" articulations, the use of fasteners such as, for example, pins, balls, screws, and set screws. Optionally, in any embodiment, the fasteners are affixed in one component and travel in a mating feature (such as a track) of another component thereby limiting the range of motion of the first component to the amount permissible by the track feature thereby preventing the components from disassembly.

By way of example, at least one of the first endplate 22a, the second endplate 22b, the third endplate 22c, and the fourth endplate 22d contacts at least one of the distal wedge 14 and the proximal wedge 16 when the expandable fusion device 10 is in its collapsed state. Alternatively, at least one of the first endplate 22a, the second endplate 22b, the third endplate 22c, and the fourth endplate 22d does not contact at least one of the distal wedge 14 and the proximal wedge 16 when the expandable fusion device 10 is in its collapsed state. The contact between at least one of the first endplate 22a, the second endplate 22b, the third endplate 22c, and the fourth endplate 22d and at least one of the distal wedge 18a and the proximal wedge 18b affects the expansion of the expandable fusion device 10.

The expandable fusion device 10 has a width w comprising an external width of at least one of the upper endplate assembly (e.g. endplates 22a, 22b) and the lower endplate assembly (e.g. endplates 22c, 22d). Optionally, in any embodiment, the device has a height h comprising an external distance between the upper endplate assembly and the lower endplate assembly (e.g. between endplates 22a, 22c and/or 22b, 22d).

Optionally, in any embodiment, actuation of the drive feature 32 by a first number of actuations in a first actuation direction increases the width w without increasing the height h. Optionally, in any embodiment, actuation of the drive feature 32 by a second number of actuations beyond the first number of actuations in the first actuation direction increases at least one of the height h and the width w. Optionally, in any embodiment, actuation of the drive feature 32 by a second number of actuations beyond the first number of actuations in the first actuation direction increases both the height h and the width w, wherein actuation of the drive feature 32 by a third number of actuations beyond the second number of actuations in the first actuation direction increases the height h without increasing the width w. Optionally, in any embodiment, actuation of the drive feature 32 by a second number of actuations beyond the first number of actuations in the first actuation direction increases neither the height h nor the width w, wherein actuation of the drive feature 32 by a third number of actuations beyond the second number of actuations in the first actuation direction increases the height h without increasing the width w. Optionally, in any embodiment, the width w of the device 10 reaches an apex once the drive feature 32 is actuated by at least the first number of actuations. Optionally, in any embodiment, the height h of the device 10 reaches an apex once the drive feature 32 is actuated by at least the first and second number of actuations.

Optionally, in any embodiment, actuation of the drive feature 32 by a second number of actuations beyond the first number of actuations in the first actuation direction increases both the height h and the width w. Optionally, in any embodiment, actuation of the drive feature 32 by a second number of actuations beyond the first number of actuations in the first actuation direction increases the height h without increasing the width w.

Optionally, in any embodiment, actuation of the drive feature 32 in the first actuation direction by at least the first number of actuations increases the height h of the device 10 by about 30% to about 400%. Optionally, in any embodiment, actuation of the drive feature 32 in the first actuation direction by at least the first and the second number of actuations increases the width w of the device by about 14% to about 150%.

The expandable fusion device 10 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 10.

FIGS. 35-43 illustrate an example of an expandable fusion device 210 for implantation between two adjacent vertebrae according to another embodiment of the disclosure. By way of example only, the expandable fusion device 210 of the present embodiment includes an actuator 212, a distal wedge 214, a proximal wedge 216, a pair of identical distal ramps 218, a pair of identical proximal ramps 220, a plurality of endplates 222a-222d, and a plurality of optional guide pins 224. As with the previously-described embodiment, the distal and proximal wedges 214, 216 are coupled with the actuator 212. The distal ramps 218 are slideably coupled with the distal wedge 214. The proximal ramps 220 are slideably coupled with the proximal wedge 216. The plurality of endplates 222a-222d are slideably coupled with the ramps 218, 220. Generally, the expandable fusion device 210 is substantially similar to expandable fusion device 10 described above, and any/all of the features described above with respect to fusion device 10 (and any other expandable fusion device described herein) may apply to fusion device 210 unless otherwise noted. By way of example only, the expandable fusion device 210 is illustrative of an expandable fusion device that expands in width, height, and lordotic expansion that may be applied to any expandable fusion device examples described herein, according to some embodiments.

By way of example, the actuator 212, distal wedge 214, and proximal wedge 216 may be identical or substantially similar to corresponding elements disclosed herein with respect to other embodiments.

Figure 39:
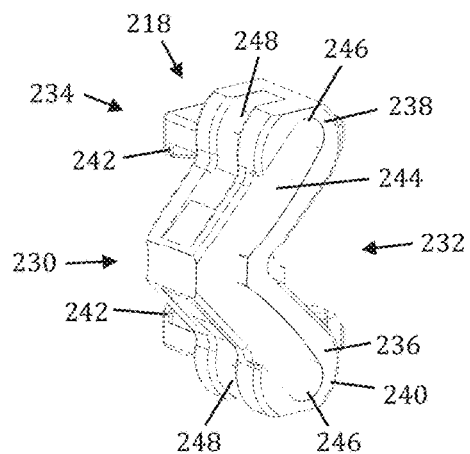
FIG. 39 is a perspective view of an example of a distal ramp forming part of the expandable fusion device of FIG. 35, according to some embodiments.

FIG. 39 illustrates an example of a distal ramp 218 according to the present example embodiment. By way of example only, the distal ramp 218 has a proximal end 230, distal end 232, medial side 234, lateral side 236, upper portion 238, and lower portion 240. The medial side 234 of the upper and lower portions 238, 240 each have a tongue and groove connector 242 configured to slideably interact with the corresponding tongue and groove connectors on the distal wedge 214 as described with respect to expandable fusion device 10 above. The distal ramp 218 has a recessed slot 244 formed within the lateral side 236 and configured to slideably receive one or more guide pins 224 therein to help stabilize the construct during lordotic expansion, as well as provide a hard stop 246 for lordotic expansion. The guide pin 224 functions as a lordosis-expansion limiting member as it will stop lordosis expansion when the guide pin 224 reaches the end of the slot 244. The distal ramp 218 may further include a pair of rail slots 248 formed within proximal-facing surfaces and configured to slideably engage inclined rails 250 of the endplates 222a-222d (see e.g. FIG. 40) during lordosis expansion.

Figure 40:
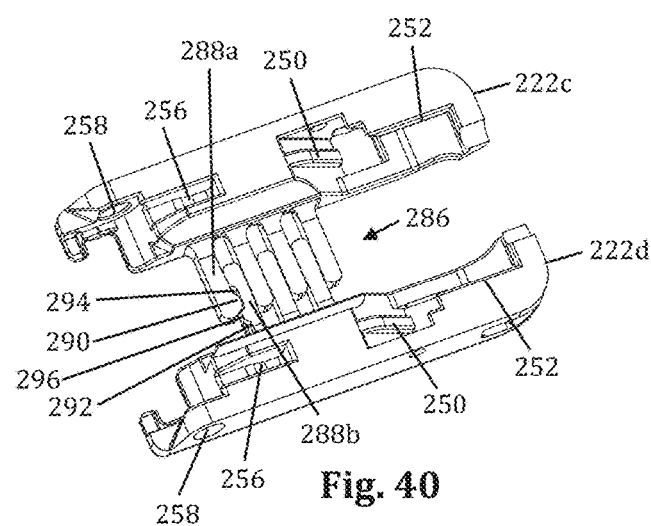
FIG. 40 is a perspective view of an example of a lower endplate assembly forming part of the expandable fusion device of FIG. 35, according to some embodiments.

FIG. 40 illustrates the bottom endplates 222c, 222d in a width-expanded configuration. By way of example only, the distal medial aspects of each of the endplates 222c, 222d (as well as endplates 222a and 222b) may include medial flanges 252 configured to engage lateral slots 254 on the distal wedge 214 when the expandable fusion device 210 is collapsed in width (e.g. FIG. 42), and prevent height and/or lordotic expansion until the device 210 has expanded sufficiently in width for the medial flanges 252 to be clear of the lateral slots 254. By way of example, this sufficient width expansion may include full width expansion or a width expansion amount that is less than full expansion. The proximal aspect of each of the endplates 222a-222d may include an elongated recess 256 configured to receive distal flange 272 of the proximal ramps 220 therein. The proximal aspect of each of the endplates 222a-222d may each further include a boss aperture 258 configured to receive a cylindrical boss 270 of the proximal ramp 220 therein.

By way of example, the endplates 222a-222d of the present embodiment may include a width stabilizer feature 286 substantially similar to those described with respect to expandable fusion device 10 above and other embodiments disclosed herein. By way of example, the width stabilizer feature 704 may comprise a plurality of interdigitated medial flanges 288 having stabilizing grooves and protrusions as described above. As a result, the endplates 222a and 222b overlap one another, and endplates 222c and 22d2d overlap one another. This helps provide stability with a lower profile, for example.

In some embodiments, the width stabilizer feature 286 of the instant example may be provided with a width lock feature to (among other things and by way of example only) maintain the expanded width of the implant 210 while collapsing the lordotic angle (e.g. in a revision procedure). According to one example of the width lock feature, one or more of the medial flanges 288a, 288b may include a lateral protrusion 290 positioned at the distal end of the flange 288a, and an opposing medial flange 288b adjacent the nesting slot may include an elongated lateral recess 292 and a distal recess 294 that is separated from the elongated lateral recess 292 by a deflection element 296. By way of example, the lateral protrusion 290 is configured to translate within the elongated lateral recess 292 upon width expansion of the expandable fusion device 210. As the lateral protrusion 290 encounters the deflection element 296, the medial flange 288a deflects to enable the lateral protrusion 290 to fully traverse the deflection element 296. Once the lateral protrusion 290 has cleared the deflection element 296, the medial flange 288a snaps back to its normal (e.g. non-deflected) orientation and detains the lateral protrusion 290 within the distal recess 294. In some embodiments, the width stabilizer with or without the width lock feature described above may be used instead as a height stabilizer and a height lock feature by simply arranging the flanges to span the upper and lower endplates instead of the "left" and "right" endplates shown in FIG. 40.

By way of example, when the implant 210 is expanded in both width and height, to collapse it down to initial state, it is important that the device first collapses in lordosis angle first and then in width (otherwise, the device may not be able to get back to initial state). The width lock of the medial flange 288a at full width provides resistance to collapsing width, so that upon actuation of the actuator 212 to collapse the implant 210, the implant 210 will first collapse in lordotic angle (e.g. path of least resistance). Only when the lordotic angle is fully collapsed will the actuator 212 apply enough force to overcome the resistance of the width lock to deflect the flange 288a again, unclick the width lock and collapse the implant 210 in width. By way of example only, the configuration of the width lock features described herein is not limited to the specific example shown, but rather may vary in number and/or placement without reservation.

Figure 41:
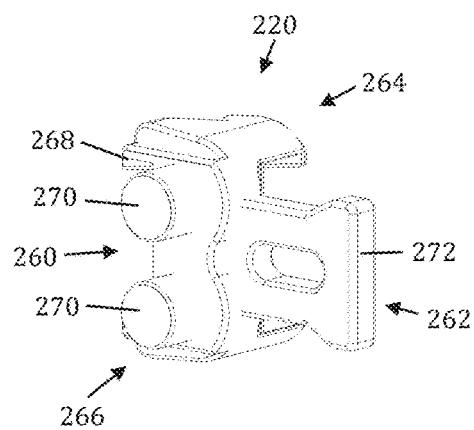
FIG. 41 is a perspective view of an example of a proximal ramp forming part of the expandable fusion device of FIG. 35, according to some embodiments.
Figure 42:
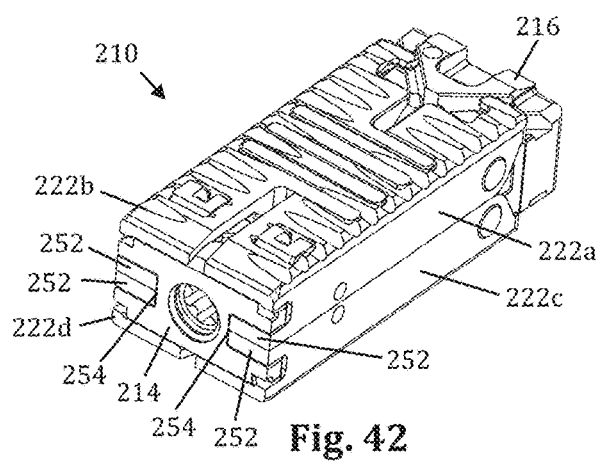
FIG. 42 is a sectional view of the expandable fusion device of FIG. 35 in a collapsed state, according to some embodiments.

FIG. 41 illustrates an example of a proximal ramp 220 according to the present example embodiment. By way of example only, the proximal ramp 220 has a proximal end 260, distal end 262, medial side 264, and lateral side 266. The medial side 264 has upper and lower tongue and groove connectors 268 configured to slideably interact with the corresponding tongue and groove connectors on the proximal wedge 216 to enable width expansion as described with respect to expandable fusion device 10 above. By way of example only, the proximal ramp 220 of the present embodiment has a pair of lateral facing cylindrical bosses 270 configured to be received within boss apertures 258 on the proximal end of each of the endplates 222a-222d such that the endplates 222a-222d are pivotally mated with the proximal ramps 220. In some embodiments, the ends of the bosses 270 may be swaged or otherwise detained within the boss apertures 258. In some embodiments, each proximal ramp 220 may include a distal flange 272 configured to nest within the elongated recesses 256 formed in the endplates 222a-222d when the lordotic expansion angle between endplate pairs (e.g. 222a and 222c, 222b and 222d) is below a predetermined threshold or within a useful/working range (e.g. any lordotic expansion angle range achieved during clinical use or limited by the guide pins 224 and slots 244), to prevent the cylindrical bosses 270 from disengaging from the boss apertures 258 during clinical use. The distal flanges 272 may be further configured for removal from the elongated recesses 256 when the lordotic expansion angle between endplate pairs (e.g. 222a and 222c, 222b and 222d) is above the predetermined threshold (e.g. outside the parameters of clinical use), enabling assembly and/or disassembly of the endplates and the proximal ramps.

Figure 35:
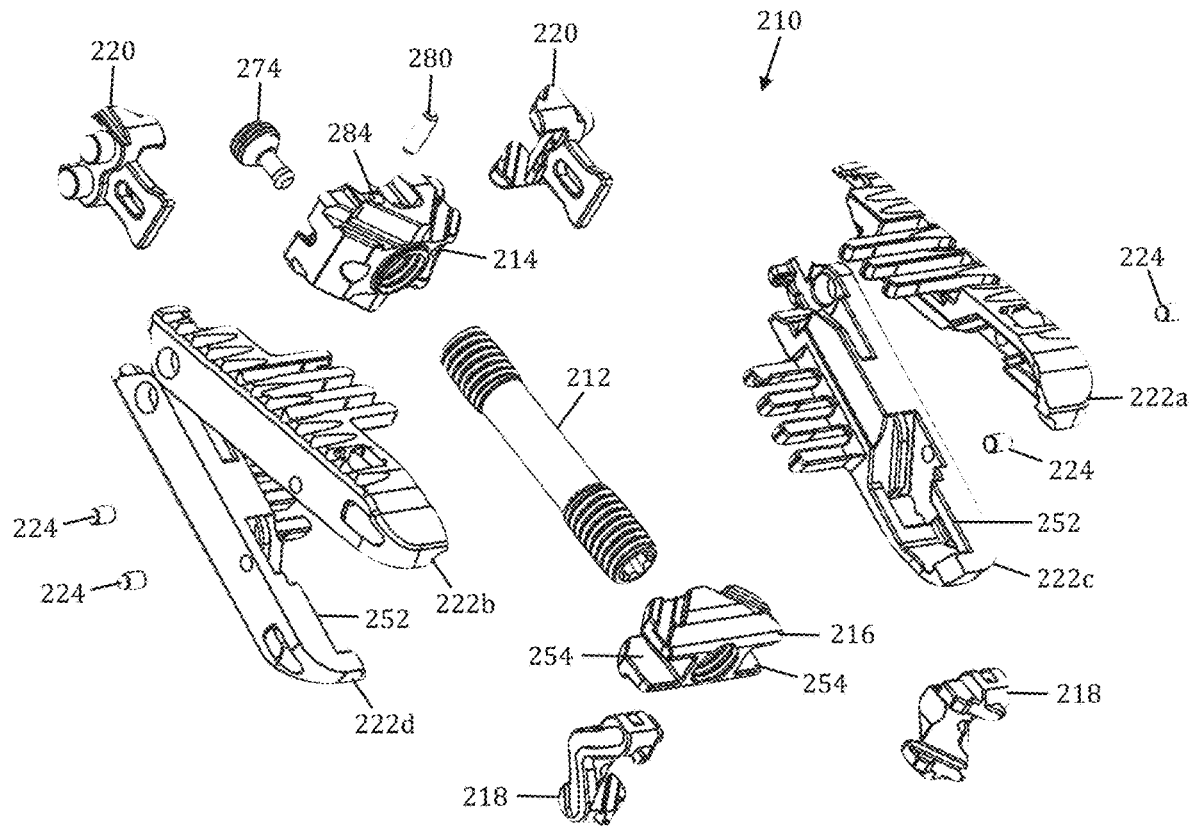
FIG. 35 is an exploded perspective view of another example of an expandable fusion device, according to some embodiments.
Figures 36, 37:
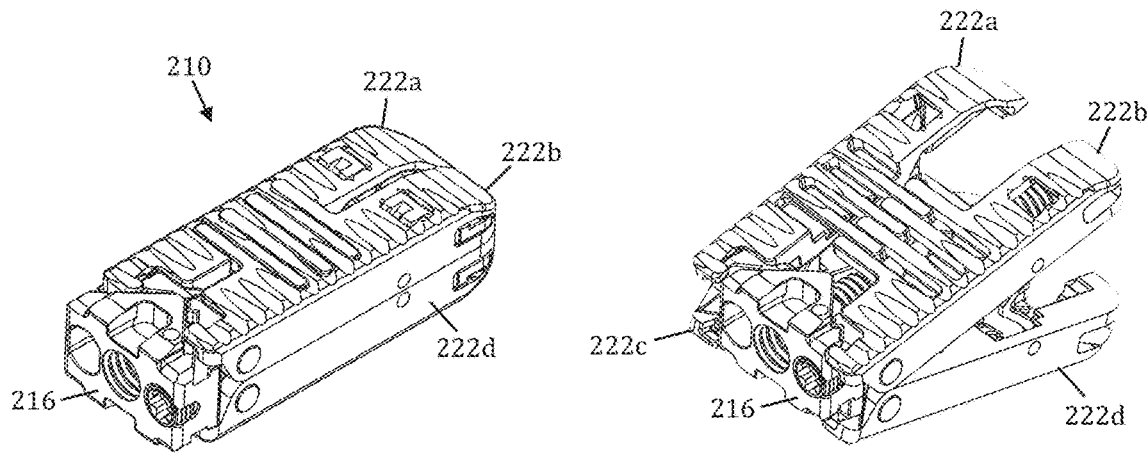
FIG. 36 is a perspective view of the expandable fusion device of FIG. 35 in a collapsed state, according to some embodiments.
FIG. 37 is a perspective view of the expandable fusion device of FIG. 35 in a lordotic expansion state, according to some embodiments.
Figure 38:
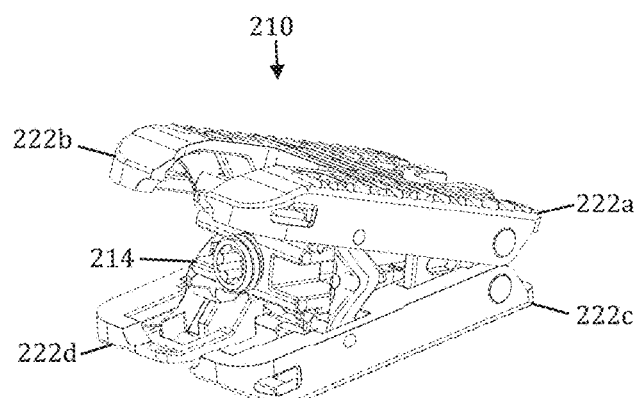
FIG. 38 is another perspective view of the expandable fusion device of FIG. 35 in a lordotic expansion state, according to some embodiments.
Figure 43:
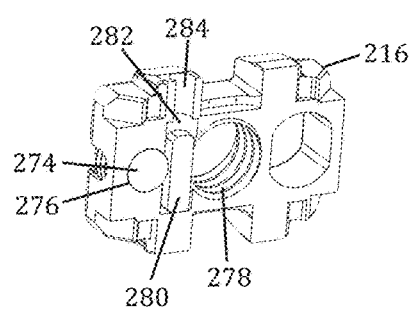
FIG. 43 is a sectional view of an example of a proximal wedge forming part of the expandable fusion device of FIG. 35, according to some embodiments.
Figure 44:
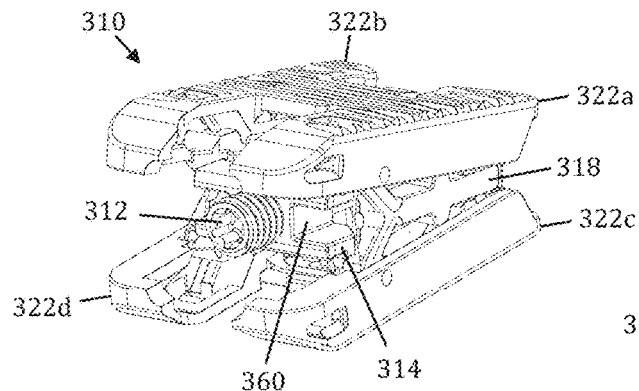
FIG. 44 is a perspective view of another example of an expandable fusion device in a fully expanded position, according to some embodiments.
Figure 45:
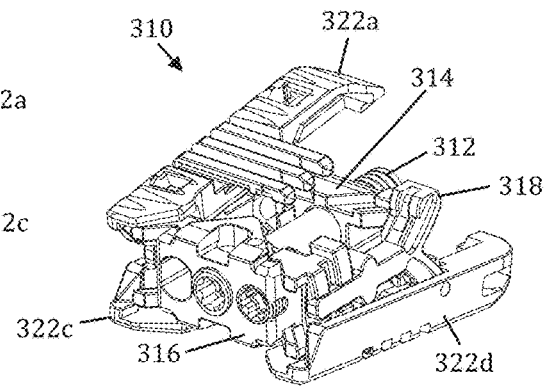
FIG. 45 is a perspective view of the expandable fusion device of FIG. 44 with an upper endplate removed, according to some embodiments.
Figure 46:
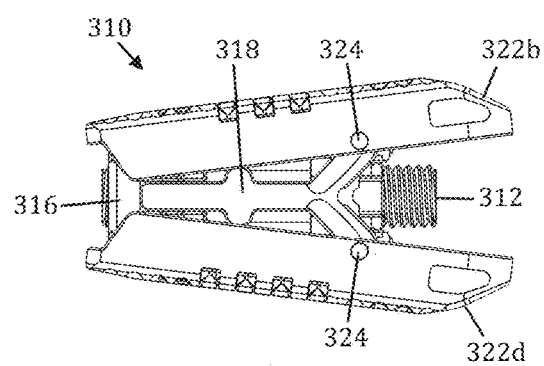
FIG. 46 is a side plan view of the expandable fusion device of FIG. 44, according to some embodiments.

With reference to FIGS. 35 and 43, in some embodiments, when the desired expansion has been achieved, the actuator 212 may be secured by a locking element (e.g. ball detent, pin detent, or other suitable feature capable of exerting immobilizing force upon the actuator shaft). To facilitate this, and by way of example only, the proximal wedge 216 may include a lock screw 274 positioned within a threaded lock screw aperture 276 positioned adjacent to the threaded bore 278 and a locking element 280 at least partially retained within a vertical chamber 282 positioned between the threaded bore 278 and the lock screw aperture 276. The vertical chamber 282 is configured to retain the locking element 280 therein while also enabling exposure to the threaded bore 278 for contacting the actuator 212 by way of a first side opening, and the lock screw aperture 276 for contacting the lock screw 274 by way of a second side opening. Upon completion of the desired expansion, the lock screw 274 may be tightened within the lock screw aperture 276, which in turn may deflect the locking element 280 medially such that the locking element 280 forcibly contacts the actuator 212 to prevent turning or translation of the actuator 212 or to increase the torque level required for the actuator to turn compared to that required before the lock screw tightening. By way of example, the lock screw 274 may be substantially similar or identical to the lock screw 63 described above. In some embodiments, the proximal wedge 216 includes a chamber aperture 284 sized and configured to enable press-fit passage of the locking element 280 therethrough. By way of example, the chamber aperture 284 has a smaller width or diameter than the vertical chamber 282 such that once the locking element 280 has been press-fit through the chamber aperture 284 and into the vertical chamber 282, the locking element 280 may move medial-laterally (e.g. in response to actuation of the lock screw 274) but remains captured within the vertical chamber 282.

In operation, first width expansion proceeds substantially as described above with respect to previous embodiments. That is, the actuator 212 is turned a select number of actuations until maximum width expansion is reached and the endplate disengages from the distal wedge 214, and optionally the medial flanges 252 disengage from the lateral slots 254 of the distal wedge 214. Once the disengagement occurs, further rotation of the actuator 212 results in the distal ramps 218 translating along the respective angled slots in the endplates and each endplate pivoting about a different cylindrical boss 270, increasing at least one of the width and lordosis angle in the process. Because the endplates pivot about the proximal ramp bosses that are received in the boss apertures, the axis of rotation of each endplate passes through that endplate's body, meaning that during lordotic expansion, the height of the device as measured at the distal ends of endplates increases, but the height measured at the proximal ends of endplates decreases. In other words, actuation of the drive feature in for a first number of actuations in the first actuation direction results in width expansion. Actuation of the drive feature by a second number of actuations beyond the first number of actuations in the first actuation direction then increases at least one of width, distal height, and lordotic angle. In other embodiments, the first number of actuations of the actuator 212 may result in at least some height expansion (and in some embodiments—exclusively height expansion), whereas further rotation of the actuator 212 then increases at least one of width, height, and lordotic angle.

The expandable fusion device 210 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 210.

FIGS. 44-49 illustrate an example of an expandable fusion device 310 for implantation between two adjacent vertebrae according to another embodiment of the disclosure. By way of example only, the expandable fusion device 310 of the present embodiment includes an actuator 312, a distal wedge 314, a proximal wedge 316, a pair of identical distal ramps 318, a pair of identical proximal ramps 320, a plurality of endplates 322*a*-322*d*, and a plurality of optional guide pins 324. As with the previously-described embodiment, the distal and proximal wedges 314, 316 are coupled with the actuator 312. The distal ramps 318 are slideably coupled with the distal wedge 314. The proximal ramps 320 are slideably coupled with the proximal wedge 316. The plurality of endplates 322*a*-322*d* are slideably coupled with the ramps 318, 320. Generally, the expandable fusion device 310 is substantially similar to expandable fusion device 10 described above, and any/all of the features described above with respect to fusion device 10 (and any other expandable fusion device described herein) may apply to fusion device 310 unless otherwise noted. By way of example only, the expandable fusion device 310 is illustrative of an expandable fusion device that expands in width, height, and lordotic expansion that may be applied to any expandable fusion device examples described herein, according to some embodiments.

By way of example, the actuator 312, distal wedge 314, and proximal wedge 316 may be identical or substantially similar to corresponding elements disclosed herein with respect to other embodiments.

Figure 47:
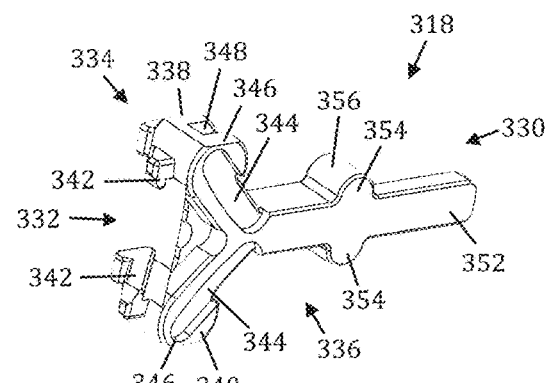
FIG. 47 is a perspective view of an example of a distal ramp forming part of the expandable fusion device of FIG. 44, according to some embodiments.

FIG. 47 illustrates an example of a distal ramp 318 according to the present example embodiment. By way of example only, the distal ramp 318 has a proximal end 330, distal end 332, medial side 334, lateral side 336, upper portion 338, and lower portion 340. The medial side 334 of the upper and lower portions 338, 340 each have a tongue and groove connector 342 configured to slideably interact with the corresponding tongue and groove connectors on the distal wedge 314 in the same manner as described with respect to corresponding features of expandable fusion device 10 above. The distal ramp 318 has a pair of angled recessed ramp slots 344 formed within the lateral side 336 and arranged in a V-shape, configured to slideably receive one or more guide pins 324 therein to help stabilize the construct during lordotic expansion, as well as provide a hard stop 346 for lordotic expansion. The guide pin 324 functions as a lordosis-expansion limiting member as it will stop lordosis expansion when the guide pin 324 reaches the end of the ramp slot 344. The distal ramp 318 may further include a pair of rail slots 348 formed within proximal-facing surfaces and configured to slideably engage inclined rails 350 of the endplates 322*a*-322*d* (see e.g. FIG. 48) during lordosis expansion. In some embodiments, the distal ramp 318 may further comprise a proximal extension 352 configured to mate with engagement slot 378 of the proximal ramp 320. By way of example only, the mating of the distal ramp 318 and proximal ramp 320 in this fashion may provide additional stability during expansion (e.g. width, height, and/or lordotic). In some embodiments, the proximal extension 352 may include one or more protrusions 354 extending toward the upper and/or lower portions 338, 340 and including a contact surface 356 configured to translate along contact surfaces 362 of the endplates 322*a*-322*d* to provide additional contact surfaces to support the assembly during height/lordotic expansion.

Figure 48:
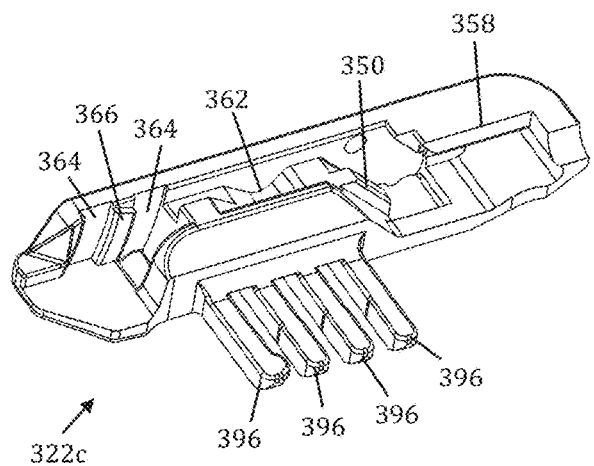
FIG. 48 is a perspective view of an example of a proximal ramp forming part of the expandable fusion device of FIG. 44, according to some embodiments.

FIG. 48 illustrates endplate 322*c* in greater detail. By way of example, the endplates 322*a*-322*d* are either identical or mirror images of one another (with the exception of the number and arrangement of the medial flanges 396 comprising a width stabilizer element that is substantially as described in previous embodiments), and thus it should be understood any structure described by way of example with respect to endplate 322*c* may also be present on the other endplates. By way of example only, the distal medial aspects of endplates 322*c* (as well as endplates 322*a*, 322*b*, and 322*d*) may include medial flanges 358 configured to engage lateral slots 360 on the distal wedge 314 when the expandable fusion device 310 is collapsed in width, and prevent height and/or lordotic expansion until the device 310 has expanded sufficiently in width for the medial flanges 358 to be clear of the lateral slots 360. By way of example, this sufficient width expansion may include full width expansion or a width expansion amount that is less than full expansion. In some embodiments, the endplate 322*c* may further include contact surface 362 configured to engage the contact surface 356 of the proximal extension 352 as described above. The proximal aspect of the endplate 322*c* may include one or more arc channels 364 oriented in concentric arcs (if more than one, as shown in the instant example embodiment) having a center point in a proximal direction and separated by an arc rail 366. The arc channels 364 are configured to slideably mate with arc ramps 372 of the corresponding proximal ramp 320, and the arc rail 366 may be configured to slideably mate with the arc rail slot 374 of the proximal ramp 320. Thus the arcs of the arc channels 364 are equal to the arcs of the respective arc ramps 372, and the arc of the arc rail 366 is equal to the arc of the arc rail slot 374.

Figure 49:
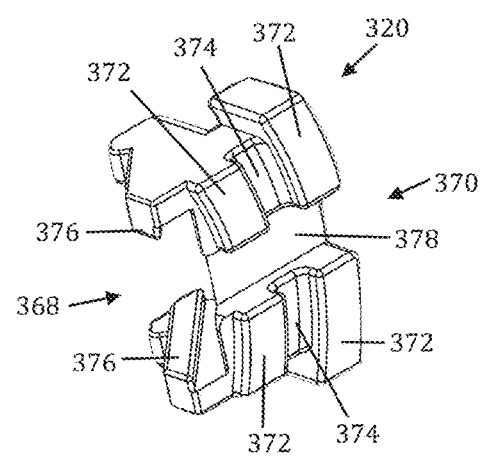
FIG. 49 is a perspective view of an example of an endplate forming part of the expandable fusion device of FIG. 44, according to some embodiments.
Figure 50:
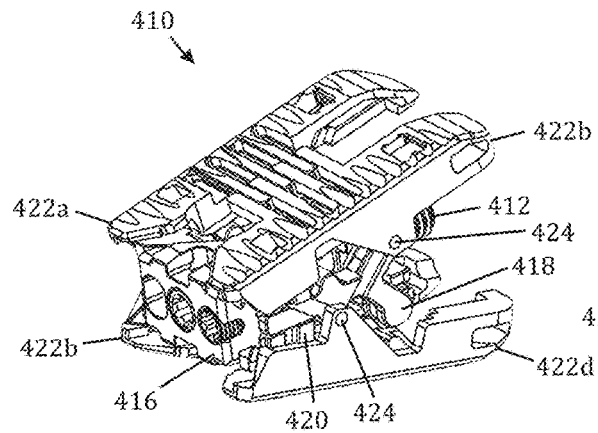
FIG. 50 is a perspective view of another example of an expandable fusion device in a fully expanded position, according to some embodiments.
Figure 51:
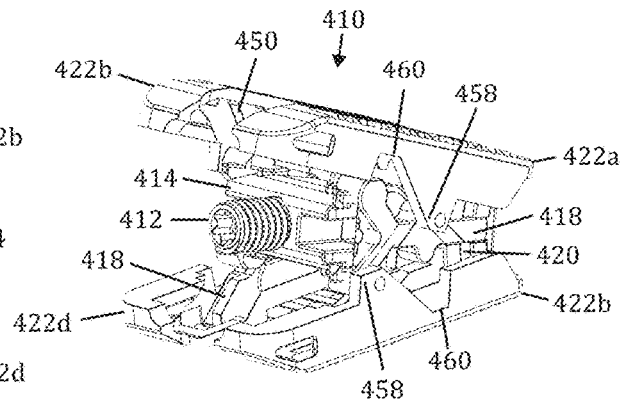
FIG. 51 is another perspective view of the expandable fusion device of FIG. 50, according to some embodiments.
Figure 52:
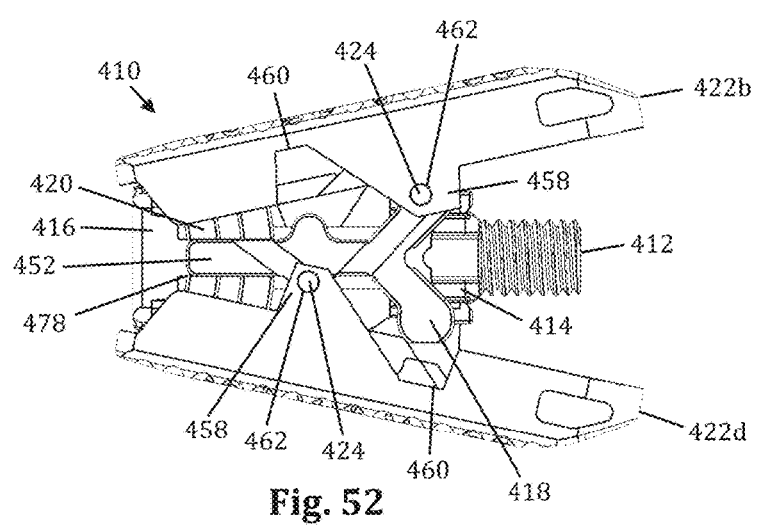
FIG. 52 is a side plan view of the expandable fusion device of FIG. 50, according to some embodiments.

FIG. 49 illustrates an example of a proximal ramp 320 according to the present example embodiment. By way of example only, the proximal ramp 320 has a proximal end 368 and a distal end 370. The proximal ramp 320 further includes at least one (e.g. first) arc ramp 372, and optionally a second (or more) arc ramp 372 (shown by way of example only) positioned distally of the first arc ramp 372 and separated from the first arc ramp 372 by a arc rail slot 374. The arc ramps 372 are curved along concentric arcs having a center point in the proximal direction. The arc ramps 372 are configured to slideably mate with first and second arc channels 364, respectively, of the corresponding endplates 322 (e.g. endplates 322*b*, 322*d*). By way of example, the arc ramps 372 essentially function as pivot guides during lordosis expansion, but also help hold the expansion angle in place once lordosis expansion is complete. By way of example, in some embodiments the radius of curvature of the arc ramps 372 (and relevant corresponding structure) may be altered to increase maximum attainable proximal (e.g. posterior) height while decreasing maximum lordosis, and vice versa. The proximal end 368 includes a pair of tongue and groove connectors 376 configured to slideably interact with the corresponding tongue and groove connectors on the proximal wedge 316 as described above. In some embodiments, the proximal ramp 320 further includes an engagement slot sized and configured to slideably mate with the proximal extension 352 of the distal ramp 314, to provide additional stability during expansion (e.g. width, height, and/or lordotic).

In operation, first width expansion proceeds substantially as described above with respect to previous embodiments. That is, the actuator 312 is turned a select number of actuations until some width expansion is reached and the endplate disengages from the distal wedge 314. Once the disengagement occurs, further rotation of the actuator 312 results in the distal ramps 318 translating along the respective angled slots in the endplates, increasing at least one of the width, height, and lordosis angle in the process. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle. Because during height/lordosis expansion, the endplates translate about arc ramps 372 and because the center of curvature of the arc ramps is located proximally outside of the proximal margin of the device assembly—the axis of rotation of each endplate does not pass through that endplates body, meaning that during lordotic expansion, the height of the device as measured at the distal ends of endplates increases, while the height measured at the proximal ends of endplates also increases. The farther away the center of curvature of arc ramps is from the proximal margin of the device, the smaller the difference in height between the distal and proximal ends of the endplates and the smaller the lordotic angle in the fully height/lordosis expanded state. The closer the center of curvature of arc ramps is to the proximal margin of the device, the greater the difference in height between the distal and proximal ends of the endplates and the greater the lordotic angle in the fully height/lordosis expanded state.

The expandable fusion device 310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 310.

FIGS. 50-53 illustrate an example of an expandable fusion device 410 for implantation between two adjacent vertebrae according to another embodiment of the disclosure. By way of example, the expandable fusion device 410 is substantially similar to the expandable fusion device 310 described above, however the expandable fusion 410 of the present example is configured to allow for a greater maximum height and/or lordotic expansion. By way of example only, the expandable fusion device 410 of the present embodiment includes an actuator 412, a distal wedge 414, a proximal wedge 416, a pair of identical distal ramps 418, a pair of identical proximal ramps 420, a plurality of endplates 422a-422d, and a plurality of optional guide pins 424. As with the previously described embodiment, the distal and proximal wedges 414, 416 are coupled with the actuator 412. The distal ramps 418 are slideably coupled with the distal wedge 414. The proximal ramps 420 are slideably coupled with the proximal wedge 416. The plurality of endplates 422a-422d are slideably coupled with the ramps 418, 420. Generally, the expandable fusion device 410 is substantially similar to expandable fusion device 10 described above, and any/all of the features described above with respect to fusion device 10 (and any other expandable fusion device embodiments described herein) may apply to fusion device 410 unless otherwise noted. By way of example only, the expandable fusion device 410 is illustrative of an expandable fusion device that expands in width, height, and lordotic expansion that may be applied to any expandable fusion device examples described herein, according to some embodiments.

By way of example, the actuator 412, distal wedge 414, proximal wedge 416, and proximal ramp 420 may be identical or substantially similar to corresponding elements disclosed herein with respect to other embodiments.

Figure 53:
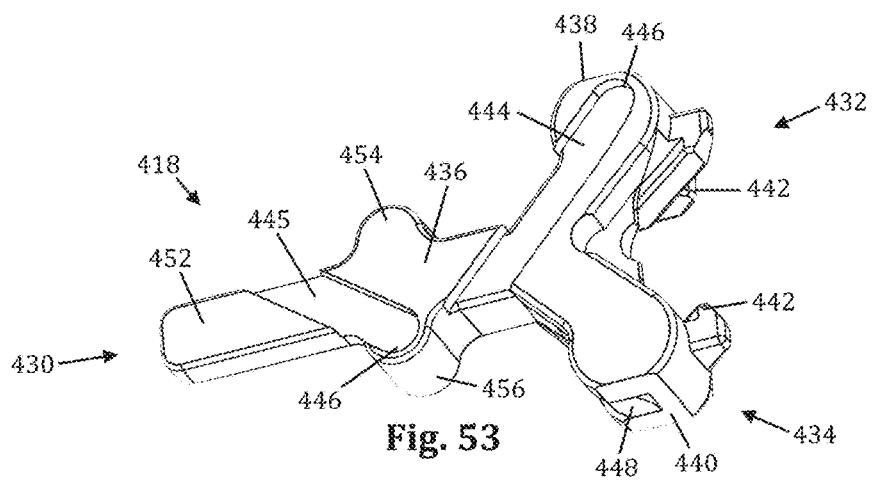
FIG. 53 is a perspective view of an example of a distal ramp forming part of the expandable fusion device of FIG. 50, according to some embodiments.
Figure 54:
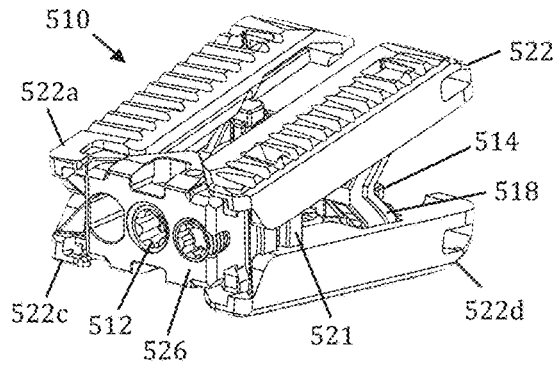
FIG. 54 is a perspective view of another example of an expandable fusion device in a fully expanded position, according to some embodiments.
Figure 55:
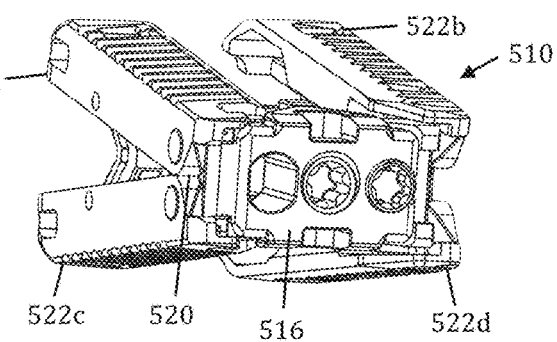
FIG. 55 is another perspective view of the expandable fusion device of FIG. 54, according to some embodiments.

FIG. 53 illustrates an example of a distal ramp 418 according to the present example embodiment. By way of example only, the distal ramp 418 has a proximal end 430, distal end 432, medial side 434, lateral side 436, upper portion 438, and lower portion 440. The medial side 434 of the upper and lower portions 438, 440 each have a tongue and groove connector 442 configured to slideably interact with the corresponding tongue and groove connectors on the distal wedge 414 in the same manner as described with respect to corresponding features of expandable fusion device 10 above. The distal ramp 418 has a pair of angled recessed ramp slots 444, 445 formed within the lateral side 436. By way of example, the ramp slot 444 is formed at the distal end 432 of one of the upper portion 438 (as shown in the example embodiment) or the lower portion 440, and is angled in a proximal direction. The ramp slot 445 is formed in the proximal extension 452 and is angled in a proximal direction. The ramp slots 444, 445 may be configured to slideably receive one or more guide pins 424 therein to help provide expansion or collapsing force, stabilize the construct during lordotic expansion, as well as provide a hard stop 446 for lordotic expansion. In other embodiments, the guide pins 424 may be replaced by integral bosses formed in the endplates. The guide pin 424 functions as a lordosis-expansion limiting member as it will stop lordosis expansion when the guide pin 424 reaches the hard stops 446 at the end of each ramp slot 444, 445. The distal ramp 418 may further include rail slots 448 formed within proximal-facing surfaces of the upper and lower portions 438, 440 that are configured to slideably engage inclined rails 450 of the endplates 422a-422d during lordosis expansion. In some embodiments, the distal ramp 418 may further comprise a proximal extension 452 configured to mate with an engagement slot 478 of the proximal ramp 420. By way of example only, the mating of the distal ramp 418 and proximal ramp 420 in this fashion may provide additional stability during expansion (e.g. width, height, and/or lordotic). In some embodiments, the proximal extension 452 may include one or more protrusions 454 extending toward the upper and/or lower portions 438, 440 and including a contact surface 456 configured to translate along complimentary contact surfaces of the endplates 432a-422d to provide additional contact surfaces to support the assembly during height/lordotic expansion.

By way of example, the endplates 422a-422d are substantially similar to endplates 322a-322d described above, and thus only different or additional features will be described. Furthermore, endplates 422a-422d are identical or mirrored equivalents of one another, and thus it should be understood any structure described by way of example with respect to any endplate may be present on the other endplates. By way of example only, each endplate 422a-422d may include a shaped projection 458 extending toward the respective vertically-opposing endplate and a shaped recess 460. The shaped projection 458 and shaped recess 460 have complimentary shapes and are arranged such that the shaped projection 458 of one endplate (e.g. endplate 422b) is configured to nest within the shaped recess 460 of the vertically-opposing endplate (e.g. endplate 422d), and vice versa, when the expandable fusion implant 410 is in a collapsed height and/or collapsed lordotic position. Each of the shaped projections 458 includes a pin aperture 462 configured to receive a guide pin 424 therein to slideably link the endplates 424a-424d with the distal ramps 418. The shaped projections allow for contact to be maintained between the endplates and the ramps while enabling a higher range of lordotic and/or height expansion.

In operation, first width expansion proceeds substantially as described above with respect to previous embodiments. That is, the actuator 412 is turned a select number of actuations until some width expansion is reached and the endplate disengages from the distal wedge 414. Once the disengagement occurs, further rotation of the actuator 412 results in the distal ramps 418 translating along the respective angled slots in the endplates, increasing at least one of the width, height, and lordosis angle in the process. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle.

The expandable fusion device 410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 410.

FIGS. 54-61 illustrate an example of an expandable fusion device 510 for implantation between two adjacent vertebrae according to another embodiment of the disclosure. By way of example, the expandable fusion device 510 is essentially a hybrid combination of expandable fusion device 210 and expandable fusion device 310 described above, configured to approximate oblique lordotic angle expansion according to some embodiments. By way of example only, the expandable fusion device 510 of the present embodiment includes an actuator 512, a distal wedge 514, a proximal wedge 516, a pair of identical distal ramps 518, a first proximal ramp 520, a second proximal ramp 521, a plurality of endplates 522a-522d, and a plurality of optional guide pins 524. As with the previously-described embodiment, the distal and proximal wedges 514, 516 are coupled with the actuator 512. The distal ramps 518 are slideably coupled with the distal wedge 514. The proximal ramps 520, 521 are slideably coupled with the proximal wedge 516. The plurality of endplates 522a-522d are slideably coupled with the ramps 518, 520, 521. Generally, the expandable fusion device 510 is substantially similar to expandable fusion device 10 described above, and any/all of the features described above with respect to fusion device 10 (and any other expandable fusion device described herein) may apply to fusion device 510 unless otherwise noted. By way of example only, the expandable fusion device 510 is illustrative of an expandable fusion device that expands in width, height, and lordotic expansion (e.g. including oblique lordotic expansion) that may be applied to any expandable fusion device examples described herein, according to some embodiments.

By way of example, the actuator 512, distal wedge 514, and proximal wedge 516 may be identical or substantially similar to corresponding elements disclosed herein with respect to other embodiments.

Figure 56:
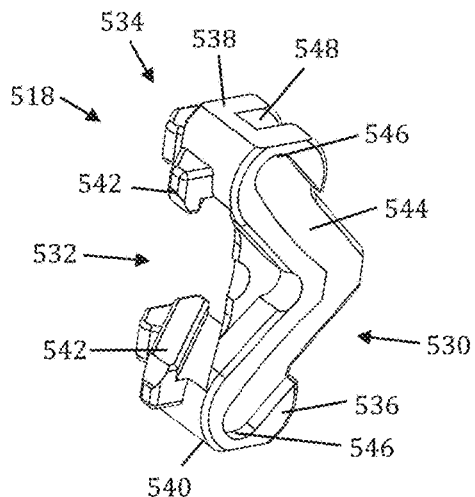
FIG. 56 is a perspective view of an example of a distal ramp forming part of the expandable fusion device of FIG. 54, according to some embodiments.

FIG. 56 illustrates an example of a distal ramp 518 according to the present example embodiment. By way of example only, the distal ramp 518 has a proximal end 530, distal end 532, medial side 534, lateral side 536, upper portion 538, and lower portion 540. The medial side 534 of the upper and lower portions 538, 540 each have a tongue and groove connector 542 configured to slideably interact with the corresponding tongue and groove connectors on the distal wedge 514 as described with respect to expandable fusion device 10 above. The distal ramp 518 has a recessed ramp slot 544 formed within the lateral side 536 and configured to slideably receive one or more guide pins 524 therein to help stabilize the construct during lordotic expansion, as well as provide a hard stop 546 for lordotic expansion. The guide pin 524 functions as a lordosis-expansion limiting member as it will stop lordosis expansion when the guide pin 524 reaches the end of the ramp slot 544. The distal ramp 518 may further include a pair of rail slots 548 formed within proximal-facing surfaces and configured to slideably engage inclined rails 550 of the endplates 222a-222d (see e.g. FIG. 57) during lordosis expansion.

Figure 57:
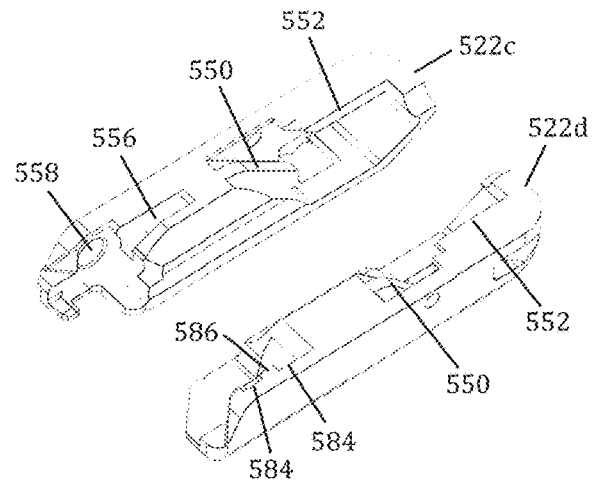
FIG. 57 is a perspective view of an example of a lower endplate assembly forming part of the expandable fusion device of FIG. 54, according to some embodiments.

FIG. 57 illustrates the bottom endplates 522c, 522d in a width-expanded configuration. In the instant embodiment, the top endplate 522a is substantially similar (e.g. mirrored equivalent) to the bottom endplate 522c, and the top endplate 522b is substantially similar (e.g. mirrored equivalent) to the bottom endplate 522d. By way of example only, the distal medial aspects of each of the endplates 522c, 522d (as well as endplates 522a and 522b) may include medial flanges 552 configured to engage lateral slots 554 on the distal wedge 514 when the expandable fusion device 510 is collapsed in width, and prevent height and/or lordotic expansion until the device 510 has expanded sufficiently in width for the medial flanges 552 to be clear of the lateral slots 554 (for example as described with respect to previous embodiments). By way of example, this sufficient width expansion may include full width expansion or a width expansion amount that is less than full expansion. In some embodiments, the proximal aspect of endplate 522c (and endplate 522a) may include an elongated recess 556 configured to receive distal flange 572 of the first proximal ramp 520 therein, and a boss aperture 558 configured to receive a cylindrical boss 570 of the first proximal ramp 520 therein. In some embodiments, the proximal aspect of endplate 522d (and endplate 522b) may include one or more arc channels 584 oriented in concentric arcs (if more than one, as shown in the instant example embodiment) having a center point in a proximal direction and separated by an arc rail 586. The arc channels 584 are configured to slideably mate with arc ramps 578 of the second proximal ramp 521, and the arc rail 586 may be configured to slideably mate with the arc rail slot 580 of the second proximal ramp 521. Thus the arcs of the arc channels 584 are equal to the arcs of the respective arc ramps 578, and the arc of the arc rail 586 is equal to the arc of the arc rail slot 580.

Figure 58:
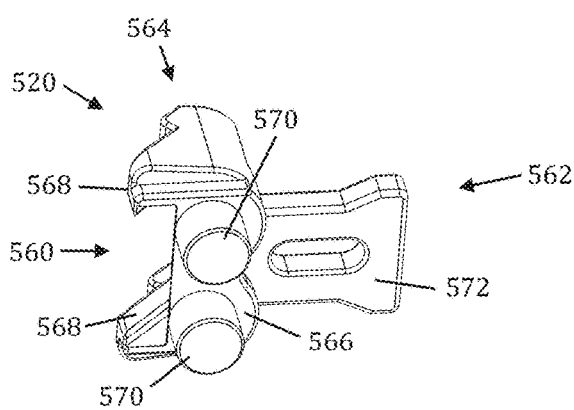
FIG. 58 is a perspective view of an example of a first proximal ramp the expandable fusion device of FIG. 54, according to some embodiments.

FIG. 58 illustrates an example of a first proximal ramp 520 according to the present example embodiment. In the instant embodiment, the first proximal ramp 520 is configured to hingedly engage the endplates 522a, 522c to enable lordotic expansion without height expansion. By way of example only, the proximal ramp 520 has a proximal end 560, distal end 562, medial side 564, and lateral side 566. The medial side 534 has upper and lower tongue and groove connectors 568 configured to slideably interact with the corresponding tongue and groove connectors on the proximal wedge 516 to enable width expansion as described with respect to expandable fusion device 10 above. By way of example only, the first proximal ramp 520 of the present embodiment has a pair of lateral facing cylindrical bosses 570 configured to be received within boss apertures 558 on the proximal end of each of the endplates 522a, 522c such that the endplates 522a, 522c are pivotally mated with the first proximal ramp 520. The ends of the bosses 570 may be swaged or otherwise detained within the boss apertures 558.

In some embodiments, each proximal ramp 520 may further include a distal flange 572 configured to nest within the elongated recesses 556 formed in the endplates 522a, 522c when the lordotic expansion angle between endplates 522a, 522c is below a predetermined threshold or within a useful/ working range (e.g. any lordotic expansion angle range achieved during clinical use), to prevent the cylindrical bosses 570 from disengaging from the boss apertures 558 during clinical use. The distal flanges 572 may be further configured for removal from the elongated recesses 556 when the lordotic expansion angle between endplates 522a, 522c is above the predetermined threshold (e.g. outside the parameters of clinical use), enabling assembly and/or disassembly of the endplates and the first proximal ramp 520.

Figure 59:
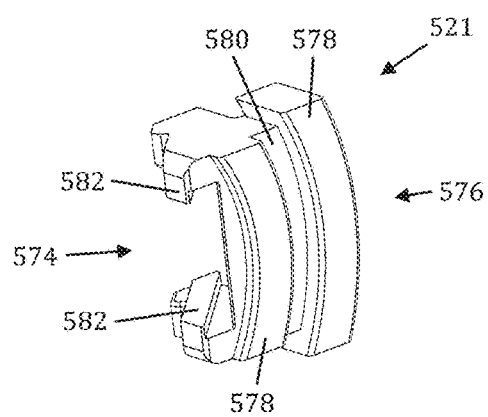
FIG. 59 is a perspective view of an example of a second proximal ramp forming part of the expandable fusion device of FIG. 54, according to some embodiments.
Figure 60:
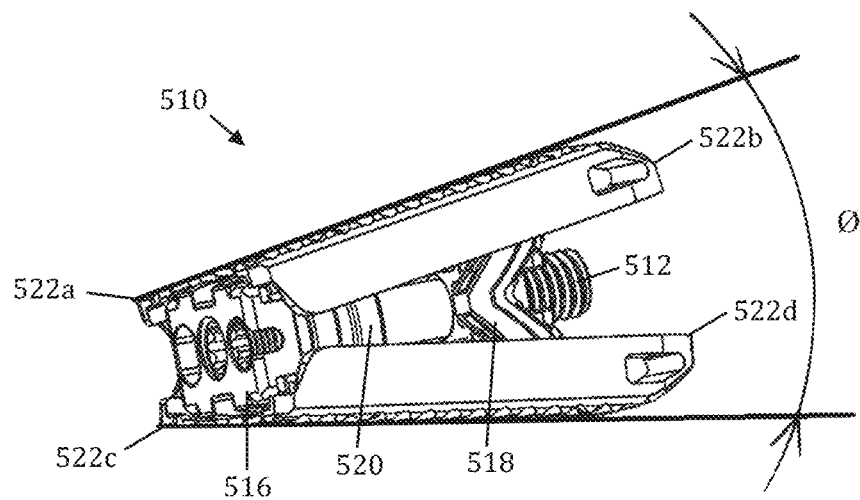
FIG. 60 is another perspective view of the expandable fusion device of FIG. 54, according to some embodiments.
Figure 61:
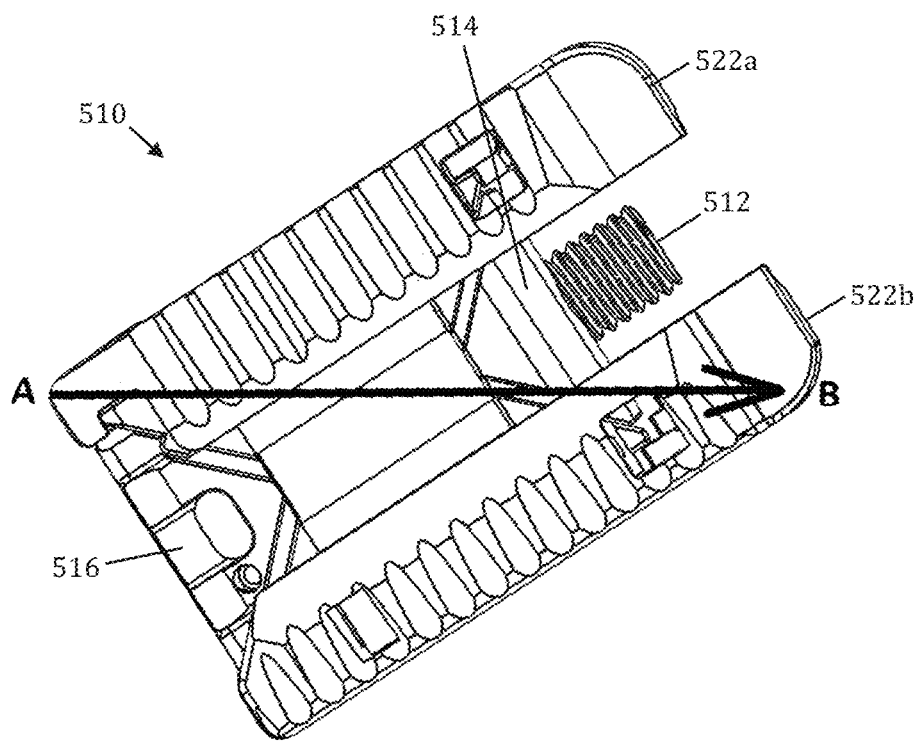
FIG. 61 is a top plan view of the expandable fusion device of FIG. 54, according to some embodiments.
Figure 62:
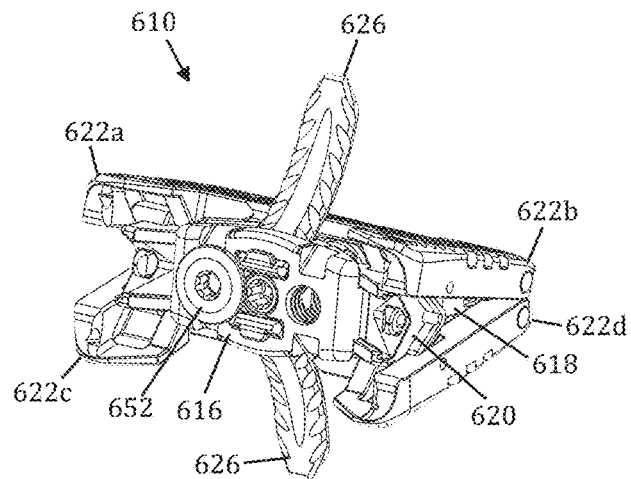
FIGS. 62-63 are perspective views of another example of an expandable fusion device in a fully expanded position, according to some embodiments.
Figure 63:
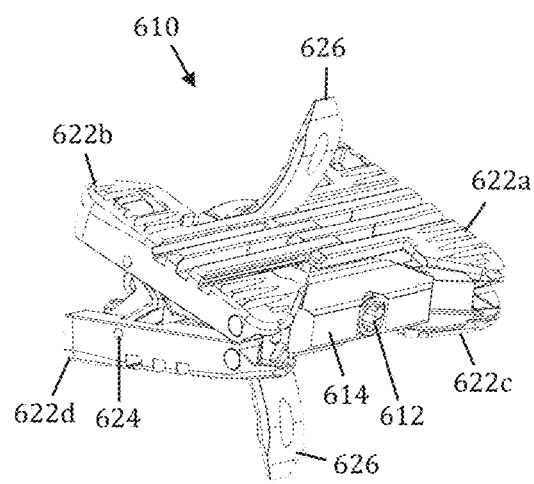

FIG. 59 illustrates an example of a second proximal ramp 521 according to the present example embodiment. In the instant embodiment, the second proximal ramp 521 is configured to slideably engage endplates 522b and 522d, enabling both lordotic and height expansion of endplates 522b, 522d. By way of example only, the proximal ramp 521 has a proximal end 574 and a distal end 576. The second proximal ramp 521 further includes at least one (e.g. first) arc ramp 578, and optionally a second (or more) arc ramp 578 (shown by way of example only) positioned distally of the first arc ramp 578 and separated from the first arc ramp 578 by a arc rail slot 580. The arc ramps 578 are curved along concentric arcs having a center point in the proximal direction. The arc ramps 578 are configured to slideably mate with first and second arc channels 584, respectively, of the corresponding endplates (e.g. endplates 522b, 522d). By way of example, the arc ramps 578 essentially function as pivot guides during lordosis expansion, but also help hold the expansion angle in place once lordosis expansion is complete. By way of example, in some embodiments the radius of curvature of the arc ramps 578 (and relevant corresponding structure) may be altered to increase maximum attainable height while decreasing maximum lordosis, and vice versa. The proximal end 574 includes a pair of tongue and groove connectors 582 configured to slideably interact with the corresponding tongue and groove connectors on the proximal wedge 516 as described above.

In operation, first width expansion proceeds substantially as described above with respect to previous embodiments. That is, the actuator 512 is turned a select number of actuations until maximum width expansion is reached and the endplate disengages from the distal wedge 514, and optionally the medial flanges 552 disengage from the lateral slots of the distal wedge 514. Once the disengagement occurs, further rotation of the actuator 512 results in the distal ramps 518 translating along the respective angled slots in the endplates, causing endplates 522a, 522c to pivot about a different cylindrical boss 570 of the first proximal ramp 520, increasing the lordosis angle between endplates 522a and 522c in the process. Simultaneously, translation of the distal ramps 518 cause the endplates 522b, 522d to translate along the arc ramps 578 of the second proximal ramp 521, increasing at least one of the height and lordosis angle between endplates 522b and 522d. This results in an asymmetric (or oblique-like) lordotic expansion of the expandable fusion device 510, as shown by way of example in FIGS. 60-61. For example, in a height/lordosis expanded position, lordotic expansion by oblique-like angle ∅ results in the minimum height differential between any endplate pairs occurring between the proximal ends of endplates 522a, 522c, and the maximum height differential between any endplate pairs occurring between the distal ends of endplates 522b, 522d. This is in contrast to the previously described embodiments 210 and 310, where at any expansion state, the proximal ends of the endplate pairs on the left and on the right side always have equal height differential and the distal ends of the endplate pairs on the left and on the right side also have equal height differential (though the height differentials on the distal and proximal ends are not the same, which is what generated the lordosis angle). In other embodiments, the height differential between the left and right pairs of endplates measured at the distal ends may be equal, but different when measured at the proximal ends. In other embodiments, the height differential between the left and right pairs of endplates measured at the proximal ends may be equal, but different when measured at the distal ends. In other words, actuation of the drive feature in for a first number of actuations in the first actuation direction results in width expansion. Actuation of the drive feature by a second number of actuations beyond the first number of actuations in the first actuation direction then increases at least one of width, height, and lordotic angle (e.g. oblique or oblique-like lordotic angle). In other embodiments, the first number of actuations of the actuator 512 may result in at least some height expansion (and in some embodiments—exclusively height expansion), whereas further rotation of the actuator 512 then increases at least one of width, height, and lordotic angle (e.g. oblique lordotic angle).

The expandable fusion device 510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 510.

FIGS. 62-75 illustrate an example of an expandable fusion device 610 for implantation between two adjacent vertebrae according to another embodiment of the disclosure, configured for example for anterior insertion. By way of example only, the expandable fusion device 610 of the present embodiment includes an actuator 612, a distal wedge 614, a proximal wedge 616, a pair of identical distal ramps 618, a pair of identical proximal ramps 620, a plurality of endplates 622a-622d, a plurality of optional guide pins 624, and at least one fixation shim 626. As with the previously-described embodiment, the distal and proximal wedges 614, 616 are coupled with the actuator 612. The distal ramps 618 are slideably coupled with the distal wedge 614 and pivotally coupled with the endplates 622a-622d. The proximal ramps 620 are slideably coupled with the proximal wedge 616 and endplates 622a-622d. Generally, the expandable fusion device 610 is substantially similar to expandable fusion device 10 described above, and any/all of the features described above with respect to fusion device 10 (and any other expandable fusion device described herein) may apply to fusion device 610 unless otherwise noted. By way of example only, the expandable fusion device 610 is illustrative of an expandable fusion device that expands in width, height, and lordotic expansion that may be applied to any expandable fusion device examples described herein, according to some embodiments.

Figure 64:
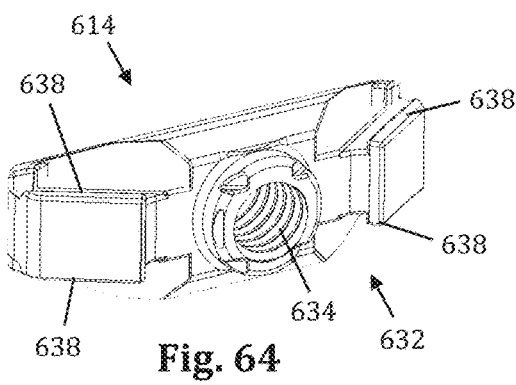
FIGS. 64-65 are perspective views of a distal wedge forming part of the expandable fusion device of FIG. 62, according to some embodiments.
Figure 65:
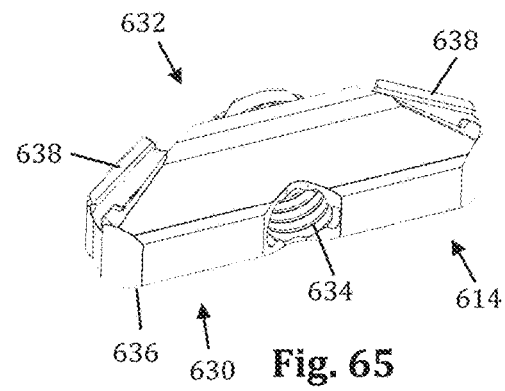

FIGS. 64-65 illustrate an example of a distal wedge 614 according to the present example embodiment. By way of example, the distal wedge 614 comprises a distal side 630, a proximal side 632, and a threaded bore 634 extending axially therethrough between the distal and proximal sides 630, 632. The distal wedge 614 includes distally tapered leading surfaces 636 that aid in the insertion process. The threaded bore 634 comprises an internal thread configured for threaded coupling with the actuator 612. The distal wedge 614 may be configured for slideable coupling with the distal ramps 618 and/or the endplates 622a-622d. By way of example only, the distal wedge 614 may include a plurality of tongue and groove connectors 638 configured to mate with corresponding features on the distal ramps 618 and the endplates 622a-622d to facilitate slideable coupling.

Figure 66:
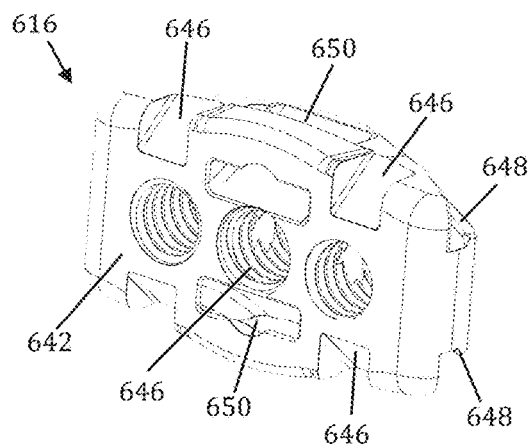
FIGS. 66-67 are perspective views of a proximal wedge forming part of the expandable fusion device of FIG. 62, according to some embodiments.
Figure 67:
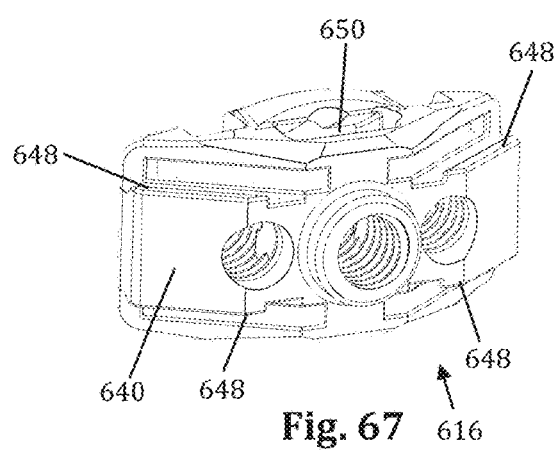

FIGS. 66-67 illustrate an example of a proximal wedge 616 according to the present example embodiment. By way of example, the proximal wedge 616 has a distal side 640, a proximal side 642, and a threaded bore 644 extending axially therethrough between the distal and proximal sides 640, 642. The proximal wedge 616 further comprises one or more engagement features 646 configured for temporary attachment to an inserter tool, for example one or more recesses 646 on the top and/or bottom sides of the distal wedge 616. The threaded bore 644 comprises an internal thread configured for threaded coupling with the actuator 612. The proximal wedge 616 may be configured for slideable coupling with the proximal ramps 620 and/or the endplates 622a-622d. By way of example only, the proximal wedge 616 may include a plurality of tongue and groove connectors 648 configured to mate with corresponding features on the proximal ramps 620 and the endplates 622a-622d to facilitate slideable coupling. In some embodiments, the proximal wedge 616 may further include shim slots 650 configured to receive fixation shims 626 therethrough, and a locking element 652 configured to secure the fixation shims 626 in place after implantation.

Figure 68:
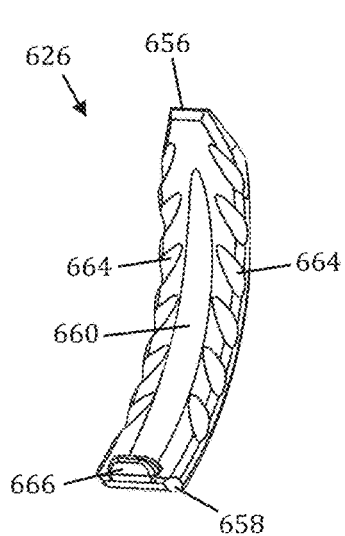
FIGS. 68-69 are perspective views of a fixation shim forming part of the expandable fusion device of FIG. 62, according to some embodiments.
Figure 69:
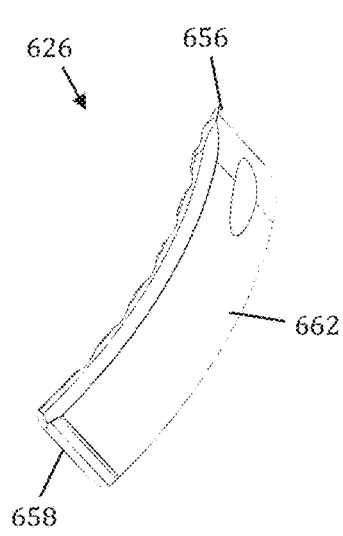
Figure 70:
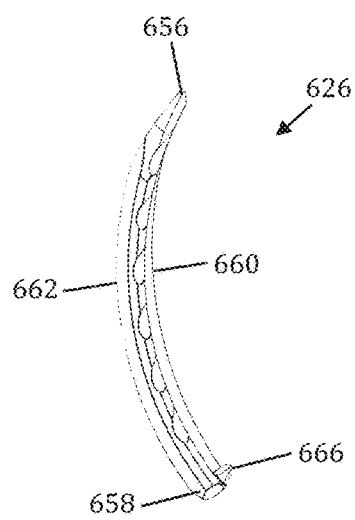
FIG. 70 is a side plan view of the fixation shim of FIG. 68, according to some embodiments.

FIGS. 68-70 illustrate an example of a fixation shim 626 according to the present example embodiment. By way of example, the fixation shim 626 comprises an elongated body 654 extending between a distal end 656 and a proximal end 658. In some embodiments, the elongated body 654 may comprise a curved member having a generally concave first surface 660 and a generally convex second surface 662. By way of example, one of the surfaces (e.g. the generally convex second surface 662) may be smooth to facilitate insertion into bony tissue, and one of the surfaces (e.g. the generally concave first surface 660) may have surface treatment 664 (e.g. roughening, recesses, ridges, protrusions, etc.) to facilitate purchase of the fixation shim 626 once inserted into adjacent bony tissue. The distal end 656 may be shaped (e.g. pointed, tapered, beveled, etc.) to facilitate insertion into the bony tissue. In some embodiments, the proximal end 658 may have a depth stop 666 configured to prevent advancement of the fixation shim when the depth stop 666 comes into contact with the proximal wedge 616.

Figure 71:
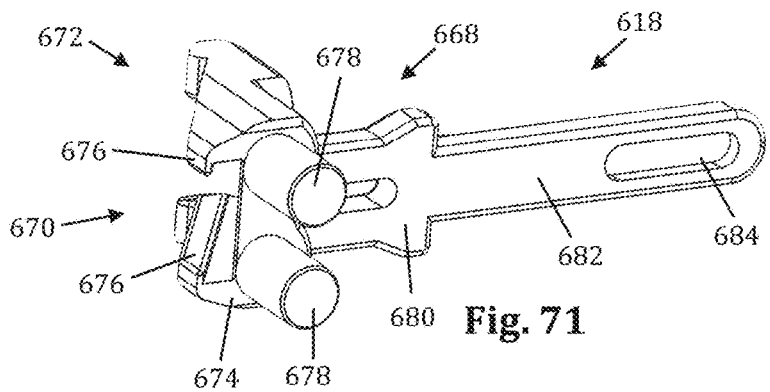
FIG. 71 is a perspective view of an example of a distal ramp forming part of the expandable fusion device of FIG. 62, according to some embodiments.

FIG. 71 illustrates an example of a distal ramp 618 according to the present example embodiment. In the instant embodiment, the distal ramp 618 is configured to hingedly engage the endplates 622a-622d to enable lordotic expansion without height expansion. By way of example only, the distal ramp 618 has a proximal end 668, distal end 670, medial side 672, and lateral side 674. The medial side 672 has upper and lower tongue and groove connectors 676 configured to slideably interact with the corresponding tongue and groove connectors on the distal wedge 616 to enable width expansion as described with respect to expandable fusion device 10 above. By way of example only, the distal ramp 618 of the present embodiment has a pair of lateral facing cylindrical bosses 678 configured to be received within boss apertures 702 on the distal end of each of the endplates 622a-622d such that the endplates 622a-622d are pivotally mated with the distal ramp 618. The ends of the bosses 678 may be swaged or otherwise detained within the boss apertures 702. In some embodiments, each distal ramp 618 may further include a proximal flange 680 configured to nest within the elongated recesses 700 formed in the endplates 622a-622d when the lordotic expansion angle between endplate pairs (e.g. 622a and 622c, 622b and 622d) is below a predetermined threshold or within a useful/working range (e.g. any lordotic expansion angle range achieved during clinical use), to prevent the cylindrical bosses 678 from disengaging from the boss apertures 702 during clinical use. The proximal flanges 680 may be further configured for removal from the elongated recesses 700 when the lordotic expansion angle between endplate pairs (e.g. 622a and 622c, 622b and 622d) is above the predetermined threshold (e.g. outside the parameters of clinical use), enabling assembly and/or disassembly of the endplates and the distal ramp 618. In some embodiments, the distal ramp 618 may further comprise a proximal extension 682 extending from the proximal flange 680 and configured to mate with engagement slot 698 of the proximal ramp 620. By way of example only, the mating of the distal ramp 618 and proximal ramp 620 in this fashion may provide additional stability during expansion (e.g. width, height, and/or lordotic). In some embodiments, the proximal extension 682 may include an elongated slot 684 near the proximal end of the proximal extension 682 configured to translatably receive a retaining pin therein to prevent dissociation from the proximal ramp 620 during height/lordotic expansion.

Figure 72:
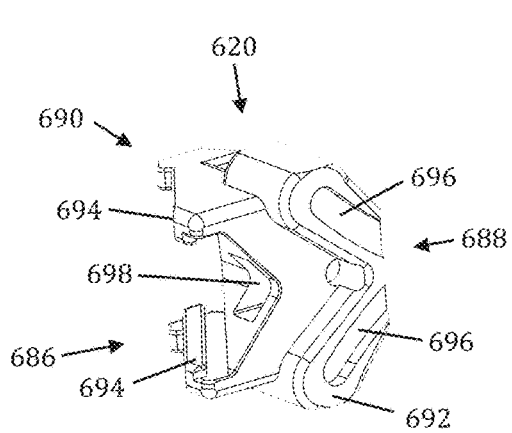
FIG. 72 is a perspective view of an example of a proximal ramp forming part of the expandable fusion device of FIG. 62, according to some embodiments.

FIG. 72 illustrates an example of a proximal ramp 620 according to the present example embodiment. By way of example only, the proximal ramp 620 has a proximal end 686, distal end 688, medial side 690, and lateral side 692. The medial side 690 includes a pair of tongue and groove connectors 694 configured to slideably interact with the corresponding tongue and groove connectors on the proximal wedge 616 as described with respect to expandable fusion device 10 above. The proximal ramp 620 has a V-shaped recessed ramp slot 696 formed within the lateral side 692 and configured to slideably receive one or more guide pins 624 therein to help stabilize the construct during lordotic expansion, as well as provide a hard stop for lordotic expansion. The guide pin 624 functions as a lordosis-expansion limiting member as it will stop lordosis expansion when the guide pin 624 reaches the end of the ramp slot 696. The proximal ramp 620 may further include an engagement slot 698 configured to receive at least a portion of the proximal extension 682 of the distal ramp 618 therethrough to stabilize the assembly during height/lordotic expansion.

Figure 73:
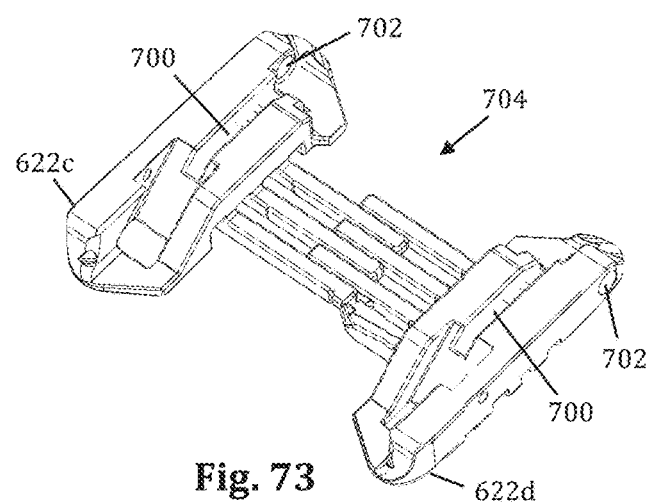
FIG. 73 is a perspective view of an example of a lower endplate assembly forming part of the expandable fusion device of FIG. 62, according to some embodiments.
Figure 74:
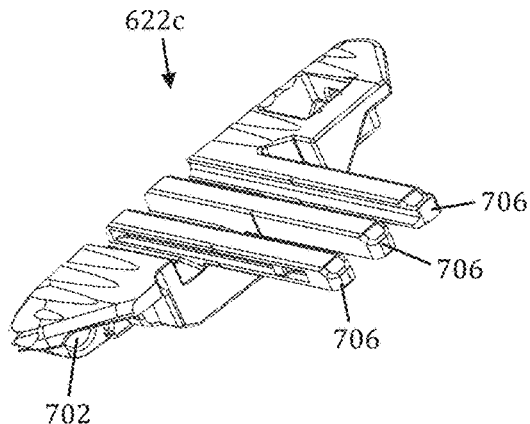
FIG. 74 is a perspective view of an example of an endplate forming part of the expandable fusion device of FIG. 62, according to some embodiments.
Figure 75:
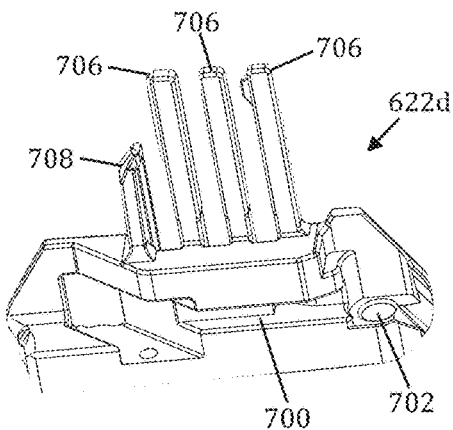
FIG. 75 is a perspective view of another example of an endplate forming part of the expandable fusion device of FIG. 62, according to some embodiments.
Figure 76:
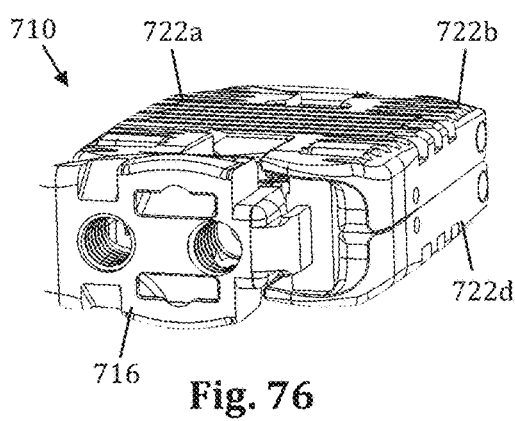
FIG. 76 is a perspective view of another example of an expandable fusion device in a collapsed position, according to some embodiments.
Figure 77:
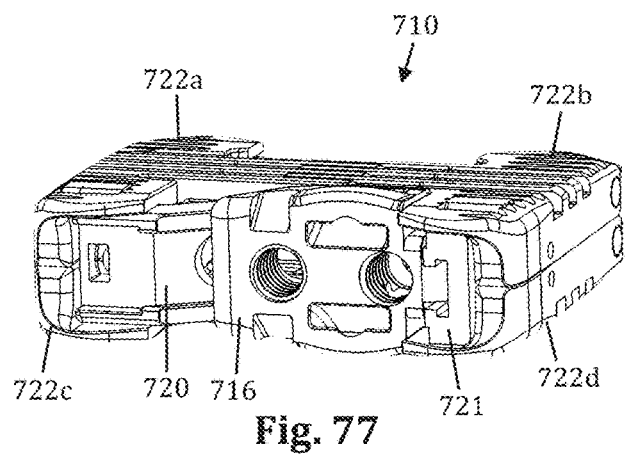
FIG. 77 is a perspective view of the expandable fusion device of FIG. 76 in a width expanded position, according to some embodiments.
Figure 78:
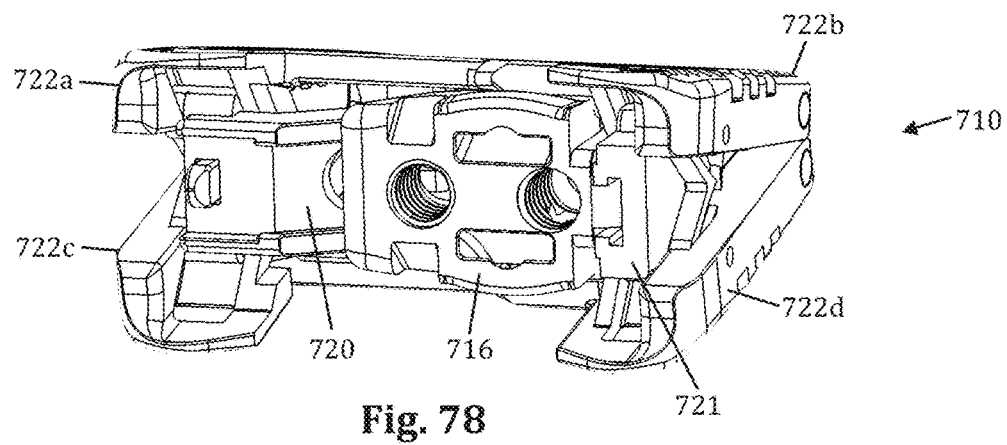
FIG. 78 is a perspective view of the expandable fusion device of FIG. 76 in a fully expanded position, according to some embodiments.
Figure 79:
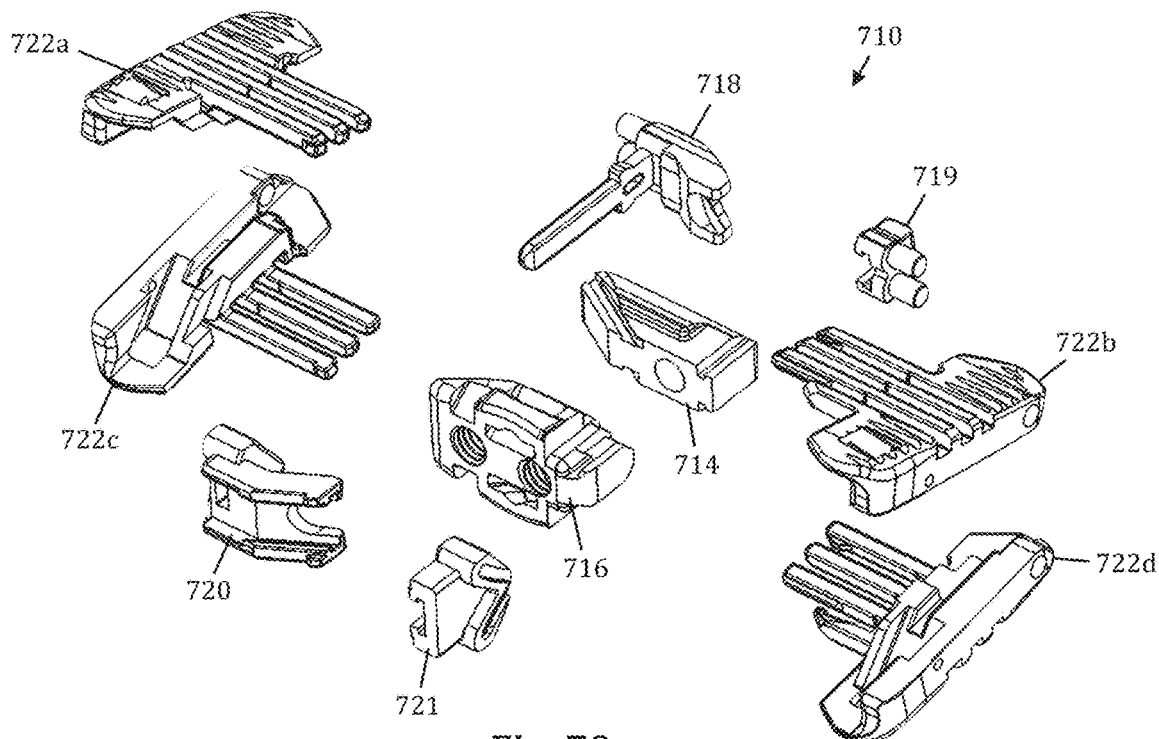
FIG. 79 is an exploded perspective view of the expandable fusion device of FIG. 76, according to some embodiments.

By way of example only, FIGS. 73-75 illustrate the bottom endplates 622c, 622d according to the present embodiment. In the instant embodiment, the top endplate 622a identical to the bottom endplate 622d, and the top endplate 622b is identical to the bottom endplate 622c. By way of example only, the distal aspects of the endplates 622a-622d may include an elongated recess 700 configured to receive proximal flange 680 and proximal extension 682 of the distal ramp 618 therein, and a boss aperture 702 configured to receive a cylindrical boss 678 of the distal ramp 618 therein. By way of example, the endplates 622a-622d of the present embodiment may include a width stabilizer feature 704 similar to those described with respect to other embodiments disclosed herein. By way of example, the width stabilizer feature 704 may comprise a plurality of interdigitated medial flanges 706 having stabilizing grooves and protrusions as described above. In the instant example embodiment, the proximal-most medial flange 708 (e.g. on top endplate 622a and/or bottom endplate 622d) may be truncated to accommodate the fixation shim 626.

In operation, first width expansion proceeds substantially as described above with respect to previous embodiments. That is, the actuator 612 is turned a select number of actuations until some width expansion is reached and the endplate disengages from the distal wedge 614. Once the disengagement occurs, further rotation of the actuator 612 results in the proximal ramps 620 translating along the respective angled slots in the endplates and each endplate pivoting about a different cylindrical boss 678, increasing at least one of the width, height, and lordosis angle in the process. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle.

The expandable fusion device 610 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 610.

FIGS. 76-89 illustrate an example of an expandable fusion device 710 for implantation between two adjacent vertebrae according to another embodiment of the disclosure, configured for example for anterior insertion. The expandable fusion device 710 of the present example embodiment is similar to the expandable fusion device 610 described herein above, but is configured (by way of example only) for unilateral width expansion. By way of example only, the expandable fusion device 710 of the present embodiment includes an actuator (not shown), a distal wedge 714, a proximal wedge 716, first and second distal ramps 718, 719, first and second proximal ramps 720, 721, a plurality of endplates 722a-722d, a plurality of optional guide pins 724, and at least one fixation shim (not shown). As with the previously-described embodiment, the distal and proximal wedges 714, 716 are coupled with the actuator. The distal ramps 718, 719 are slideably coupled with the distal wedge 714 and pivotally coupled with the endplates 722a-722d. The proximal ramps 720, 721 are slideably coupled with the proximal wedge 716 and endplates 722a-722d. Generally, the expandable fusion device 710 is substantially similar to expandable fusion device 10 described above, and any/all of the features described above with respect to fusion device 10 (and any other expandable fusion device described herein) may apply to fusion device 710 unless otherwise noted. By way of example only, the expandable fusion device 710 is illustrative of an expandable fusion device that expands in width, height, and lordotic expansion that may be applied to any expandable fusion device examples described herein, according to some embodiments.

Figure 80:
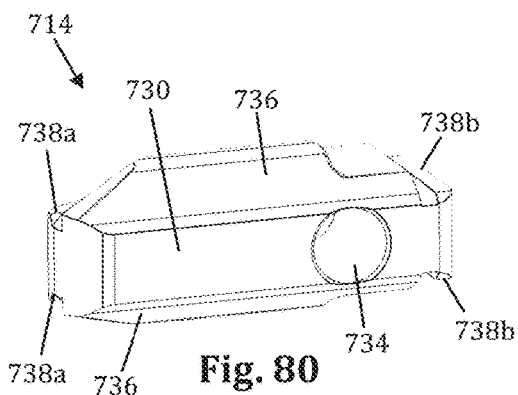
FIGS. 80-81 are perspective views of a distal wedge forming part of the expandable fusion device of FIG. 76, according to some embodiments.
Figure 81:
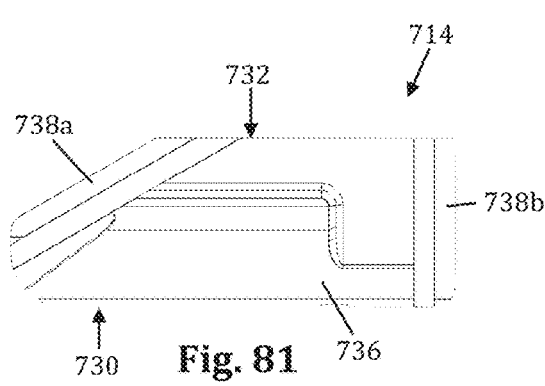

FIGS. 80-81 illustrate an example of a distal wedge 714 according to the present example embodiment. By way of example, the distal wedge 714 comprises a distal side 730, a proximal side 732, and a threaded bore 734 extending axially therethrough between the distal and proximal sides 730, 732. The distal wedge 714 includes distally tapered leading surfaces 736 that aid in the insertion process. The threaded bore 734 comprises an internal thread (for example right handed thread) configured for threaded coupling with the actuator 712. The distal wedge 714 may be configured for slideable coupling with the distal ramps 718 and/or the endplates 722a-722d. By way of example only, the distal wedge 714 may include a plurality of tongue and groove connectors 738a, 738b configured to mate with corresponding features on the distal ramps 718 and the endplates 722a, 722c to facilitate slideable coupling. By way of example, the tongue and groove connectors 738a, 738b may be arranged and configured to enable the unilateral width expansion feature of the present embodiment. More specifically, the tongue and groove connectors 738a on one side of the distal wedge 714 (e.g. that are configured to engage the width-expanding endplates 722a, 722c) may be formed at an oblique angle relative to the longitudinal axis of the device 710 so that endplates (e.g. endplates 722a, 722c) translating along them translate generally away from endplates 722b, 722d, thereby effecting width expansion. The tongue and groove connectors 738b may be arranged in an axial orientation parallel to the longitudinal axis of the expandable fusion device 710 so that no width expansion occurs on that side of the device 710.

Figure 82:
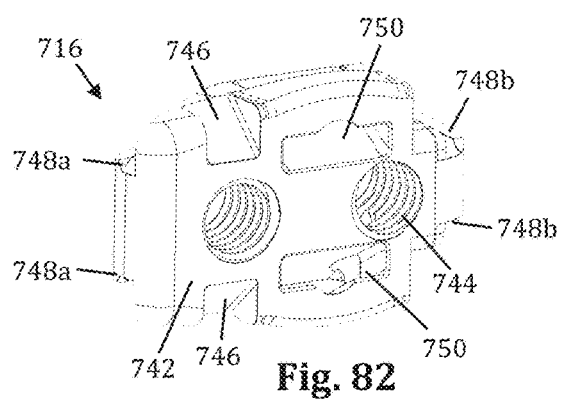
FIGS. 82-83 are perspective views of a proximal wedge forming part of the expandable fusion device of FIG. 76, according to some embodiments.
Figure 83:
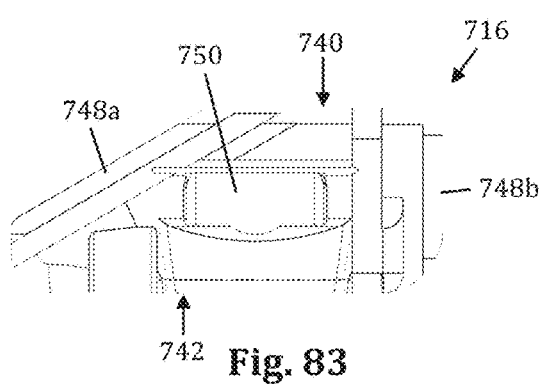
Figure 98:
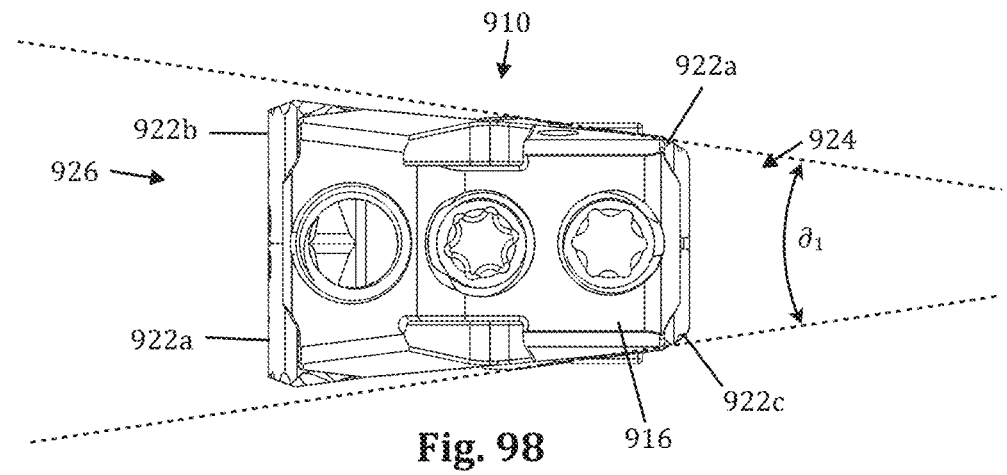
FIG. 98 is an end plan view of the expandable fusion device of FIG. 95 in a collapsed position, according to some embodiments.
Figure 99:
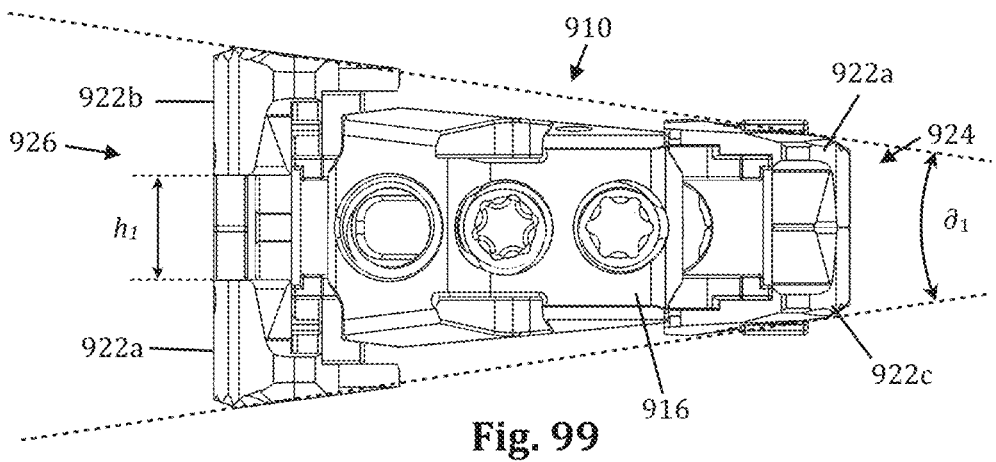
FIG. 99 is an end plan view of the expandable fusion device of FIG. 95 in a width-expanded position, according to some embodiments.
Figure 100:
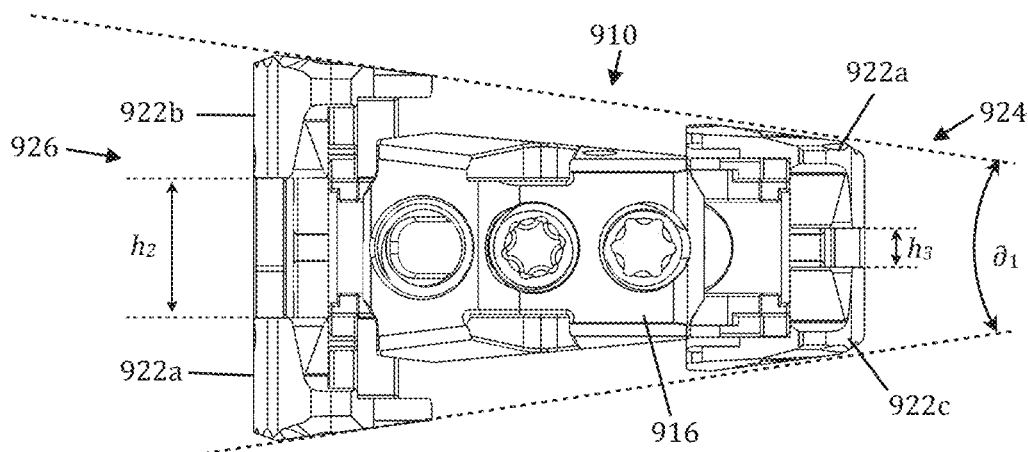
FIG. 100 is an end plan view of the expandable fusion device of FIG. 95 in a fully expanded position, according to some embodiments.
Figure 101:
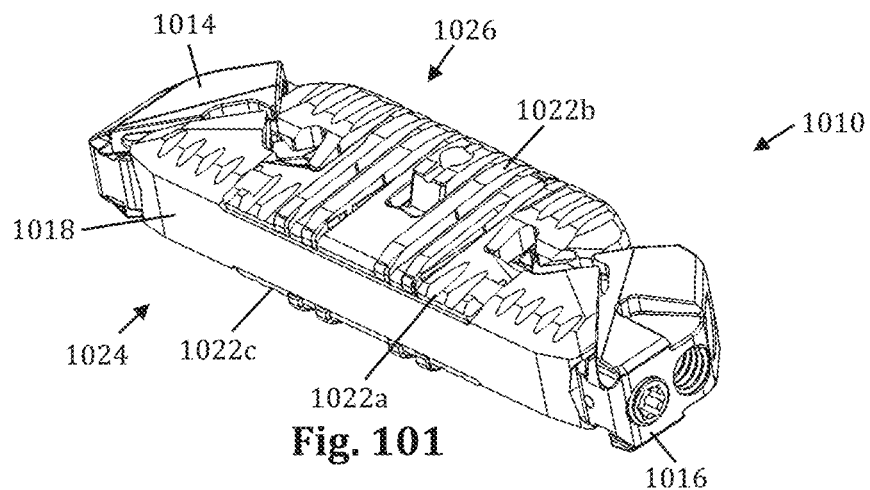
FIG. 101 is a perspective view of another example of an expandable fusion device in a collapsed position, according to some embodiments.
Figure 102:
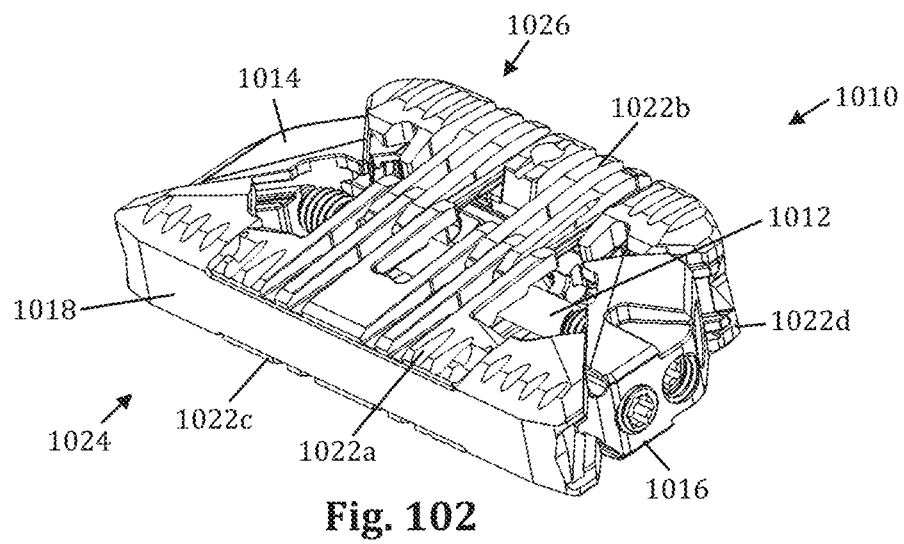
FIG. 102 is a perspective view of the expandable fusion device of FIG. 101 in a width expanded position, according to some embodiments.
Figure 103:
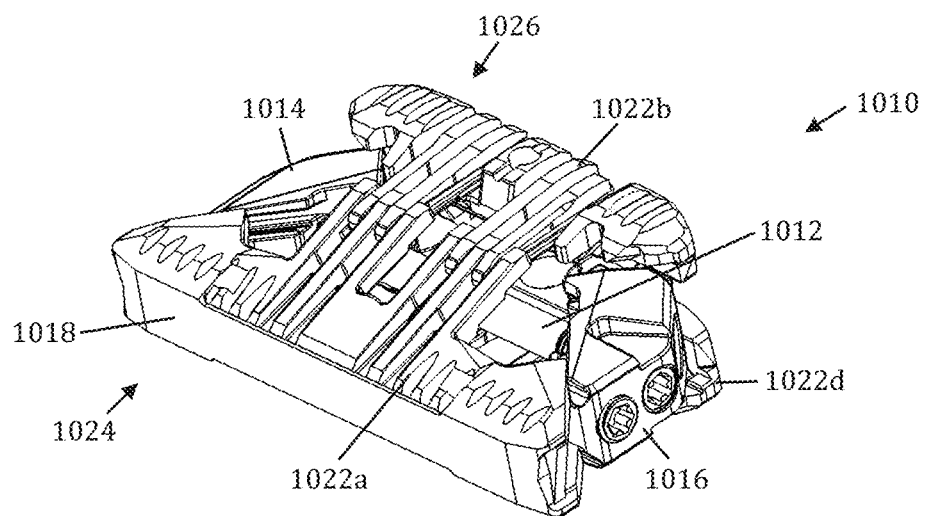
FIG. 103 is a perspective view of the expandable fusion device of FIG. 101 in a fully expanded position, according to some embodiments.
Figure 104:
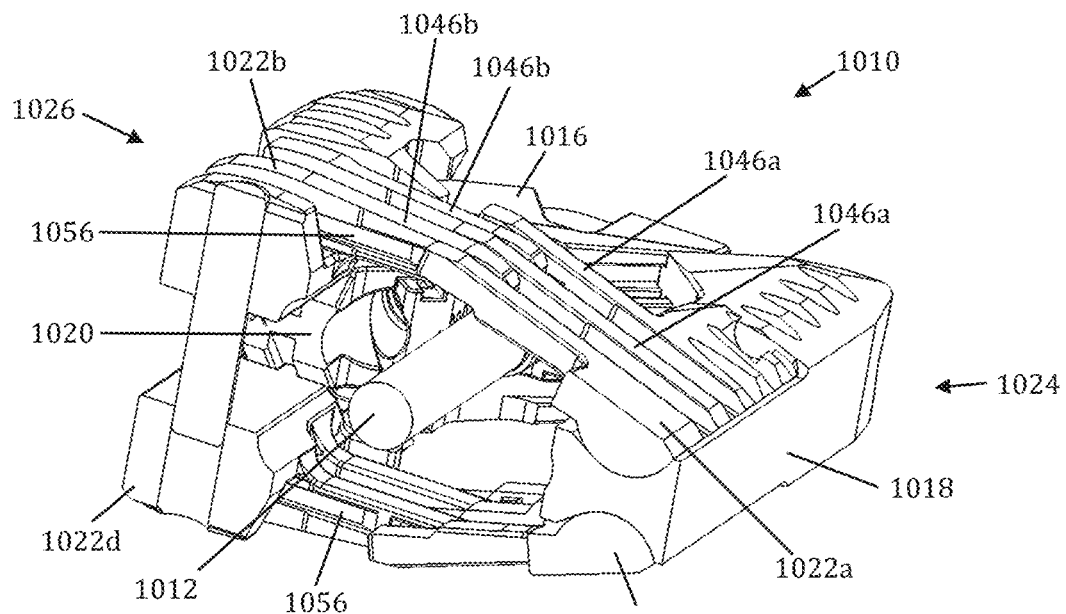
FIG. 104 is a sectional view of the expandable fusion device of FIG. 101 in a fully expanded position, according to some embodiments.
Figure 105:
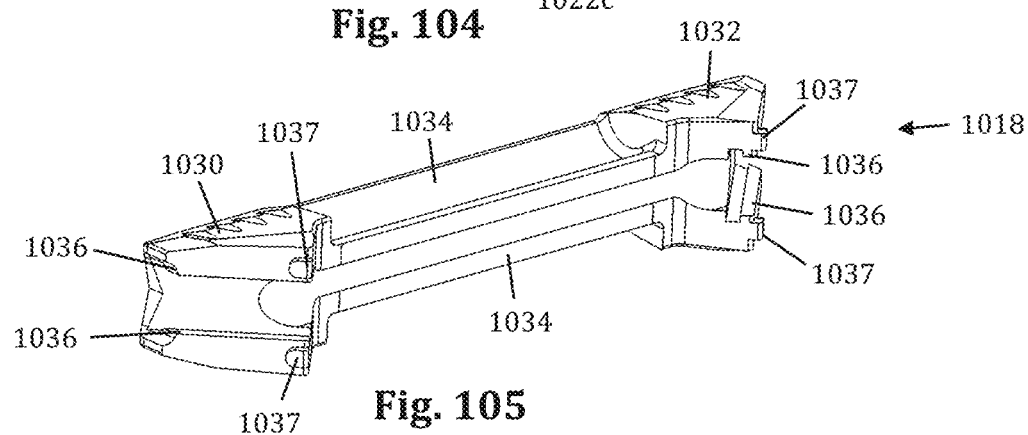
FIG. 105 is a perspective view of an example of a posterior beam forming part of the expandable fusion device of FIG. 101, according to some embodiments.
Figure 106:
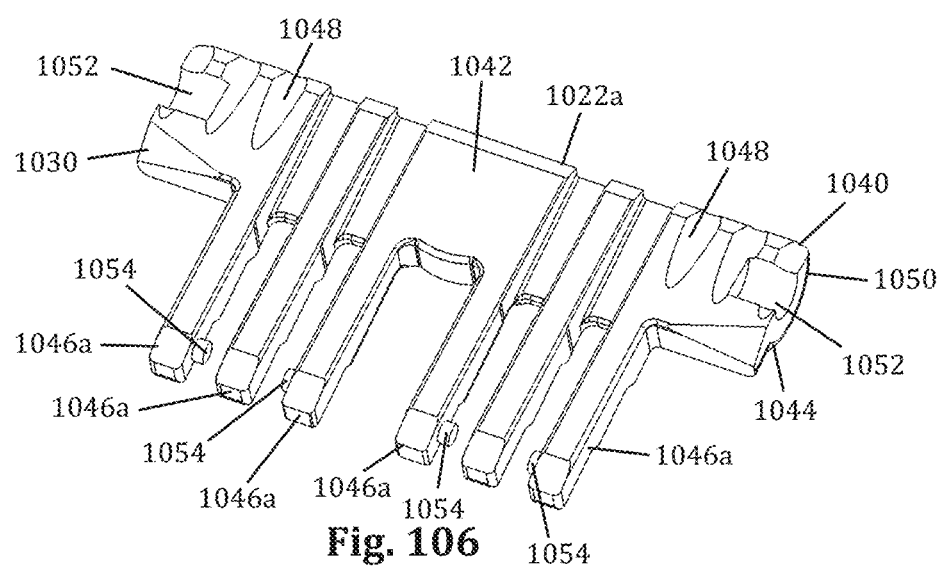
FIG. 106 is a perspective view of an example of a posterior endplate forming part of the expandable fusion device of FIG. 101, according to some embodiments.
Figure 107:
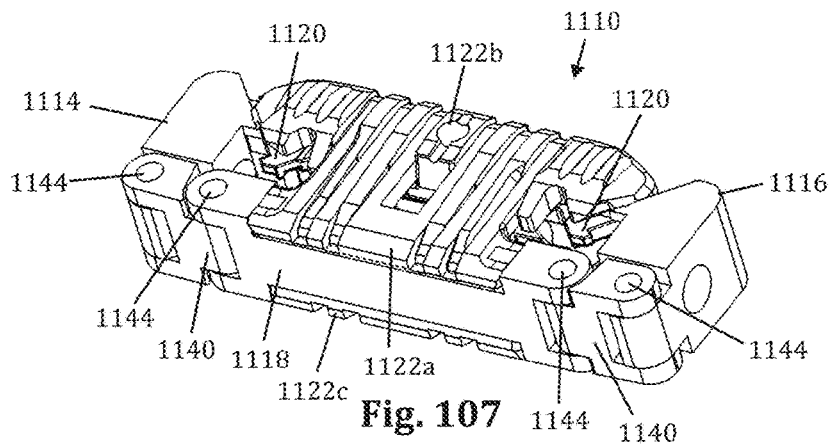
FIG. 107 is a perspective view of another example of an expandable fusion device in a collapsed position, according to some embodiments.
Figure 108:
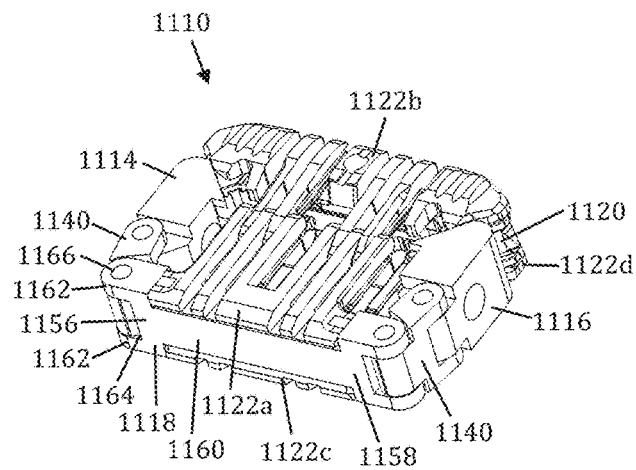
FIG. 108 is a perspective view of the expandable fusion device of FIG. 107 in a width expanded position, according to some embodiments.
Figure 109:
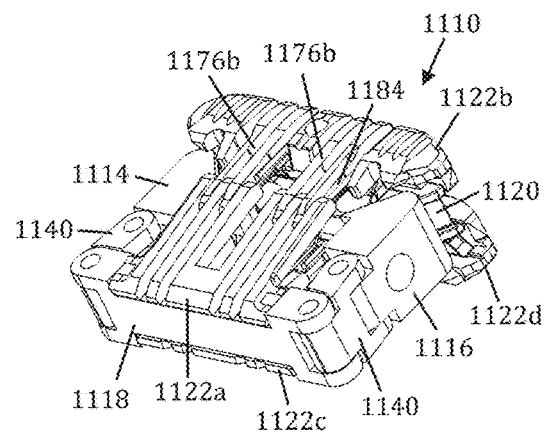
FIG. 109 is a perspective view of the expandable fusion device of FIG. 107 in a fully expanded position, according to some embodiments.
Figure 110:
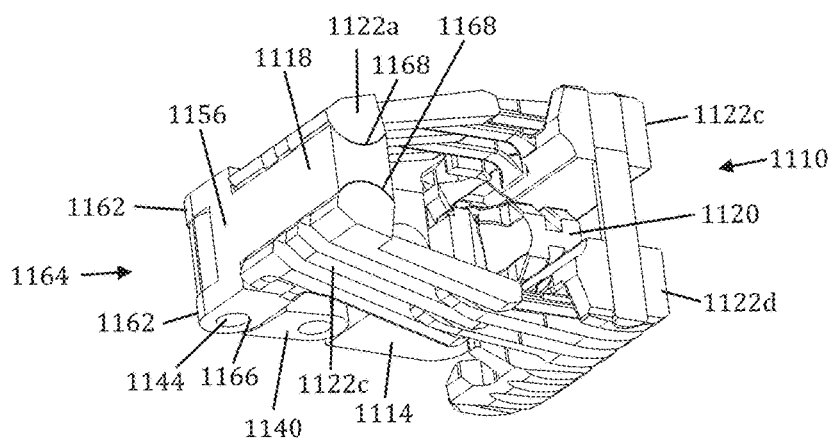
FIG. 110 is a sectional view of the expandable fusion device of FIG. 107 in a fully expanded position, according to some embodiments.
Figure 116:
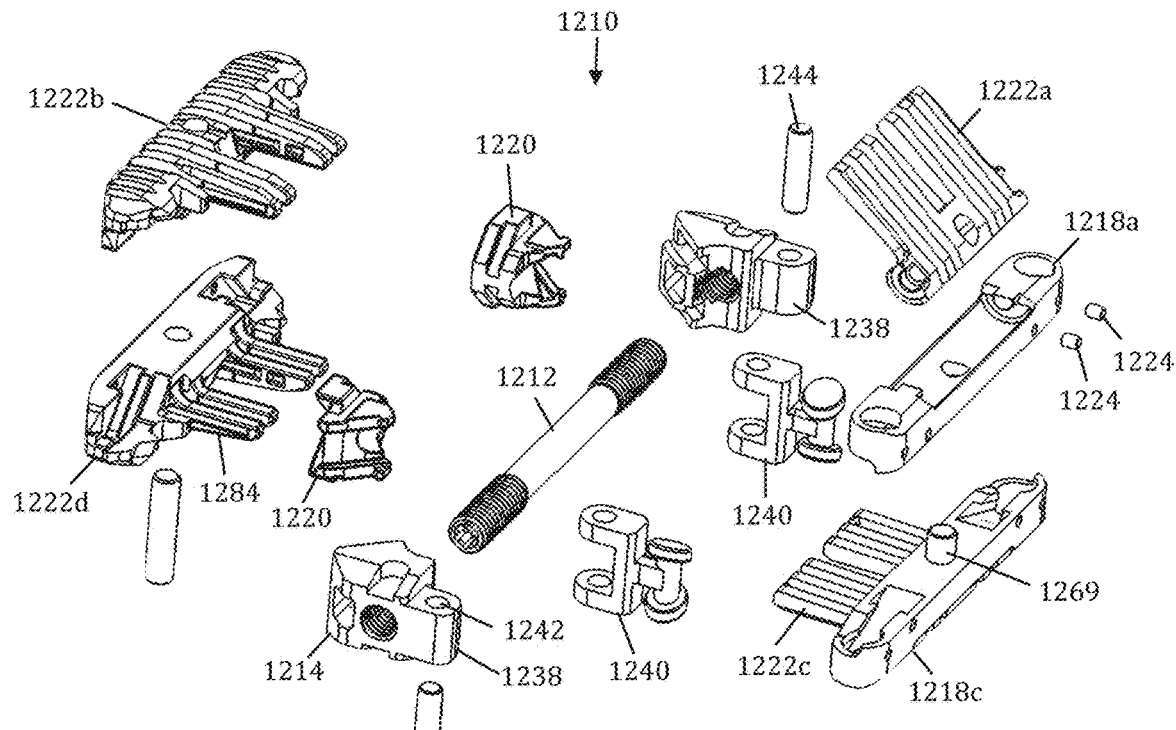
FIG. 116 is an exploded perspective view of the expandable fusion device of FIG. 113, according to some embodiments.

FIGS. 82-83 illustrate an example of a proximal wedge 716 according to the present example embodiment. By way of example, the proximal wedge 716 has a distal side 740, a proximal side 742, and a threaded bore 744 extending axially therethrough between the distal and proximal sides 740, 742. The proximal wedge 716 further comprises one or more engagement features 746 configured for temporary attachment to an inserter tool, for example one or more recesses 746 on the top and/or bottom sides of the distal wedge 716. The threaded bore 744 comprises an internal thread (for example left handed thread) configured for threaded coupling with the actuator. The proximal wedge 716 may be configured for slideable coupling with the proximal ramps 720 and/or the endplates 722a-722d. By way of example only, the proximal wedge 716 may include a plurality of tongue and groove connectors 748a, 748b configured to mate with corresponding features on the proximal ramps 720 and the endplates 722a, 722c to facilitate slideable coupling. By way of example, the tongue and groove connectors 748a, 748b may be arranged and configured to enable the unilateral width expansion feature of the present embodiment. More specifically, the tongue and groove connectors 748a on one side of the proximal wedge 716 (e.g. that are configured to engage the width-expanding endplates 722a, 722c) may be formed at an oblique angle relative to the longitudinal axis of the device 710 so that endplates (e.g. endplates 722a, 722c) translating along them translate generally away from endplates 722b, 722d, thereby effecting width expansion. The tongue and groove connectors 748b may be arranged in an axial orientation parallel to the longitudinal axis of the expandable fusion device 710 so that no width expansion occurs on that side of the device 710. In some embodiments, the proximal wedge 716 may further include shim slots 750 configured to receive fixation shims therethrough, and a locking element (not shown) configured to secure the fixation shims in place after implantation. In any embodiment, the tongue and groove connectors may be dovetailed connectors or have any other geometry allowing linear translation along substantially one axis when engaged.

FIG. 84 illustrates an example of a first distal ramp 718 according to the present example embodiment. In the instant embodiment, the distal ramp 718 is configured to hingedly engage the endplates 722a, 722c to enable lordotic expansion without height expansion. By way of example only, the distal ramp 718 has a proximal end 752, distal end 754, medial side 756, and lateral side 758. By way of example, the medial side 758 comprises a medial extension 760 having upper and lower tongue and groove connectors 762 configured to slideably interact with the oblique tongue and groove connectors 738a on the distal wedge 716 to enable width expansion as described with respect to expandable fusion device 10 above. The medial extension 760 allows the tongue and groove connectors 762 to be oriented at a wider angle relative to the longitudinal axis of the device 710, enabling a greater distance of width expansion, which may be beneficial in a unilateral expansion embodiment. By way of example only, the distal ramp 718 of the present embodiment has a pair of lateral facing cylindrical bosses 764 configured to be received within boss apertures 765 on the distal end of each of the endplates 722a, 722c (e.g. the width-expanding endplates) such that the endplates 722a, 722c are pivotally mated with the first distal ramp 718 to enable lordotic expansion. The ends of the bosses 764 may be swaged or otherwise detained within the boss apertures 765. In some embodiments, the first distal ramp 718 may further include a proximal flange 766 configured to nest within the elongated recesses 767 formed in the endplates 722a, 722c when the lordotic expansion angle between the endplate pair is below a predetermined threshold or within a useful/working range, as described above. In some embodiments, the distal ramp 718 may further comprise a proximal extension 768 extending from the proximal flange 766 and configured to mate with engagement slot 798 of the first proximal ramp 720. By way of example only, the mating of the distal ramp 718 and first proximal ramp 720 in this fashion may provide additional stability during expansion (e.g. width, height, and/or lordotic). In some embodiments, the proximal extension 768 may include an elongated slot 770 near the proximal end of the proximal extension 768 configured to translatably receive a retaining pin therein to prevent dissociation from the proximal ramp 720 during height/lordotic expansion.

FIG. 85 illustrates an example of a second distal ramp 719 according to the present example embodiment. In the instant embodiment, the second distal ramp 719 is configured to hingedly engage the endplates 722b, 722d to enable lordotic expansion without height expansion. By way of example only, the second distal ramp 719 has a proximal end 772, a distal end 774, a medial side 776, and a lateral side 778. By way of example, the medial side 776 comprises upper and lower tongue and groove connectors 780 configured to slideably interact with the axial tongue and groove connectors 738b on the distal wedge 716 to prohibit width expansion of the endplates 722b, 722d. The second distal ramp 719 of the present embodiment further includes a pair of lateral facing cylindrical bosses 782 configured to be received within boss apertures 765 on the distal end of each of the endplates 722b, 722d (e.g. the width-stable endplates) such that the endplates 722b, 722d are pivotally mated with the second distal ramp 719 to enable lordotic expansion. The ends of the bosses 782 may be swaged or otherwise detained within the boss apertures 765.

FIGS. 86-87 illustrate an example of a first proximal ramp 720 according to the present example embodiment. By way of example only, the first proximal ramp 720 has a proximal end 786, distal end 788, medial side 790, and lateral side 792. The medial side 790 comprises a medial extension 784 having a pair of tongue and groove connectors 794 configured to slideably interact with the oblique tongue and groove connectors 748a on the proximal wedge 716 as described with respect to expandable fusion device 10 above. The medial extension 784 allows the tongue and groove connectors 794 to be oriented at a wider angle relative to the longitudinal axis of the device 710, enabling a greater distance of width expansion, which may be beneficial in a unilateral expansion embodiment. The proximal ramp 720 has a recessed ramp slot 796 formed within the lateral side 792 and configured to slideably receive one or more guide pins 724 therein to help stabilize the construct during lordotic expansion, as well as provide a hard stop for lordotic expansion. The proximal ramp 720 may further include an engagement slot 798 configured to receive at least a portion of the proximal extension 768 of the first distal ramp 718 therethrough to stabilize the assembly during height/lordotic expansion.

FIG. 88 illustrates an example of a second proximal ramp 721 according to the present example embodiment. By way of example only, the second proximal ramp 721 has a proximal end 800, a distal end 802, a medial side 804, and a lateral side 806. By way of example, the medial side 804 comprises upper and lower tongue and groove connectors 808 configured to slideably interact with the axial tongue and groove connectors 748b on the proximal wedge 716 to prohibit width expansion of the endplates 722b, 722d while the endplates 722a, 722c do expand in width. The second proximal ramp 721 of the present embodiment further includes a recessed ramp slot 809 formed within the lateral side 806 and configured to slideably receive one or more guide pins 724 therein to help stabilize the construct during lordotic expansion, as well as provide a hard stop for lordotic expansion.

In operation, first width expansion proceeds substantially as described above with respect to previous embodiments, however due to the relevant structure of the present embodiment (e.g. oblique tongue and groove connectors 738a, 748a and axial tongue and groove connectors 738b, 748b and their corresponding interaction with the endplates 722a-722d), only the endplates 722a, 722c participate in width expansion. That is, the actuator is turned a select number of actuations until some width expansion of endplates 722a, 722c is reached and the endplates disengage from the wedges 714, 716. Once the disengagement occurs, further rotation of the actuator results in the proximal ramps 720, 721 translating along the respective angled slots in the endplates and each endplate pivoting about a different cylindrical boss 764, 782, increasing at least one of the width, height, and lordosis angle in the process. In other words, actuation of the drive feature in for a first number of actuations in the first actuation direction results in at least some unilateral width expansion. Actuation of the drive feature by a second number of actuations beyond the first number of actuations in the first actuation direction then increases at least one of width and lordotic angle, but may also increase height.

The expandable fusion device 710 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 710.

FIGS. 90-94 illustrate an example of a modular fixation plate 810 configured for use with the expandable fusion device 10 (and other embodiments thereof) described herein, according to some embodiments. By way of example only, the modular fixation plate 810 comprises a proximal side 812, a distal side 814, and one or more shim slots 816. The shim slots 816 may be positioned at or near the middle of the proximal side 812, and are configured to receive fixation shims 818 such that at least a portion of the fixation shims 818 pass through the shim slots 816 and into patient tissue, while at least a portion of the fixation shim 818 remains on the proximal side of the modular fixation plate 810 to secure the fixation shim 818 to the modular fixation plate 810. In the instant example embodiment, the fixation shims 818 are identical to fixation shims 626 described above, however the modular fixation plate 810 may be configured to employ any suitable fixation shim 818, including but not limited to curved, straight, smooth, roughened, threaded, and the like. By way of example, the shim slots 816 may be curved to accommodate the shape of curved fixation shims 818, and may be configured such that the fixation shims 818 are advanced through a proximal opening of the shim slot 816 and at least a portion of the fixation shim 818 exits through a distal opening of the shim slot 816.

The proximal side 812 may further include a coupling aperture 820, a lock screw aperture 822, and a plurality of engagement elements 824. By way of example only, the coupling aperture 820 may be positioned on one side of the shim slots 816, and is configured to optionally receive a coupling element 826 therethrough. The coupling element 826 may be any structure configured to couple the modular fixation plate 810 to the expandable fusion device 10 (for example). In the instant embodiment, the coupling element 826 comprises a head 828 including a drive feature 830 and a threaded shaft 832 configured to engage a receiving element on the expandable fixation plate 10, (e.g., the auxiliary aperture 61 of the proximal wedge 16). In some embodiments, the coupling element 826 may be retained within the modular fixation plate 810, for example by way of a press-fit engagement with the coupling aperture 820. The lock screw aperture 822 may be configured to threadedly receive a lock screw 834 therein (or other suitable anti-backout mechanism), the lock screw 834 having a head portion configured to at least partially cover the proximal ends of the fixation shims 818 when the fixation shims 818 are fully inserted, providing a physical barrier to backout of the fixation shims 818. By way of example, a plurality of engagement elements 824 may be provided that are configured to receive at least a portion of an inserter tool (for example).

The distal side 814 may be shaped to complement the shape and contour of the portion of the expandable fixation device 10 (or any embodiment described herein) that the modular fixation plate 810 is attached to. In some embodiments, the distal side 814 may include additional features to aid in coupling the modular fixation plate 810 to the expandable fusion device 10. By way of example only, the distal side 814 may include one or more flanges 836 sized and configured to mate with the engagement feature or recess 58 of the proximal wedge 16 (for example).

Optionally, in any embodiment, the modular fixation plate 810 may be coupled to the expandable fusion device 10 after the expandable fusion device 10 has been fully implanted in the patient, and optionally after graft material has been added. Thus, the modular fixation plate 810 may function not only to secure the expandable fusion device 10 to the patient anatomy, but also as a graft containment device.

FIGS. 95-100 illustrate an example of an expandable fusion device 910 for implantation between two adjacent vertebrae according to another embodiment of the disclosure. By way of example only, the expandable fusion device 910 of the present embodiment includes an actuator 912, a distal wedge 914, a proximal wedge 916, a pair of posterior ramps 918a, 918b (e.g. comprising distal posterior ramp 918a and proximal posterior ramp 918b), a pair of anterior ramps 920a, 920b (e.g. comprising distal anterior ramp 920a and proximal anterior ramp 920b), a plurality of endplates 922a-922d, and optionally a plurality of guide pins. As with previously-described embodiments, the distal and proximal wedges 914, 916 are coupled with the actuator 912. The distal ramps 918a, 920a are slideably coupled with the distal wedge 914. The proximal ramps 918b, 920b are slideably coupled with the proximal wedge 916. The plurality of endplates 922a-922d are slideably coupled with the ramps 918a, 918b, 920a. 920b. Generally, the expandable fusion device 910 is substantially similar to expandable fusion device 10 described above, and any/all of the features described above with respect to fusion device 10 (and any other expandable fusion device described herein) may apply to fusion device 910 unless otherwise noted. By way of example only, the expandable fusion device 910 is illustrative of a lateral lordotic expansion mechanism that may be applied to any expandable fusion device examples described herein, according to some embodiments. By way of example only, the expandable fusion device 910 of the present embodiment has a posterior side 924 and an anterior side 926.

The expandable fusion implant 910 is configured to have a minimized or optimized total insertion height in the fully collapsed position such that when the device 910 is initially inserted into the intervetebral space, it wouldn't require a limited distraction of the vertebral bodies. Also, it should be noted that the outer contact surfaces of the upper endplates 922a, 922b, and the outer contact surfaces of the lower endplates 922c, 922d, are generally parallel but not coplanar in this initial collapsed state. The reason they are not coplanar in the collapsed state is that the anterior (i.e. the taller) side of the device is shorter than it would need to be in order for the upper and lower endplates to be coplanar. While the above is also true for the fusion device 10, the difference is that whereas in the fusion device 10, when the device reaches full width expansion, the outer contact surfaces of the upper and lower endplate pairs do become generally coplanar, in the fusion device 910, they do not, because of the fact that the collapsed insertion height (i.e. the collapsed height of the anterior endplates) in fusion device 910 is reduced in order to minimize tissue disruption during implantation—an important clinical consideration. This allows the device 910 to have lower insertion height than the device 10, but in order for the target lordosis of the device to affect the bony anatomy, the outer contact surfaces do need to be coplanar and subsequent height expansion will not fix the problem if the endplates expand in height at the same rate. To solve this problem, expandable fusion device 910 of the present example is configured to delay the height expansion of the posterior endplates 922a, 922c until the anterior endplates 910b, 910d has expanded in height ($h_1$) enough to establish the desired lordotic angle $\partial_1$ (e.g. FIG. 96 and FIG. 99) and bring the outer contact surfaces of the upper and lower endplate pairs into alignment. Once this occurs, the posterior endplates 910a, 910c expand in height at the same rate as the anterior endplates 910b, 910d, and still maintain the desired lordotic angle $\partial_1$. Thus the maximum height expansion ($h_2$) of the anterior endplates 910b, 910d will be greater than the maximum height expansion ($h_3$) of the posterior endplates 910a, 910c (e.g. FIG. 97 and FIG. 100).

By way of example, the actuator 912, distal wedge 914, proximal wedge 916, distal ramps 918a, 920a, and proximal ramps 918b, 920b may be identical or substantially similar to corresponding elements disclosed herein with respect to other embodiments (e.g. expandable fusion device 10), and therefore their specific structure will not be described unless necessary.

By way of example, the endplates comprise posterior endplates 922a, 922c, and anterior endplates 922b, 922d. Endplate 922a will be described herein as representative of the posterior endplates, as endplate 922c is identical or a mirrored equivalent and has the same elements as endplate 922a. Similarly, endplate 922b will be described herein as representative of the anterior endplates, as endplate 922d is identical or a mirrored equivalent and has the same elements as endplate 922b. By way of example, each of the endplates 922a-922d has a distal end 930, a proximal end 932, an outer facing contact surface 934 and a plurality of angled slots (not shown, but same or similar as previously described) that interact with inclined surfaces on the distal and proximal ramps (not shown, but same or similar as previously described) to facilitate height expansion in the same manner as described previously with respect to other embodiments. As with other embodiments disclosed herein, height expansion may begin as soon as the endplates 922a-922d dissociate from the wedges 914, 916. This may be controlled in a number of ways. In the instant example embodiment, for example, the distal and proximal ends 930, 932 of the endplates include cutaway portions 936a-936d that truncate the tongue and groove interface between the endplates 922a-922d and the proximal and distal wedges 914, 916, and thus enable height expansion to begin when translation of the wedges 914, 916 relative to the endplates 922a-922d encounter a cutaway portion 936a-936d. Differences in the sizes of the cutaway portions 936a-936d dictate when height expansion can begin for the posterior plates 922a, 922c and the anterior plates 922b, 922d. By way of example, the cutaway portions 936b, 936d of the anterior endplates 922b, 922d may be much larger than the cutaway portions 936a, 936c of the posterior endplates 922a, 922c, resulting in the anterior endplates 922b, 922d dissociating from the distal and proximal wedges 914, 916 before the posterior endplates 922a, 922c, and therefore causing the anterior endplates 922b, 922d to begin height expansion before the posterior endplates 922a, 922c.

In operation, first width expansion proceeds substantially as described above with respect to previous embodiments. That is, the actuator 912 is turned a select number of actuations until a predetermined width expansion is reached wherein the distal and proximal wedges 914, 916 encounter the cutaway portions 936b, 936d of the anterior endplates 922b, 922d, at which point the anterior endplates 922b, 922d dissociate from the distal and proximal wedges 914, 916, and turning the actuator 912 additional actuations in the same actuation direction causes height expansion of the anterior endplates 922b, 922d as well as continued width expansion. Width expansion continues until the distal and proximal wedges 914, 916 encounter the cutaway portions 936a, 936c of the posterior endplates 922a, 922c, at which point the posterior endplates 922a, 922c dissociate from the distal and proximal wedges 914, 916, and turning the actuator 912 additional actuations in the same actuation direction causes height expansion of the posterior endplates 922a, 922c as well as continued height expansion of the anterior endplates 922b, 922d.

The expandable fusion device 910 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 910.

FIGS. 101-106 illustrate an example of an expandable fusion device 1010 for implantation between two adjacent vertebrae according to another embodiment of the disclosure. By way of example only, the expandable fusion device 1010 of the present embodiment includes an actuator 1012, a distal wedge 1014, a proximal wedge 1016, a posterior beam 1018, a pair of anterior ramps 1020, a plurality of endplates 1022a-1022d, and optionally a plurality of guide pins. As with previously-described embodiments, the distal and proximal wedges 1014, 1016 are coupled with the actuator 1012. The anterior ramps 1020 are slideably coupled with the distal and proximal wedges 1014, 1016, which are also slideably coupled with the posterior beam 1018. The posterior endplates 1022a, 1022c are pivotably coupled with the posterior beam 1018. The anterior endplates 1022b, 1022d are slideably coupled with the anterior ramps 1020. Generally, the expandable fusion device 1010 is substantially similar to expandable fusion device 10 described above, and any/all of the features described above with respect to fusion device 10 (and any other expandable fusion device described herein) may apply to fusion device 1010 unless otherwise noted. By way of example only, the expandable fusion device 1010 is illustrative of a lateral lordosis-approximating expansion mechanism that may be applied to any expandable fusion device examples described herein, according to some embodiments. By way of example only, the expandable fusion device 1010 of the present embodiment has a posterior side 1024 and an anterior side 1026.

By way of example, the actuator 1012, distal wedge 1014, proximal wedge 1016, anterior ramps 1020, and anterior endplates 1022b, 1022d may be identical or substantially similar to corresponding elements disclosed herein with respect to other embodiments.

By way of example, the posterior beam 1018 comprises first and second end portions 1030, 1032 separated by an elongated central portion 1034. The first and second end portions 1030, 1032 each include tongue and groove connectors 1036 configured to slideably engage the corresponding tongue and groove connectors on the distal and/or proximal wedges 1014, 1016 to enable width expansion as described herein throughout. The central portion 1034 comprises a pair of elongated semi-cylindrical recesses 1038 positioned on opposite sides (e.g. top and bottom) of the posterior beam 1018, configured to pivotally receive the posterior endplates 1022a, 1022c therein.

By way of example, the posterior endplates 1022a, 1022c are identical or mirrored equivalents, so only endplate 1022a will be described herein. By way of example, the posterior endplate 1022a comprises an elongated body 1040 having a superior surface 1042, an inferior surface 1044, and a plurality of medially-extending flanges 1046. By way of example, the superior surface 1042 is configured to engage tissue, and thus may comprise one or more friction elements to secure the endplate to the tissue once fully expanded, including but not limited to surface treatment 1048 (shown by way of example), ridges, teeth, bumps, and the like. By way of example, the inferior surface 1044 is generally convex in shape, and is sized and configured to pivotally mate with an elongated recess 1038 of the posterior beam 1018, enabling the endplate 1022a to pivot or rotate about an axis of rotation extending longitudinally through the elongated recesses 1038. The ends 1050 of the elongated body 1040 may be configured to enable retention within the elongated recess 1038, for example by a snap fit retention, or by capture of a pin or other suitable retention element within retention recesses 1052 formed at the ends 1050.

By way of example, the expandable fusion device 1010 has a width stabilizer feature that is substantially similar to the width stabilizer feature described with respect to the expandable fusion device 10 above. More specifically, the posterior endplates 1022a, 1022c each have a plurality of medial flanges 1046a, 1046c that are interdigitally associated with medial flanges 1046b, 1046d of the anterior endplates 1022b, 1022d. At least one (and preferably a few) of each of the medial flanges 1046a, 1046c include a lateral protrusion 1054 positioned near the medial ends of the medial flanges 1046a, 1046c, the lateral protrusion(s) 1054 each being sized and configured to translate within a corresponding lateral recess 1056 formed in adjacent medial flanges 1046b, 1046d during width expansion. In the instant example embodiment, the lateral protrusions 1054 are generally cylindrical in shape, or otherwise have a generally circular cross-section, to enable at least partial rotation of the lateral protrusions 1054 within the elongated recesses 1056 during height expansion.

In operation, first width expansion proceeds substantially as described above with respect to previous embodiments. That is, the actuator 1012 is turned a select number of actuations causing the distal and proximal wedges 1014, 1016 to translate along the various tongue and groove connectors of the posterior beam 1018 and anterior ramps 1020 until a predetermined width expansion is reached, wherein the distal and proximal wedges 1014, 1016 disassociate from the anterior endplates 1022b, 1022d but remain associated with the proximal beam 1018. Turning the actuator 1012 additional actuations in the same actuation direction then causes height expansion of the anterior endplates 1022b, 1022d (in parallel) as well as continued width expansion due to the continued association with the posterior beam 1018. As the anterior endplates 1022b, 1022d expand in height (remaining parallel to one another), the posterior endplates 1022a, 1022c pivot outward (e.g included angle increases) because the lateral protrusions 1054 at the medial ends of the medial flanges 1046a, 1046c on the posterior endplates 1022a, 1022c are retained within the lateral recesses 1056 on the anterior endplates 1022b, 1022d, while at the same time the elongated bodies 1040 of the posterior endplates 1022a, 1022c remain captured (and pivot) within the elongated recesses 1038 of the posterior beam 1018, which does not experience any height differential. Width and height expansion continues in this fashion until the translation stops of the distal and proximal wedges 1014, 1016 (e.g., the end of control slots) encounter protrusions 1037 on the posterior beam 1018 at which point translation of the distal and proximal wedges 1014, 1016 stops entirely, with the expandable fusion device 1010 at maximum width, maximum height, and maximum lordosis approximation. Thus, turning the actuator 1012 a select number of rotations in a first actuation direction causes width expansion. Turning the actuator 1012 additional actuations in the same actuation direction causes height expansion of the anterior endplates 1022b, 1022d, continued width expansion, as well as lordotic-approximating expansion of the posterior endplates 1022a, 1022c.

The expandable fusion device 1010 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1010.

In some embodiments, the devices include a 3-beam cage. These devices can provide asymmetric vertical expansion. In some embodiments, the cage can comprise a beam assembly having a first end, a second end, a first beam, a second beam, a spanning beam, and a long axis; a width expansion assembly positioned between the first beam and the spanning beam and having a first spacer rotatably connected to a first pivotal link, the first pivotal link rotatably connected to the spanning beam at the first end of the cage; and, a second spacer rotatably connected to a second pivotal link, the second pivotal link rotatably connected to the spanning beam at the second end of the cage; wherein a first movement of the first spacer in the direction of the long axis rotates the first pivotal link to expand the width of the first end of the cage, and a first movement of the second spacer in the direction of the long axis rotates the second pivotal link to expand the width of the second end of the cage; and, a height expansion assembly positioned between the first beam and the second beam and having a ramp movably connected to the first beam and the second beam, wherein a movement of the ramp in the direction of the long axis expands the height of the cage only at the first beam and the second beam.

In some embodiments, the 3-beam cage can further comprise a pivotal endplate in a pivotal connection with the spanning beam; a first set of interdigitating fingers attached to the first beam; and, a second set of interdigitating fingers attached to the spanning beam; wherein, the first set of interdigitating fingers are slidably and pivotably attached to the second set of interdigitating fingers for sliding during the width expansion and pivoting during the height expansion.

FIGS. 107-112 illustrate an example of an expandable fusion device 1110 for implantation between two adjacent vertebrae according to another embodiment of the disclosure. By way of example only, the expandable fusion device 1110 of the present embodiment includes an actuator (not shown but identical or substantially similar to actuator 12 described above), a distal wedge 1114, a proximal wedge 1116, a posterior beam 1118, a pair of anterior ramps 1120, a plurality of endplates or beams 1122a-1122d, and optionally a plurality of guide pins. As with previously-described embodiments, the distal and proximal wedges 1114, 1116 can be coupled with an actuator in some embodiments. The anterior ramps 1120 are slideably coupled with the distal and proximal wedges 1114, 1116, which are coupled with the posterior beam or spanning beam 1118 via a pin linkage or pivotal linkage mechanism. The posterior endplates 1122a, 1122c are pivotably coupled with the posterior beam or spanning beam 1118. The anterior endplates or beams 1122b, 1122d are slideably coupled with the anterior ramps 1120, the ramps movable in the direction of the long axis relative to the beam assembly 1118, 1122b, 1122d. Generally, the expandable fusion device 1110 is substantially similar to expandable fusion device 10 described above, and any/all of the features described above with respect to fusion device 10 (and/or any other expandable fusion device described herein) may apply to fusion device 1110 unless otherwise noted. Notably, the expandable fusion device 1110 is substantially similar to expandable fusion device 1010 described above, modified to use a pin linkage or pivotal linkage connection between the wedges 1114, 1116 and the posterior beam 1118 to effect width expansion on the posterior side 1124 (as opposed to the wedge tongue and groove connection of device 1010). By way of example only, the expandable fusion device 1110 is illustrative of a lateral lordosis-approximating expansion mechanism that may be applied to any expandable fusion device examples described herein, according to some embodiments. By way of example only, the expandable fusion device 1110 of the present embodiment has a posterior side 1124 and an anterior side 1126.

By way of example, the actuator, anterior ramps 1120, and anterior endplates 1122b, 1122d may be identical or substantially similar to corresponding elements disclosed herein with respect to other embodiments.

By way of example only, the distal and proximal wedges 1114, 1116 are substantially similar to one another, having differences unique to orientation (e.g. tapered leading surfaces on the distal wedge, tool engagement features on the proximal wedge) that, while shown and described with respect to other embodiments herein, are not shown with respect to the instant example embodiment. The wedges can be referred to, in some embodiments, as a first wedge and a second wedge to relieve description of the device from the proximal and distal orientation restrictions. However, it should be understood that any feature shown and described with regard to any embodiment may apply to all embodiments herein without reservation.

FIG. 111 illustrates an example of a proximal wedge 1116 (and/or distal wedge 1114, which is identical as to the elements described) according to the present example embodiment. By way of example, the proximal wedge 1116 comprises a distal side 1130, a proximal side 1132, and a threaded bore 1134 extending axially therethrough between the distal and proximal sides 1130, 1132. The threaded bore 1134 comprises an internal thread configured for threaded coupling with the actuator. The proximal wedge 1116 may be configured for slideable coupling with the anterior ramps 1120 and/or the anterior endplates 1122b, 1122d. By way of example only, the proximal wedge 1116 may include a plurality of tongue and groove connectors 1136 positioned on an anterior-facing side and configured to mate with corresponding features on the anterior ramps 1120 and the anterior endplates 1122b, 1122d to facilitate slideable coupling and therefore width and height expansion in a manner consistent with other embodiments described herein. The proximal wedge 1116 may further include a lateral extension 1138 configured to engage a link element 1140 and extending toward the posterior side 1124. By way of example only, the lateral extension 1138 may further include a pin aperture 1142 for receiving a pivot pin 1144 extending therethrough, to pivotally couple the proximal wedge 1116 to the link element 1140.

FIG. 111A illustrates an example of a link element 1140 according to the present example embodiment. By way of example, the link elements 1140 each comprise a linkage base 1146 and a pair of link flanges 1148 separated by a cavity 1150 that is sized and configured to receive at least a portion of the lateral extension 1138 of the proximal wedge 1116 (and/or distal wedge 1114). The linkage base 1146 may further include a pin aperture 1152 for receiving a pivot pin 1144 extending therethrough, to pivotally couple the link element 1140 to the posterior beam 1118 (and/or another link element 1140). Similarly, each link flange 1148 may include a pin aperture 1154 configured to axially align with pin aperture 1142 of the proximal wedge 1116 (and/or distal wedge 1114) and receive a pivot pin 1144 therethrough, to pivotally couple the link element 1140 to the proximal wedge 1116 (and/or distal wedge 1114).

By way of example, the posterior beam 1118 comprises first and second end portions 1156, 1158 separated by an elongated central portion 1160. The first and second end portions 1156, 1158 each include a pair of link flanges 1162 separated by a cavity 1164 sized and configured to receive at least a portion of the corresponding linkage base 1146 on an adjacent link element 1140 to enable width expansion. Each link flange 1162 may include a pin aperture 1164 configured to axially align with pin aperture 1152 of the link element 1140 and receive a pivot pin 1144 therethrough, to pivotally couple posterior beam 1118 and the link element 1140. The central portion 1160 comprises a pair of elongated semi-cylindrical recesses 1168 positioned on opposite sides (e.g. top and bottom) of the posterior beam 1118, configured to pivotally receive the posterior endplates 1122a, 1122c therein.

By way of example, the posterior endplates 1122a, 1122c are identical or mirrored equivalents, so only endplate 1122a will be described herein. By way of example, the posterior endplate 1122a comprises an elongated body 1170 having a superior surface 1172, an inferior surface 1174, and a plurality of medially-extending flanges 1176a. By way of example, the inferior surface 1174 is generally convex in shape, and is sized and configured to pivotally mate with an elongated recess 1168 of the posterior beam 1118, enabling the endplate 1122a to pivot or rotate about an axis of rotation extending longitudinally through the elongated recesses 1138. The ends 1178 of the elongated body 1170 may be configured to enable retention within the elongated recess 1168, for example by a snap fit retention, or by capture of a pin or other suitable retention element within retention recesses 1180 formed at the ends 1178.

By way of example, the expandable fusion device 1110 has a width stabilizer feature that is substantially similar to the width stabilizer feature described with respect to the expandable fusion device 10 above. More specifically, the posterior endplates 1122a, 1122c each have a plurality of medial flanges 1176a, 1176c that are interdigitally associated with medial flanges 1176b, 1176d of the anterior endplates 1122b, 1122d. At least one (and preferably a few) of each of the medial flanges 1176a, 1176c include a lateral protrusion 1182 positioned near the medial ends of the medial flanges 1176a, 1176c, the lateral protrusion(s) 1182 each being sized and configured to translate within a corresponding lateral recess 1184 formed in adjacent medial flanges 1176b, 1176d during width expansion. In the instant example embodiment, the lateral protrusions 1182 are generally cylindrical in shape, or otherwise have a generally circular cross-section, to enable at least partial rotation of the lateral protrusions 1182 within the elongated recesses 1184 during height expansion.

In operation, first width expansion proceeds substantially as described above with respect to previous embodiments. That is, the actuator is turned a select number of actuations causing the distal and proximal wedges 1114, 1116 to translate along the tongue and groove connectors of the anterior ramps 1120 (effecting width expansion of the anterior endplates 1122b, 1122d by way of the tongue and groove interaction, and causing width expansion of the posterior beam 1118 and posterior endplates 1122a, 1122c by way of the pin linkage) until a predetermined width expansion is reached, wherein the distal and proximal wedges 1114, 1116 disassociate from the anterior endplates 1122b, 1122d but remain associated with the posterior beam 1118 (e.g. by way of link elements 1140). Turning the actuator additional actuations in the same actuation direction then causes height expansion of the anterior endplates 1122b, 1122d (in parallel) as well as continued width expansion due to the continued association with the proximal beam 1118. As the anterior endplates 1122b, 1122d expand in height (remaining parallel to one another), the posterior endplates 1122a, 1122c pivot outward (e.g included angle increases) because the lateral protrusions 1182 at the medial ends of the medial flanges 1176a, 1176c on the posterior endplates 1122a, 1122c are retained within the lateral recesses 1184 on the anterior endplates 1122b, 1122d, while at the same time the elongated bodies 1170 of the posterior endplates 1122a, 1122c remain captured (and pivot) within the elongated recesses 1168 of the posterior beam 1118, which does not experience any height differential. Width and height expansion continues in this fashion until the wedges cannot translate any further, with the expandable fusion device 1110 at maximum width, maximum height, and maximum lordosis approximation. Thus, turning the actuator a select number of rotations in a first actuation direction causes width expansion. Turning the actuator additional actuations in the same actuation direction causes height expansion of the anterior endplates 1122b, 1122d, continued width expansion, as well as lordotic-approximating expansion of the posterior endplates 1122a, 1122c.

The expandable fusion device 1110 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1110.

FIGS. 113-121 illustrate an example of an expandable fusion device 1210 for implantation between two adjacent vertebrae according to another embodiment of the disclosure. By way of example only, the expandable fusion device 1210 of the present embodiment includes an actuator 1212, a distal wedge 1214, a proximal wedge 1216, a pair of posterior beams 1218a, 1218c, a pair of anterior ramps 1220, a plurality of endplates 1222a-1222d, and optionally a plurality of guide pins 1224. As with previously-described embodiments, the distal and proximal wedges 1214, 1216 are coupled with the actuator 1212. The anterior ramps 1220 are slideably coupled with the distal and proximal wedges 1214, 1216, which are coupled with the posterior beam 1218 via a pin linkage mechanism. The posterior endplates 1222a, 1222c are pivotably coupled with the posterior beams 1218a, 1218c, respectively. The anterior endplates 1222b, 1222d are slideably coupled with the anterior ramps 1220. Generally, the expandable fusion device 1210 is substantially similar to expandable fusion device 10 described above, and any/all of the features described above with respect to fusion device 10 (and/or any other expandable fusion device described herein) may apply to fusion device 1210 unless otherwise noted. Notably, the expandable fusion device 1210 is substantially similar to expandable fusion device 1110 described above, modified so that the posterior endplates 1222a, 1222c are capable of parallel height expansion. By way of example only, the expandable fusion device 1210 is illustrative of a lateral lordosis-approximating expansion mechanism that may be applied to any expandable fusion device examples described herein, according to some embodiments. By way of example only, the expandable fusion device 1210 of the present embodiment has a posterior side 1226 and an anterior side 1228.

By way of example, the actuator 1212, distal wedge 1214, proximal wedge 1216, anterior ramps 1220, posterior endplates 1222a, 1222c, and anterior endplates 1222b, 1222d may be identical or substantially similar to corresponding elements disclosed herein with respect to other embodiments, and thus will not be described in detail here.

Figure 117:
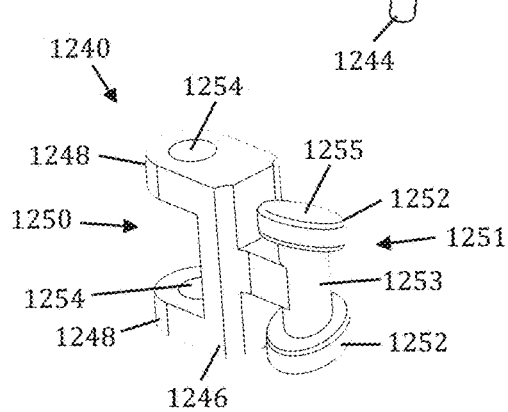
FIG. 117 is a perspective view of an example of a link element forming part of the expandable fusion device of FIG. 113, according to some embodiments.

FIG. 117 illustrates an example of a link element 1240 according to the present example embodiment. By way of example, the link elements 1240 each comprise a linkage base 1246 and a pair of link flanges 1248 separated by a cavity 1250 that is sized and configured to receive at least a portion of the lateral extension 1238 of the proximal wedge 1216 (and/or distal wedge 1214). The linkage base 1246 may further include a posterior ramp element 1251 extending in a direction opposite the link flanges 1248. By way of example only, the posterior ramp element 1251 comprises a pair of vertically separated circular flanges 1252 at opposite ends of a vertical post 1253. The circular flanges 1252 are oriented at an angle that matches the incline angle of the inclined surfaces 1264 on the posterior beams 1218a, 1281c such that outer translation surfaces 1255 on the circular flanges 1252 may be coplanar with the inclined surfaces 1264 of the posterior beams 1218a, 1218c when the circular flanges 1252 are properly aligned (e.g. upon maximum width expansion). By way of example only, the circular flanges 1252 are sized and configured to mate with and nest in link recess 1262 on the posterior beams 1218a, 1218c to pivotally couple the link element 1240 to the posterior beams 1218a, 1218c. Each link flange 1248 may include a pin aperture 1254 configured to axially align with pin aperture 1242 of the proximal wedge 1216 (and/or distal wedge 1214) and receive a pivot pin 1244 therethrough, to pivotally couple the link element 1240 to the proximal wedge 1216 (and/or distal wedge 1214).

Figure 118:
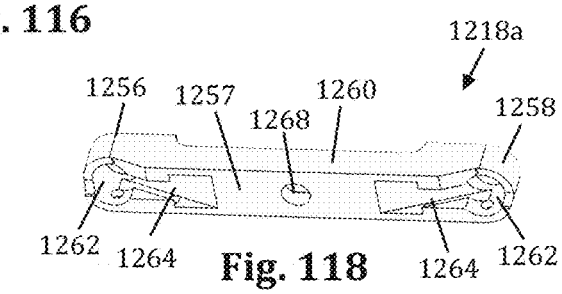
FIGS. 118-119 are perspective views of an example of a posterior beam forming part of the expandable fusion device of FIG. 113, according to some embodiments.
Figure 119:
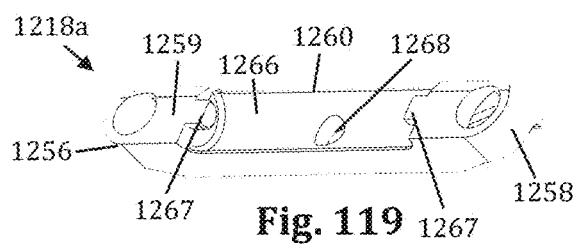
Figure 120:
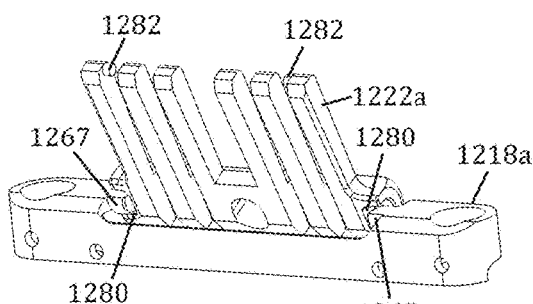
FIGS. 120-121 are perspective views of an example of a posterior beam and posterior endplate forming part of the expandable fusion device of FIG. 113, according to some embodiments.
Figure 121:
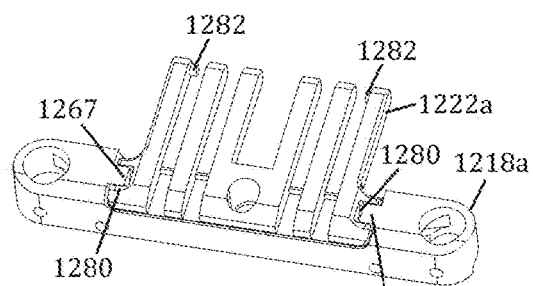
Figure 122:
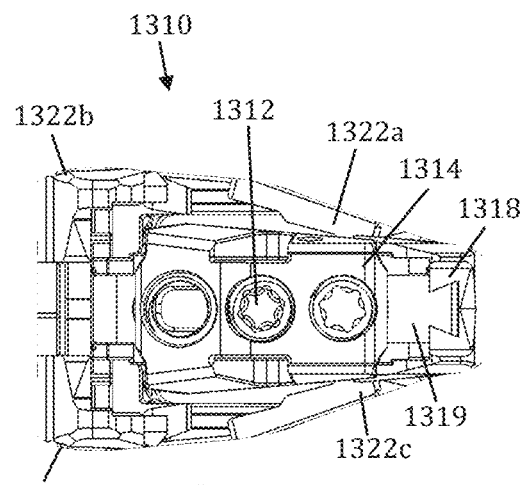
FIG. 122 is an end plan view of another example of an expandable fusion device in a fully expanded position, according to some embodiments.
Figure 123:
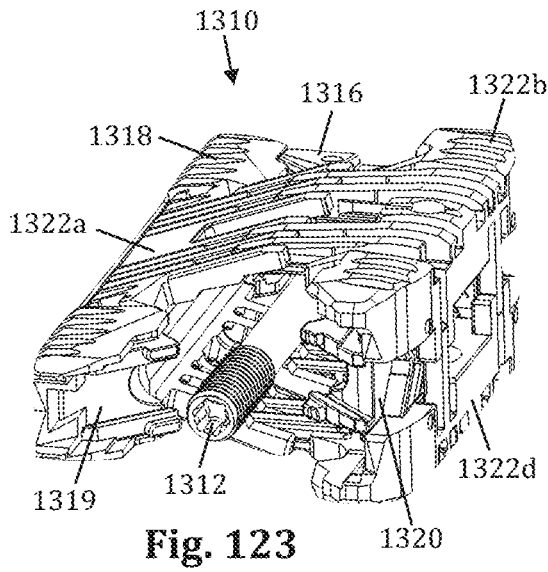
FIG. 123 is a perspective view of the expandable fusion device of FIG. 122, according to some embodiments.
Figure 124:
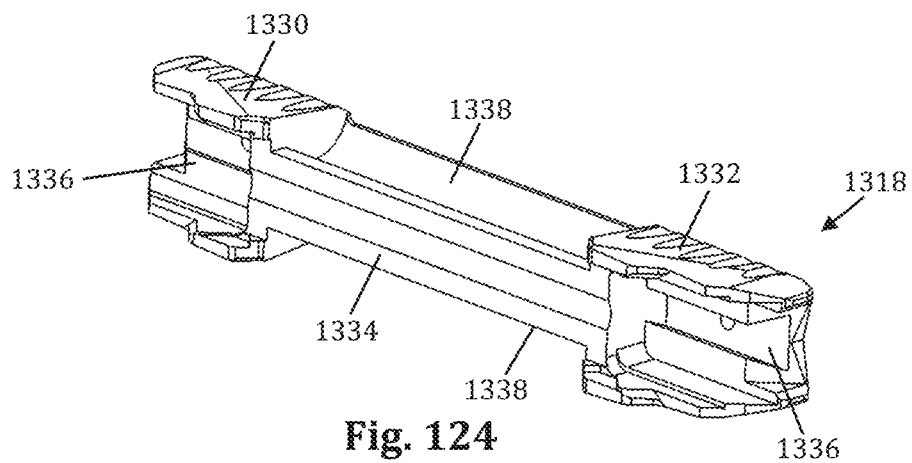
FIG. 124 is a perspective view of a posterior beam forming part of the expandable fusion device of FIG. 122, according to some embodiments.
Figure 125:
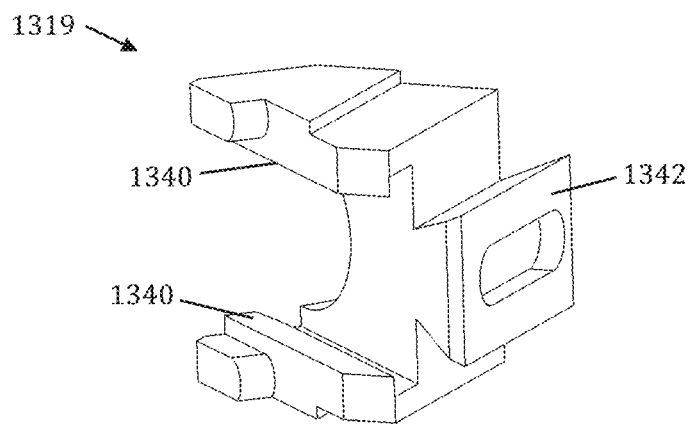
FIG. 125 is a perspective view of an example of a posterior ramp forming part of the expandable fusion device of FIG. 122, according to some embodiments.
Figure 126:
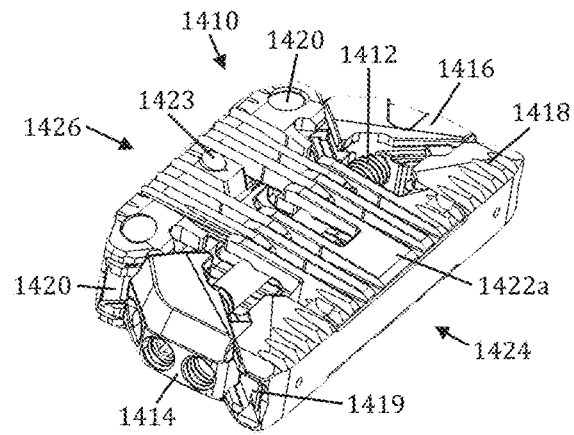
FIG. 126 is a perspective view of another example of an expandable fusion device in a width expanded position, according to some embodiments.
Figure 127:
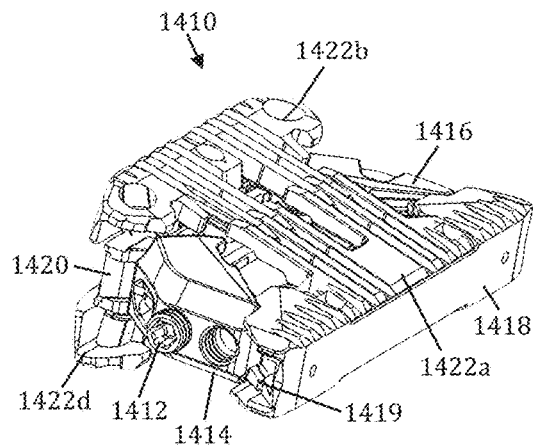
FIG. 127 is a perspective view of the expandable fusion device of FIG. 126 in a fully expanded position, according to some embodiments.
Figure 128:
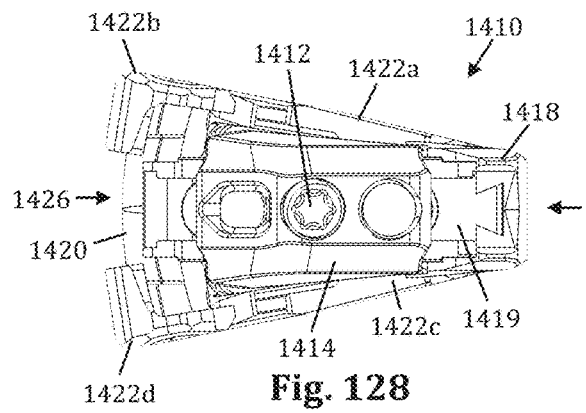
FIG. 128 is an end plan view of the expandable fusion device of FIG. 126 in a fully expanded position, according to some embodiments.
Figure 129:
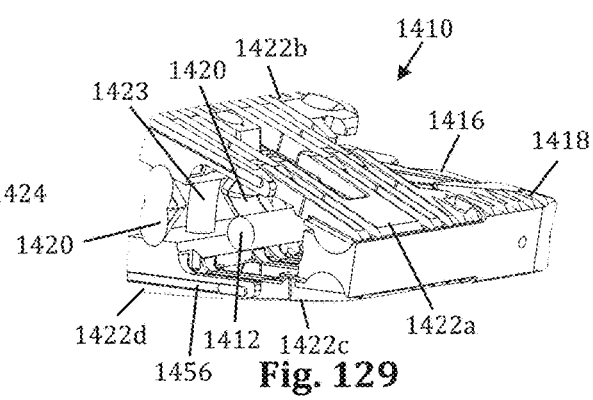
FIG. 129 is a sectional view of the expandable fusion device of FIG. 126 in a fully expanded position, according to some embodiments.

By way of example, the posterior beams 1218a, 1218c are substantially identical in form and function, and thus only posterior beam 1218a is described in detail. By way of example only, FIGS. 118-119 illustrate an example of posterior beam 1218a according to the instant example embodiment. Posterior beam 1218a is configured to engage the upper posterior endplate 1222a, and poster beam 1218c is configured to engage the lower posterior endplate 1222c. By way of example, the posterior beam 1218a comprises first and second end portions 1256, 1258 separated by an elongated central portion 1260, a first or inner side 1257, and a second or outer side 1259. The first and second end portions 1256, 1258 each include a link recess 1262 and an inclined translation surface 1264 on the inner side 1257. The link recess 1262 may be sized and configured to receive a circular flange 1252 of the link element 1240 therein, and further allow the circular flange 1252 to rotate while nesting within the link recess 1262. Upon sufficient rotation (e.g. when maximum width expansion is achieved) the circular flanges 1252 will be aligned such that the outer translation surfaces 1255 are aligned and coplanar with the inclined translation surfaces 1264, enabling height expansion on the posterior side 1226. The central portion 1260 comprises an elongated semi-cylindrical recess 1266 positioned on the outer side 1259 of the posterior beam 1218a, configured to pivotally receive the posterior endplates 1222a therein. The central portion 1260 may further include a retaining flange 1267 extending axially over each end of the elongated recess 1266, configured to engage a retention recess 1280 provided on the endplate 1222a, to prevent the endplate 1222a from dissociating from the posterior beam 1218a unless and until the endplate 1222a is rotated beyond a predetermined useful range (see, e.g. FIGS. 120-121). In some embodiments, the posterior beam 1218a may have central bore 1268 extending vertically therethrough, and configured to receive a stabilization post 1269 therein.

In operation, first width expansion proceeds substantially as described above with respect to previous embodiments. That is, the actuator 1212 is turned a select number of actuations causing the distal and proximal wedges 1214, 1216 to translate along the tongue and groove connectors of the anterior ramps 1220 (effecting width expansion of the anterior endplates 1222b, 1222d by way of the tongue and groove interaction, and causing width expansion of the posterior beams 1218a, 1218c and posterior endplates 1222a, 1222c by way of the pin linkage) until a predetermined width expansion (e.g. maximum width expansion) is reached, wherein the distal and proximal wedges 1214, 1216 disassociate from the anterior endplates 1222b, 1222d but remain associated with the posterior beams 1218a, 1218c (e.g. by way of link elements 1240). During width expansion, as the link angle between the wedges and associated link elements 1240 increases (see, e.g. FIGS. 113-115), the circular flanges 1252 (that link the link elements 1240 to the posterior beams 1218a, 1218c) are rotating within the link recesses 1262, and the angles of the circular flanges 1252 are not in alignment with the inclined surfaces 1264, preventing height expansion of the posterior beams 1218a, 1218c. Upon reaching maximum width expansion, the circular flanges 1252 become angularly aligned with the inclined translation surfaces 1264, enabling height expansion of the posterior beams 1218a, 1218c (and therefore the posterior endplates 1222a, 1222c) to proceed. Turning the actuator 1212 additional actuations in the same actuation direction then causes height expansion of the anterior endplates 1222b, 1222d (in parallel) as well as height expansion of the posterior endplates 1222a, 1222c (in parallel). In the instant example embodiment, the anterior endplates expand in height at a different rate than the posterior beams/endplates. Thus, as the anterior endplates 1222b, 1222d expand in height (remaining parallel to one another), the posterior endplates 1222a, 1222c pivot outward (e.g. inclusive angle increases) because the lateral protrusions 1282 at the medial ends of the medial flanges on the posterior endplates 1222a, 1222c are retained within the lateral recesses 1284 on the anterior endplates 1222b, 1222d, while at the same time the elongated bodies 1270 of the posterior endplates 1222a, 1222c remain captured (and pivot) within the elongated recesses 1266 of the posterior beams 1218a, 1218c, even as the posterior beams 1218a, 1218c expand in height (in parallel). Height expansion continues in this fashion until the wedges cannot translate any further, with the expandable fusion device 1210 at maximum width, maximum height, and maximum lordosis approximation. Thus, turning the actuator 1212 a select number of rotations in a first actuation direction causes width expansion. Turning the actuator 1212 additional actuations in the same actuation direction causes height expansion of both the anterior endplates 1222b, 1222d, and the posterior endplates 1222a, 1222c, as well as lordotic-approximating expansion of the posterior endplates 1222a, 1222c.

The expandable fusion device 1210 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1210.

FIGS. 122-125 illustrate an example of an expandable fusion device 1310 for implantation between two adjacent vertebrae according to another embodiment of the disclosure. By way of example only, the expandable fusion device 1310 of the present embodiment includes an actuator 1312, a distal wedge 1314, a proximal wedge 1316, a posterior beam 1318, a pair of posterior ramps 1319, a pair of anterior ramps 1320, a plurality of endplates 1322a-1322d, and optionally a plurality of guide pins. As with previously-described embodiments, the distal and proximal wedges 1314, 1316 are coupled with the actuator 1312. The posterior ramps 1319 and anterior ramps 1320 are slideably coupled with the distal and proximal wedges 1314, 1316. By way of example, the posterior endplates 1322a, 1322c are pivotably coupled with the posterior beam 1318. The anterior endplates 1322b, 1322d are slideably coupled with the anterior ramps 1320. Generally, the expandable fusion device 1310 is substantially similar to expandable fusion device 10 described above, and any/all of the features described above with respect to fusion device 10 (and any other expandable fusion device described herein) may apply to fusion device 1310 unless otherwise noted. Notably, the expandable fusion device 1310 is substantially similar to expandable fusion device 1010, modified so that the posterior ramps 1319 are not integrated with the posterior beam 1318 but rather are configured to translate along the posterior beam 1318 parallel to the longitudinal axis of the actuator 1312, thereby enabling full width expansion before initiation of height expansion. By way of example only, the expandable fusion device 1310 is illustrative of a lateral lordosis-approximating expansion mechanism that may be applied to any expandable fusion device examples described herein, according to some embodiments. By way of example only, the expandable fusion device 1310 of the present embodiment has a posterior side 1324 and an anterior side 1326.

By way of example, the actuator 1312, distal wedge 1314, proximal wedge 1316, anterior ramps 1320, and endplates 1322a-1322d may be identical or substantially similar to corresponding elements disclosed herein with respect to other embodiments.

By way of example, the posterior beam 1318 comprises first and second end portions 1330, 1332 separated by an elongated central portion 1334. The first and second end portions 1330, 1332 each include female dovetail connectors 1336 configured to slideably engage the corresponding male dovetail connectors 1342 on the posterior ramps 1319 to enable height expansion to occur after maximum width expansion has been achieved. By way of example, the female dovetail connectors 1336 are oriented axially parallel to the longitudinal axis of the actuator 1312. The central portion 1334 comprises a pair of elongated semi-cylindrical recesses 1338 positioned on opposite sides (e.g. top and bottom) of the posterior beam 1318, configured to pivotally receive the posterior endplates 1322a, 1322c therein.

By way of example, the anterior ramps 1319 each include tongue and groove connectors 1340 configured to slideably engage the corresponding tongue and groove connectors on the distal and/or proximal wedges 1314, 1316 to enable width expansion as described herein throughout. Additionally, the anterior ramps 1319 each include a male dovetail connector 1342 configured to slideably engage the female dovetail connectors 1336 of the proximal beam 1319.

In operation, first width expansion proceeds substantially as described above with respect to previous embodiments. That is, the actuator 1312 is turned a select number of actuations causing the distal and proximal wedges 1314, 1316 to translate along the various tongue and groove connectors of the posterior ramps 1319 and anterior ramps 1320 until a predetermined width expansion (e.g. maximum width expansion) is reached, wherein the distal and proximal wedges 1314, 1316 disassociate from the anterior endplates 1322b, 1322d but remain associated with the posterior ramps 1319. Turning the actuator 1312 additional actuations in the same actuation direction then causes height expansion of the anterior endplates 1322b, 1322d (in parallel), which is possible due to the longitudinally parallel orientation of the dovetail connection between the posterior ramps 1319 and the posterior beam 1319. This is because, even after maximum width expansion has been reached, the distal and proximal wedges 1314, 1316 are still able to move toward one another as the posterior ramps 1319 translate axially within the posterior beam 1318 along the dovetail connection to enable height expansion. As the anterior endplates 1322*b*, 1322*d* expand in height (remaining parallel to one another), the posterior endplates 1322*a*, 1322*c* pivot outward (e.g inclusive angle increases) because (as described above with respect to device 1010) the lateral protrusions at the medial ends of the medial flanges on the posterior endplates 1322*a*, 1322*c* are retained within the lateral recesses on the anterior endplates 1322*b*, 1322*d*, while at the same time the elongated bodies of the posterior endplates 1322*a*, 1322*c* remain captured (and pivot) within the elongated recesses 1338 of the posterior beam 1318, which does not experience any height differential. Height expansion continues in this fashion until translation of the distal and proximal wedges 1314, 1316 stops entirely, with the expandable fusion device 1310 at maximum width, maximum height, and maximum lordosis approximation. Thus, turning the actuator 1312 a select number of rotations in a first actuation direction causes width expansion. Turning the actuator 1312 additional actuations in the same actuation direction causes height expansion of the anterior endplates 1322*b*, 1322*d*, width expansion, and/or lordotic-approximating expansion of the posterior endplates 1322*a*, 1322*c*.

The expandable fusion device 1310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1310.

FIGS. 126-134 illustrate an example of an expandable fusion device 1410 for implantation between two adjacent vertebrae according to another embodiment of the disclosure. By way of example only, the expandable fusion device 1410 of the present embodiment includes an actuator 1412, a distal wedge 1414, a proximal wedge 1416, a posterior beam 1418, a pair of posterior ramps 1419, a pair of anterior ramps 1420, a plurality of endplates 1422*a*-1422*d*, and optionally a plurality of guide pins. As with previously-described embodiments, the distal and proximal wedges 1414, 1416 are coupled with the actuator 1412. The posterior ramps 1419 and anterior ramps 1420 are slideably coupled with the distal and proximal wedges 1414, 1416. The posterior endplates 1422*a*, 1422*c* are pivotably coupled with the posterior beam 1418. The anterior endplates 1422*b*, 1422*d* are slideably coupled with the anterior ramps 1420. Generally, the expandable fusion device 1410 is substantially similar to expandable fusion device 10 described above, and any/all of the features described above with respect to fusion device 10 (and any other expandable fusion device described herein) may apply to fusion device 1410 unless otherwise noted. Notably, the expandable fusion device 1410 is substantially similar to expandable fusion device 1310, modified so that the anterior endplates 1422*b*, 1422*d* change angle during height expansion, thereby enabling true lordosis correction as opposed to a lordosis-approximating correction of the previous embodiments. By way of example only, the expandable fusion device 1410 is illustrative of a lateral lordosis expansion mechanism that may be applied to any expandable fusion device examples described herein, according to some embodiments. By way of example only, the expandable fusion device 1410 of the present embodiment has a posterior side 1424 and an anterior side 1426.

By way of example, the actuator 1412, distal wedge 1414, proximal wedge 1416, posterior beam 1418, posterior ramps 1419, and endplates 1422*a*-1422*d* may be identical or substantially similar to corresponding elements disclosed herein with respect to other embodiments.

Figure 130A:
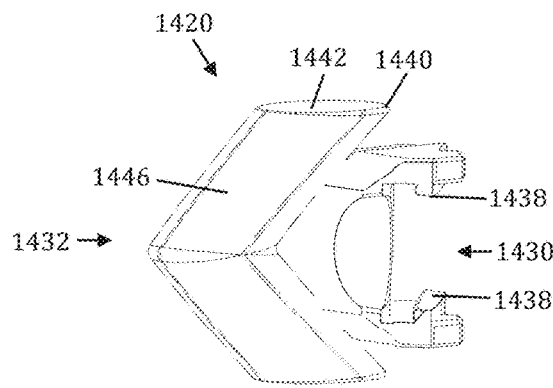
Figure 130B:
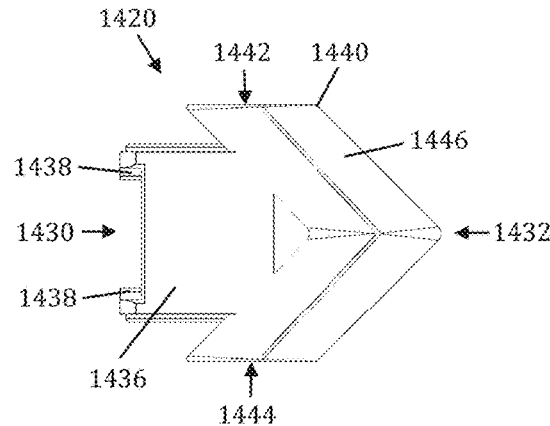
Figure 135:
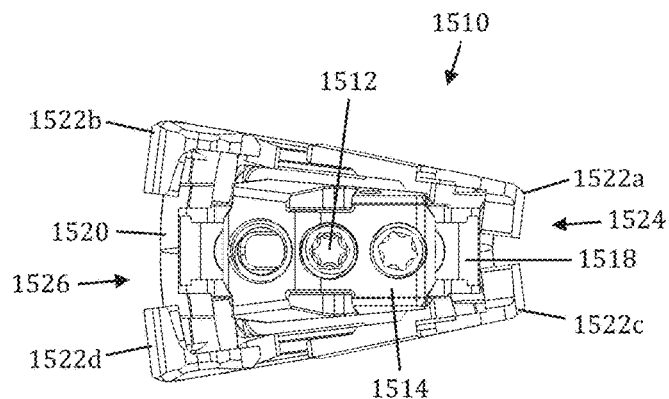

FIGS. 130A-130C illustrate an example of an anterior ramp 1420 according to some embodiments. By way of example, the anterior ramp 1420 of the present embodiment has a first end 1430 configured for engagement with the distal wedge 1414 (and/or proximal wedge 1416), a second end 1432 oriented toward the center of the assembled expandable fusion device 1410, a medial side 1434 (e.g. oriented toward the actuator 1412 in the assembled expandable fusion device 1410), and a lateral side 1436 (e.g. oriented away from the actuator 1412 in the assembled expandable fusion device 1410).

The anterior ramp 1420 may be configured for slideable coupling with the distal wedge 1414, proximal wedge 1416, and/or the anterior endplates 1422*b*, 1422*d*. To facilitate slideable coupling, the first end 1430 includes tongue and groove connectors 1438 configured to slideably engage the corresponding tongue and groove connectors on the distal and/or proximal wedges 1414, 1416 to enable width expansion as described herein throughout.

The anterior ramp 1420 further includes an endplate engagement lobe 1440 comprising a curved V-shape having an apex oriented away from the first end 1430. The endplate engagement lobe 1440 includes a top surface 1442, a bottom surface 1444, and a lateral surface 1446. By way of example, the engagement lobe 1440 has a generally round or oval cross-sectional shape, however it should be noted that the engagement lobe 1440 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). By way of example, the lateral surface 1446 functions as a translation surface that slideably engages inclined surfaces 1448 of the anterior endplates 1422*b*, 1422*d* to facilitate height expansion. By way of example, the endplate engagement lobe 1440 has a general outward medial-lateral curve, as best shown in FIG. 130C, that enables the anterior endplates 1422*b*, 1422*d* to change in angle as height expansion occurs.

By way of example only, the anterior endplates 1422*b*, 1422*d* are substantially as previously described but for the inclined surfaces 1448 that slideably engage the anterior ramps 1420. By way of example only, the inclined surfaces 1448 have a cross-sectional shape to match that of the engagement lobe 1440, for example generally round or oval in the current embodiment. This enables consistent translational contact during height expansion while also enabling the anterior endplates 1422*b*, 1422*d* to change angle during height expansion, which creates a true lordotic expansion. The anterior endplates 1422*b*, 1422*d* may also include a generally curved stabilizer aperture 1450 configured to receive the curved stabilization post 1423 therein.

By way of example only, the posterior endpates 1422*a*, 1422*c* of the present example embodiment are substantially similar as previously described with respect to other embodiments, however in the instant embodiment, the lateral projections 1452 on the medial flanges 1454*a*, 1454*c* may be elongated (e.g. elliptical, rectangular, etc) rather than circular because the posterior endplates 1422*a*, 1422*c* do not pivot relative to the anterior endplates 1422b, 1422d during height expansion. Rather, the interface between the medial flanges 1454a, 1454c on the posterior ramps 1422a, 1422c and the medial flanges 1454b, 1454d on the anterior ramps 1422b, 1422d remain coplanar during height expansion.

In operation, first width expansion proceeds substantially as described above with respect to previous embodiments. That is, the actuator 1412 is turned a select number of actuations causing the distal and proximal wedges 1414, 1416 to translate along the various tongue and groove connectors of the posterior ramps 1419 and anterior ramps 1420 until a predetermined width expansion is reached (e.g. maximum width expansion), wherein the distal and proximal wedges 1414, 1416 disassociate from the anterior endplates 1422b, 1422d but remain associated with the proximal ramps 1419. Turning the actuator 1412 additional actuations in the same actuation direction then causes height expansion of the anterior endplates 1422b, 1422d, which unlike previous embodiments now enables the anterior endplates 1422b, 1422d to change in angle. As the anterior endplates 1422b, 1422d expand in height, the posterior endplates 1422a, 1422c pivot outward (e.g inclusive angle increases) because the lateral protrusions 1452 at the medial ends of the medial flanges 1454a, 1546c on the posterior endplates 1422a, 1422c are retained within the lateral recesses 1456 on the anterior endplates 1422b, 1422d, while at the same time the elongated bodies of the posterior endplates 1422a, 1422c remain captured (and pivot) within the elongated recesses of the posterior beam 1418, which does not experience any height differential. Height expansion continues in this fashion until translation of the distal and proximal wedges 1414, 1416 stops entirely, with the expandable fusion device 1410 at maximum width, maximum height, and maximum lordosis expansion. Thus, turning the actuator 1412 a select number of rotations in a first actuation direction causes width expansion. Turning the actuator 1412 additional actuations in the same actuation direction causes at least one of height expansion, width expansion, and lordotic expansion.

The expandable fusion device 1410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1410.

FIGS. 135-137B illustrate an example of an expandable fusion device 1510 for implantation between two adjacent vertebrae according to another embodiment of the disclosure. By way of example only, the expandable fusion device 1510 of the present embodiment includes an actuator 1512, a distal wedge 1514, a proximal wedge 1516, a pair of posterior ramps 1518, a pair of anterior ramps 1520, a plurality of endplates 1522a-1522d, and optionally a plurality of guide pins. As with previously-described embodiments, the distal and proximal wedges 1514, 1516 are coupled with the actuator 1512. The posterior ramps 1518 and anterior ramps 1520 are slideably coupled with the distal and proximal wedges 1514, 1516. The posterior endplates 1522a, 1522c are slideably coupled with the posterior ramps 1518. The anterior endplates 1522b, 1522d are slideably coupled with the anterior ramps 1520. Generally, the expandable fusion device 1510 is substantially similar to expandable fusion device 10 described above, and any/all of the features described above with respect to fusion device 10 (and any other expandable fusion device described herein) may apply to fusion device 1510 unless otherwise noted. Notably, the expandable fusion device 1510 is hybrid of expandable fusion device 1310, and expandable fusion device 10, modified so that the posterior endplates 1522a, 1522c change angle during height expansion to match the changing angle of the anterior endplates 1522b, 1522d, thereby enabling true lordosis correction. By way of example only, the expandable fusion device 1510 is illustrative of a lateral lordosis expansion mechanism that may be applied to any expandable fusion device examples described herein, according to some embodiments. By way of example only, the expandable fusion device 1510 of the present embodiment has a posterior side 1524 and an anterior side 1526.

By way of example, the actuator 1512, distal wedge 1514, proximal wedge 1516, anterior ramps 1520, and endplates 1522a-1522d may be identical or substantially similar to corresponding elements disclosed herein with respect to other embodiments.

Figure 136A:
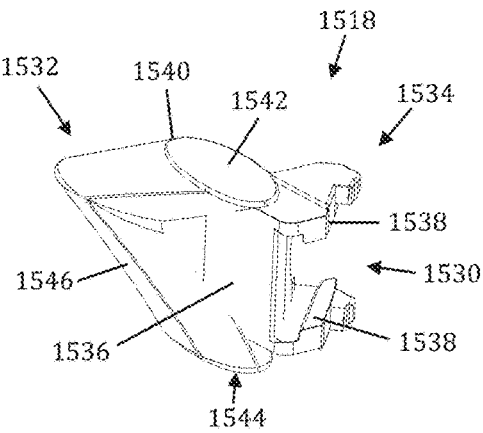

FIG. 136A illustrates an example of a posterior ramp 1518 according to some embodiments. By way of example, the posterior ramp 1518 of the present embodiment has a first end 1530 configured for engagement with the distal wedge 1514 (and/or proximal wedge 1516), a second end 1532 oriented toward the center of the assembled expandable fusion device 1510, a medial side 1534 (e.g. oriented toward the actuator 1512 in the assembled expandable fusion device 1510), and a lateral side 1536 (e.g. oriented away from the actuator 1512 in the assembled expandable fusion device 1510).

The posterior ramp 1518 may be configured for slideable coupling with the distal wedge 1514, proximal wedge 1516, and/or the posterior endplates 1522a, 1522c. To facilitate slideable coupling, the first end 1530 includes tongue and groove connectors 1538 configured to slideably engage the corresponding tongue and groove connectors on the distal and/or proximal wedges 1514, 1516 to enable width expansion as described herein throughout.

The posterior ramp 1518 further includes an endplate engagement lobe 1540 comprising a curved V-shape having an apex oriented away from the first end 1530. The endplate engagement lobe 1540 includes a top surface 1542, a bottom surface 1544, and a lateral surface 1546. By way of example, the engagement lobe 1540 has a generally round or oval cross-sectional shape, however it should be noted that the engagement lobe 1540 may have any suitable cross-sectional shape including but not limited to (and by way of example only a circle, an oval, an ellipse, a triangle, a square, a T-shape, a V-shape, a regular polygon, an irregular polygon, or an irregular shape, or any combination thereof). By way of example, the lateral surface 1546 functions as a translation surface that slideably engages inclined surfaces 1548 of the posterior endplates 1522a, 1522c to facilitate height expansion. By way of example, the endplate engagement lobe 1540 has a general outward medial-lateral curve that enables the posterior endplates 1522a, 1522c to change in angle as height expansion occurs.

Figure 136B:
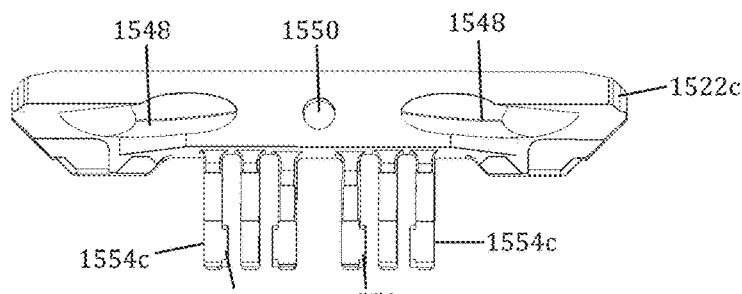
Figure 137A:
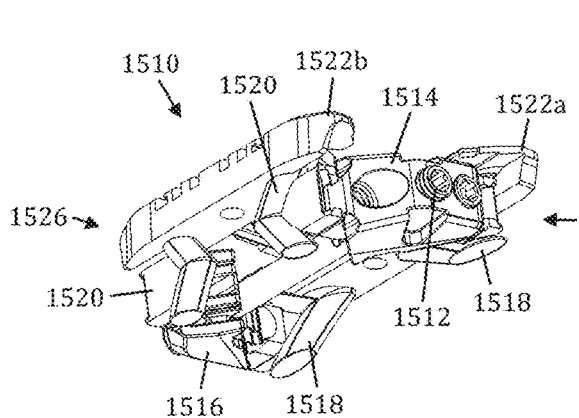
Figure 137B:
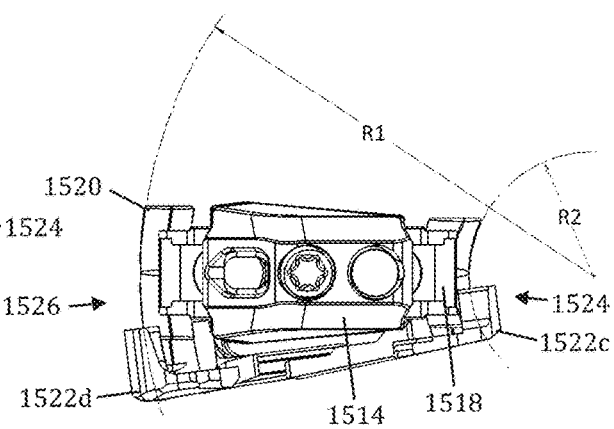

By way of example only, the posterior endplates 1522a, 1522c are substantially as previously described but for the inclined surfaces 1548 that slideably engage the posterior ramps 1518 (e.g. FIG. 136B). By way of example only, the inclined surfaces 1548 have a cross-sectional shape to match that of the engagement lobe 1540, for example generally round in the current embodiment. This enables consistent translational contact during height expansion while also enabling the posterior endplates 1522a, 1522c to change angle during height expansion, which creates a true lordotic expansion. As illustrated by way of example only in FIG. 137B, in order for the posterior endplates 1522a, 1522c to remain coplanar with the anterior endplates 1522b, 1522d during height expansion, the arc of curvature R2 for the posterior side 1524 must be greater than the arc of curvature R1 for the anterior side 1526. The posterior endplates 1522a, 1522c may also include a generally curved stabilizer aperture 1550 configured to receive the curved stabilization post (not shown) therein.

In the instant embodiment, the lateral projections 1452 on the medial flanges 1554a, 1554c may be elongated (e.g. elliptical, rectangular, etc) rather than circular because the posterior endplates 1522a, 1522c do not pivot relative to the anterior endplates 1522b, 1522d during height expansion. Rather, the interface between the medial flanges on the posterior ramps and the medial flanges on the anterior ramps remain coplanar during height expansion.

In operation, first width expansion proceeds substantially as described above with respect to previous embodiments. That is, the actuator 1512 is turned a select number of actuations causing the distal and proximal wedges 1514, 1516 to translate along the various tongue and groove connectors of the posterior ramps 1518 and anterior ramps 1520 until a predetermined width expansion is reached (e.g. maximum width expansion), wherein the distal and proximal wedges 1514, 1516 disassociate from the endplates. Turning the actuator 1512 additional actuations in the same actuation direction then causes height expansion of all endplates 1522-1522d, which unlike previous embodiments now enables all endplates to change in angle during height expansion. Height expansion continues in this fashion until translation of the distal and proximal wedges 1514, 1516 stops entirely, with the expandable fusion device 1510 at maximum width, maximum height, and maximum lordosis expansion. Thus, turning the actuator 1512 a select number of rotations in a first actuation direction causes width expansion. Turning the actuator 1512 additional actuations in the same actuation direction causes at least one of height expansion, width expansion, and lordotic expansion.

The expandable fusion device 1510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1510.

FIGS. 138-142 illustrate an example of an expandable fusion device 1610 for implantation between two adjacent vertebrae according to another embodiment of the disclosure. By way of example only, the expandable fusion device 1610 of the present embodiment includes an actuator 1612, a distal wedge 1614, a proximal wedge 1616, a pair of identical posterior ramps 1618, a pair of identical anterior ramps 1620, a plurality of endplates 1622a-1622d, and a width stabilizer assembly 1624. As with previously-described embodiments, the distal and proximal wedges 1614, 1616 are coupled with the actuator 1612. The posterior ramps 1618 and anterior ramps 1620 are each slideably coupled with the distal wedge 1614, the proximal wedge 1616, and/or the endplates 1622a-1622d. Generally, the expandable fusion device 1610 is substantially similar to expandable fusion device 10 described above, and any/all of the features described above with respect to fusion device 10 (and any other expandable fusion device described herein) may apply to fusion device 1610 unless otherwise noted. By way of example only, the expandable fusion device 1610 is illustrative of an expandable fusion device that expands in width and height, and includes a parallel-link width stabilizer assembly 1624 that may be applied to any expandable fusion device examples described herein, according to some embodiments. By way of example only, the expandable fusion device 1610 of the present embodiment has a posterior side 1626 and an anterior side 1628.

By way of example, the actuator 1612, distal wedge 1614, proximal wedge 1616, posterior ramps 1618, anterior ramps 1620, and endplates 1622a-1622d may be identical or substantially similar to corresponding elements disclosed herein with respect to other embodiments.

In the instant embodiment, the expandable fusion device 1610 includes a width stabilizer assembly 1624 configured to maintain the width-expanded state of the expandable fusion device 1610 during height expansion or collapsing. By way of example only, the width stabilizer 1624 of the present embodiment comprises a plurality of rigid link bars 1630 pivotally associated with a sliding carriage 1632 and extending between the sliding carriage 1632 and a plurality of pivot pins 1634 extending between vertically adjacent endplate pairs (e.g. posterior endplates 1622a/1622c and anterior endplates 1622b/1622d). The sliding carriage 1632 is associated with the actuator 1612, and includes a central lumen 1636 configured to enable the actuator 1612 to pass through the carriage 1632. The carriage includes a plurality of carriage pins 1638 configured to pivotally couple one end (e.g. "medial end") of the link bars 1630 to the sliding carriage 1632. By way of example only, the pivot pins 1634 may be immovably coupled with pin apertures 1640 (e.g. by press fit, swaging, etc) provided on endplates 1622a-1622d. The pivot pins 1634 are configured to pivotally couple one end (e.g. "lateral end") of the link bars 1630 to an endplate pair (e.g. posterior endplates 1622a/1622c or anterior endplates 1622b/1622d).

By way of example, the embodiment shown and described herein includes a single link bar 1630 extending between the sliding carriage 1632 and anterior pivot pins 1634, and a two link bars 1630 extending between the sliding carriage 1632 and posterior pivot pins 1634. This configuration shown is the minimum configuration required to for the width stabilizer assembly 1624 to function, however additional configurations including at least two link bars 1630 per side, and preferably at least three (or more) link bars 1630 per side are possible. The endplates 1622a-1622d may each be provided with an inferior recess 1642 configured to house at least a portion of the link bars 1630 when the expandable fusion device 1610 is in an initial, collapsed state (e.g. FIG. 140).

Figure 140:
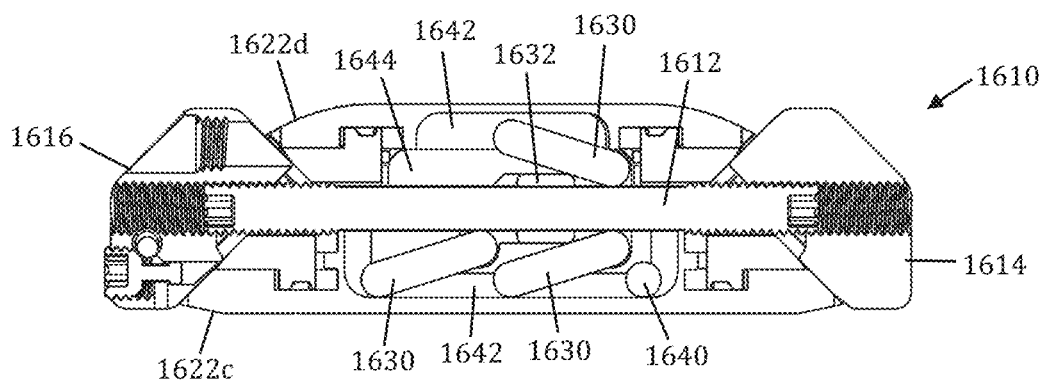

In use, when the expandable fusion device 1610 is in an initial, collapsed state, the slideable carriage 1632 may be positioned along the actuator 1612 within a distal aspect of the interior cavity 1644 of the device 1610, as shown by way of example in FIG. 140. In this orientation, the link bars 1630 are angled distally from the endplates to the carriage. As the expandable fusion device 1610 undergoes width expansion, the expansion force is transferred through the pivoting link bars 1630 to the sliding carriage 1632, which is caused to translate proximally along the actuator 1612. When maximum width expansion has been achieved, the link bars 1630 may be angled in a slight proximal direction, as shown in FIG. 142. The force required to overcome this directional orientation of the link bars 1630 (e.g. proximally oriented) is greater than the force required to collapse the device 1610 in height, and so only after the device 1610 is collapsed in height first will enough force be applied to the link bars 1630 to cause them to translate distally to effectuate width collapse. In some embodiments, directly advancing or retracting the carriage would result in width expansion or collapse. In such embodiments, the distal and proximal wedges may have included angles of approximately 180 degrees or may not make sliding contact with the endplates, resulting in width expansion to be more independent or completely independent of height expansion.

The expandable fusion device 1610 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1610.

FIGS. 143-146 illustrate an example of an expandable fusion device 1710 for implantation between two adjacent vertebrae according to another embodiment of the disclosure. By way of example only, the expandable fusion device 1710 of the present embodiment includes an actuator 1712, a distal wedge 1714, a proximal wedge 1716, a pair of identical posterior ramps 1718, a pair of identical anterior ramps 1720, a plurality of endplates 1722a-1722d, and a width stabilizer 1724. As with previously-described embodiments, the distal and proximal wedges 1714, 1716 are coupled with the actuator 1712. The posterior ramps 1718 and anterior ramps 1720 are each slideably coupled with the distal wedge 1714, the proximal wedge 1716, and/or the endplates 1722a-1722d. Generally, the expandable fusion device 1710 is substantially similar to expandable fusion device 10 described above, and any/all of the features described above with respect to fusion device 10 (and any other expandable fusion device described herein) may apply to fusion device 1710 unless otherwise noted. By way of example only, the expandable fusion device 1710 is illustrative of an expandable fusion device that expands in width and height, and includes a width stabilizer 1724 that may be applied to any expandable fusion device examples described herein, according to some embodiments. By way of example only, the expandable fusion device 1710 of the present embodiment has a posterior side 1726 and an anterior side 1728.

By way of example, the actuator 1712, distal wedge 1714, proximal wedge 1716, posterior ramps 1718, anterior ramps 1720, and endplates 1722a-1722d may be identical or substantially similar to corresponding elements disclosed herein with respect to other embodiments.

In the instant embodiment, the expandable fusion device 1710 includes a width stabilizer 1724 configured to maintain the width-expanded state of the expandable fusion device 1710 during height expansion or collapsing. By way of example only, the width stabilizer 1724 of the present embodiment comprises a carriage 1730 having a plurality of laterally extending flanges 1732 for engaging the endplates 1722a-1722d, and a U-shaped channel configured to receive at least a portion of the actuator 1712 therein. By way of example only, at least one flange 1732 engages each one of the endplates 1722a-1722d. The endplates 1722a-1722d may have a plurality of lateral channels 1736, each configured to slidingly receive at least a portion of one of the lateral flanges 1732 therein when the expandable fusion device 1710 is in a collapsed width state. By way of example only, the carriage 1730 shown and described herein has a pair of lateral flanges 1732 extending to each endplate 1722a-1722d, and each endplate has a pair of lateral channels 1736 configured to receive them. However, any number of lateral flanges 1732 and lateral channels 1736 may be used if needed. In some embodiments, the carriage 1730 may be centered with respect to natural midplane of the expandable fusion device 1710 due to the engagement of the actuator 1712 with the U-shaped channel 1734.

By way of example only, the lateral flanges 1732 of the present embodiment may prevent the expandable fusion device 1710 from expanding in height until a predetermined width expansion (e.g. at least substantial) has occurred. In the width-collapsed state, the lateral flanges 1732 engage the endplates 1722a-1722d and prevent height expansion while engaged with the lateral channels 1736. By way of example only, In the instant embodiment the lateral flanges 1732 that are configured to engage the upper endplates (e.g. upper posterior endplate 1722a and upper anterior endplate 1722b) each include a cutout portion 1738 that allows the flanges 1738 to disengage from their respective endplates (e.g. upper posterior endplate 1722a and upper anterior endplate 1722b) when a predetermined maximum width expansion is achieved, allowing height expansion to proceed. The lateral flanges 1732 that are configured to engage the lower endplates (e.g. lower posterior endplate 1722c and the lower posterior endplate 1722d) do not have cutout portions and therefore remain captured within the respective lateral channels 1736. When height expansion occurs, the carriage 1730 moves together with the endplates with which the flanges 1732 remain engaged (e.g. lower posterior endplate 1722c and the lower posterior endplate 1722d in the instant example). The U-shaped channel 1734 on the carriage 1730 allows the carriage 1730 to translate vertically relative to the actuator 12 while maintaining alignment with midplane of the expandable fusion device 1710. It should be noted that, while in the described example the cutout portions 1738 are located on the upper flanges 1732 configured to engage the upper endplates 1722a, 1722b, the carriage 1730 could be provided wherein the cutout portions 1738 are positioned on the lower flanges 1732 configured to engage the lower endplates 1722c, 1722d, so long as the upper flanges 1732 in such an embodiment do not have cutout portions, and the carriage 1730 is arranged so that the opening of the U-shaped channel 1736 is oriented toward the flanges 1736 with the cutout portions 1738.

By way of example only, the expandable fusion device 1710 of the present embodiment further includes height stabilizer pins 1740 having midline lateral projections 1742 that engage mating channels 1744 in the posterior ramps 1718 and the anterior ramps 1720 and keep the pins centered as the expandable fusion device 1710 expands in height (e.g. maintaining the height stabilizer pin 1740 engaged to an equal depth into the upper and the lower endplates 1722a-1722d). In some embodiments, the endplates 1722a-1722d may further include interior-facing protrusions 1746 that mate with the carriage 1730 and increase the engagement length between the endplates 1722a-1722d and the carriage 1730, which may be particularly important at or near fully width-expanded state.

The expandable fusion device 1710 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1710.

FIGS. 147-155 illustrate an example of an expandable fusion device 1810 for implantation between two adjacent vertebrae according to another embodiment of the disclosure. By way of example only, the expandable fusion device 1810 of the present embodiment includes an actuator 1812, a distal wedge 1814, a proximal wedge 1816, a pair of identical posterior ramps 1818, a pair of identical anterior ramps 1820, a plurality of endplates 1822a-1822d, and a width stabilizer 1824. As with previously-described embodiments, the distal and proximal wedges 1814, 1816 are coupled with the actuator 1812. The posterior ramps 1818 and anterior ramps 1820 are each slideably coupled with the distal wedge 1814, the proximal wedge 1816, and/or the endplates 1822a-1822d. Generally, the expandable fusion device 1810 is substantially similar to expandable fusion device 10 described above, and any/all of the features described above with respect to fusion device 10 (and any other expandable fusion device described herein) may apply to fusion device 1810 unless otherwise noted. By way of example only, the expandable fusion device 1810 is illustrative of an expandable fusion device that expands in width and height, and includes a width stabilizer 1824 that may be applied to any expandable fusion device examples described herein, according to some embodiments. By way of example only, the expandable fusion device 1810 of the present embodiment has a posterior side 1826 and an anterior side 1828.

By way of example, the actuator 1812, distal wedge 1814, proximal wedge 1816, posterior ramps 1818, anterior ramps 1820, and endplates 1822a-1822d may be identical or substantially similar to corresponding elements disclosed herein with respect to other embodiments.

In the instant embodiment, the expandable fusion device 1810 includes a width stabilizer 1824 configured to maintain the width-expanded state of the expandable fusion device 1810 during height expansion or collapsing. Referring to FIG. 149, the width stabilizer 1824 of the present embodiment comprises (by way of example) a carriage 1830 having a plurality of laterally extending flanges 1832 for engaging the endplates 1822a-1822d, and a U-shaped channel 1834 configured to receive at least a portion of the actuator 1812 therein. By way of example only, at least one flange 1832 engages each one of the endplates 1822a-1822d. The endplates 1822a-1822d may have a plurality of lateral channels 1836, each sized and configured to slidingly receive at least a portion of one of the lateral flanges 1832 therein when the expandable fusion device 1810 is in a collapsed width state. By way of example only, the carriage 1830 shown and described herein has a pair of lateral flanges 1832 extending in one direction to one endplate pair (e.g. anterior endplates 1822b, 1822d), and one lateral flange 1832 extending in the opposite direction to the other endplate pair (e.g. posterior endplates 1822a, 1822c). The receiving endplates have corresponding structure configured to receive the specific configuration of the carriage 1830. For example, in addition to the lateral flanges 1832, the carriage 1830 of the present embodiment may comprise lateral lips 1838 on either side of the flanges configured to slideably engage elongated recesses 1840 on the sides of lateral channels 1836, and a central cutaway portion 1842 configured to provide clearance for the height stabilizer pin 1844.

FIGS. 150-155 illustrate several alternative examples of carriage configurations that may be used with expandable fusion device 1810. In some embodiments, the expandable fusion device 1810 may include a carriage 1850 having a pair of lateral flanges 1852 extending to one side, a single flange 1852 extending to the opposite side, a U-shaped channel 1854 for registering to the actuator 1812, and tapered sides 1856, as shown by way of example only in FIG. 150. In some embodiments, the expandable fusion device 1810 may include a carriage 1860 having a pair of lateral flanges 1862 extending to each side, and a central lumen 1864 extending transversely therethough for registering to the actuator 1812, as shown by way of example only in FIG. 151. In some embodiments, the expandable fusion device 1810 may include a carriage 1870 having a single lateral flange 1872 extending to each side, and a U-shaped channel 1874 extending transversely therethough for registering to the actuator 1812, as shown by way of example only in FIG. 152. In some embodiments, the expandable fusion device 1810 may include a carriage 1880 having a single lateral flange 1882 extending to each side, and a central lumen 1884 extending transversely therethough for registering to the actuator 1812, as shown by way of example only in FIG. 153. In some embodiments, the expandable fusion device 1810 may include a carriage 1890 having a pair of lateral flanges 1892 extending to one side, a single lateral flange 1892 extending to the opposite side, and a central lumen 1894 extending transversely therethough for registering to the actuator 1812, as shown by way of example only in FIG. 154. In some embodiments, the expandable fusion device 1810 may include a carriage 1900 having a single lateral flange 1902 (e.g. of different thickness) extending to each side, and a U-shaped channel 1904 extending transversely therethough for registering to the actuator 1812, as shown by way of example only in FIG. 155.

The expandable fusion device 1810 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1810.

FIGS. 156-161 illustrate an example of an expandable fusion device 1910 for implantation between two adjacent vertebrae according to another embodiment of the disclosure. By way of example only, the expandable fusion device 1910 of the present embodiment includes an actuator 1912, a distal wedge 1914, a proximal wedge 1916, a pair of distal ramps 1918, a pair of proximal ramps 1920, a plurality of endplates 1922a-1922d, and a (optionally) plurality of guide pins. As with previously-described embodiments, the distal and proximal wedges 1914, 1916 are coupled with the actuator 1912. The distal ramps 1918 are slideably coupled with the distal wedge 1914. The proximal ramps 1920 are slideably coupled with the proximal wedge 1916. The plurality of endplates 1922a-1922d are slideably coupled with the ramps 1918, 1920. Generally, the expandable fusion device 1910 is substantially similar to expandable fusion device 10 described above, and any/all of the features described above with respect to fusion device 10 (and any other expandable fusion device described herein) may apply to fusion device 1910 unless otherwise noted. By way of example only, the expandable fusion device 1910 is illustrative of another example of a width stabilizer that may be applied to any expandable fusion device examples described herein, according to some embodiments.

By way of example, the actuator 1912, distal wedge 1914, proximal wedge 1916, posterior ramps 1918, anterior ramps 1920, and endplates 1922a-1922d may be identical or substantially similar to corresponding elements disclosed herein with respect to other embodiments.

Referring first to FIGS. 156-157, one example of a width stabilizer 1924 is shown. By way of example only, the width stabilizer 1924 of the present example comprises a crossbar 1926 sized and configured to extend between upper endplates 1922a, 1922b and/or lower endplates 1922c, 1922d. The crossbar 1926 may have any cross-sectional shape that ensures the endplates 1922a-1922d remain generally parallel to one another during width expansion, including but not limited to elliptical, rectangular, trapezoidal, polygonal, and the like. By way of example, the crossbar 1926 has a generally chevron shape comprising an apex 1928 and a pair of angled struts 1930. The angled struts 1930 are self-centering between the endplates and may be advantageous in embodiments with a ramp structure that would preclude straight struts at the midline (for example). Additionally, the angled struts 1930 are prevented from disengaging from the lateral slots 1932 during height expansion because the angled struts 1930 cannot translate within lateral slots 1932 in the absence of the endplates moving closer together or farther apart. By way of example, the crossbar 1926 may be "free floating" (e.g. not registered to the actuator 1912) and have an included angle matching that of the distal and proximal wedges 1914, 1916, or alternatively they may have a different included angle.

By way of example, the endplates 1922a-1922d each have a lateral slot 1932 for each width stabilizer 1924 extending therethrough at an oblique angle relative to a longitudinal axis of the actuator 1912, the lateral slot(s) 1932 configured to slideably receive at least a portion of the crossbar 1926 therein. By way of example, the instant example embodiment comprises a pair of lateral slots 1932 positioned on either side of the midpoint of each endplate but angled toward both the longitudinal and the transverse centerlines of the device 1910, however this position may vary depending on how many width stabilizers are in use per endplate and the ramp configuration of the specific embodiment being used. Because the width stabilizer 1924 is a single crossbar, a pair of width stabilizers 1924 spanning both the upper and lower endplate pairs is used at each crossbar location in the current embodiment to force the endplates to remain parallel during width expansion. By way of example, the lateral slots 1932 are sized and shaped to snugly receive the angled struts 1930 therein without allowing for any wiggle motion. This snug interaction maintains the endplates 1922a-1922d in a parallel orientation during width expansion. The width stabilizers 1924 of the current example do not inhibit height expansion at any time because they are not attached to the actuator 1912. By way of example, at least a portion of the crossbar 1926 may remain engaged within the lateral slots 1932 even after completion of width expansion.

In some embodiments, multiple width stabilizers engaged with the same endplate may be oriented in different directions, for example with the apex 1928 of one width stabilizer oriented in the proximal direction and the apex of another stabilizer oriented in the distal direction. In other embodiments, width stabilizer may comprise two or more chevrons connected with bridges apex-to-apex and with the apexes all pointing in the same direction. In other embodiments, directly advancing or retracting the width stabilizer or cross-bar or crossbars would result in width expansion or collapse. In those embodiments the distal and proximal wedges may have included angles of approximately 180° or may not make sliding contact with the endplates, resulting in width expansion to be more independent or completely independent from height expansion.

Referring to FIGS. 158-159, in some embodiments, two opposing crossbars 1926 may be stabilized via prong and groove interaction (e.g. one crossbar 1926 including an extension or prong 1934 that is received within a corresponding groove 1936 on the opposing crossbar 1926) may be used for added stability.

Referring to FIGS. 160-161, in some embodiments, the width stabilizer 1924 may include a crossbar 1938 having an included angle of 180 degrees (e.g. a linear crossbar) connected to a chevron shaped crossbar 1926 by a prong and groove connection as described above (e.g. the chevron crossbar 1926 including an extension or prong 1934 that is received within a corresponding groove 1936 on the straight crossbar 1938). The prong and groove interaction in this example keep the straight crossbar 1938 properly aligned or centered during width expansion.

The expandable fusion device 1910 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 1910.

FIGS. 162-168 illustrate an example of an expandable fusion device 2010 for implantation between two adjacent vertebrae according to another embodiment of the disclosure. By way of example only, the expandable fusion device 2010 of the present embodiment includes an actuator 2012, a distal wedge 2014, a proximal wedge 2016, a pair of distal ramps 2018, a pair of proximal ramps 2020, a plurality of endplates 2022a-2022d, and a (optionally) plurality of guide pins. As with previously-described embodiments, the distal and proximal wedges 2014, 2016 are coupled with the actuator 2012. The distal ramps 2018 are slideably coupled with the distal wedge 2014. The proximal ramps 2020 are slideably coupled with the proximal wedge 2016. The plurality of endplates 2022a-2022d are slideably coupled with the ramps 2018, 2020. Generally, the expandable fusion device 2010 is substantially similar to expandable fusion device 10 described above, and any/all of the features described above with respect to fusion device 10 (and any other expandable fusion device described herein) may apply to fusion device 2010 unless otherwise noted. By way of example only, the expandable fusion device 2010 is illustrative of an example of a height stabilizer that may be applied to any expandable fusion device examples described herein, according to some embodiments.

By way of example, the actuator 2012, distal wedge 2014, proximal wedge 2016, posterior ramps 2018, anterior ramps 2020, and endplates 2022a-2022d may be identical or substantially similar to corresponding elements disclosed herein with respect to other embodiments.

Referring first to FIGS. 162-163, one example of a height stabilizer 2024 is shown. By way of example only, the height stabilizer 2024 of the present example comprises a crossbar 2026 sized and configured to extend between upper and lower endplate pairs 2022a/2022c, 2022b/2022d. The crossbar 2026 may have any cross-sectional shape that ensures the endplates 2022a-2022d remain generally parallel to one another during height expansion, including but not limited to elliptical, rectangular, trapezoidal, polygonal, and the like. By way of example, the crossbar 2026 has a generally chevron shape comprising an apex 2028 and a pair of angled struts 2030. The angled struts 2030 are self-centering between the endplates. Additionally, the angled struts 2030 are prevented from disengaging from the vertical slots 2032 during width or height expansion because the angled struts 2030 cannot translate within vertical slots 2032 in the absence of the endplates moving closer together or farther apart. By way of example, the crossbar 2026 may be "free floating" and have an included angle matching that of the distal and proximal ramps 2018, 2020, or alternatively they may have a different included angle. In other embodiments, directly advancing one or more of the crossbars would result in height expansion (similar functionality to that on FIG. 252).

By way of example, the endplates 2022a-2022d each have a vertical slot 2032 for each height stabilizer 2024 extending therethrough at an oblique angle relative to a longitudinal axis of the respective endplate, the vertical slot(s) 2032 configured to slideably receive at least a portion of the crossbar 2026 therein. By way of example, the instant example embodiment comprises a pair of vertical slots 2032 positioned on either side of the midpoint of each endplate but angled toward the transverse centerline of the device 2010, however this position may vary depending on how many width stabilizers are in use per endplate and the ramp configuration of the specific embodiment being used. Because the height stabilizer 2024 is a single crossbar, a pair of height stabilizers 2024 spanning both the upper and lower endplate pairs is used at each crossbar location in the current embodiment to force the endplates to remain parallel during height expansion. By way of example, the vertical slots 2032 are sized and shaped to snugly receive the angled struts 2030 therein without allowing for any wiggle motion. This snug interaction maintains the endplates 2022a-2022d in a parallel orientation during height expansion. The height stabilizers 2024 of the current example do not inhibit expansion at any time because they are not attached to the actuator 2012. By way of example, at least a portion of the crossbar 2026 may remain engaged within the lateral slots 2032 even after completion of height expansion.

In some embodiments, multiple height stabilizers engaged with the same endplate may be oriented in different directions, for example with the apex 2028 of one height stabilizer oriented in the proximal direction and the apex of another stabilizer oriented in the distal direction.

Referring to FIGS. 164-168, in some embodiments, two opposing crossbars 2026 may be stabilized via prong and groove interaction with the adjacent distal ramps 2018 and/or proximal ramps 2020 (e.g. one crossbar 2026 including an extension or prong 2034 that is received within a mating slot 2036 on a distal ramp 2018 and the other crossbar 2026 including an extension or prong 2034 that is received within a mating slot 2036 on a proximal ramp 2020) may be used for added stability. In some embodiments, the crossbar 2026 may have a chevron shape but include a prong 2034 extending from the apex 2028 (e.g. FIG. 167). In some embodiments, the height stabilizer may comprise a straight crossbar 2038 having a prong 2036 extending therefrom (e.g. FIG. 168). In this case, the prong and groove connection with the distal or proximal ramp 2018, 2020 is critical because without such an interaction, the straight crossbar 2038 would become easily disengaged from one of the vertical slots 2032 by becoming uncentered between the endplates.

The expandable fusion device 2010 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2010.

In some embodiments, it may be desirable and/or advantageous to anchor the expandable fusion device 10 or a specific part thereof to the vertebral body during a surgical procedure. By way of example only, FIGS. 169-197 illustrate several examples of adding anchor elements or anti-migration features to various components of the expandable fusion device 10. To simplify the disclosure, all such anti-migration features are disclosed in the context of expandable fusion device 10 described above. However, it should be understood that any feature or element disclosed in the context of expandable fusion device 10 may be applied to any other embodiment or combination of embodiments disclosed herein (or any other width expandable device) without reservation.

As described above, the expandable fusion device 10 of the present embodiment is configured for lateral insertion into a target disc space, and is described as having an anterior side (e.g. configured for positioning within an anterior aspect of the target disc space) and a posterior side (e.g. configured for positioning within a posterior aspect of the target disc space). By way of example only, the expandable fusion device 10 of the present embodiment includes an actuator 12, a distal wedge 14, a proximal wedge 16, a pair of posterior ramps 18a, 18b (e.g., distal posterior ramp 18a and proximal posterior ramp 18b), a pair of anterior ramps 20a, 20b, (e.g., distal anterior ramp 20a and proximal anterior ramp 20b), a plurality of endplates 22a-22d (e.g., first or upper posterior endplate 22a, first or upper anterior endplate 22b, second or lower posterior endplate 22c, second or lower anterior endplate 22d), a plurality of stabilization posts, and a plurality of guide pins. The distal and proximal wedges 14, 16 are coupled with the actuator 12. The distal ramps 18a, 20a are slideably coupled with the distal wedge 14. The proximal ramps 18b, 20b are slideably coupled with the proximal wedge 16. The plurality of endplates 22a-22d are slideably coupled with the ramps 18a, 18b, 20a, 20b.

By way of example only, FIGS. 169-174 illustrate several examples of anti-migration features provided on the distal wedge and/or proximal wedge 16. In some embodiments, anti-migration features on the distal wedge 14 and/or proximal wedge 16 may help keep the expandable fusion device 10 centered during width expansion by providing an anchor in the vertebral bodies (e.g. vertebral endplates) adjacent the surgical target site (e.g. intervertebral disc space), for example to resist or reduce side-to-side movement of the wedges during width expansion. By way of example, the various anti-migration features described herein may be positioned on the upper and/or lower facing surfaces of the wedges in any combination. In some embodiments, the anti-migration features may be provided in the form of fins or elongated penetration elements 2110 positioned on one side of the wedge (e.g. distal or proximal), as shown by way of example only in FIGS. 169-171. In some embodiments, the anti-migration features may be a plurality of spikes 2112 positioned on both sides of the wedges, as shown by way of example only in FIG. 172. In some embodiments, the anti-migration features may be in the form of a plurality of fins 2114 provided on both sides of the wedge, as shown by way of example in FIG. 173. In some embodiments, the anti-migration features may be in the form of a plurality of elongated spines 2116 distributed across the top and/or bottom of the wedges, as shown by way of example only in FIG. 174.

By way of example only, FIGS. 175-183 illustrate several examples of anti-migration elements on device endplates 22a-22d. In some embodiments, anti-migration features on one of the endplates or an upper-lower endplate pair (e.g. 22a/22c or 22b/22d) help keep that/those endplates in place during width expansion by penetrating the vertebral bodies. This may be advantageous if one needs to bias the direction of width expansion of the expandable fusion device 10. For example, fins 2020 positioned on the posterior endplates 22*a*, 22*c* (e.g. as shown in FIGS. 175-177) may provide resistance to width expansion in the posterior direction, making width expansion in the anterior direction a more likely result as the path of least resistance. Alternatively, the fins may be positioned on the anterior endplates and act to make posterior expansion more likely as a path of least resistance.

In some embodiments, providing fins with a specific cross-sectional shape (e.g. directional) may provide more resistance to motion in one direction than the other, thereby urging width expansion in a particular direction. By way of example only, anti-migration fins may have any useful cross-sectional shape, including but not limited to (and by way of example only) rectangular, rectangular with one bevel (e.g. fin 2122 of FIGS. 178-179), rectangular with two bevels (e.g. fin 2110 of FIGS. 169-171), trapezoidal, triangular, regular or irregular quadrilateral, or other polygonal or curvilinear cross-sectional shapes.

In some embodiments, it may be advantageous to locate the directional fins 2124 on the outer margin of endplates (e.g. posterior endplates 22*a*, 22*c*, as shown by way of example only in FIGS. 180-182). In a lateral lordotic application like the present example embodiment, locating the anti-migration fin 2124 in this way is advantageous because adding anti-migration fins 2124 here may not add total initial height to the expandable fusion device 10, which is beneficial during the implantation process.

In some embodiments, the expandable fusion device 10 may be provided with a plurality of elongated, directional anti-migration fins 2126 distributed on at least one endplate, as shown by way of example only in FIG. 183.

By way of example only, FIGS. 184-187 illustrate anti-migration elements in the form of directional cleats 2130 provided on width stabilizers (e.g. medial flanges 196*a*, 196*c* on the posterior endplates 22*a*, 22*c*). During width expansion (for example), the cleats 2130 dig into the vertebral bodies and cause the expandable fusion device 10 to preferentially expand in the direction opposite the cleats 2130 (e.g. in the anterior direction). This approach may be advantageous in that in the collapsed state the cleats 2130 are "hidden" by the adjacent medial flanges 196*b*, in that the cleats 2130 do not exceed the vertical height of the collapsed expandable fusion device 10 (see, e.g. FIGS. 184 & 186). Thus, the expandable fusion device 10 may be inserted into the target site (e.g. intervertebral disc space) without the cleats 2130 damaging vertebral endplates. During the width expansion state, the cleats 2130 emerge from the interflange recesses of the anterior endplates 22*b*, 22*d*, and engage the vertebral endplates.

By way of example only, FIGS. 188-195 illustrate several examples of anti-migration features 2140 provided on height-expanding ramps, for example posterior ramps 18*a*, 18*b*. This may be advantageous in that in most cases these anti-migration features are at their most prominent at initial height (due to the lordotic configuration of the expandable fusion device 10 in the collapsed state), prior to or during width expansion when the anti-migration features are most useful to bias width expansion in a particular direction (see e.g. FIGS. 188-189). As the height expansion subsequently takes place, the prominence of these anti-migration features decreases due to the elevation of structure around them, as shown by way of example only in FIG. 190. By way of example, FIGS. 191-195 illustrate several examples of a posterior ramp 18*a* (or 18*b*) with different configurations of anti-migration features 2140 provided thereon.

By way of example only, FIGS. 196-197 illustrate on way to achieve a biasing effect without using additional anti-migration features, by adjusting the height of the posterior ramps 18*a*, 18*b* so that the top portions of first and second lobes 84, 86 are configured to extend beyond the endplate surfaces the initial collapsed height state. This may achieve the same biasing effect (e.g. biased width expansion) as described above with regard to providing anti-migration features.

FIGS. 198-201 illustrate an example of an insertion instrument 2210 configured for use with the expandable fusion implant 10 and other embodiments disclosed herein, according to one example embodiment. In some embodiments, the insertion instrument 2210 is configured to engage the proximal wedge 16 of the expandable fusion implant 10 in a manner such that a longitudinal axis of the insertion instrument 2210 is coaxial with the longitudinal axis of the actuator 12. By way of example only, the insertion instrument 2210 includes an elongated housing 2212 having a generally rectangular outer perimeter shape, with smoothed or rounded edges 2214 to minimize trauma to patient tissue during use. The insertion instrument 2210 further comprises a distal end 2216 having a shape complimentary to the shape of the proximal face 52 of the proximal wedge 16 such that the distal end 2216 has a flush interface with the proximal wedge 16 when coupled. The distal end 2216 further comprises a pair of distal flanges or tangs 2218 extending distally from the distal end 2216 and configured to engage the engagement features 58 (e.g. recesses) on the proximal wedge 16.

The insertion instrument 2210 may have at least one interior lumen or channel extending longitudinally through the housing 2212 to enable passage of various instrumentation that are needed to insert, expand, and lock down the expandable fusion device 10 during use, including but not limited to device holder 2220, an expansion driver 2222, and a lock screw driver (not shown). By way of example only the insertion instrument 2210 may have three separate but parallel channels extending longitudinally through the housing 2212, including a first channel 2224 positioned on the anterior side (when attached to the device 10), a second channel 2226 extending through the middle of the housing 2212, and a third channel 2228 positioned on the posterior side (when attached to the device 10). By way of example only, the first channel 2224 may be aligned with the auxiliary aperture 61 of the proximal wedge 16 when attached to the device 10 and sized and configured to enable passage of a device holder 2220 therethough so that the device holder 2220 may engage the auxiliary aperture 61 (e.g. by threaded engagement, press fit, snap fit, and the like) to secure the device 10 for insertion. The second or middle channel 2226 may be aligned with the threaded bore 56 of the proximal wedge 16 when attached to the device 10 so that the expansion driver 2222 may traverse the threaded bore 56 and engage the drive feature 32 of the actuator 12 to drive width and height expansion as described herein. The third channel 2228 may be aligned with the lock screw aperture 65 of the proximal wedge 16 when attached to the device 10, and is sized and configured to allow passage of a lock screw driver (not shown) therethrough so that the lock screw driver may engage the lock screw 63.

By way of example, due to the positioning of the device holder 2220 on one side of the housing 2212, the insertion instrument 2210 may have a tendency to tilt away from the engagement location when the device holder 2220 is engaged to the device 10. This phenomenon may be counteracted by a negative angle surface 2230 on the distal flange 2218 (FIG. 200) that helps to keep the inserter 2210 in the proper alignment during use.

As previously mentioned, in some embodiments it may be useful to register the proximal wedge 16 to the bony structure to maintain alignment during width expansion of the expandable fusion device 10. FIG. 201 illustrates an example embodiment that achieves a similar result by providing anti-migration features 2232 on the distal end 2216 of the housing 2212. By way of example only, the anti-migration features 2232 may comprise any structure capable of penetrating the bony tissue and preventing relative movement (e.g. side-to-side) of the distal end 2216 during width expansion of the device 10, including but not limited to fins, ridges, spikes, and the like.

FIGS. 202-204 illustrate an example of an expandable fusion device 2310 for implantation between two adjacent vertebrae according to another embodiment of the disclosure. By way of example only, the expandable fusion device 2310 of the present embodiment includes an actuator 2312, a distal wedge 2314, a proximal wedge 2316, a pair of identical distal ramps 2318, a pair of identical proximal ramps 2320, a plurality of endplates 2322a-2322d, and a plurality of optional guide pins 2324. As with the previously described embodiment, the distal and proximal wedges 2314, 2316 are coupled with the actuator 2312. The distal ramps 2318 are slideably coupled with the distal wedge 2314. The proximal ramps 2320 are slideably coupled with the proximal wedge 2316. The plurality of endplates 2322a-2322d are slideably coupled with the distal ramps 2318 and slideably associated with the proximal ramps 2320. Generally, the expandable fusion device 2310 is substantially similar to expandable fusion device 10 described above, and any/all of the features described above with respect to fusion device 10 (and any other expandable fusion device embodiments described herein) may apply to fusion device 2310 unless otherwise noted. More specifically, the expandable fusion device 2310 is substantially similar to the expandable fusion device 210 described above, however the expandable fusion device 2310 of the present example includes a pair of flexible bridges 2326 connecting the proximal ends of endplates 2322a and 2322c, and endplates 2322b and 2322d, which may deform (e.g. elastically or plastically) during lordotic expansion. By way of example only, the expandable fusion device 2310 is illustrative of an expandable fusion device that expands in width, height, and lordotic expansion that may be applied to any expandable fusion device examples described herein, according to some embodiments.

By way of example, the actuator 2312, distal wedge 2314, proximal wedge 2316, and distal ramps 2318 may be identical or substantially similar to corresponding elements disclosed herein with respect to other embodiments.

FIG. 204 illustrates an example of a proximal ramp 2320 according to the present example embodiment. By way of example only, the proximal ramp 2320 has a proximal end 2330, distal end 2332, medial side 2334, and lateral side 2336. The medial side 2334 has upper and lower tongue and groove connectors 2338 configured to slideably interact with the corresponding tongue and groove connectors on the proximal wedge 2316 to enable width expansion as described with respect to expandable fusion device 10 above. By way of example only, the proximal ramp 2320 of the present embodiment has a distal-facing curved or cam surface 2340 configured to slideably interface with the curved surfaces 2344 on the proximal end of each of the endplates 2322a-2322d such that the endplates 2322a-2322d are pivotally associated with the proximal ramps 2320, and the distal-facing curved or cam surfaces 2340 are in continuous tangential contact with curved surfaces 2344. In some embodiments, each proximal ramp 2320 may further include a distal flange 2342 configured to nest within elongated recesses on the endplates 2322a-2322d (e.g. in the same manner as described with respect to analogous features of device 210 above) to detain the endplates 2322a-2322d during clinical use.

By way of example, the endplates 2322a-2322d are substantially similar to endplates 222a-222d described above, and thus only different or additional features will be described. In the instant example embodiment, the proximal ends of the upper and lower endplates on each side of the device 2310 are connected by way of a flexible bridge 2326, which may deform (e.g. elastically or plastically) during lordotic expansion. For example, the proximal end of upper endplate 2322a is connected to the proximal end of lower endplate 2322c by a first flexible bridge member 2326, and the proximal end of upper endplate 2322b is connected to the proximal end of the lower endplate 2322d by a second flexible bridge member 2326. In some embodiments, the flexible bridge 2326 may be an integral part of the endplates 2322a and 2322c, and endplates 2322b and 2322d such that each vertical endplate pairing comprises a single endplate component comprising an upper portion (e.g. upper portions 2322a, 2322b) and a lower portion (e.g. 2322c, 2322d). By way of example, the flexible bridges 2326 function to accommodate the angular relationship between the connected portions of the endplate components during lordotic expansion. The proximal ends of each of the endplates (or endplate portions) 2322a-2322d further include a curved surface 2344 configured to slideably associate with the curved or cam surfaces 2340 of the proximal ramps 2320.

In operation, first width expansion proceeds substantially as described above with respect to previous embodiments. That is, the actuator 2312 is turned a select number of actuations until some width expansion is reached and the endplate disengages from the distal wedge 2314. Once the disengagement occurs, further rotation of the actuator 2312 results in the distal ramps 2318 translating along the respective angled slots in the endplates, increasing at least one of the width, height, and lordosis angle in the process. Meanwhile, the curved surfaces 2344 of the endplates 2322a-2322d translate with continuous contact along curved or cam surfaces 2340 of the proximal ramps 2230 to provide a pivot surface for lordosis expansion. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle.

The expandable fusion device 2310 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2310.

FIGS. 205-207 illustrate an example of an expandable fusion device 2410 for implantation between two adjacent vertebrae according to another embodiment of the disclosure. By way of example only, the expandable fusion device 2410 of the present embodiment includes an actuator (not shown), distal and proximal wedge (not shown), a pair of identical distal ramps 2418, a pair of identical proximal ramps 2420, a plurality of endplates 2422a-2422d, and a plurality of optional guide pins (not shown). As with the previously described embodiment, the distal and proximal wedges 2414, 2416 are coupled with the actuator 2412. The distal ramps 2418 are slideably coupled with the distal wedge 2414. The proximal ramps 2420 are slideably coupled with the proximal wedge 2416. The plurality of endplates 2422a-2422d are slideably coupled with the distal ramps 2418 and slideably associated with the proximal ramps 2420. Generally, the expandable fusion device 2410 is substantially similar to expandable fusion device 10 described above, and any/all of the features described above with respect to fusion device 10 (and any other expandable fusion device embodiments described herein) may apply to fusion device 2410 unless otherwise noted. More specifically, the expandable fusion device 2410 is substantially similar to the expandable fusion device 310 described above, however the expandable fusion device 2410 of the present example includes additional protrusions (e.g. cylindrical bosses 2448) on the proximal ramps 2418 that travel in mating tracks in endplates 2422a-2422d to improve the expanding and collapsing behavior of the device. By way of example only, the expandable fusion device 2410 is illustrative of an expandable fusion device that expands in width, height, and lordotic expansion that may be applied to any expandable fusion device examples described herein, according to some embodiments.

By way of example, the actuator, distal wedge, proximal wedge, distal ramps 2418, proximal ramps 2420, and endplates 2422a-2422d may be identical or substantially similar to corresponding elements disclosed herein with respect to other embodiments. Notable differences between the elements of the current example embodiment and elements of the previously-described substantially similar example embodiments are described below.

FIG. 206 illustrates an example of a distal ramp 2418 according to the present example embodiment. By way of example only, the distal ramp 2418 of the present embodiment is substantially similar to distal ramp 318 described in detail above, and thus any features described above with respect to distal ramp 318 may be applied to distal ramp 2418. By way of example only, the distal ramp 2418 has a proximal end 2430, distal end 2432, medial side 2434, lateral side 2436, and a pair of tongue and groove connectors 2438 configured to slideably interact with the corresponding tongue and groove connectors on the distal wedge in the same manner as described with respect to corresponding features of expandable fusion device 10 above. The distal ramp 2418 may further include a pair of rail slots 2440 formed within proximal-facing surfaces and configured to slideably engage inclined rails 2442 of the endplates 2422a-2422d during lordosis expansion. In some embodiments, the distal ramp 2418 may further comprise a proximal extension 2444 configured to mate with an engagement slot of the proximal ramp 2420 in the same manner as described above with respect to similar embodiments (e.g. device 310). By way of example only, the mating of the distal ramp 2418 and proximal ramp 2420 in this fashion may provide additional stability during expansion (e.g. width, height, and/or lordotic).

In some embodiments, the proximal extension 2444 may include one or more protrusions 2446 extending toward the upper and/or lower endplates, each including a medially-extending cylindrical boss 2448 configured to translate along mating tracks 2450 of the endplates 2432a-2422d to provide additional contact surfaces to support the assembly during height/lordotic expansion (see FIG. 207). The cylindrical bosses 2448 translating within mating tracks 2450 during lordosis expansion may make the expanding and/or collapsing behavior more consistent and predictable, by providing more than one contact point per endplate portion during expanding or collapsing movements. In some embodiments, the mating tracks 2450 may have a different slope (e.g. less inclined) than the inclined rails 2442 that drive lordosis expansion.

In operation, first width expansion proceeds substantially as described above with respect to previous embodiments. That is, the actuator is turned a select number of actuations until some width expansion is reached and the endplate disengages from the distal wedge. Once the disengagement occurs, further rotation of the actuator results in the distal ramps 2418 translating along the respective angled slots in the endplates, increasing at least one of the width, height, and lordosis angle in the process. In other words, actuation of the drive feature in for a first number of actuations in the first actuation direction results in at least some width expansion. Actuation of the drive feature by a second number of actuations beyond the first number of actuations in the first actuation direction then increases at least one of width, height, and lordotic angle.

The expandable fusion device 2410 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2410.

In some embodiments, the devices include a 4-beam cage. In some embodiments, the 4-beam cage can provide asymmetric vertical expansion. The cages can include a pivotal linkage for width expansion. In some embodiments, the cage comprises a beam assembly having a first end, a second end, a first beam, a second beam, a third beam, a fourth beam, and a long axis; a width expansion assembly positioned between the first beam and the third beam and having a first spacer rotatably connected to a first pivotal link and a second pivotal link; a second spacer rotatably connected to third pivotal link and a fourth pivotal link; the first pivotal link rotatably connected at the first end to the first beam and the third beam; the second pivotal link rotatably connected at the first end to the second beam and the fourth beam; the third pivotal link rotatably connected at the second end to the first beam and the third beam; the fourth pivotal link rotatably connected at the second end to the second beam and the fourth beam; wherein, a first movement of the first spacer in the direction of the long axis rotates the first pivotal link and the second pivotal link to expand the first end of the cage, and a first movement of the second spacer in the direction of the long axis rotates the third pivotal link and the fourth pivotal link to expand the second end of the cage; and, a height expansion assembly positioned (i) between the first beam and the third beam, and (ii) between the second beam and the fourth beam; wherein, the height expansion assembly has a first ramp connected to the first pivotal link; a second ramp connected to the second pivotal link; a first post connected to the third pivotal link; and a second post connected to the fourth pivotal link; wherein, a second movement of the first spacer in the direction of the long axis moves the first pivotal link and the second pivotal link to expand the first end of the cage; the second spacer does not have a second movement in the direction of the long axis and the first post and the second post do not expand the second end of the cage.

In some embodiments, the wedge assembly expands the distal end more than the proximal end. In some embodiments, the wedge assembly expands the proximal end more than the distal end. In some embodiments, the wedge assembly expands the first beam away from the third beam more than the second beam away from the fourth beam. In some embodiments, the wedge assembly expands the second beam away from the fourth beam more than the first beam away from the third beam.

FIGS. 208-216 illustrate an example of an expandable fusion device 2510 for implantation between two adjacent vertebrae according to another embodiment of the disclosure. In some embodiments, the height of the device can be greater on the proximal end than on the distal end, greater on the distal end than on the proximal end, greater on one side than on the other, or greater on one corner than another. By way of example only, the expandable fusion device 2510 of the present embodiment includes an actuator 2512, a distal wedge 2514, a proximal wedge 2516, a pair of distal link elements 2518, a pair of proximal link elements 2520, a plurality of endplates 2522a-2522d, and one or more optional height stabilizers 2524. As with previously-described embodiments, the distal and proximal wedges 2514, 2516 are coupled with the actuator 2512. The distal and proximal link elements 2518, 2520 connect the distal and proximal wedges 2514, 2516 to the endplates 2522a-2522d by way of via a pin linkage mechanism. Generally, the expandable fusion device 2510 is substantially similar to expandable fusion device 1210 described above, and any/all of the features described above with respect to fusion device 1210 (and/or any other expandable fusion device described herein) may apply to fusion device 2510 unless otherwise noted.

By way of example, the actuator 2512, distal wedge 2514, proximal wedge 2516, distal link elements or pivotal links 2518, proximal link elements or pivotal links 2520, and endplates 1222a-1222d may be identical or substantially similar to corresponding elements disclosed herein with respect to other embodiments. Notable differences (and/or similarities) between the elements of the current example embodiment and analogous elements of the previously-described substantially similar example embodiments are described below.

FIG. 213 illustrates an example of a distal link element 2518 according to the present example embodiment. By way of example, the distal link elements 2518 each comprise a linkage base 2532 and a pair of link flanges 2534 separated by a cavity 2536 that is sized and configured to receive at least a portion of the lateral extension 2526 of the proximal wedge 2514 (see, e.g., FIG. 208). The linkage base 2532 may further include a distal ramp element 2538 extending in a direction opposite the link flanges 2534. By way of example only, the distal ramp element 2538 comprises a post 2540, which can be oriented as desired, vertical in some embodiments, having a generally cylindrical surface 2542 at one or both ends. The generally cylindrical surfaces 2542 are configured to translate along the distal inclined surfaces 2576 on the endplates 2522a-2522d when the distal link elements 2518 are properly aligned (e.g. fully rotated upon maximum width expansion). By way of example only, the vertical posts 2540 are sized and configured to mate with and nest in distal link recess 2574 on the endplates 2522a-2522d to pivotally couple the distal link elements 2518 to the endplates 2522a-2522d. Each link flange 2534 may include a pin aperture 2544 configured to axially align with a pin aperture (not shown) of the distal wedge 2514 and receive a pivot pin 2530 therethrough, to pivotally couple the distal link element 2518 to the distal wedge 2514.

FIGS. 214-215 illustrate an example of a proximal link element 2520 according to the present example embodiment. By way of example, the proximal link elements 2520 each comprise a linkage base 2546 and a pair of link flanges 2548 separated by a cavity 2550 that is sized and configured to receive at least a portion of the lateral extension 2528 of the proximal wedge 2516 (see, e.g., FIG. 208). The linkage base 2546 may further include a proximal ramp element 2552 extending in a direction opposite the link flanges 2548. By way of example only, the proximal ramp element 2552 comprises a pair of vertically separated end portions 2554 at opposite ends of a vertical post 2556. In some embodiments, the end portions 2554 may include one or more cylindrical surfaces 2558 that, when the end portions 2554 are properly aligned with the endplates 2522a-2522d (e.g. upon maximum width expansion), enable lordotic expansion to occur. By way of example only, the end portions 2554 are sized and configured to mate with and nest in proximal link recesses 2578 on the endplates 2522a-2522d to pivotally couple the proximal link elements 2520 to the endplates 2522a-2522d. Each link flange 2548 may include a pin aperture 2560 configured to axially align with a pin aperture (not shown) on the proximal wedge 2516 and receive a pivot pin 2530 therethrough, to pivotally couple the proximal link elements 2520 to the proximal wedge 2516. Optionally, each end portion may include a cylindrical boss 2562 extending laterally therefrom, the cylindrical bosses configured to migrate into retention slots 2584 on the endplates 2522a-2522d upon rotation of the proximal link elements 2520 during width expansion (see, e.g. FIGS. 208-210), to provide stability during lordotic expansion.

By way of example, the endplates 2522a-2522d are substantially identical in form and function, and thus only posterior beam 2522a is described in detail, but it should be understood that endplates 2522b-2522d have the same features and function as described with respect to endplate 2522a. By way of example only, FIG. 216 illustrates an example of an endplate 2522a according to the instant example embodiment. By way of example, the endplate 2522a comprises distal and proximal end portions 2564, 2566 separated by an elongated central portion 2568, a first or inner-facing side 2570 oriented toward the vertically opposing endplate, and a second or outer-facing side 2572 including a vertebral contact surface. The distal end portion 2564 includes a distal link recess 2574 and an inclined translation surface 2576 on the inner-facing side 2570. The distal link recess 2574 may be sized and configured to receive at least a portion of the vertical post 2540 of the distal link element 2518 therein, and further allow the distal link element 2518 to rotate while nesting within the distal link recess 2574. Upon sufficient rotation (e.g. when maximum width expansion is achieved) the generally cylindrical surfaces 2542 will be aligned with the inclined translation surface 2576, enabling lordotic (and/or height) expansion on the distal end of the expandable fusion device 2510. The proximal end portion 2566 includes a proximal link recess 2578 and an angled cutout 2580 on the inner-facing side 2570. The proximal link recess 2578 may be sized and configured to receive at least a portion of the vertical post 2556 of the proximal link element 2520 therein, and further allow the proximal link element 2520 to rotate while nesting within the proximal link recess 2578 during width expansion. The proximal link recess 2578 may include a pivot surface 2582 configured to engage the generally cylindrical surface 2558 of the proximal link element 2520 during lordotic expansion. Upon sufficient rotation (e.g. when maximum width expansion is achieved) the generally cylindrical surface 2558 will be aligned with the pivot surface 2582, enabling lordotic (and/or height) expansion on the proximal end of the expandable fusion device 2510. By way of example, the angled cutout 2580 may be sized and configured to receive an end portion 2554 of the proximal link element 2520 therein prior to lordosis expansion. In some embodiments, the endplate 2522*a* includes a retention slot 2584 formed in a lateral aspect of the endplate 2522*a* and configured to receive a cylindrical boss 2562 of the proximal link element 2520 therein. In some embodiments, the endplate 2522*a* may have bore 2586 extending vertically therethrough and configured to receive the height stabilizer 2524 therein. In some embodiments, the height stabilizer 2524 may be curved to accommodate the lordotic expansion of the expandable fusion device 2510.

In operation, first width expansion proceeds substantially as described above with respect to previous embodiments. That is, the actuator 2512 is turned a select number of actuations causing the distal and proximal wedges 2514, 2516 to translate toward one another along the actuator 2512, causing rotation of the distal and proximal link elements 2518, 2520 within the distal and proximal link recesses 2574, 2578 of the endplates 2522*a*-2522*d* and forcing the endplates 2522*a*-2522*d* laterally away from the actuator 2512, thereby effecting width expansion. During width expansion, as the link angle between the wedges 2514, 2516 and associated link elements 2518, 2520 increases (see, e.g. FIGS. 208-210), the vertical posts 2540, 2556 are rotating within the link recesses 2574, 2578, and the generally cylindrical surfaces 2542, 2558 are not in alignment with the inclined surfaces 2576 and/or pivot surfaces 2582, preventing lordotic expansion of the endplates 2522*a*-2522*d*. Upon reaching maximum width expansion (or another predetermined width expansion), the generally cylindrical surfaces 2542, 2558 become aligned with the inclined surfaces 2576 and/or pivot surfaces 2582, enabling lordotic expansion of the endplates 2522*a*-2522*d* to proceed upon turning the actuator 2512 additional actuations in the same actuation direction. Thus, turning the actuator 2512 a select number of rotations in a first actuation direction causes width expansion. Turning the actuator 2512 additional actuations in the same actuation direction causes at least one of width, height, and lordotic expansion.

The expandable fusion device 2510 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 2510.

FIGS. 217-228 illustrate an example of a method of inserting an expandable fusion device 10 into an intervertebral disc 2600 in a manner that promotes biased expansion. In the instant example, the method is shown as introducing an expandable fusion device 10 into a posterior aspect of an intervertebral disc 2600, and thereafter expanding the device 10 in an anterior direction, even though expansion of the individual components of the device occurs in an unbiased manner. Alternatively, the device 10 may be inserted into an anterior aspect of an intervertebral disc 2600 and expanded in a posterior direction (see, e.g. FIGS. 227-228), using substantially the same method.

As illustrated in FIG. 217, the first step in the method is to perform an annulotomy procedure to create an annulotomy opening 2602 in the disc 2600, for example within a lateral aspect. By way of example, the annulotomy opening may have a width component $w_1$ approximately equal to the width of the device 10 in collapsed form, for example as defined by a distance between outside lateral surfaces of width-opposing endplates (e.g. upper endplates 22*a*-22*b* and/or lower endplates 22*c*-22*d*). The next step is to perform a channel discectomy procedure to create an insertion corridor 2604 through the disc 2600, as illustrated by way of example only in FIG. 218. In the instant example, the insertion corridor 2604 is essentially a continuation of the annulotomy opening and thus may have a width component WI approximately equal to the width of the device 10 in collapsed form. The next step in the exemplary method is to perform a directional discectomy through the annulotomy opening 2602 to remove disc material and create a directional void 2606 that has a width component $w_2$ approximately the size of the device 10 in expanded width form, as shown by way of example only in FIG. 219.

As shown by way of example in FIG. 220, the next step is to advance the expandable fusion device 10 through the annulotomy opening 2602 and into the insertion corridor 2604. By way of example, the device 10 is inserted in a fully collapsed-width form, with the inserter housing 2608 initially biased to the posterior side of the annulotomy opening 2602 and the posterior endplates (e.g. endplates 22*a*, 22*c*) adjacent the posterior wall of the insertion corridor 2604. Upon rotation of the actuator 12 to effectuate width expansion, the device 10 will start to expand anteriorly into the directional void 2606, as the path of least resistance. As this occurs, the posterior endplates 22*a*, 22*c* remain substantially in place and the rest of the implant, including the actuator 12, wedges 14, 16, and anterior endplates 22*b*, 22*d* (among other things) shift anteriorly. The inserter housing 2608, being engaged with the proximal wedge 16 (for example by a threaded coupling, however other coupling means are possible) by way of threaded inserter shaft 2610, migrates anteriorly within the annulotomy opening 2602, as shown by way of example in FIG. 221. Upon reaching full width expansion, the inserter housing 2608 is fully biased anteriorly within the initial annulotomy opening 2602, and the fully width-expanded device 10 occupies the insertion corridor 2604 and directional void 2606, as shown by way of example in FIGS. 222-223. At this point, the inserter shaft 2610 is engaged with anterior threaded aperture on the proximal wedge 16, the expansion driver 2612 is engaged with the actuator 12.

The next step in the exemplary method is to disengage the inserter shaft 2610 from the proximal wedge 16 and remove from the inserter housing 2608, vacating the side channel 2614 in the inserter housing 2608, as shown by way of example only in FIG. 224. By way of example only, a lock screw driver 2616 may then be inserted through the side channel 2614 and the device 10 to engage the locking mechanism (e.g. comprising a lock screw 2618 and pin detent 2620). In the instant embodiment, the locking mechanism is positioned on the distal wedge 14 as shown in FIGS. 223-226. In some embodiments, this allows fusion-promoting material 2622 (e.g. synthetic bone graft material, allograft material and/or autograft material, biologics, etc.) to be delivered into the interior of the expanded device 10 through the same aperture used to access the locking mechanism with the locking driver 2616 (and to engage the inserter shaft 2610). In this embodiment the fusion-promoting material 2622 is delivered after the locking mechanism is activated and the lock screw driver 2616 has been removed from the device 10, however in other embodiments and/or methods, the locking mechanism may be engaged after delivery of the fusion-promoting material.

In the instant embodiment, the locking mechanism is provided in duplicate—one on either side of the actuator 12. This configuration may facilitate directional expansion in either the anterior direction (e.g. as shown in FIGS. 217-226) or in the posterior direction (as shown in FIGS. 227-228). Thus, the proximal wedge 16 may have a threaded aperture on either side of the central aperture to which the inserter shaft 2610 may attach depending on whether an anterior-expanding or posterior-expanding inserter is used. It is important to note that this method is made possible by the fact that the distal width of the inserter body is smaller than the initial collapsed width of the expandable device. If the width of the inserter is smaller than the initial collapsed width of the expandable device by exactly half the difference between the device's fully expanded width and the device's fully collapsed width, and that width difference is all applied to one side (i.e. one side of the inserter is aligned or co-planar with one side of the device when collapsed), then there will be exactly enough room for the inserter body to travel and stay within the annulotomy opening as the implant expands fully in width. In practice, having e.g. left side of the inserter aligned with left side of expandable device, with its overall width being narrower—allows for some expansion biasing to the right side of the device. It should further be understood that this method applies to any width-expanding interbody device, whether or not also capable of height expansion.

FIGS. 229-232 illustrate an example of an alternative embodiment of an expansion mechanism 2700 configured for use with the expandable fusion device 10 (and/or any other embodiment disclosed herein), according to some embodiments. By way of example only, the expansion mechanism 2700 includes a threaded bolt 2702, distal wedge 2704, proximal wedge 2706, and an actuation nut 2708. By way of example, the threaded bolt 2702, distal wedge 2704, and proximal wedge 2706 may be identical or substantially similar in form and/or function to corresponding elements disclosed herein with respect to other embodiments. Notable differences (and/or similarities) between the elements of the current example embodiment and analogous elements of the previously-described substantially similar example embodiments are described below.

By way of example only, the threaded bolt 2702 comprises a generally cylindrical elongated member having a threaded distal end 2710, threaded proximal end 2712, and a drive feature 2714. By way of example, the threads of threaded ends 2710, 2712 may be formed in the same direction. The distal wedge 2704 includes a threaded central bore 2716 configured to threadedly engage the threaded distal end 2710 of the threaded bolt 2702. The proximal wedge 2704 includes a nonthreaded central bore 2718 extending axially through the proximal wedge 2706 and in axial alignment with the threaded central bore 2716 of the distal wedge 2704. The proximal wedge 2706 further includes a proximal recess 2720 formed in the proximal side of the proximal wedge 2706 and including the proximal opening of the nonthreaded central bore 2718. By way of example only, the proximal recess 2720 is sized and configured to receive the actuation nut 2708 therein. In some embodiments, the proximal wedge 2706 further includes a side bore 2722 extending through the wedge 2706 generally parallel to the central bore 2718, the side bore 2722 configured to enable passage of additional instrumentation therethrough, including but not limited to drivers, locking bolts, fusion-promoting material, etc. In some embodiments, the actuation nut 2708 comprises a generally cylindrical member sized and configured nest within the proximal recess 2720 and having a threaded lumen 2724 configured to threadedly engage the threaded bolt 2702 and a drive feature 2726 configured to engage a driver instrument (not shown). In some embodiments, the thread direction of the threaded bore 2716 and the thread direction of the threaded lumen 2724 are the same, for example right-handed.

In order to effectuate width expansion, the actuator 2702 is held stationary and the actuation nut 2708 may be rotated about the threaded bolt 2702 in a clockwise direction. Since the confines of the proximal recess 2720 prevent the actuation nut 2708 from translating distally along the actuator 2702, rotation of the actuation nut 2708 "pulls" the threaded bolt 2702 and the distal wedge 2704 proximally, causing width expansion, as shown by way of example in FIG. 230. Upon completion of width expansion (and/or height expansion and/or lordotic expansion), a portion of the proximal end 2712 of the threaded bolt 2702 may be protruding proximally from the proximal wedge 2706. In some embodiments, the device 10 may be left in such a state. However, if the user prefers, the threaded bolt 2702 may be rotated with the actuation nut 2708 held stationary to thread the actuator 2702 farther into the distal wedge 2704 without causing additional width expansion. This simply shifts the threaded bolt 2702 distally into the device 10 so that no portion (or at least very little) is extending beyond the perimeter of the proximal wedge 2706 (and/or distal wedge 2704).

In some embodiments, the actuation nut 2708 may be captured within the proximal recess 2720 to allow rotational movement of the actuation nut 2708 while preventing separation from the proximal wedge 2706. For example, as illustrated in FIGS. 233-234, the proximal wedge 2706 may be provided with a retaining element 2728 (e.g. pin, ring, split ring, welded flange, etc.) coupled with or integrally formed within the proximal recess 2720 and configured to engage a circumferential recess 2730 formed on the outer perimeter of the actuation nut 2708. This interaction will allow the actuation nut 2708 to rotate freely within the proximal recess 2720 while securely retaining the actuation nut 2708 within the recess 2720.

FIGS. 235-238 illustrate another example of an expansion mechanism 2800 configured for use with the expandable fusion device 10 (and/or any other embodiment disclosed herein), in which the expansion element or actuator may be removed after full device expansion, according to some embodiments. By way of example only, the expansion mechanism 2800 includes a distal wedge 2802, proximal wedge 2804, a removable expansion instrument 2806, which in some embodiments may also be at least a portion of an insertion instrument, and at least one locking bolt 2808. The distal wedge 2802 may include a threaded central bore 2810 configured to threadedly receive a threaded distal end 2812 of the expansion instrument 2806 to securely mate the distal wedge 2802 with the expansion instrument 2806. The distal wedge 2802 may further include at least one threaded side aperture 2814 positioned adjacent the central bore 2810. Preferably, the distal wedge 2802 includes a threaded side aperture 2814 positioned on each side of the central bore 2810, as shown by way of example in FIGS. 235-238. The proximal wedge 2804 may include a nonthreaded central bore 2816 configured to enable passage of the expansion instrument 2806 therethrough. The proximal wedge 2804 may further include at least one threaded side aperture 2818 positioned adjacent the central bore 2816 and in axial alignment with threaded side aperture 2814 of the distal wedge 2802. Preferably, the proximal wedge 2804 includes a threaded side aperture 2818 positioned on each side of the central bore 2816, as shown by way of example in FIGS. 235-238. By way of example only, the locking bolt 2808 may comprise a generally cylindrical elongated member having a threaded distal end 2820 configured to engage a threaded side aperture 2814 on distal wedge 2802, a threaded proximal end 2822 configured to engage a threaded side aperture 2818 on proximal wedge 2804, and a drive feature 2824.

Figure 235:
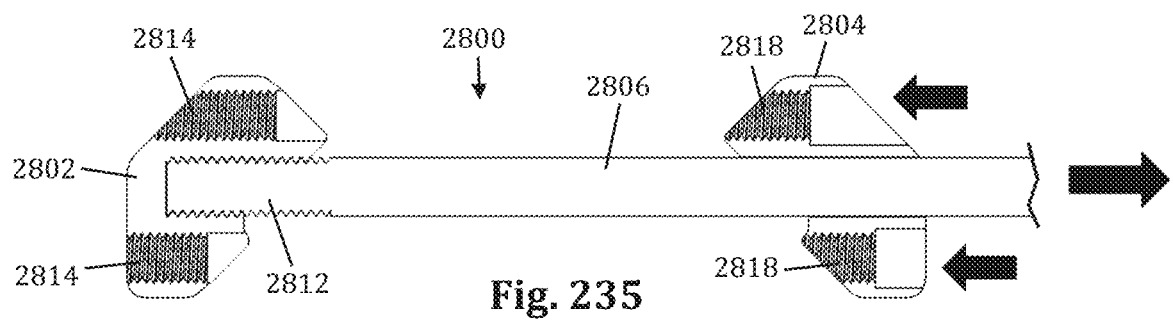
Figure 236:
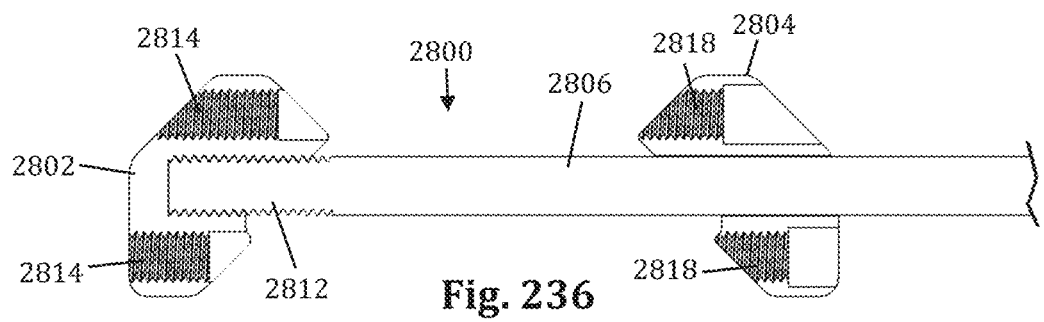
Figure 237:
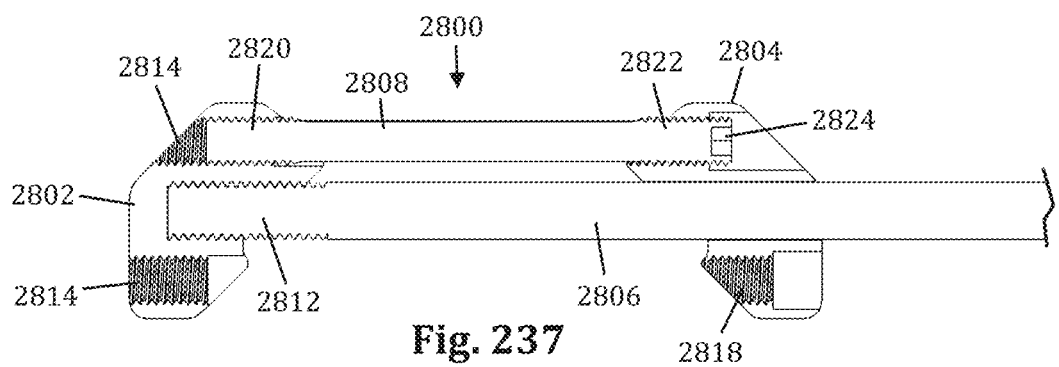
Figure 238:
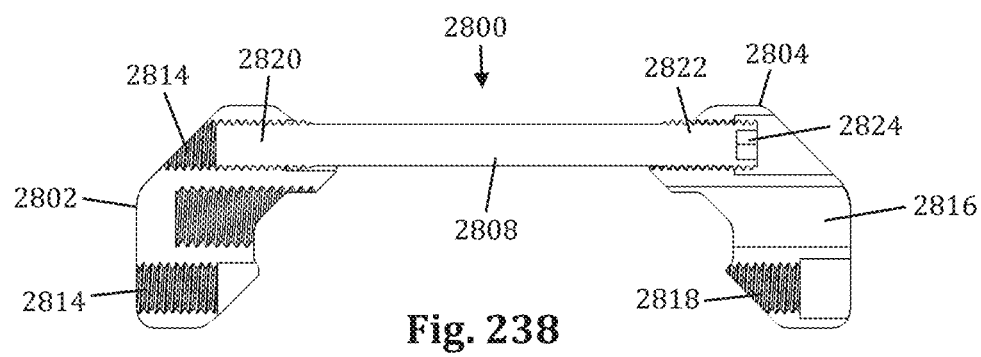

By way of example only, expansion may be effected by exerting a proximal force (e.g. "pulling") on the expansion instrument 2806 (e.g. which may also be the insertion instrument) while exerting a distal force (e.g. "pushing") on the proximal wedge 2804, as shown in FIG. 235. As a result, the distal and proximal wedges 2802, 2804 are caused to move toward one another, resulting in at least one of width expansion, height expansion, and lordosis expansion, substantially as described with respect to the various embodiments above. Upon completion of the desired expansion (e.g. width, height, and/or lordosis), the locking bolt 2808 must be employed before the expansion instrument 2806 may be removed. By way of example only, the locking bolt 2808 may be inserted through a threaded side aperture 2818 in the proximal wedge 2804 and into the axially aligned threaded side aperture 2814 of the distal wedge 2802 such that the threaded distal end 2820 is engaged with threaded side aperture 2814, while the threaded proximal end 2822 is simultaneously engaged with the threaded side aperture 2818, as shown by way of example only in FIG. 237. Once the locking bolt 2808 has been properly positioned, the expansion instrument 2806 may be removed, as shown in FIG. 238. In some embodiments fusion-promoting material may then be inserted into the device 10 through the vacant nonthreaded central bore 2816 of the proximal wedge 2804.

In some embodiments, the wedges may need to move apart in order to expand the expandable fusion device. In such embodiments, expansion is effected by pushing on the expansion instrument 2806 while simultaneously pulling on the proximal wedge 2804.

Figure 239:
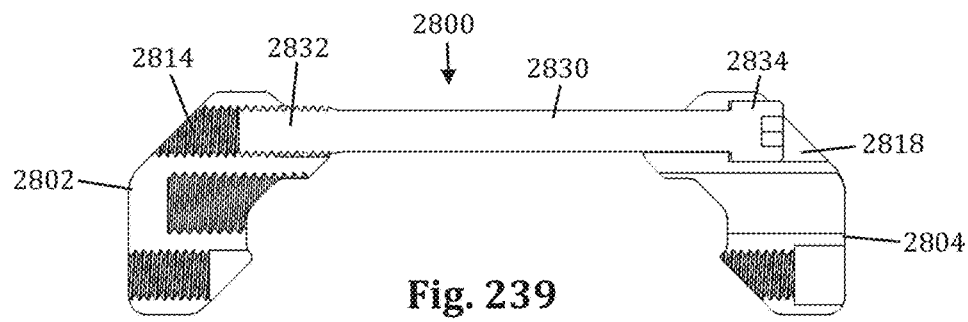
Figure 240:
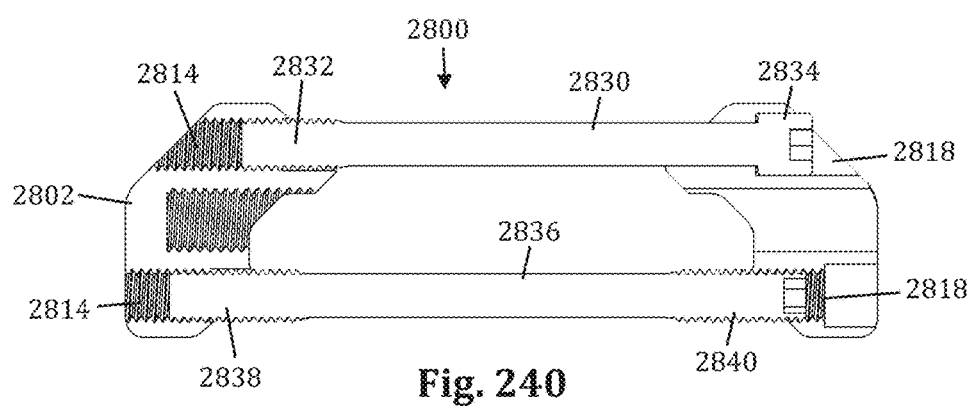

In some embodiments, the locking element may comprise a lag bolt 2830 comprising a threaded distal end 2832 configured to threadedly engage the threaded side aperture 2814 of the distal wedge 2802 and a shaped head 2834 configured to nest within side aperture 2818 of the proximal wedge 2804, as shown by way of example only in FIG. 239. The shaped head 2834 is pulled against the proximal wedge 2804, effectively locking the device. In some embodiments, a double threaded bolt 2836 may be inserted through the second set of axially aligned threaded side apertures 2814, 2818 such that a threaded distal end 2838 of the bolt 2836 engages the second threaded side aperture 2814 on distal wedge 2802 and a threaded proximal end 2840 engages the second threaded side aperture 2818 of the proximal wedge 2804, as shown by way of example only in FIG. 240. Because the double threaded bolt 2836 prevents the wedges 2802, 2804 from further movement, the shaped head 2834 of the lag bolt 2830 may be further turned to apply thread tension to the device, potentially creating a stronger locking effect.

In some embodiments, the connection between the expansion instrument and the distal wedge may be other than a threaded engagement, for example in instances in which the expansion instrument is not the same as the insertion instrument. By way of example only, FIGS. 241-243 illustrate an example in which the expansion instrument 2850 has a shaped distal end 2852 configure to engage a retention recess 2854 in the distal wedge 2802. In the instant example, the shaped distal end 2852 has a generally elliptical shaped transverse flange 2856 oriented transverse to the longitudinal axis of the expansion instrument 2850, as shown in FIG. 242. However, it should be understood that other shapes are possible for the transverse flange 2856. The retention recess 2854 is configured to receive the shaped distal end 2852 therein in a first orientation and, upon rotation of the expansion instrument 2850 (e.g. approximately 90°), the retention recess 2854 is further configured to prevent separation of the expansion instrument 2850 from the distal wedge 2802. Once desired expansion has been achieved, the distal and proximal wedges 2802, 2804 may be locked in position as described above, and the expansion instrument 2806 may be removed.

In some embodiments (e.g. as shown in FIGS. 244-245), the distal wedge may have a shaped central bore 2858 configured to allow passage of the shaped distal end 2852 the expansion instrument 2850 completely therethrough such that the shaped distal end 2852 extends beyond the distal end of the distal wedge 2802, as shown. Thus, upon rotating the expansion instrument 2850 (e.g. by 90°), the transverse flange 2856 abuts the distal end of the distal wedge 2802, preventing the shaped end 2852 from reentering the shaped central bore 2858 and enabling a user to exert a proximal force (e.g. "pull") on the distal wedge 2802 (while also exerting a distal force on the proximal wedge 2804) to effect device expansion. Once desired expansion has been achieved, the distal and proximal wedges 2802, 2804 may be locked in position as described above, and the expansion instrument 2806 may be removed.

Figure 246:
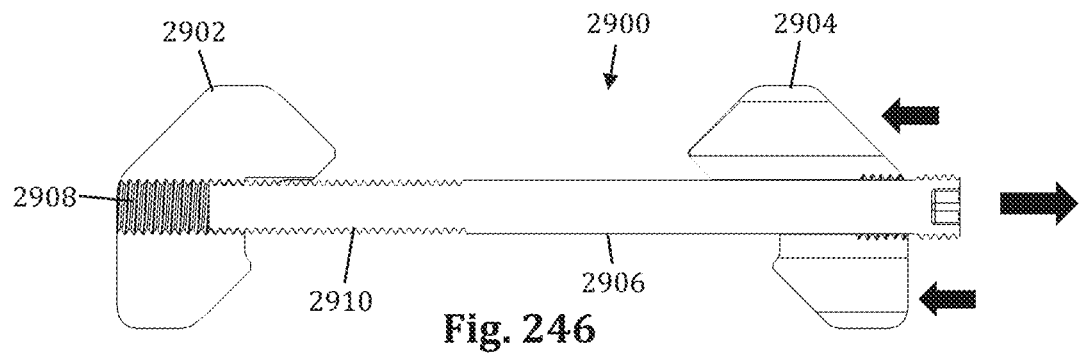
Figure 247:
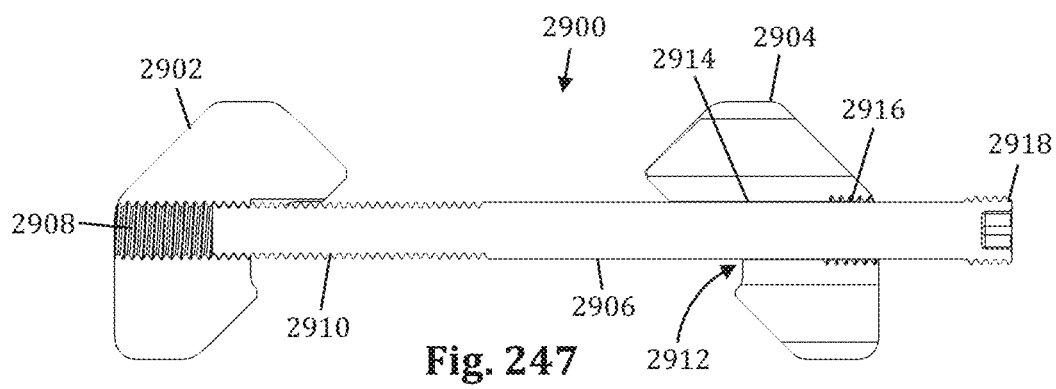
Figure 248:
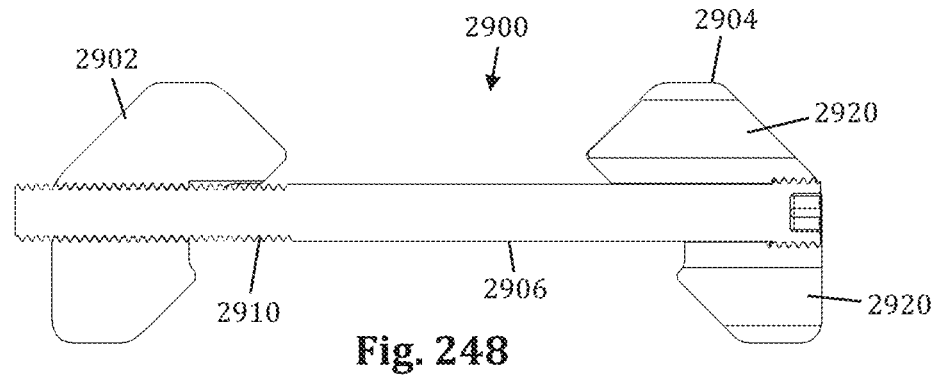

FIGS. 246-248 illustrate an example of an expansion mechanism 2900 configured for use with the expandable fusion device 10 (and/or any other embodiment disclosed herein), in which the expansion element facilitates using a linear "pull" force application to effect expansion, but then remains associated with the device after full expansion (e.g. is not removed as in previous examples), according to some embodiments. By way of example only, the expansion mechanism 2900 includes a distal wedge 2902, proximal wedge 2904, an expansion element 2906, which in some embodiments may also be the locking element. The distal wedge 2902 may include a threaded central bore 2908 configured to threadedly receive a threaded distal end 2910 of the expansion element 2906 to securely mate the distal wedge 2902 with the expansion element 2906. The proximal wedge 2904 may include a central bore 2912 configured to enable passage of the expansion element 2906 therethrough. By way of example, the central bore 2912 may have an unthreaded portion 2914 and a threaded portion 2916 adjacent the proximal end of the central bore 2912. The unthreaded portion 2914 is sized and configured to enable passage of the smooth cylindrical shaft of the expansion element 2906 therethrough. The threaded portion 2916 is sized and configured to engage the threaded head 2918 of the expansion element 2906. The proximal wedge 2804 may further include at least one side aperture 2920 positioned adjacent the central bore 2912 to enable introduction of fusion-promoting material after the device is fully expanded.

By way of example only, expansion may be effected by exerting a linear proximal force (e.g. "pulling") on the expansion element 2906 (e.g. by way of an expansion instrument mated with the threaded proximal end 2918) while exerting a linear distal force (e.g. "pushing") on the proximal wedge 2904, as illustrated in FIG. 246. As a result, the distal and proximal wedges 2902, 2904 are caused to move toward one another, resulting in at least one of width expansion, height expansion, and lordosis expansion, substantially as described with respect to the various embodiments above. Upon completion of the desired expansion (e.g. width, height, and/or lordosis), the expansion element 2906 may be threaded distally further into the distal wedge 2902, and distal threading continues until the threaded proximal end 2918 is engaged with the threaded portion 2916 of the central bore 2912 of the proximal wedge 2904, as illustrated by way of example only in FIG. 248. Once the wedge thread is bottomed out, the expansion element 2906 may be locked by applying locking torque.

In some embodiments, the wedges may need to move apart in order to expand the expandable fusion device. In such embodiments, expansion is effected by pushing on the expansion element 2906 while simultaneously pulling on the proximal wedge 2904.

In some embodiments, a cage with independent width and height expansion is provided, the cage can comprise, for example, a beam assembly having a proximal end, a distal end, and a long axis disposed between the proximal end and the distal end; a first beam with a proximal end and a distal end, a second beam with a proximal end and a distal end, and a third beam with a proximal end and a distal end; and, a collapsed state and an expanded state; a wedge assembly having a first wedge and a second wedge, the first wedge movably connected to a first guide and configured for increasing the width of the cage when the first wedge is moved in the direction of the long axis relative to the beam assembly; wherein, the first wedge is positioned between the first beam and the third beam; and, the first guide (i) is movably positioned between the first beam and the second beam, and, (ii) does not provide an expansion in height by being moved in the direction of the long axis relative to the beam assembly; and, a ramp assembly having a ramp movably positioned between the first beam and the second beam and configured for increasing the height of the cage with a movement of the ramp in the direction of the long axis relative to the beam assembly; wherein, the translation of the wedge increases the width of the cage without increasing the height of the cage; the translation of the ramp increases the height of the cage without increasing the width of the cage; and, the ramp is configured to translate independently of the wedge assembly in the direction of the long axis.

In some embodiments, the wedge assembly is configured to retain the first beam, the second beam, and the third beam from expanding beyond a desired width in the expanded state; the wedge is configured with a retaining mechanism to retain the first guide from separating from the wedge in the expanded state; the first guide is configured with a retaining mechanism to retain the first beam and the second beam from separating from the first guide in the expanded state; and, the wedge assembly is configured with a retaining mechanism to retain the third beam from separating from the wedge assembly in the expanded state.

FIGS. 249-253 illustrate an example of an expandable fusion device 3010 for implantation between two adjacent vertebrae, according to some embodiments. By way of example only, the expandable fusion device 3010 of the present embodiment includes an actuator 3012, a distal wedge 3014, a proximal wedge 3016, a pair of distal guides 3018, a pair of proximal guides 3020, a plurality of endplates 3022a-3022d, a plurality of guide pins 3024, and a height expansion core 3026. As with previously-described embodiments, the distal and proximal wedges 3014, 3016 are coupled with the actuator 3012. The distal guides 3018 are slideably coupled with the distal wedge 3014. The proximal guides 3020 are slideably coupled with the proximal wedge 3016. The plurality of endplates 3022a-3022d are slideably coupled with the guides 3018, 3020. Generally, the expandable fusion device 3010 is substantially similar to expandable fusion device 10 described above, and any/all of the features described above with respect to fusion device 10 (and any other expandable fusion device described herein) may apply to fusion device 3010 unless otherwise noted. However, in the instant embodiment the endplates 3022a-3022d are not coupled with the distal and proximal wedges 3014, 3016, and therefore width expansion occurs by the wedges 3014, 3016 pushing on the guides 3018, 3020 (upon rotation of the actuator 3012), which in turn force the endplates 3022a-3022d laterally apart. Height expansion is caused by movement of the height expansion core 3026, which is independent of movement of the actuator 3012, wedges 3014, 3016, and guides 3018, 3020, and may occur before maximum width expansion has occurred. Thus, the expandable fusion device 3010 is an illustrative example of an expandable fusion device having height expansion that is independent of the width expansion and actuator, according to some embodiments.

By way of example, the actuator 3012, distal wedge 3014, proximal wedge 3016, posterior guides 3018, anterior guides 3020, and endplates 3022a-3022d may be identical or substantially similar in form and/or function to corresponding elements disclosed herein with respect to other embodiments. Notable differences (and/or similarities) between the elements of the current example embodiment and analogous elements of the previously-described substantially similar example embodiments are described below. The guides can be referred to as first guide, second guide, third guide, and fourth guide, for example, for ease of labeling in some embodiments, in any order desired.

Moreover, the guides and wedges can be configured to retain the first beam, the second beam, and the third beam from expanding beyond a desired width in the expanded state. In some embodiments, the wedge assembly is configured to retain the first beam, the second beam, and the third beam from expanding beyond a desired width in the expanded state; the wedge is configured with a retaining mechanism to retain the first guide from separating from the wedge in the expanded state; the first guide is configured with a retaining mechanism to retain the first beam and the second beam from separating from the first guide in the expanded state; and, the wedge assembly is configured with a retaining mechanism to retain the third beam from separating from the wedge assembly in the expanded state.

In some embodiments, the beam assembly can further comprise a fourth beam; and, the wedge assembly can have a second guide that is (i) movably positioned between the third beam and the fourth beam, and, (ii) does not provide an expansion in height by being moved in the direction of the long axis relative to the beam assembly. There can also be a third guide and a fourth guide. Likewise, the wedge can be configured with a retaining mechanism to retain the first guide from separating from the wedge in the expanded state; the first guide and the third guide are each configured with a retaining mechanism to retain the first beam and the second beam from separating from the first guide and the second guide in the expanded state; the second guide and the fourth guide can each be configured with a retaining mechanism to retain the third beam and the fourth beam from separating the second guide and the fourth guide in the expanded state; the first wedge can be configured to retain the first guide and the second guide in the expanded state; and, the second wedge can be configured to retain the third guide and the fourth guide in the expanded state. In some embodiments, the retaining mechanism can be, for example, any mechanism that holds the components together, such as a complementary mechanism in which one component interlocks with another component in an interfering manner, holding the two components together. In some embodiments, the retaining mechanism can be an interlocking mechanism, for example. Any retaining mechanism can fix the two components together at least substantially, or it can allow the components to move while holding the connection between the two components, the movements including, for example, sliding, translating, and rotating.

In the instant embodiment, the proximal and distal guides 3018, 3020 are identical or mirrored equivalents of one another. By way of example only, the guides 3018, 3020 each have tongue and groove connectors 3030 for slideable coupling with the wedges 3014, 3016, and an endplate engagement lobe 3032 for engaging the endplates 3022a-3022d. Unlike previously-described embodiments, however, the endplate engagement lobe 3032 of the instant embodiment comprises a vertical post (e.g. instead of ramped surfaces) that provides stability of the endplates during height expansion, and also limits height expansion by way of the guide pins 3024 traveling within vertical guide recesses 3034 formed within lateral aspects of the engagement lobes 3032. The endplate engagement lobes 3032 are sized and configured for vertical translation within vertical guide slots 3036 formed within endplates 3022a-3022d.

Figure 253:
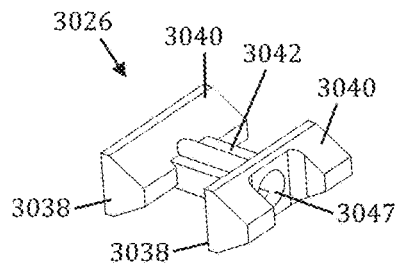
Figure 254:
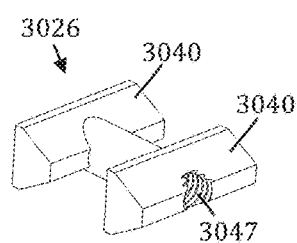
Figure 255:
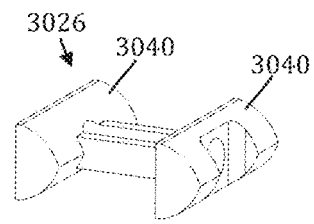
Figure 256:
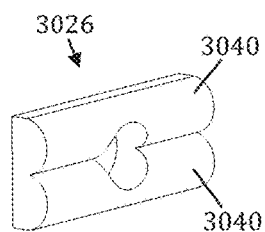
Figure 257:
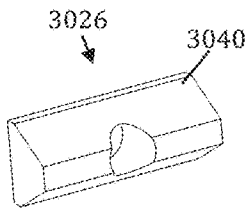
Figure 258:
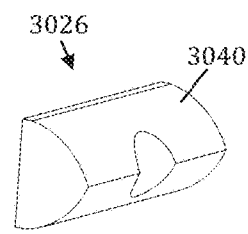
Figure 259:
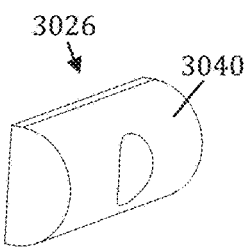
Figure 260:
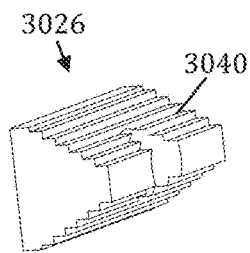
Figure 261:
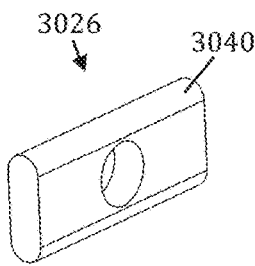
Figure 262:
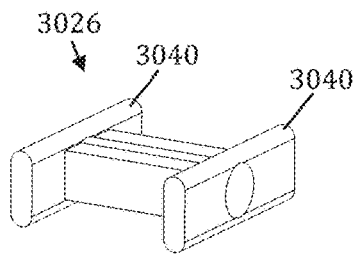
Figure 263:
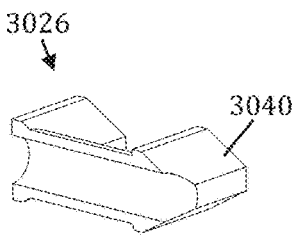
Figure 264:
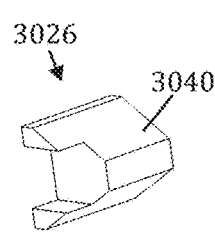
Figure 265:
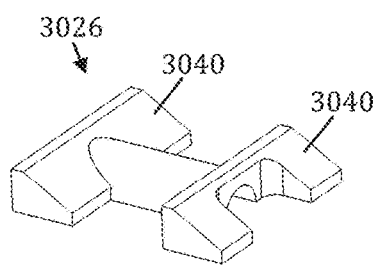
Figure 266:
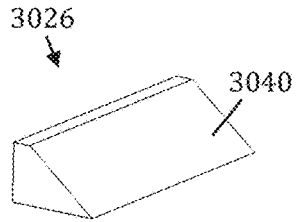
Figure 267:
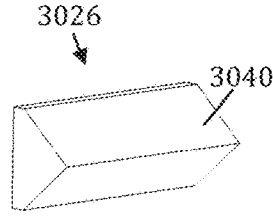

Referring to FIG. 253, the height expansion core 3026 comprises at least one shaped crossbeam 3038 having one or more expansion surfaces 3040 configured to engage corresponding expansion surfaces on the endplates 3022a-3022d. In the instant embodiment, the height expansion core 3026 includes a pair of shaped crossbeams 3038 connected by an axial connector 3042. In some embodiments, the height expansion core 3026 may have only one shaped crossbeam 3038. In some embodiments, the height expansion core 3026 may have more than two shaped crossbeams 3038 connected in series by axial connectors 3042. Each end of the shaped crossbeams 3038 are configured to nest within lateral recesses 3044 formed within the endplates 3022a-3022d when the expandable fusion device 3010 is in a fully collapsed position. During width expansion, the endplates 3022a-3022d translate laterally along the crossbeams 3038, which in this capacity may also serve as width stabilizers. In some embodiments, the height expansion core may be detained or located in between the endplates on at least one side of the device and move together with the endplates during width expansion (as opposed to translating within lateral recesses), while still being able to translate in the distal-proximal direction to cause height or lordotic expansion (e.g. height expansion cores shown in FIGS. 263, 264, 266 and 267). During height expansion, the expansion surfaces 3040 of the shaped crossbeams 3038 engage and translate along ramped surfaces 3046 of the lateral recesses 3044 to effect height expansion. The height expansion core 3026 further comprises an axial lumen 3047 extending therethrough and configured to allow passage of the actuator 3012. In some embodiments, the axial lumen 3047 may be nonthreaded (e.g. as shown in FIG. 253) to remain independent from the actuator 3012. In some embodiments, the axial lumen 3047 may be threaded (e.g. as shown in FIG. 254) to associate the height expansion core 3026 with the actuator 3012 for assembly purposes or, in some embodiments, to advance or retract upon actuation of the actuator 3012.

The present embodiment allows for completely independent width and height expansion. The device 3010 may be expanded in height first or in width first, provided that the height expansion core is accessible from the proximal end at the time that height expansion is desired. By way of example only, in any embodiment, height expansion may commence upon achievement of enough width expansion such that the height expansion core 3026 is accessible through side bores 3048 of the distal and proximal wedges 3014, 3016 to provide access for a height expansion element 3050 to engage the height expansion core 3026 to apply sufficient push or pull force to effect height expansion. By way of example only, the height expansion element 3050 may be a part of the implantable device 3010 (e.g. bolt, screw, rod, ratchet post, flexible or tensionable member, etc.), or the height expansion element 3050 may be moved/actuated by a removable instrument such as tamp rod, screw, bolt, etc. In some embodiments, the height expansion element 3050 may be introduced into the device 3010 during height expansion and left in place to ensure that the height doesn't collapse. For example, FIGS. 268-269 illustrate a device 3010 in which the height expansion element 3050 includes a threaded head portion 3052 configured to threadedly engage the side bore 3048 to lock in the height expansion.

FIGS. 254-267 illustrate various examples of height expansion cores 3026 configured for use with the expandable fusion device 3010, according to some embodiments. By way of example, height expansion cores 3026 with generally planar expansion surfaces 3040, or with double curved expansion surfaces 3040 (e.g. FIG. 256) are particularly, but not exclusively, suited for height expansion of the endplates 3022a-3022d. Height expansion cores 3026 with single curved expansion surfaces 3040 are particularly, but not exclusively, suited for lordotic expansion of the endplates 3022a-3022d.

In the implementations in which the height expansion element 3050 is removed after use, the expandable fusion device 3010 may be provided with structure capable of maintaining the desired height expansion. By way of example only, FIGS. 270-271 illustrate one such embodiment, in which the ramped surfaces 3046 have a plurality of ramp recesses 3056 spaced along the ramp surface 3046 to capture the expansion core 3026 (e.g. expansion core 3026 of FIG. 261 or FIG. 262) at predetermined intervals such that the expansion core 3026 may be pushed to a particular level and will remain at that level even when the height expansion element is removed. Either version of height expansion cores could be used for either parallel or lordotic expansion of the endplates.

FIGS. 272-273 illustrate an example of expandable fusion device 3010 modified for lordotic expansion. By way of example only, the device 3010 of the current example uses the height expansion core 3026 of FIG. 258, having a curved expansion surface 3040. The proximal ramps 3020 may have a pair of cylindrical bosses 3058 on them mating with bores in the endplates 3022a-3022d allowing the endplates to pivot similar to expandable fusion device 210 described above. The distal ramp 3018 may have a vertical endplate engagement lobe as described above, in some embodiments the endplate engagement lobe may be curved or bi-curved, for example where the portion of the ramp engaging each of the opposing endplates is curved to be concentric with that endplate's boss-bore articulation on the proximal side.

In some embodiments of a lordotically expandable device 3010, distal and/or proximal ramps 3018, 3020 may have endplate engagement lobes with curvatures concentric with each other, with the shared curvature center serving as the axis of lordotic expansion.

In some embodiments of a lordotically expandable device 3010, lordotic expansion may be enabled by ensuring that the vertical endplate engagement lobes have enough room within the mating vertical guide slots on the endplates to pivot and accommodate varying angular relationships between endplates. Although a height expansion core with a curved expansion surface is preferable in lordotic embodiments, a height expansion core with a ramped surface may also be used.

The expandable fusion device 3010 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 3010.

FIGS. 274-280 illustrate an example of an expandable fusion device 3110 for implantation between two adjacent vertebrae according to another embodiment of the disclosure. By way of example only, the expandable fusion device 3110 of the present embodiment includes an actuator 3112, a distal wedge 3114, a proximal wedge 3116, a pair of identical distal ramps 3118, a pair of identical proximal ramps 3120, a plurality of endplates 3122a-3122d, and a plurality of optional guide pins 3123. As with the previously-described embodiment, the distal and proximal wedges 3114, 3116 are coupled with the actuator 3112. The distal ramps 3118 are slideably coupled with the distal wedge 3114. The proximal ramps 3120 are slideably coupled with the proximal wedge 3116. The plurality of endplates 3122a-3122d are slideably coupled with the ramps 3118, 3120. Generally, the expandable fusion device 3110 is substantially similar to expandable fusion device 310 described above, and any/all of the features described above with respect to fusion device 310 (and any other expandable fusion device described herein) may apply to fusion device 3110 unless otherwise noted. By way of example only, the expandable fusion device 3110 is illustrative of an expandable fusion device that expands in width, height, and lordotic expansion that may be applied to any expandable fusion device examples described herein, according to some embodiments.

By way of example only, the actuator 3112 comprises a cylindrically shaped elongate shaft having a distal end 3124, a proximal end 3126, and a longitudinal axis L. At least a portion of the distal end 3124 includes a thread feature 3128. In some embodiments, the proximal end 3126 a circumferential recess 3130 (or other suitable capture feature) configured to engage with a complimentary capture feature on the proximal wedge 3116. By way of example, the complimentary capture features enable the actuator 3112 to rotate freely relative to the proximal wedge 3116 while preventing axial translation of the actuator 3112 relative to the proximal wedge 3116. At least one of the distal and proximal ends 3124, 3126 includes a drive feature 3132 coincident with the longitudinal axis L and configured to engage with a driver instrument (not shown) to operate the actuator 3112. In some embodiments, the proximal end 3126 may have a nonthreaded outer cylindrical surface 3134. The thread feature 3128 comprises a thread disposed externally around the shaft of the actuator 3112. In some embodiments, the thread feature 3128 may comprise a right-handed threading. In some embodiments, the thread feature 3128 may comprise a left-handed threading. By way of example only, the drive feature 3132 comprises a recessed region configured to receive a driving instrument.

Optionally, in any embodiment, the actuator can have a distal end and a proximal end. Optionally, in any embodiment, at least a portion of the distal end can comprise a thread feature. Optionally, in any embodiment, the proximal end can be rotatably captured within the proximal wedge. Optionally, in any embodiment, the proximal end can comprise a drive feature. Optionally, in any embodiment, the thread feature can comprise a thread disposed externally around the actuator.

By way of example, distal wedge 3114 and proximal wedge 3116 may be identical or substantially similar to corresponding elements disclosed herein with respect to other embodiments. In some embodiments, the proximal wedge 3116 includes a capture feature configured to engage the capture feature of the actuator 3112 described above. In some embodiments the capture feature of the distal wedge 3116 comprises a protrusion 3136, at least portion of which is sized and configured to be received within the circumferential recess 3130 of the actuator 3112. By way of example, the protrusion 3136 may be configured to enable rotational movement of the actuator 3112 but prevent axial translation of the actuator 3112 while the protrusion 3136 is engaged with the circumferential recess 3130. Thus, rotation of the actuator 3112 in a first direction will cause the distal wedge 3114 and proximal wedge 3116 to translate toward one another, causing expansion of the device. Rotation of the actuator 3112 in a second direction will cause the distal wedge 3114 and proximal wedge 3116 to translate away from one another, causing the device to collapse.

FIG. 276 illustrates an example of a distal ramp 3118 according to the present example embodiment. The distal ramp 3118 is substantially similar to the distal ramp 318 described above (and shown by way of example in FIG. 47), and thus a description of features common to both distal ramp 318 and distal ramp 3118 will not be repeated, except as necessary to illustrate the features unique to the distal ramp 3118 of the present embodiment. In some embodiments, the distal ramp 3118 may further comprise a proximal extension 3138 similar to the proximal extension 352 described above. In some embodiments, the proximal extension 3138 may include one or more protrusions 3140 extending toward the upper and/or lower endplates 3122a-d. In some embodiments, the one or more protrusions 3140 may include one or more medial flanges 3142 including contact surfaces 3144 configured to translate within angled guide tracks 3146 of the endplates 3122a-3122d to provide additional contact surfaces to support the assembly during height/lordotic expansion and contraction.

FIG. 277 illustrates an example of a locking element 3150 according to some embodiments. By way of example only, the locking element 3150 may be a cam style lock positioned within a lock aperture 3148 in the proximal wedge 3116. In some embodiments, the locking element 3150 may have a first portion 3152 and a second portion 3154. In some embodiments, the first portion 3152 may comprise a cylindrical outer surface. In some embodiments, the first portion may have a helical thread wound about the cylindrical outer surface. In some embodiments, the second portion 3154 may comprise a flat surface interrupting the cylindrical outer surface of the first portion 3152. In some embodiments, the locking element 3150 may include a drive aperture 3156 configured to receive at least a portion of an actuator instrument.

In some embodiments, the lock aperture 3148 includes a lateral opening in communication with the central bore of the wedge 3116 through which the actuator 3112 is inserted. Optionally, in any embodiment, the locking element 3150 may be positioned within the lock aperture 3148 in an initial position in which the second portion or flat surface 3154 is facing the medial aspect of the proximal wedge 3116 so that no part of the locking element 3150 is extending into the central bore of the proximal wedge 3116. In some embodiments, with the locking element 3150 in this initial position, the actuator 3112 may be inserted into the construct and/or actuated to effect device expansion or contraction as explained herein above with respect to many embodiments. When the desired expansion profile is achieved, the locking element 3150 may be rotated (e.g., using an actuator coupled with the drive aperture 3156) so that a portion including the major diameter of the locking element 3150 (e.g., defined by the maximum diameter of the outer surface) extends into the central bore and exerts a lateral force against the proximal end 3126 of the actuator, preventing further rotation of the actuator and thereby locking the expandable fusion device 3110 (or any embodiment described herein) in place (See, e.g., FIGS. 279-280).

FIG. 278 illustrates another example of a locking element 3160 according to some embodiments. By way of example only, the locking element 3160 may be a cam style lock positioned within a lock aperture 3148 in the proximal wedge 3116. In some embodiments, the locking element 3160 may have a first portion 3162 and a second portion 3164. In some embodiments, the first portion 3162 may comprise a cylindrical outer surface. In some embodiments, the cylindrical outer surface may be smooth. In some embodiments, the second portion 3164 may comprise a flat surface interrupting the cylindrical outer surface of the first portion 3162. In some embodiments, the locking element 3150 may include a drive aperture 3166 configured to receive at least a portion of an actuator instrument. In some embodiments, the locking element 3160 may have a stem portion 3168 extending therefrom, the stem portion 3168 having a radial groove 3170 formed therein. In some embodiments, the radial groove 3170 may extend circumferentially around the stem 3168. In some embodiments, the radial groove 3170 may extend partially around the stem 3168. In some embodiments, the radial groove 3170 may be configured to receive a portion of a retention pin 3172 therein to prevent ejection of the locking element 3160 from the proximal wedge 3116 (See, e.g., FIGS. 279-280). In some embodiments, the locking element 3160 may be configured for use with an actuator 3112 having a threaded proximal end. In some embodiments, the locking element 3160 may be configured for use with an actuator 3112 having a nonthreaded proximal end.

Optionally, in any embodiment, the locking element 3160 may be positioned within the lock aperture 3148 in an initial position in which the second portion or flat surface 3164 is facing the medial aspect of the proximal wedge 3116 so that no part of the locking element 3160 is extending into the central bore of the proximal wedge 3116. In some embodiments, with the locking element 3160 in this initial position, the actuator 3112 may be inserted into the construct and/or actuated to effect device expansion or contraction as explained herein above with respect to many embodiments. When the desired expansion profile is achieved, the locking element 3160 may be rotated (e.g., using an actuator coupled with the drive aperture 3166) so that a portion including the major diameter of the locking element 3160 (e.g., defined by the maximum diameter of the outer surface) extends into the central bore and exerts a lateral force against the proximal end 3126 of the actuator, preventing further rotation of the actuator and thereby locking the expandable fusion device 3110 (or any embodiment described herein) in place (See, e.g., FIGS. 279-280).

The expandable fusion device 3110 of the present example embodiment can further or alternatively include any features, components, or characteristics of any of the various example embodiments of expandable fusion devices described herein. Furthermore, any of the additionally described expandable fusion devices can further include any features, components, or characteristics of the expandable fusion device 3110.

Optionally, in any embodiment, the actuator may comprise a flexible member 3230 configured to effect expansion as shown by way of example only in FIGS. 281 and 282. In some embodiments, for example as shown in FIG. 281, the flexible member 3230 may pass through a first or ingress opening 3232 in the proximal wedge 3216, loop around a fulcrum element 3234 in the distal wedge 3214, and pass through a second or egress opening 3236 in the proximal wedge 3216 so that both ends of the flexible member 3230 extend proximal of proximal wedge 3216. In some embodiments, a user may hold both free ends of the flexible member 3230 while exerting a distal oriented force on the proximal wedge 3216. This force causes the proximal and distal wedges 3216, 3214, respectively, to translate toward one another thereby effecting expansion. Once the desired expansion is achieved, a locking element 3238 may be actuated to lock the flexible member in place.

In some embodiments, for example as shown in FIG. 282, one end of the flexible member 3230 may be secured to the proximal wedge 3216, and the flexible member 3230 may loop around a fulcrum element 3234 in the distal wedge 3214 and pass through an egress opening 3236 in the proximal wedge 3216 so that the free end of the flexible member 3230 extends proximal of proximal wedge 3216. In this embodiment, a user may effect expansion of the expandable fusion device by pulling on the free end of the flexible member 3230, which causes the proximal and distal wedges 3216, 3214, respectively, to translate toward one another thereby effecting expansion. Once the desired expansion is achieved, a locking element 3238 may be actuated to lock the flexible member in place.

In some embodiments, the flexible member 3230 may pass into and out of the same opening in the proximal wedge 3216. In some embodiments, the fulcrum element 3234 may comprise a portion of the distal wedge 3214 positioned between a pair of openings through which the flexible member 3230 passes (e.g., an egress opening and an ingress opening). In some embodiments, the fulcrum element 3234 may comprise a rigid member (e.g., pin, bar, etc.) extending across a single opening. In some embodiments, the flexible member 3230 may comprise at least one of suture, tape, braided cable, flexible shaft, rope, line, titanium cable, and the like.

By way of example only, FIGS. 283-290 illustrate several embodiments in which the proximal wedges, distal wedges, proximal ramps, and/or distal ramps may be partially or fully split in half, according to some embodiments.

In some embodiments, the proximal wedge 3300 and/or distal wedge 3302 may have one or more vertically oriented splits 3304, separating the wedge into two or more lateral portions, as shown by way of example in FIG. 283. In some embodiments, the proximal wedge 3300 and/or distal wedge 3302 may be may have one or more horizontally oriented splits 3306, separating the wedge into two or more vertical portions, as shown by way of example in FIG. 284. In either case, each portion may have a recess 3308 configured to engage with the actuator 12 (e.g. instead of a threaded bore as described above). By way of example, the recesses 3308 may be threaded or unthreaded. By way of example, the recesses 3308 complement one another to form a generally cylindrical opening when the split wedge portions are positioned adjacent one another. In some embodiments, the proximal and/or distal wedge may have one or more vertical splits and one or more horizontal splits.

In some embodiments, the proximal wedge 3310 and/or distal wedge 3312 may be at least partially, and preferably substantially split in half so that they are connected by a living hinge element 3314 (or fully split and joined with a hinge element). In such an embodiment, the proximal ramp 3316 and or distal ramp (not shown) may be fully split, with each half engaged with and translating along a respective portion of the wedges as with intact versions described above. In some embodiments, the split ramps 3316 may each have a projection 3318 configured to extend into and travel within the void of the wedge created by the split to capture the ramp portion relative to the respective wedge portion. In some embodiments, this interaction may comprise a dovetail connection or a tongue and groove connection.

In some embodiments, splitting the wedges and/or ramps to create a living hinge may enable an additional mode of expansion that may be performed independently of the translation-based expansion described herein. In some embodiments, this additional mode of expansion may comprise a lordotic expansion. In some embodiments, the additional mode of expansion may be performed prior to, during, or after completion of the translation-based expansion described herein.

In some embodiments, a spacer element may be provided for insertion between the split portions to force them apart. In some embodiments, the spacer element may be implantable within the split wedges. In some embodiments, the spacer may be non-implantable and must be removed after use. In some embodiments, the spacer may comprise a wedge shape. In some embodiments, the spacer may be threaded. In some embodiments, the spacer may be threadedly attached to one portion and have a nonthreaded engagement with another portion. In some embodiments, the spacer element may have a tapered thread and a threaded engagement with more than one split portion.

In some embodiments, a control element may be provided to ensure that the two or more portions move relative to one another in a predictable manner. In some embodiments, the control member is attached or connected to each of the split portions. In some embodiments, the control member may be a hinge element. In some embodiments, the control member may be a plate pivotally or translationally connected to each of the split portions.

By way of example only, FIGS. 288-290 illustrate an example of a fully split distal wedge 3300 that is split into four "quadrant" portions 3300a-3300d by a vertical split 3304 and a horizontal split 3306, according to some embodiments. Each wedge portion 3300a-3300d includes a coupling element 3322 configured to couple to a control member 3320. By way of example, the coupling elements 3322 of the present example embodiment comprise proximal protrusions configured to mate with mating slots 3324 of the control member 3320. In some embodiments (e.g. as shown in FIG. 288), the control member 3320 may comprise a generally rectangular plate member having a plurality of mating slots 3324 and a central opening 3326 configured to enable passage of (and/or access to) the actuator 12 therethrough.

By way of example only, the mating slots 3324 are configured to control movement of the wedge portions 3300a-d by defining the direction(s) in which the coupling elements 3322 are able to translate relative to the control member 3320. In some embodiments, the mating slots 3324 may be configured to effect movement in a particular fashion. For example, in some embodiments (e.g., FIG. 288), the mating slots 3324 may be configured to effect width expansion of the expandable fusion device first, then height expansion. In some embodiments (e.g. FIG. 289), the mating slots 3324 may be configured to effect height expansion first, and then width expansion. In some embodiments (e.g. FIG. 290), the mating slots 3324 may be configured to effect simultaneous width and height expansion.

FIGS. 291-294 illustrate an example of an expandable fusion device 3410 for implantation between two adjacent vertebrae, according some embodiments. By way of example only, the expandable fusion device 3410 of the present embodiment includes an actuator 3412, a pair of identical spacer elements 3414, a plurality of endplates 3122, and a pair of control members 3424. As with the previously-described embodiments, the spacer elements 3414 are coupled with the actuator 3412 and slideably associated with the endplates 3422. By way of example only, the expandable fusion device 3110 is illustrative of an expandable fusion device that expands in width and height that may be applied to any expandable fusion device examples described herein, according to some embodiments.

In some embodiments, each endplate 3422 may include a coupling element 3426 configured to couple to a control member 3424. By way of example, the coupling elements 3426 of the present example embodiment comprise proximal protrusions configured to mate with mating slots 3428 of the control member 3424. In some embodiments (e.g. as shown in FIG. 291), the control member 3424 may comprise a generally rectangular plate member having a plurality of mating slots 3428 and a central opening 3430 configured to enable passage of (and/or access to) the actuator 3412 and spacer 3414 therethrough.

In some embodiments, the spacer element 3426 may include a vertical wedge element 3432 and a horizontal wedge element 3434. In some embodiments, each of the vertical and horizontal wedge elements 3432, 3434 may include one or more beveled surfaces 3436 that are configured to slideably engage with corresponding ramped translation surfaces (not shown) formed in the respective endplates 3422. In some embodiments, the staged expansion, including the order, amount, and/or degree of expansion of each endplate may be controlled by the interaction between the wedge elements 3432, 3434 and the ramped translation surfaces of the endplates 3422. For example, in some embodiments, the vertical wedge element 3432 effects horizontal expansion or separation of the endplates 3422. In some embodiments, the horizontal wedge element 3434 affects vertical expansion or separation of the endplates 3422.

In some embodiments, the expandable fusion device 3410 may be configured to expand first in width, then in height by extending the vertical wedge element 3432 beyond the horizontal wedge element 3434 so that the beveled surfaces 3436 on the vertical wedge element 3432 contact the corresponding ramped translation surfaces in the endplates 3422 before the beveled surfaces 3436 of the horizontal wedge element 3434 make similar contact with corresponding ramped translation surfaces, as shown by way of example in FIG. 292. Once the beveled surfaces 3436 of the horizontal wedge element 3434 contact and translate along the corresponding ramped translation surfaces of the endplates 3422, then the expandable fusion device 3410 will expand in height, as shown by way of example only in FIG. 293. Alternatively, the same result may be achieved by providing a symmetrical spacer element 3414 but recessing one pair of corresponding ramped translation surfaces in the endplates 3422 so that contact with the recessed pair is delayed relative to contact with the non recessed pair. In some embodiments, the expandable fusion device 3410 may be configured to expand first in width, then in height, as described. In some embodiments, the expandable fusion device 3410 may be configured to expand first in height, then in width, for example by extending the horizontal wedge elements 3434 beyond the vertical wedge elements 3432, or by recessing the ramped translation surfaces of the endplates 3422 that correspond to the vertical wedge elements 3432 to delay contact. In some embodiments, the expandable fusion device 3410 may be configured to expand in width and height simultaneously, for example by providing a symmetrical spacer element 3414 that interacts with symmetrical corresponding ramped translation surfaces of the endplates 3422. In some embodiments, asymmetrical expansion may be achieved in a similar fashion, namely by configuring at least one of the spacer element 3414 and the ramped translation surfaces to achieve that result.

In some embodiments, for example as shown in FIG. 294, the endplates 3422 may be connected by flexible members that stabilize the endplates during expansion. In such an embodiment, the control member 3424 may be optional.

In some embodiments, rotation of the actuator 3412 in a first rotational direction causes the spacer elements 3414 to translate toward one another along the actuator 3412. As this translation occurs the beveled surfaces 3436 of the vertical and/or horizontal wedge elements 3432, 3434 translate within ramped translation surfaces of the endplates, causing expansion of the endplates in width and/or height.

The teachings contained herein include descriptions that are merely exemplary in nature and are in no way intended to limit the teachings, their applications, or uses. While directed generally towards embodiments of the expandable fusion device and method for its implantation between two adjacent lumbar vertebrae using a lateral, posterior and transforaminal approaches to spine, it should be appreciated that similar mechanisms and arrangements of the same are also used in treatment of cervical, thoracic and sacral spine segments, utilizing other surgical approaches including but not limited to transpedicular, transiliac, anterior and anterior-lateral approaches and configured to interface with respective anatomies and approach angles. Similarly, while the teachings are directed generally towards embodiments of the expandable fusion device which might include, for example, a drive system having an actuator drawing wedges together to cause expansion, perhaps in combination with a spacer system that is independent of the drive system, it should be appreciated that in other embodiments the same functionality can be achieved through actuator forcing the wedges apart, or perhaps the spacer or spacers can be any suitable object, of any shape size or configuration that can separate structural components in a manner similar, or substantially similar, to the teachings set-forth herein.

The present disclosure provides a plurality of example embodiments of an expandable fusion device configured for insertion between adjacent vertebral bodies, each example embodiment intended to illustrate one or more specific features, components, and/or characteristics of the expandable fusion device. These features, components, and/or characteristics are interchangeable between and within example embodiments. Thus, as previously noted herein throughout, the expandable fusion device of any example embodiment can further or alternatively include any features, components, or characteristics of any of the various example embodiments of expandable fusion devices described herein. Furthermore, it is specifically contemplated that various example embodiments may be combined with various other example embodiments to form hybrid embodiments with a first portion of the hybrid embodiment resembling a first example embodiment, a second portion of the hybrid embodiment resembling a second example embodiment, a third portion of the hybrid embodiment resembling a third example embodiment, etc. For example, this may mean that specific components (e.g., wedges, ramps, endplates, etc.) may be asymmetric in that they have different features that interact with different parts of the device (e.g. a wedge component having a tongue and groove connector on one side and a pin linkage on another side). A few such examples are provided herein. However, this is not limited to combinations shown and described herein. As illustrated in FIGS. 295-296, for example, the expandable fusion devices shown herein may be hypothetically divided into sectors, with each sector comprising an axial quadrant (e.g., L1, L2, R1, or R2, which accounts for a transverse half (e.g. L or R) and a vertical half (e.g. 1 or 2)), and a longitudinal portion (e.g. A, B, or C, which longitudinal portions may or may not be unequal). Thus, the provided example is divided into for example, 12 sectors (e.g. L1A, L1B, L1C, L2A, L2B, L2C . . . ). The expandable fusion device described herein is interchangeable by sector such that the features of any one sector of one example embodiment may be applied to the corresponding sector of any other embodiment, in any combination. For example, the above means among other things, that if embodiments Z1, Z2, Z3, Z4 and Z5 are shown or described herein, then an embodiment is contemplated in which for example, the L1A and L2A sectors of the wedge may have the features of the wedge from Z1, the R1A and R2A sectors of the wedge may have the features of the wedge from Z2, the half of the ramp in R1A sector may have the features of the ramp from Z3, the half of the ramp in R2A sector may have the features of the ramp from Z4, the R1A sector of the endplate may be 20% of its length and have features of the endplate from Z3, the R1B sector of the endplate may be 50% of its length and have the features of the endplate from Z1 and R1C sector of the endplate may be 30% of its length and have the features of the endplate from Z5.

Unless otherwise defined, all technical terms used herein are intended to have the same meaning as commonly understood by one of ordinary skill in the art to which this disclosure belongs. The singular forms "a," "an," and "the" include plural references unless the context clearly dictates otherwise. Any reference to "or" herein is intended to encompass "and/or" unless otherwise stated. The term "about" can be used to refer to a variance around the stated amount that is near the stated amount by 10%, 9%, 8%, 7%, 6%, 5%, 4%, 3%, 2%, or 1%, including amounts or ranges therein in amount of 0.1%. The term "longitudinal axis" can be used to refer to a theoretical axis in space comprising an axis of revolving symmetry of an object. The term "slidably coupled" can be used to refer to a relationship between two or more components whereby the components share at least one degree of freedom. The term "external width" can be used to refer to the width between the outermost surfaces of an object. The term "external distance" can be used to refer to the distance between the outermost surfaces of an object. The term "apex" can be used to refer to the maximum value of a distance, measurement, or parameter. The term "thread feature" can be used to refer to one or more helical or spiral protrusions or recesses capable of acting as, or coupling with another thread feature.

Moreover, it should be appreciated that the devices taught herein are expandable, which means that they can also be collapsible in some embodiments. One of the benefits is that each of the embodiments can have a collapsed configuration for insertion into a target space through a small surgical corridor which can be, for example, an intervertebral space. As such, they have an expanded configuration for expansion in the target space to serve as a scaffolding to support surrounding tissue which can be, for example, the tissue surrounding an intervertebral space, as well as bone graft material in a spinal fusion procedure. In some embodiments, the devices can be designed to expand in the cephalocaudal direction only, "cephalocaudal" expansion, also referred to as "craniocaudal" expansion and, perhaps, "vertical" expansion. In some embodiments, the devices can be designed to expand in the transverse direction only, "transverse" expansion, also referred to as "lateral" expansion. That is, one of skill will appreciate that the designs can be designed to include, and thus to operate with, only one of the expansions systems described herein. That is, this teaching is expressly intended to represent unilaterally expandable device, cephalocaudally expandable only, and transversely expandable only, in which one of skill can use any one of the expansion systems taught herein to expand the endplates of the devices either laterally only or vertically only. The embodiments that are illustrated and described in most detail, however, are the devices that include both of the expansion systems taught herein, a concerted design that includes the drive system and the spacer system, in which each system is designed to work independent of the other in a single device to obtain the improvements, and address the problems in the art, at least as set-forth herein.

Moreover, the methods, devices, and systems taught herein can be used on any subject for experimental purposes, or for medical treatments, for example. The terms "subject" and "patient" can be used interchangeably in some embodiments and can be used to refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like.

Moreover, terms of degree are used herein to provide relative relationships between the position and/or movements of components of the systems taught herein. For example, the phrase "at least substantially" can be used to refer to an approximation, perhaps relevant to an amount, position, or function one amount, position, or function relative to another. For example, an axis that is at least substantially parallel to another axis can be used to refer to an orientation that is intended, for all practical purposes to be parallel, but it is understood that this is just a convenient reference and that there can be variations due to stresses internal to the system and imperfections in the devices and systems. Likewise, the phrase "at least substantially parallel", "at least substantially on a plane", or "at least substantially coincident", for example, can each refer to a type of an orientation or movement that is intended, for all practical purposes, to be on or near, for example, an axis or a plane, or a point, as the case may be, as a convenient measure of the orientation or movement without having to suffer the hard definition, the ultimate measure, unless otherwise defined is known to one of skill as just a convenient reference, allowing variance until there are variations due to stresses internal to the system and imperfections in the devices and systems that affect the operation of the methods, devices and systems to the point that they are no longer of use and, in some embodiments, to the point of being non-functional. In some embodiments, the term "at least substantially parallel", "at least substantially on a plane", or "at least substantially coincident", for example, can be described as any deviation from "0°" (meaning "parallel" or "on the plane, in some embodiments), such as a deviation from the parallel or plane in an amount of about 1°, about 2°, about 3°, about 4°, about 5°, or any range or amount therein in increments of 0.1° with respect to angular deviations, and in an amount of about 1 mm, about 2 mm, about 3 mm, about 4 mm, about 5 mm, or any range or amount therein in increments of 0.1 mm, with respect to distance deviations.

I claim:

1. A cage with independent width and height expansion, the cage comprising:
    a beam assembly having a proximal end, a distal end, and a long axis disposed between the proximal end and the distal end, a first beam with a proximal end and a distal end, a second beam with a proximal end and a distal end, and a third beam with a proximal end and a distal end, and a collapsed state and an expanded state;
    a wedge assembly having a first wedge and a second wedge, the first wedge movably connected to a first guide and configured for increasing the width of the cage when the first wedge is moved in the direction of the long axis relative to the beam assembly, wherein the first wedge is positioned between the first beam and the third beam, and the first guide (i) comprises a vertical post slideably coupled directly to the first beam and the second beam such that the first beam and second beam move vertically along the vertical post, and (ii) does not provide an expansion in height by being moved in the direction of the long axis relative to the beam assembly; and
    a ramp assembly having a ramp movably positioned between the first beam and the second beam and configured for increasing the height of the cage with a movement of the ramp in the direction of the long axis relative to the beam assembly;
    wherein the translation of the first wedge increases the width of the cage without increasing the height of the cage, the translation of the ramp increases the height of the cage without increasing the width of the cage, and the ramp is configured to translate independently of the wedge assembly in the direction of the long axis.

2. The cage of claim 1, wherein the ramp is not in contact with the first wedge through at least a first distance moved by the first wedge.

3. The cage of claim 1, wherein the ramp is not in contact with the first wedge through at least a final distance moved by the first wedge.

4. The cage of claim 1, wherein the ramp is not in contact with the first wedge through the entirety of the distance moved by the first wedge.

5. The cage of claim 1, wherein:

the wedge assembly is configured to retain the first beam, the second beam, and the third beam from expanding beyond a desired width in the expanded state;

the first wedge is configured with a retaining mechanism to retain the first guide from separating from the first wedge in the expanded state;

the first guide is configured with a retaining mechanism to retain the first beam and the second beam from separating from the first guide in the expanded state; and, the wedge assembly is configured with a retaining mechanism to retain the third beam from separating from the wedge assembly in the expanded state.

6. The cage of claim 5, wherein:

the wedge assembly is configured to retain the first beam, the second beam, and the third beam from expanding beyond a desired width in the expanded state;

the first wedge is configured with a first retaining mechanism to retain the first guide from separating from the first wedge in the expanded state;

the wedge assembly is configured with a second retaining mechanism to retain a second guide from separating from the first wedge in the expanded state;

the first guide is configured with a retaining mechanism to retain the first beam and the second beam from separating from the first guide in the expanded state; and, the second guide is configured with a retaining mechanism to retain the third beam from separating from the second guide in the expanded state.

7. The cage of claim 1, wherein:

the beam assembly further comprises a fourth beam; and the wedge assembly has a second guide that is (i) slideably coupled with the third beam and the fourth beam, (ii) does not provide an expansion in height by being moved in the direction of the long axis relative to the beam assembly, and (iii) comprises a vertical post.

* * * * *